US010059959B2

(12) United States Patent
Baum et al.

(10) Patent No.: US 10,059,959 B2
(45) Date of Patent: Aug. 28, 2018

(54) LEPIDOPTERAN-ACTIVE CRY1DA1 AMINO ACID SEQUENCE VARIANT PROTEINS

(71) Applicant: Monsanto Technology LLC, St. Louis, MO (US)

(72) Inventors: James A. Baum, Webster Groves, MO (US); Thomas Cerruti, Newton, MA (US); Stanislaw Flasinski, Chesterfield, MO (US); Xiaoran Fu, Belmont, MA (US); Arlene R. Howe, Chesterfield, MO (US); Sara Ann Salvador, Wildwood, MA (US)

(73) Assignee: Monsanto Technology LLC, St. Louis, MO (US)

( * ) Notice: Subject to any disclaimer, the term of this patent is extended or adjusted under 35 U.S.C. 154(b) by 287 days.

(21) Appl. No.: 14/884,432

(22) Filed: Oct. 15, 2015

(65) Prior Publication Data
US 2016/0108426 A1  Apr. 21, 2016

Related U.S. Application Data

(60) Provisional application No. 62/065,017, filed on Oct. 17, 2014, provisional application No. 62/064,994, filed on Oct. 16, 2014.

(51) Int. Cl.
| C07K 14/325 | (2006.01) |
| C12N 15/82 | (2006.01) |
| A01H 5/10 | (2018.01) |
| C12N 15/32 | (2006.01) |
| A01N 47/08 | (2006.01) |
| A01N 63/02 | (2006.01) |

(52) U.S. Cl.
CPC ......... *C12N 15/8286* (2013.01); *A01N 47/08* (2013.01); *A01N 63/02* (2013.01); *C07K 14/325* (2013.01); *Y02A 40/162* (2018.01)

(58) Field of Classification Search
CPC .................. C07K 14/325; C12N 15/8286
See application file for complete search history.

(56) References Cited

U.S. PATENT DOCUMENTS

| 5,500,365 | A | 3/1996 | Fischhoff et al. |
| 5,880,275 | A | 3/1999 | Fischhoff et al. |
| 6,033,874 | A | 3/2000 | Baum et al. |
| 6,501,009 | B1 | 12/2002 | Romano |
| 6,713,063 | B1 | 3/2004 | Malvar et al. |
| 6,962,705 | B2 | 11/2005 | Malvar et al. |
| 7,064,249 | B2 | 6/2006 | Corbin et al. |
| 7,070,982 | B2 | 7/2006 | Malvar et al. |
| 7,510,878 | B2 | 3/2009 | Abad et al. |
| 7,772,465 | B2 | 8/2010 | Abad et al. |
| 7,812,129 | B1 | 10/2010 | Abad et al. |
| 7,927,598 | B2 | 4/2011 | Malvar et al. |
| 8,344,207 | B2 | 1/2013 | Bogdanova et al. |
| 8,609,936 | B2 | 12/2013 | Baum et al. |

| 2004/0058860 | A1* | 3/2004 | Payne ............... A01N 63/00 435/418 |
| 2005/0155103 | A1 | 7/2005 | Baum et al. |
| 2006/0021087 | A1 | 1/2006 | Baum et al. |
| 2006/0112447 | A1 | 5/2006 | Bogdanova et al. |
| 2008/0172762 | A1 | 7/2008 | Cerf et al. |
| 2009/0313721 | A1 | 12/2009 | Abad et al. |
| 2010/0004176 | A1 | 1/2010 | Sampson et al. |
| 2010/0017914 | A1 | 1/2010 | Hart et al. |
| 2010/0077507 | A1 | 3/2010 | Abad et al. |
| 2010/0077508 | A1 | 3/2010 | Abad et al. |
| 2010/0137216 | A1 | 6/2010 | Carozzi et al. |
| 2010/0160231 | A1 | 6/2010 | Sampson et al. |
| 2010/0192256 | A1 | 7/2010 | Abad et al. |
| 2010/0197592 | A1 | 8/2010 | Heinrichs |
| 2010/0269221 | A1 | 10/2010 | Abad et al. |
| 2010/0317569 | A1 | 12/2010 | Lira et al. |
| 2010/0319092 | A1 | 12/2010 | Lira et al. |
| 2010/0319093 | A1 | 12/2010 | Lira et al. |
| 2011/0030096 | A1 | 2/2011 | Sampson et al. |
| 2011/0055968 | A1 | 3/2011 | Cerf et al. |
| 2011/0112013 | A1 | 5/2011 | Abad et al. |
| 2011/0154536 | A1 | 6/2011 | Abad et al. |
| 2012/0047606 | A1 | 2/2012 | Abad et al. |
| 2012/0117690 | A1 | 5/2012 | Cerf et al. |

(Continued)

FOREIGN PATENT DOCUMENTS

| EP | 0 358 557 A2 | 3/1990 |
| WO | WO 2011/041256 A2 | 4/2011 |

(Continued)

OTHER PUBLICATIONS

Tounsi et al (J. Appl. MicrobioL 95:23-28; 2003) (Year: 2003).*
de Maagd et al (Appl Environ. Microbiol 65:4369-4374, 1999) (Year: 1999).*
Aronson et al ((FEMS Microbiol. Lett. 2001, 195:1-8) (Year: 2001).*
Bravo et al (Microbial Biotechnology, 6, (2012) 17-26 (Year: 2012).*
Crickmore et al., "Revision of the Nomenclature for *Bacillus thuringiensis* Pesticidal Crystal Proteins," *Microbiology and Molecular Biology Reviews*, 62(3):807-813 (1998).
Höfte et al., "Insecticidal Crystal Proteins of *Bacillus thuringiensis*," *Microbiological Reviews*, 53:242-255 (1989).
Höfte et al., "Nucleotide sequence and deduced amino acid sequence of a new Lepidoptera-specific crystal protein gene from *Bacillus thuringiensis*," *Nucleic Acids Research*, 18(18):5545 (1990).

(Continued)

*Primary Examiner* — Lee A Visone
(74) *Attorney, Agent, or Firm* — Timothy K. Ball; Carine M. Doyle; Arnold & Porter Kaye Scholer LLP

(57) ABSTRACT

Engineered Cry1Da amino acid sequences are provided that exhibit improved Lepidopteran insecticidal activity and an enhanced Lepidopteran spectrum compared to the naturally occurring Cry1Da protein toxin. Polynucleotide sequences intended for use in expression of the improved proteins in plants are also provided. Particular embodiments provide compositions containing insect inhibitory amounts of the engineered proteins, as well as recombinant plants, plant parts, and seeds containing polynucleotide constructs encoding one or more of the improved engineered proteins.

20 Claims, 1 Drawing Sheet

Specification includes a Sequence Listing.

(56) References Cited

U.S. PATENT DOCUMENTS

| | | |
|---|---|---|
| 2012/0167259 A1 | 6/2012 | Liu et al. |
| 2012/0192310 A1 | 7/2012 | Abad et al. |
| 2012/0210462 A1 | 8/2012 | Bermudez et al. |
| 2012/0233726 A1 | 9/2012 | Abad et al. |
| 2013/0055469 A1 | 2/2013 | Sampson et al. |
| 2013/0097735 A1 | 4/2013 | Bowen et al. |
| 2013/0104259 A1 | 4/2013 | Sampson et al. |
| 2013/0117884 A1 | 5/2013 | Hargiss et al. |
| 2013/0167264 A1 | 6/2013 | Sampson et al. |
| 2013/0219570 A1 | 8/2013 | Lira et al. |
| 2013/0269060 A1 | 10/2013 | Baum et al. |
| 2013/0303440 A1 | 11/2013 | Sampson et al. |
| 2013/0310543 A1 | 11/2013 | Sampson et al. |
| 2014/0007292 A1 | 1/2014 | Cerf et al. |
| 2014/0033361 A1 | 1/2014 | Altier et al. |
| 2014/0033363 A1 | 1/2014 | Sampson |
| 2014/0196175 A1 | 7/2014 | Samspson et al. |
| 2014/0223598 A1 | 8/2014 | Sampson et al. |
| 2014/0223599 A1 | 8/2014 | Sampson et al. |
| 2014/0245491 A1 | 8/2014 | Sampson et al. |
| 2014/0298538 A1 | 10/2014 | Heinrichs et al. |
| 2014/0366227 A1 | 12/2014 | Gatehouse et al. |
| 2014/0373195 A1 | 12/2014 | Sampson et al. |

FOREIGN PATENT DOCUMENTS

| | | |
|---|---|---|
| WO | WO 2012/139004 A2 | 10/2012 |
| WO | WO 2014/008054 A2 | 1/2014 |
| WO | WO 2014/055881 A1 | 4/2014 |

OTHER PUBLICATIONS

International Search Report dated Jun. 20, 2016, in International Patent Application No. PCT/US2015/055779.

Kim et al., "Mutagenesis of *Bacillus thuringiensis* cry1Ac gene and its insecticidal activity against *Plutella xylostella* and *Ostrinia furnacalis*," *Biological Control*, 47(2):222-227 (2008).

Lucena et al., "Molecular Approaches to Improve the Insecticidal Activity of *Bacillus thuringiensis* Cry toxins," *Toxins*, 6(8):2393-2423 (2014).

Pardo-Lopez et al., "Strategies to improve the insecticidal activity of Cry toxins from *Bacillus thuringiensis*," *Peptides*, 30(3):589-595 (2008).

Rajamohan et al., "Protein engineering of *Bacillus thuringiensis* Δ-endotoxin: Mutations at domain II of CryIAb enhance receptor affinity and toxicity toward gypsy moth larvae," *Proceedings of the National Academy of Sciences U.S.A.*, 93(25):14338-14343 (1996).

Saraswathy et al., "Protein engineering of delta-endotoxins of *Bacillus thuringiensis*," *Electronic Journal of Biotechnology*, 7(2):178-188 (2004).

Yu et al., "Effect of Cry1Ca7 protein modified by site-directed mutagenesis on inhibiting Spodoptera exigua Hubner," *Acta Microbiologica Sinica*, 48(6):733-738 (2008).

Höfte et al., "Nucleotide sequence and deduced amino acid sequence of a new Lepidoptera-specific crystal protein gene from *Bacillus thuringiensis*," *Nucleic Acids Research*, 18:5545 (1990).

IUPAC-IUB Joint Commission on Biochemical Nomenclature, "Nomenclature and Symbolism for Amino Acids and Peptides," *Eur. J. Biochem.* 138:9-37(1984).

Tabashnik et al., "Cross-Resistance of Pink Bollworm (*Pectinophora gossypiella*) to *Bacillus thuringiensis* Toxins," *Applied and Environmental Microbiology*, 66:4582-4584 (2000).

Tabashnik et al., "Cross-Resistance to *Bacillus thuringiensis* Toxin Cry1Ja in a Strain of Diamondback Moth Adapted to Artificial Diet," *Journal of Invertebrate Pathology*, 76:81-83 (2000).

Thompson et al., "CLUSTAL W: improving the sensitivity of progressive multiple sequence alignment through sequence weighting, position-specific gap penalties and weight matrix choice," *Nucleic Acids Research*, 22:4673-4680 (1994).

\* cited by examiner

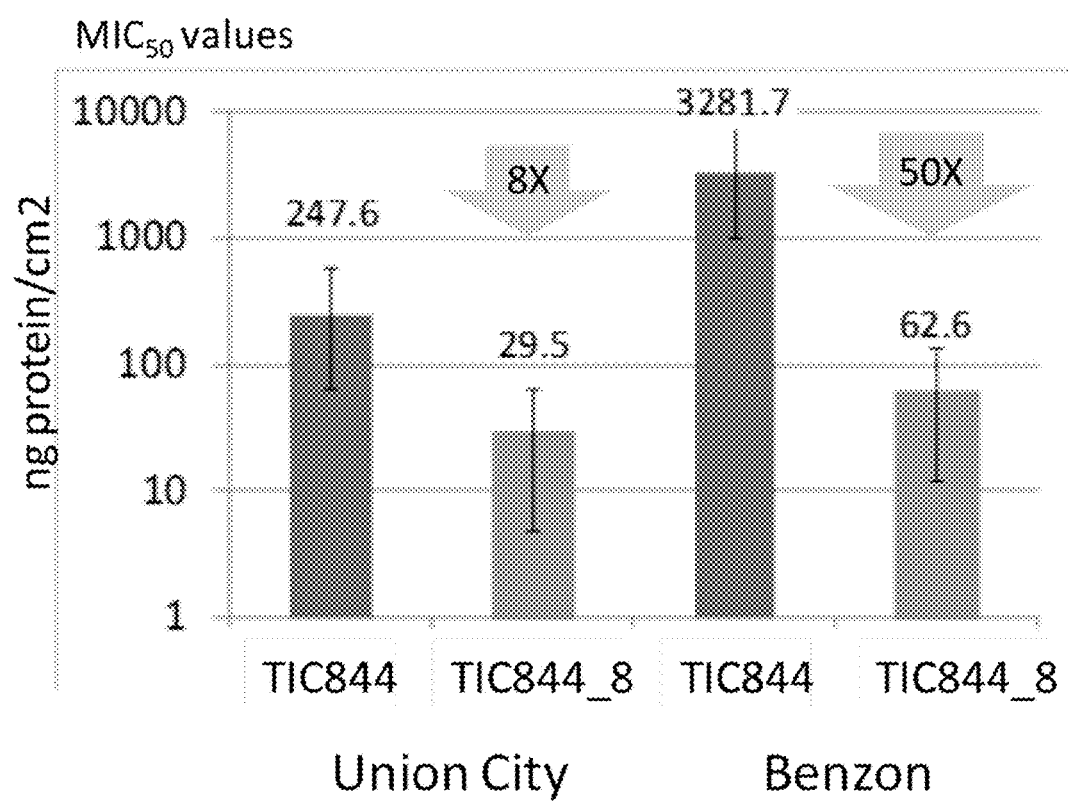

SEQUENCE LISTING

```
<160> NUMBER OF SEQ ID NOS: 44

<210> SEQ ID NO 1
<211> LENGTH: 3498
<212> TYPE: DNA
<213> ORGANISM: Bacillus thuringiensis
<220> FEATURE:
<221> NAME/KEY: misc_feature
<222> LOCATION: (1)..(3498)
<223> OTHER INFORMATION: Nucleotide sequence used for expression in a
      bacterial cell encoding Cry1Da1.

<400> SEQUENCE: 1
atggaaataa ataatcaaaa ccaatgtgtg ccttacaatt gtttaagtaa tcctaaggag      60
ataatattag gcgaggaaag gctagaaaca gggaatactg tagcagacat ttcattaggg     120
cttattaatt ttctatattc taattttgta ccaggaggag gatttatagt aggtttacta     180
gaattaatat ggggatttat agggccttcg caatgggata ttttttttagc tcaaattgag     240 caattgatta gtcaaagaat agaagaattt gctaggaatc aggcaatttc aagattggag     300
gggctaagca atctttataa ggtctatgtt agagcgttta gcgactggga gaaagatcct     360
actaatcctg cttaaggga agaaatgcgt atacaattta tgacatgaa tagtgctctc     420 ataacggcta ttccactttt tagagttcaa aattatgaag ttgctctttt atctgtatat     480
```

```
gttcaagccg caaacttaca tttatctatt ttaagggatg tttcagtttt cggagaaaga    540
tggggatatg atacagcgac tatcaataat cgctatagtg atctgactag ccttattcat    600
gtttatacta accattgtgt ggatacgtat aatcagggat taaggcgttt ggaaggtcgt    660
tttcttagcg attggattgt atataatcgt ttccggagac aattgacaat ttcagtatta    720
gatattgttg cgttttttcc aaattatgat attagaacat atccaattca aacagctact    780
cagctaacga gggaagtcta tctggattta cctttttatta atgaaaatct ttctcctgca    840
gcaagctatc caacctttc agctgctgaa agtgctataa ttagaagtcc tcatttagta    900 gacttttaa atagctttac catttataca gatagtctgg cacgttatgc atattgggga    960
gggcacttgg taaattcttt ccgcacagga accactacta atttgataag atccccttta   1020
tatggaaggg aaggaaatac agagcgcccc gtaactatta ccgcatcacc tagcgtacca   1080
atatttagaa cactttcata tattacaggc cttgacaatt caaatcctgt agctggaatc   1140
gagggagtgg aattccaaaa tactataagt agaagtatct atcgtaaaag cggtccaata   1200
gattctttta gtgaattacc acctcaagat gccagcgtat ctcctgcaat tgggtatagt   1260
caccgtttat gccatgcaac attttttagaa cggattagtg gaccaagaat agcaggcacc   1320
gtattttctt ggacacaccg tagtgccagc cctactaacg aagtaagtcc atctagaatt   1380
acacaaattc catgggtaaa ggcgcatact cttgcatctg gtgcctccgt cattaaaggt   1440
cctggattta caggtggaga tattctgact aggaatagta tgggcgagct ggggaccttta   1500 cgagtaaccct tcacaggaag attaccacaa agttattata tacgtttccg ttatgcttcg   1560
gtagcaaata ggagtggtac atttagatat tcacagccac cttcgtatgg aatttcattt   1620
ccaaaaacta tggacgcagg tgaaccacta acatctcgtt cgttcgctca tacaacactc   1680
ttcactccaa taacctttc acgagctcaa gaagaatttg atctatacat ccaatcgggt   1740
gtttatatag atcgaattga atttataccg gttactgcaa catttgaggc agaatatgat   1800
ttagaaagag cgcaaaaggt ggtgaatgcc ctgtttacgt ctacaaacca actagggcta   1860
aaaacagatg tgacggatta tcatattgat caggtatcca atctagttgc gtgtttatcg   1920
gatgaatttt gtctggatga aaagagagaa ttgtccgaga agttaaaaca tgcaaagcga   1980
ctcagtgatg agcggaattt acttcaagat ccaaacttca gagggatcaa taggcaacca   2040
gaccgtggct ggagaggaag tacggatatt actatccaag gaggagatga cgtattcaaa   2100
gagaattacg ttacgctacc gggtaccttt gatgagtgct atccaacgta tttatatcaa   2160
aaaatagatg agtcgaaatt aaaagcctat acccgttatc aattaagagg gtatatcgaa   2220
gatagtcaag acttagaaat ctatttaatt cgttacaatg caaaacacga aatagtaaat   2280
gtaccaggta caggaagttt atggcctctt tctgtagaaa atcaaattgg accttgtgga   2340
gaaccgaatc gatgcgcgcc acaccttgaa tggaatcctg atttacactg ttcctgcaga   2400 gacgggaaa atgtgcaca tcattctcat catttctctt tggacattga tgttggatgt   2460
acagacttaa atgaggactt aggtgtatgg gtgatattca agattaagac gcaagatggc   2520
cacgcacgac tagggaatct agagtttctc gaagagaaac cattattagg agaagcacta   2580
gctcgtgtga aaagagcgga gaaaaatgg agagacaaac gcgaaacatt acaattggaa   2640
acaactatcg tttataaaga ggcaaaagaa tctgtagatg ctttatttgt aaactctcaa   2700
tatgatagat tacaagcgga tacgaacatc gcgatgattc atgcggcaga taaacgcgtt   2760
catagaattc gagaagcgta tctgccggag ctgtctgtga ttccgggtgt caatgcggct   2820 attttttgaag aattagaaga gcgtatttc actgcatttt ccctatatga tgcgagaaat   2880
```

-continued

```
attattaaaa atggcgattt caataatggc ttattatgct ggaacgtgaa agggcatgta    2940
gaggtagaag aacaaaacaa tcaccgttca gtcctggtta tcccagaatg ggaggcagaa    3000
gtgtcacaag aggttcgtgt ctgtccaggt cgtggctata tccttcgtgt tacagcgtac    3060
aaagagggat atggagaagg ttgcgtaacg atccatgaga tcgagaacaa tacagacgaa    3120
ctgaaattca caactgtgt agaagaggaa gtatatccaa caacacggt aacgtgtatt     3180 aattatactg cgactcaaga agaatatgag ggtacgtaca cttctcgtaa tcgaggatat    3240
gacgaagcct atggtaataa cccttccgta ccagctgatt atgcgtcagt ctatgaagaa    3300
aaatcgtata cagatagacg aagagagaat ccttgtgaat ctaacagagg atatggagat    3360
tacacaccac taccagctgg ttatgtaaca aaggaattag agtacttccc agagaccgat    3420
aaggtatgga ttgagattgg agaaacagaa ggaacattca tcgtggacag cgtggaatta    3480
ctccttatgg aggaatag                                                  3498
```

```
<210> SEQ ID NO 2
<211> LENGTH: 1165
<212> TYPE: PRT
<213> ORGANISM: Bacillus thuringiensis
<220> FEATURE:
<221> NAME/KEY: MISC_FEATURE
<222> LOCATION: (1)..(1165)
<223> OTHER INFORMATION: Amino acid sequence of the protein Cry1Da1.

<400> SEQUENCE: 2

Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Lys Val Tyr Val Arg Ala
            100                 105                 110

Phe Ser Asp Trp Glu Lys Asp Pro Thr Asn Pro Ala Leu Arg Glu Glu
        115                 120                 125

Met Arg Ile Gln Phe Asn Asp Met Asn Ser Ala Leu Ile Thr Ala Ile
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
        195                 200                 205

Thr Tyr Asn Gln Gly Leu Arg Arg Leu Glu Gly Arg Phe Leu Ser Asp
    210                 215                 220

Trp Ile Val Tyr Asn Arg Phe Arg Arg Gln Leu Thr Ile Ser Val Leu
225                 230                 235                 240
```

```
Asp Ile Val Ala Phe Pro Asn Tyr Asp Ile Arg Thr Tyr Pro Ile
            245                 250                 255

Gln Thr Ala Thr Gln Leu Thr Arg Glu Val Tyr Leu Asp Leu Pro Phe
        260                 265                 270

Ile Asn Glu Asn Leu Ser Pro Ala Ala Ser Tyr Pro Thr Phe Ser Ala
        275                 280                 285

Ala Glu Ser Ala Ile Ile Arg Ser Pro His Leu Val Asp Phe Leu Asn
        290                 295                 300

Ser Phe Thr Ile Tyr Thr Asp Ser Leu Ala Arg Tyr Ala Tyr Trp Gly
305                 310                 315                 320

Gly His Leu Val Asn Ser Phe Arg Thr Gly Thr Thr Asn Leu Ile
                325                 330                 335

Arg Ser Pro Leu Tyr Gly Arg Glu Gly Asn Thr Glu Arg Pro Val Thr
                340                 345                 350

Ile Thr Ala Ser Pro Ser Val Pro Ile Phe Arg Thr Leu Ser Tyr Ile
            355                 360                 365

Thr Gly Leu Asp Asn Ser Asn Pro Val Ala Gly Ile Glu Gly Val Glu
        370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
            405                 410                 415

Ile Gly Tyr Ser His Arg Leu Cys His Ala Thr Phe Leu Glu Arg Ile
            420                 425                 430

Ser Gly Pro Arg Ile Ala Gly Thr Val Phe Ser Trp Thr His Arg Ser
            435                 440                 445

Ala Ser Pro Thr Asn Glu Val Ser Pro Ser Arg Ile Thr Gln Ile Pro
            450                 455                 460

Trp Val Lys Ala His Thr Leu Ala Ser Gly Ala Ser Val Ile Lys Gly
465                 470                 475                 480

Pro Gly Phe Thr Gly Gly Asp Ile Leu Thr Arg Asn Ser Met Gly Glu
            485                 490                 495

Leu Gly Thr Leu Arg Val Thr Phe Thr Gly Arg Leu Pro Gln Ser Tyr
            500                 505                 510

Tyr Ile Arg Phe Arg Tyr Ala Ser Val Ala Asn Arg Ser Gly Thr Phe
            515                 520                 525

Arg Tyr Ser Gln Pro Pro Ser Tyr Gly Ile Ser Phe Pro Lys Thr Met
            530                 535                 540

Asp Ala Gly Glu Pro Leu Thr Ser Arg Ser Phe Ala His Thr Thr Leu
545                 550                 555                 560

Phe Thr Pro Ile Thr Phe Ser Arg Ala Gln Glu Glu Phe Asp Leu Tyr
            565                 570                 575

Ile Gln Ser Gly Val Tyr Ile Asp Arg Ile Glu Phe Ile Pro Val Thr
            580                 585                 590

Ala Thr Phe Glu Ala Glu Tyr Asp Leu Glu Arg Ala Gln Lys Val Val
            595                 600                 605

Asn Ala Leu Phe Thr Ser Thr Asn Gln Leu Gly Leu Lys Thr Asp Val
            610                 615                 620

Thr Asp Tyr His Ile Asp Gln Val Ser Asn Leu Val Ala Cys Leu Ser
625                 630                 635                 640

Asp Glu Phe Cys Leu Asp Glu Lys Arg Glu Leu Ser Glu Lys Val Lys
            645                 650                 655
```

-continued

His Ala Lys Arg Leu Ser Asp Glu Arg Asn Leu Leu Gln Asp Pro Asn
        660                 665                 670

Phe Arg Gly Ile Asn Arg Gln Pro Asp Arg Gly Trp Arg Gly Ser Thr
        675                 680                 685

Asp Ile Thr Ile Gln Gly Gly Asp Val Phe Lys Glu Asn Tyr Val
        690                 695                 700

Thr Leu Pro Gly Thr Phe Asp Glu Cys Tyr Pro Thr Tyr Leu Tyr Gln
705                 710                 715                 720

Lys Ile Asp Glu Ser Lys Leu Lys Ala Tyr Thr Arg Tyr Gln Leu Arg
                725                 730                 735

Gly Tyr Ile Glu Asp Ser Gln Asp Leu Glu Ile Tyr Leu Ile Arg Tyr
            740                 745                 750

Asn Ala Lys His Glu Ile Val Asn Val Pro Gly Thr Gly Ser Leu Trp
        755                 760                 765

Pro Leu Ser Val Glu Asn Gln Ile Gly Pro Cys Gly Glu Pro Asn Arg
        770                 775                 780

Cys Ala Pro His Leu Glu Trp Asn Pro Asp Leu His Cys Ser Cys Arg
785                 790                 795                 800

Asp Gly Glu Lys Cys Ala His His Ser His His Phe Ser Leu Asp Ile
                805                 810                 815

Asp Val Gly Cys Thr Asp Leu Asn Glu Asp Leu Gly Val Trp Val Ile
            820                 825                 830

Phe Lys Ile Lys Thr Gln Asp Gly His Ala Arg Leu Gly Asn Leu Glu
        835                 840                 845

Phe Leu Glu Glu Lys Pro Leu Leu Gly Glu Ala Leu Ala Arg Val Lys
850                 855                 860

Arg Ala Glu Lys Lys Trp Arg Asp Lys Arg Glu Thr Leu Gln Leu Glu
865                 870                 875                 880

Thr Thr Ile Val Tyr Lys Glu Ala Lys Glu Ser Val Asp Ala Leu Phe
                885                 890                 895

Val Asn Ser Gln Tyr Asp Arg Leu Gln Ala Asp Thr Asn Ile Ala Met
            900                 905                 910

Ile His Ala Ala Asp Lys Arg Val His Arg Ile Arg Glu Ala Tyr Leu
        915                 920                 925

Pro Glu Leu Ser Val Ile Pro Gly Val Asn Ala Ala Ile Phe Glu Glu
930                 935                 940

Leu Glu Glu Arg Ile Phe Thr Ala Phe Ser Leu Tyr Asp Ala Arg Asn
945                 950                 955                 960

Ile Ile Lys Asn Gly Asp Phe Asn Asn Gly Leu Leu Cys Trp Asn Val
                965                 970                 975

Lys Gly His Val Glu Val Glu Glu Gln Asn Asn His Arg Ser Val Leu
            980                 985                 990

Val Ile Pro Glu Trp Glu Ala Glu Val Ser Gln Glu Val Arg Val Cys
        995                 1000                1005

Pro Gly Arg Gly Tyr Ile Leu Arg Val Thr Ala Tyr Lys Glu Gly
        1010                1015                1020

Tyr Gly Glu Gly Cys Val Thr Ile His Glu Ile Glu Asn Asn Thr
        1025                1030                1035

Asp Glu Leu Lys Phe Asn Asn Cys Val Glu Glu Glu Val Tyr Pro
        1040                1045                1050

Asn Asn Thr Val Thr Cys Ile Asn Tyr Thr Ala Thr Gln Glu Glu
        1055                1060                1065

Tyr Glu Gly Thr Tyr Thr Ser Arg Asn Arg Gly Tyr Asp Glu Ala

```
    1070                1075                1080

Tyr Gly  Asn Asn Pro Ser Val  Pro Ala Asp Tyr Ala  Ser Val Tyr
    1085                1090                1095

Glu Glu  Lys Ser Tyr Thr Asp  Arg Arg Arg Glu Asn  Pro Cys Glu
    1100                1105                1110

Ser Asn  Arg Gly Tyr Gly Asp  Tyr Thr Pro Leu Pro  Ala Gly Tyr
    1115                1120                1125

Val Thr  Lys Glu Leu Glu Tyr  Phe Pro Glu Thr Asp  Lys Val Trp
    1130                1135                1140

Ile Glu  Ile Gly Glu Thr Glu  Gly Thr Phe Ile Val  Asp Ser Val
    1145                1150                1155

Glu Leu  Leu Leu Met Glu Glu
    1160                1165

<210> SEQ ID NO 3
<211> LENGTH: 3498
<212> TYPE: DNA
<213> ORGANISM: Artificial Sequence
<220> FEATURE:
<223> OTHER INFORMATION: Nucleotide sequence used for expression in a
      bacterial cell encoding Cry1Da1_3.

<400> SEQUENCE: 3
atggaaataa ataatcaaaa ccaatgtgtg ccttacaatt gtttaagtaa tcctaaggag     60
ataatattag gcgaggaaag gctagaaaca gggaatactg tagcagacat ttcattaggg    120
cttattaatt ttctatattc taattttgta ccaggaggag gatttatagt aggtttacta    180
gaattaatat ggggatttat agggccttcg caatgggata tttttttagc tcaaattgag    240
caattgatta gtcaaagaat agaagaattt gctaggaatc aggcaatttc aagattggag    300
gggctaagca atctttataa ggtctatgtt agagcgttta gcgactggga gaaagatcct    360
actaatcctg ctttaaggga agaaatgcgt atacaattta atgacatgaa tagtgctctc    420
ataacggcta ttccactttt tagagttcaa aattatgaag ttgctctttt atctgtatat    480
gttcaagccg caaacttaca tttatctatt ttaagggatg tttcagtttt cggagaaaga    540
tggggatatg atacagcgac tatcaataat cgctatagtg atctgactag ccttattcat    600
gtttatacta accattgtgt ggatacgtat aatcagggat taaggcgttt ggaaggtcgt    660
tttcttagcg attggattgt atataatcgt ttccggagac aattgacaat ttcagtatta    720
gatattgttg cgtttttttcc aaattatgat attagaacat atccaattca aacagctact    780
cagctaacga gggaagtcta tctggattta ccttttatta atgaaaatct ttctcctgca    840
gcaagctatc caaccttttc agctgctgaa agtgctataa ttagaagtcc tcatttagta    900
gactttttaa atagctttac catttataca gatagtctgg cacgtagtgc atattgggga    960
gggcacttgg taaattcttt ccgcacagga accactacta atttgataag atcccctttta   1020 tatggaaggg aaggaaatac agagcgcccc gtaactatta ccgcatcacc tagcgtacca   1080
atatttagaa cactttcata tattacaggc cttgacaatt caaatcctgt agctggaatc   1140
gagggagtgg aattccaaaa tactataagt agaagtatct atcgtaaaag cggtccaata   1200
gattctttta gtgaattacc acctcaagat gccagcgtat ctcctgcaat tgggtatagt   1260
caccgtttat gccatgcaac atttttagaa cggattagtg gaccaagaat agcaggcacc   1320
gtattttctt ggacacaccg tagtgccagc cctactaacg aagtaagtcc atctagaatt   1380
acacaaattc catgggtaaa ggcgcatact cttgcatctg gtgcctccgt cattaaaggt   1440
```

```
cctggattta caggtggaga tattctgact aggaatagta tgggcgagct ggggacctta   1500
cgagtaacct tcacaggaag attaccacaa agttattata tacgtttccg ttatgcttcg   1560
gtagcaaata ggagtggtac atttagatat tcacagccac cttcgtatgg aatttcattt   1620
ccaaaaacta tggacgcagg tgaaccacta acatctcgtt cgttcgctca tacaacactc   1680
ttcactccaa taccttttc acgagctcaa gaagaatttg atctatacat ccaatcgggt    1740
gtttatatag atcgaattga atttataccg gttactgcaa catttgaggc agaatatgat   1800
ttagaaagag cgcaaaaggt ggtgaatgcc ctgtttacgt ctacaaacca actagggcta   1860
aaaacagatg tgacggatta tcatattgat caggtatcca atctagttgc gtgtttatcg   1920
gatgaatttt gtctggatga aagagagaa ttgtccgaga aagttaaaca tgcaaagcga    1980
ctcagtgatg agcggaattt acttcaagat ccaaacttca gagggatcaa taggcaacca   2040
gaccgtggct ggagaggaag tacggatatt actatccaag gaggagatga cgtattcaaa   2100
gagaattacg ttacgctacc gggtaccttt gatgagtgct atccaacgta tttatatcaa   2160
aaaatagatg agtcgaaatt aaaagccat acccgttatc aattaagagg gtatatcgaa    2220
gatagtcaag acttagaaat ctatttaatt cgttacaatg caaaacacga atagtaaat    2280
gtaccaggta caggaagttt atggcctctt tctgtagaaa atcaaattgg accttgtgga   2340
gaaccgaatc gatgcgcgcc acaccttgaa tggaatcctg atttacactg ttcctgcaga   2400
gacgggaaa atgtgcaca tcattctcat catttctctt tggacattga tgttggatgt     2460
acagacttaa atgaggactt aggtgtatgg gtgatattca agattaagac gcaagatggc   2520
cacgcacgac tagggaatct agagtttctc gaagagaaac cattattagg agaagcacta   2580
gctcgtgtga aaagagcgga gaaaaaatgg agagacaaac gcgaaacatt acaattggaa   2640
acaactatcg tttataaaga ggcaaaagaa tctgtagatg ctttatttgt aaactctcaa   2700
tatgatagat acaagcgga tacgaacatc gcgatgattc atgcggcaga taaacgcgtt    2760
catagaattc gagaagcgta tctgccggag ctgtctgtga ttccgggtgt caatgcggct   2820
attttgaag aattagaaga gcgtattttc actgcatttt ccctatatga tgcgagaaat    2880
attattaaaa atggcgattt caataatggc ttattatgct ggaacgtgaa agggcatgta   2940
gaggtagaag aacaaaacaa tcaccgttca gtcctggtta tcccagaatg ggaggcagaa   3000
gtgtcacaag aggttcgtgt ctgtccaggt cgtggctata tccttcgtgt tacagcgtac   3060
aaagagggat atggagaagg ttgcgtaacg atccatgaga tcgagaacaa tacagacgaa   3120
ctgaaattca caactgtgt agaagaggaa gtatatccaa caacacggt aacgtgtatt     3180
aattatactg cgactcaaga gaatatgag ggtacgtaca cttctcgtaa tcgaggatat    3240
gacgaagcct atggtaataa ccccttccgta ccagctgatt atgcgtcagt ctatgaagaa  3300
aaatcgtata cagatagacg aagagagaat ccttgtgaat ctaacagagg atatggagat   3360
tacacaccac taccagctgg ttatgtaaca aaggaattag agtacttccc agagaccgat   3420
aaggtatgga ttgagattgg agaaacagaa ggaacattca tcgtggacag cgtggaatta   3480
ctccttatgg aggaatag                                                 3498
```

<210> SEQ ID NO 4
<211> LENGTH: 1165
<212> TYPE: PRT
<213> ORGANISM: Artificial Sequence
<220> FEATURE:
<223> OTHER INFORMATION: Amino acid sequence of the engineered
      insecticidal protein Cry1Da1_3.

<400> SEQUENCE: 4

```
Met Glu Ile Asn Asn Gln Asn Gln Cys Val Pro Tyr Asn Cys Leu Ser
1               5                   10                  15
Asn Pro Lys Glu Ile Ile Leu Gly Glu Glu Arg Leu Glu Thr Gly Asn
            20                  25                  30
Thr Val Ala Asp Ile Ser Leu Gly Leu Ile Asn Phe Leu Tyr Ser Asn
            35                  40                  45
Phe Val Pro Gly Gly Gly Phe Ile Val Gly Leu Leu Glu Leu Ile Trp
        50                  55                  60
Gly Phe Ile Gly Pro Ser Gln Trp Asp Ile Phe Leu Ala Gln Ile Glu
65                  70                  75                  80
Gln Leu Ile Ser Gln Arg Ile Glu Glu Phe Ala Arg Asn Gln Ala Ile
                85                  90                  95
Ser Arg Leu Glu Gly Leu Ser Asn Leu Tyr Lys Val Tyr Val Arg Ala
            100                 105                 110
Phe Ser Asp Trp Glu Lys Asp Pro Thr Asn Pro Ala Leu Arg Glu Glu
            115                 120                 125
Met Arg Ile Gln Phe Asn Asp Met Asn Ser Ala Leu Ile Thr Ala Ile
130                 135                 140
Pro Leu Phe Arg Val Gln Asn Tyr Glu Val Ala Leu Leu Ser Val Tyr
145                 150                 155                 160
Val Gln Ala Ala Asn Leu His Leu Ser Ile Leu Arg Asp Val Ser Val
                165                 170                 175
Phe Gly Glu Arg Trp Gly Tyr Asp Thr Ala Thr Ile Asn Asn Arg Tyr
            180                 185                 190
Ser Asp Leu Thr Ser Leu Ile His Val Tyr Thr Asn His Cys Val Asp
        195                 200                 205
Thr Tyr Asn Gln Gly Leu Arg Arg Leu Glu Gly Arg Phe Leu Ser Asp
210                 215                 220
Trp Ile Val Tyr Asn Arg Phe Arg Arg Gln Leu Thr Ile Ser Val Leu
225                 230                 235                 240
Asp Ile Val Ala Phe Phe Pro Asn Tyr Asp Ile Arg Thr Tyr Pro Ile
                245                 250                 255
Gln Thr Ala Thr Gln Leu Thr Arg Glu Val Tyr Leu Asp Leu Pro Phe
            260                 265                 270
Ile Asn Glu Asn Leu Ser Pro Ala Ala Ser Tyr Pro Thr Phe Ser Ala
        275                 280                 285
Ala Glu Ser Ala Ile Ile Arg Ser Pro His Leu Val Asp Phe Leu Asn
290                 295                 300
Ser Phe Thr Ile Tyr Thr Asp Ser Leu Ala Arg Ser Ala Tyr Trp Gly
305                 310                 315                 320
Gly His Leu Val Asn Ser Phe Arg Thr Gly Thr Thr Thr Asn Leu Ile
                325                 330                 335
Arg Ser Pro Leu Tyr Gly Arg Glu Gly Asn Thr Glu Arg Pro Val Thr
            340                 345                 350
Ile Thr Ala Ser Pro Ser Val Pro Ile Phe Arg Thr Leu Ser Tyr Ile
        355                 360                 365
Thr Gly Leu Asp Asn Ser Asn Pro Val Ala Gly Ile Glu Gly Val Glu
370                 375                 380
Phe Gln Asn Thr Ile Ser Arg Ser Ile Tyr Arg Lys Ser Gly Pro Ile
385                 390                 395                 400
Asp Ser Phe Ser Glu Leu Pro Pro Gln Asp Ala Ser Val Ser Pro Ala
                405                 410                 415
```

```
Ile Gly Tyr Ser His Arg Leu Cys His Ala Thr Phe Leu Glu Arg Ile
            420                 425                 430

Ser Gly Pro Arg Ile Ala Gly Thr Val Phe Ser Trp Thr His Arg Ser
        435                 440                 445

Ala Ser Pro Thr Asn Glu Val Ser Pro Ser Arg Ile Thr Gln Ile Pro
450                 455                 460

Trp Val Lys Ala His Thr Leu Ala Ser Gly Ala Ser Val Ile Lys Gly
465                 470                 475                 480

Pro Gly Phe Thr Gly Gly Asp Ile Leu Thr Arg Asn Ser Met Gly Glu
                485                 490                 495

Leu Gly Thr Leu Arg Val Thr Phe Thr Gly Arg Leu Pro Gln Ser Tyr
            500                 505                 510

Tyr Ile Arg Phe Arg Tyr Ala Ser Val Ala Asn Arg Ser Gly Thr Phe
        515                 520                 525

Arg Tyr Ser Gln Pro Pro Ser Tyr Gly Ile Ser Phe Pro Lys Thr Met
530                 535                 540

Asp Ala Gly Glu Pro Leu Thr Ser Arg Ser Phe Ala His Thr Thr Leu
545                 550                 555                 560

Phe Thr Pro Ile Thr Phe Ser Arg Ala Gln Glu Glu Phe Asp Leu Tyr
                565                 570                 575

Ile Gln Ser Gly Val Tyr Ile Asp Arg Ile Glu Phe Ile Pro Val Thr
            580                 585                 590

Ala Thr Phe Glu Ala Glu Tyr Asp Leu Glu Arg Ala Gln Lys Val Val
        595                 600                 605

Asn Ala Leu Phe Thr Ser Thr Asn Gln Leu Gly Leu Lys Thr Asp Val
610                 615                 620

Thr Asp Tyr His Ile Asp Gln Val Ser Asn Leu Val Ala Cys Leu Ser
625                 630                 635                 640

Asp Glu Phe Cys Leu Asp Glu Lys Arg Glu Leu Ser Glu Lys Val Lys
                645                 650                 655

His Ala Lys Arg Leu Ser Asp Glu Arg Asn Leu Leu Gln Asp Pro Asn
            660                 665                 670

Phe Arg Gly Ile Asn Arg Gln Pro Asp Arg Gly Trp Arg Gly Ser Thr
        675                 680                 685

Asp Ile Thr Ile Gln Gly Gly Asp Asp Val Phe Lys Glu Asn Tyr Val
690                 695                 700

Thr Leu Pro Gly Thr Phe Asp Glu Cys Tyr Pro Thr Tyr Leu Tyr Gln
705                 710                 715                 720

Lys Ile Asp Glu Ser Lys Leu Lys Ala Tyr Thr Arg Tyr Gln Leu Arg
                725                 730                 735

Gly Tyr Ile Glu Asp Ser Gln Asp Leu Glu Ile Tyr Leu Ile Arg Tyr
            740                 745                 750

Asn Ala Lys His Glu Ile Val Asn Val Pro Gly Thr Gly Ser Leu Trp
        755                 760                 765

Pro Leu Ser Val Glu Asn Gln Ile Gly Pro Cys Gly Glu Pro Asn Arg
770                 775                 780

Cys Ala Pro His Leu Glu Trp Asn Pro Asp Leu His Cys Ser Cys Arg
785                 790                 795                 800

Asp Gly Glu Lys Cys Ala His His Ser His His Phe Ser Leu Asp Ile
                805                 810                 815

Asp Val Gly Cys Thr Asp Leu Asn Glu Asp Leu Gly Val Trp Val Ile
            820                 825                 830
```

Phe Lys Ile Lys Thr Gln Asp Gly His Ala Arg Leu Gly Asn Leu Glu
            835                 840                 845

Phe Leu Glu Glu Lys Pro Leu Leu Gly Glu Ala Leu Ala Arg Val Lys
    850                 855                 860

Arg Ala Glu Lys Lys Trp Arg Asp Lys Arg Glu Thr Leu Gln Leu Glu
865                 870                 875                 880

Thr Thr Ile Val Tyr Lys Glu Ala Lys Glu Ser Val Asp Ala Leu Phe
                885                 890                 895

Val Asn Ser Gln Tyr Asp Arg Leu Gln Ala Asp Thr Asn Ile Ala Met
            900                 905                 910

Ile His Ala Ala Asp Lys Arg Val His Arg Ile Arg Glu Ala Tyr Leu
        915                 920                 925

Pro Glu Leu Ser Val Ile Pro Gly Val Asn Ala Ala Ile Phe Glu Glu
    930                 935                 940

Leu Glu Glu Arg Ile Phe Thr Ala Phe Ser Leu Tyr Asp Ala Arg Asn
945                 950                 955                 960

Ile Ile Lys Asn Gly Asp Phe Asn Asn Gly Leu Leu Cys Trp Asn Val
                965                 970                 975

Lys Gly His Val Glu Val Glu Glu Gln Asn Asn His Arg Ser Val Leu
            980                 985                 990

Val Ile Pro Glu Trp Glu Ala Glu  Val Ser Gln Glu Val  Arg Val Cys
        995                 1000                 1005

Pro Gly Arg Gly Tyr Ile Leu  Arg Val Thr Ala Tyr  Lys Glu Gly
    1010                1015                1020

Tyr Gly Glu Gly Cys Val Thr  Ile His Glu Ile Glu  Asn Asn Thr
    1025                1030                1035

Asp Glu Leu Lys Phe Asn Asn  Cys Val Glu Glu Glu  Val Tyr Pro
    1040                1045                1050

Asn Asn Thr Val Thr Cys Ile  Asn Tyr Thr Ala Thr  Gln Glu Glu
    1055                1060                1065

Tyr Glu Gly Thr Tyr Thr Ser  Arg Asn Arg Gly Tyr  Asp Glu Ala
    1070                1075                1080

Tyr Gly Asn Asn Pro Ser Val  Pro Ala Asp Tyr Ala  Ser Val Tyr
    1085                1090                1095

Glu Glu Lys Ser Tyr Thr Asp  Arg Arg Arg Glu Asn  Pro Cys Glu
    1100                1105                1110

Ser Asn Arg Gly Tyr Gly Asp  Tyr Thr Pro Leu Pro  Ala Gly Tyr
    1115                1120                1125

Val Thr Lys Glu Leu Glu Tyr  Phe Pro Glu Thr Asp  Lys Val Trp
    1130                1135                1140

Ile Glu Ile Gly Glu Thr Glu  Gly Thr Phe Ile Val  Asp Ser Val
    1145                1150                1155

Glu Leu Leu Leu Met Glu Glu
    1160                1165

<210> SEQ ID NO 5
<211> LENGTH: 3498
<212> TYPE: DNA
<213> ORGANISM: Artificial Sequence
<220> FEATURE:
<223> OTHER INFORMATION: Nucleotide sequence used for expression in a
      bacterial cell encoding Cry1Da1_4.

<400> SEQUENCE: 5
atggaaataa ataatcaaaa ccaatgtgtg ccttacaatt gtttaagtaa tcctaaggag       60

```
ataatattag gcgaggaaag gctagaaaca gggaatactg tagcagacat tcattaggg      120 cttattaatt ttctatattc taattttgta ccaggaggag gatttatagt aggtttacta      180
gaattaatat ggggatttat agggccttcg caatgggata ttttttttagc tcaaattgag     240 caattgatta gtcaaagaat agaagaattt gctaggaatc aggcaatttc aagattggag      300
gggctaagca atctttataa ggtctatgtt agagcgttta gcgactggga gaaagatcct      360
actaatcctg ctttaaggga gaaaatgcgt atacaattta atgacatgaa tagtgctctc      420
ataacggcta ttccactttt tagagttcaa aattatgaag ttgctctttt atctgtatat      480
gttcaagccg caaacttaca tttatctatt ttaagggatg tttcagtttt cggagaaaga      540
tggggatatg atacagcgac tatcaataat cgctatagtg atctgactag ccttattcat      600
gtttatacta accattgtgt ggatacgtat aatcagggat taaggcgttt ggaaggtcgt      660
tttcttagcg attggattgt atataatcgt ttccggagac aattgacaat tcagtatta      720 gatattgttg cgttttttcc aaattatgat attagaacat atccaattca aacagctact      780
cagctaacga gggaagtcta tctggattta ccttttatta atgaaaatct ttctcctgca      840
gcaagctatc caacctttc agctgctgaa agtgctataa ttagaagtcc tcatttagta      900 gacttttaa atagctttac catttataca gatagtctgg cacgttatgc atattgggga     960
gggcacttgg taaattcttt ccgcacagga accactacta atttgataag atccccttta    1020
tatgaagggg aaggaaatac agagcgcccc gtaactatta ccgcatcacc tagcgtacca    1080
atatttagaa cactttcata tattacaggc cttgacaatc gtaatcctgt agctggaatc    1140
gagggagtgg aattccaaaa tactataagt agaagtatct atcgtaaaag cggtccaata    1200 gattcttta gtgaattacc acctcaagat gccagcgtat ctcctgcaat tgggtatagt     1260
caccgtttat gccatgcaac attttttagaa cggattagtg gaccaagaat agcaggcacc    1320
gtattttctt ggacacaccg tagtgccagc cctactaacg aagtaagtcc atctagaatt    1380
acacaaattc catgggtaaa ggcgcatact cttgcatctg gtgcctccgt cattaaaggt    1440
cctggattta caggtggaga tattctgact aggaatagta gggcgagct ggggacctta     1500 cgagtaacct tcacaggaag attaccacaa agttattata tacgtttccg ttatgcttcg    1560
gtagcaaata ggagtggtac atttagatat tcacagccac cttcgtatgg aatttcattt    1620
ccaaaaacta tggacgcagg tgaaccacta acatctcgtt cgttcgctca tacaacactc    1680
ttcactccaa taacctttc acgagctcaa gaagaatttg atctatacat ccaatcgggt     1740
gtttatatag atcgaattga atttataccg gttactgcaa catttgaggc agaatatgat    1800
ttagaaagag cgcaaaaggt ggtgaatgcc ctgtttacgt ctacaaacca actagggcta    1860
aaaacagatg tgacggatta tcatattgat caggtatcca atctagttgc gtgtttatcg    1920
gatgaatttt gtctggatga aaagagagaa ttgtccgaga agttaaaaca tgcaaagcga    1980
ctcagtgatg agcggaattt acttcaagat ccaaacttca gagggatcaa taggcaacca    2040
gaccgtggct ggagaggaag tacggatatt actatccaag gaggagatga cgtattcaaa    2100
gagaattacg ttacgctacc gggtacccttt gatgagtgct atccaacgta tttatatcaa    2160
aaaatagatg agtcgaaatt aaaagcctat acccgttatc aattaagagg gtatatcgaa    2220
gatagtcaag acttagaaaat ctatttaatt cgttacaatg caaaacacga aatagtaaat    2280
gtaccaggta caggaagttt atggcctctt tctgtagaaa atcaaattgg accttgtgga    2340
gaaccgaatc gatgcgcgcc acaccttgaa tggaatcctg atttacactg ttcctgcaga    2400
gacggggaaa aatgtgcaca tcattctcat catttctctt tggacattga tgttggatgt    2460
```

-continued

```
acagacttaa atgaggactt aggtgtatgg gtgatattca agattaagac gcaagatggc      2520
cacgcacgac tagggaatct agagtttctc gaagagaaac cattattagg agaagcacta      2580
gctcgtgtga aaagagcgga gaaaaaatgg agagacaaac gcgaaacatt acaattggaa      2640
acaactatcg tttataaaga ggcaaaagaa tctgtagatg ctttatttgt aaactctcaa      2700
tatgatagat tacaagcgga tacgaacatc gcgatgattc atgcggcaga taaacgcgtt      2760
catagaattc gagaagcgta tctgccggag ctgtctgtga ttccgggtgt caatgcggct      2820 attttgaag aattagaaga gcgtattttc actgcatttt ccctatatga tgcgagaaat       2880
attattaaaa atggcgattt caataatggc ttattatgct ggaacgtgaa agggcatgta      2940
gaggtagaag aacaaaacaa tcaccgttca gtcctggtta tcccagaatg ggaggcagaa      3000
gtgtcacaag aggttcgtgt ctgtccaggt cgtggctata tccttcgtgt tacagcgtac      3060
aaagagggat atggagaagg ttgcgtaacg atccatgaga tcgagaacaa tacagacgaa      3120
ctgaaattca acaactgtgt agaagaggaa gtatatccaa acaacacggt aacgtgtatt      3180
aattatactg cgactcaaga agaatatgag ggtacgtaca cttctcgtaa tcgaggatat      3240
gacgaagcct atggtaataa ccccttccgta ccagctgatt atgcgtcagt ctatgaagaa     3300
aaatcgtata cagatagacg aagagagaat ccttgtgaat ctaacagagg atatggagat      3360
tacacaccac taccagctgg ttatgtaaca aaggaattag agtacttccc agagaccgat      3420
aaggtatgga ttgagattgg agaaacagaa ggaacattca tcgtggacag cgtggaatta      3480
ctccttatgg aggaatag                                                   3498
```

```
<210> SEQ ID NO 6
<211> LENGTH: 1165
<212> TYPE: PRT
<213> ORGANISM: Artificial Sequence
<220> FEATURE:
<223> OTHER INFORMATION: Amino acid sequence of the engineered
      insecticidal protein Cry1Da1_4.

<400> SEQUENCE: 6

Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Lys Val Tyr Val Arg Ala
            100                 105                 110

Phe Ser Asp Trp Glu Lys Asp Pro Thr Asn Pro Ala Leu Arg Glu Glu
        115                 120                 125

Met Arg Ile Gln Phe Asn Asp Met Asn Ser Ala Leu Ile Thr Ala Ile
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
```

```
                    165                 170                 175
Phe Gly Glu Arg Trp Gly Tyr Asp Thr Ala Thr Ile Asn Asn Arg Tyr
                180                 185                 190

Ser Asp Leu Thr Ser Leu Ile His Val Tyr Thr Asn His Cys Val Asp
            195                 200                 205

Thr Tyr Asn Gln Gly Leu Arg Leu Glu Gly Arg Phe Leu Ser Asp
        210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
                260                 265                 270

Ile Asn Glu Asn Leu Ser Pro Ala Ala Ser Tyr Pro Thr Phe Ser Ala
                275                 280                 285

Ala Glu Ser Ala Ile Ile Arg Ser Pro His Leu Val Asp Phe Leu Asn
            290                 295                 300

Ser Phe Thr Ile Tyr Thr Asp Ser Leu Ala Arg Tyr Ala Tyr Trp Gly
305                 310                 315                 320

Gly His Leu Val Asn Ser Phe Arg Thr Gly Thr Thr Asn Leu Ile
                325                 330                 335

Arg Ser Pro Leu Tyr Gly Arg Glu Gly Asn Thr Glu Arg Pro Val Thr
            340                 345                 350

Ile Thr Ala Ser Pro Ser Val Pro Ile Phe Arg Thr Leu Ser Tyr Ile
                355                 360                 365

Thr Gly Leu Asp Asn Arg Asn Pro Val Ala Gly Ile Glu Gly Val Glu
        370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
                405                 410                 415

Ile Gly Tyr Ser His Arg Leu Cys His Ala Thr Phe Leu Glu Arg Ile
                420                 425                 430

Ser Gly Pro Arg Ile Ala Gly Thr Val Phe Ser Trp Thr His Arg Ser
            435                 440                 445

Ala Ser Pro Thr Asn Glu Val Ser Pro Ser Arg Ile Thr Gln Ile Pro
            450                 455                 460

Trp Val Lys Ala His Thr Leu Ala Ser Gly Ala Ser Val Ile Lys Gly
465                 470                 475                 480

Pro Gly Phe Thr Gly Gly Asp Ile Leu Thr Arg Asn Ser Met Gly Glu
                485                 490                 495

Leu Gly Thr Leu Arg Val Thr Phe Thr Gly Arg Leu Pro Gln Ser Tyr
            500                 505                 510

Tyr Ile Arg Phe Arg Tyr Ala Ser Val Ala Asn Arg Ser Gly Thr Phe
            515                 520                 525

Arg Tyr Ser Gln Pro Pro Ser Tyr Gly Ile Ser Phe Pro Lys Thr Met
        530                 535                 540

Asp Ala Gly Glu Pro Leu Thr Ser Arg Ser Phe Ala His Thr Thr Leu
545                 550                 555                 560

Phe Thr Pro Ile Thr Phe Ser Arg Ala Gln Glu Glu Phe Asp Leu Tyr
                565                 570                 575

Ile Gln Ser Gly Val Tyr Ile Asp Arg Ile Glu Phe Ile Pro Val Thr
            580                 585                 590
```

```
Ala Thr Phe Glu Ala Glu Tyr Asp Leu Glu Arg Ala Gln Lys Val Val
            595                 600                 605

Asn Ala Leu Phe Thr Ser Thr Asn Gln Leu Gly Leu Lys Thr Asp Val
    610                 615                 620

Thr Asp Tyr His Ile Asp Gln Val Ser Asn Leu Val Ala Cys Leu Ser
625                 630                 635                 640

Asp Glu Phe Cys Leu Asp Glu Lys Arg Glu Leu Ser Glu Lys Val Lys
            645                 650                 655

His Ala Lys Arg Leu Ser Asp Glu Arg Asn Leu Leu Gln Asp Pro Asn
            660                 665                 670

Phe Arg Gly Ile Asn Arg Gln Pro Asp Arg Gly Trp Arg Gly Ser Thr
            675                 680                 685

Asp Ile Thr Ile Gln Gly Gly Asp Asp Val Phe Lys Glu Asn Tyr Val
690                 695                 700

Thr Leu Pro Gly Thr Phe Asp Glu Cys Tyr Pro Thr Tyr Leu Tyr Gln
705                 710                 715                 720

Lys Ile Asp Glu Ser Lys Leu Lys Ala Tyr Thr Arg Tyr Gln Leu Arg
                725                 730                 735

Gly Tyr Ile Glu Asp Ser Gln Asp Leu Glu Ile Tyr Leu Ile Arg Tyr
            740                 745                 750

Asn Ala Lys His Glu Ile Val Asn Val Pro Gly Thr Gly Ser Leu Trp
            755                 760                 765

Pro Leu Ser Val Glu Asn Gln Ile Gly Pro Cys Gly Glu Pro Asn Arg
770                 775                 780

Cys Ala Pro His Leu Glu Trp Asn Pro Asp Leu His Cys Ser Cys Arg
785                 790                 795                 800

Asp Gly Glu Lys Cys Ala His His Ser His His Phe Ser Leu Asp Ile
                805                 810                 815

Asp Val Gly Cys Thr Asp Leu Asn Glu Asp Leu Gly Val Trp Val Ile
            820                 825                 830

Phe Lys Ile Lys Thr Gln Asp Gly His Ala Arg Leu Gly Asn Leu Glu
            835                 840                 845

Phe Leu Glu Glu Lys Pro Leu Leu Gly Glu Ala Leu Ala Arg Val Lys
            850                 855                 860

Arg Ala Glu Lys Lys Trp Arg Asp Lys Arg Glu Thr Leu Gln Leu Glu
865                 870                 875                 880

Thr Thr Ile Val Tyr Lys Glu Ala Lys Glu Ser Val Asp Ala Leu Phe
                885                 890                 895

Val Asn Ser Gln Tyr Asp Arg Leu Gln Ala Asp Thr Asn Ile Ala Met
            900                 905                 910

Ile His Ala Ala Asp Lys Arg Val His Arg Ile Arg Glu Ala Tyr Leu
            915                 920                 925

Pro Glu Leu Ser Val Ile Pro Gly Val Asn Ala Ala Ile Phe Glu Glu
            930                 935                 940

Leu Glu Glu Arg Ile Phe Thr Ala Phe Ser Leu Tyr Asp Ala Arg Asn
945                 950                 955                 960

Ile Ile Lys Asn Gly Asp Phe Asn Asn Gly Leu Leu Cys Trp Asn Val
                965                 970                 975

Lys Gly His Val Glu Val Glu Glu Gln Asn Asn His Arg Ser Val Leu
            980                 985                 990

Val Ile Pro Glu Trp Glu Ala Glu  Val Ser Gln Glu Val  Arg Val Cys
            995                 1000                1005
```

```
Pro Gly  Arg Gly Tyr Ile Leu  Arg Val Thr Ala Tyr  Lys Glu Gly
    1010                 1015                 1020

Tyr Gly  Glu Gly Cys Val Thr  Ile His Glu Ile Glu  Asn Asn Thr
    1025                 1030                 1035

Asp Glu  Leu Lys Phe Asn Asn  Cys Val Glu Glu Glu  Val Tyr Pro
    1040                 1045                 1050

Asn Asn  Thr Val Thr Cys Ile  Asn Tyr Thr Ala Thr  Gln Glu Glu
    1055                 1060                 1065

Tyr Glu  Gly Thr Tyr Thr Ser  Arg Asn Arg Gly Tyr  Asp Glu Ala
    1070                 1075                 1080

Tyr Gly  Asn Asn Pro Ser Val  Pro Ala Asp Tyr Ala  Ser Val Tyr
    1085                 1090                 1095

Glu Glu  Lys Ser Tyr Thr Asp  Arg Arg Arg Glu Asn  Pro Cys Glu
    1100                 1105                 1110

Ser Asn  Arg Gly Tyr Gly Asp  Tyr Thr Pro Leu Pro  Ala Gly Tyr
    1115                 1120                 1125

Val Thr  Lys Glu Leu Glu Tyr  Phe Pro Glu Thr Asp  Lys Val Trp
    1130                 1135                 1140

Ile Glu  Ile Gly Glu Thr Glu  Gly Thr Phe Ile Val  Asp Ser Val
    1145                 1150                 1155

Glu Leu  Leu Leu Met Glu Glu
    1160                 1165
```

<210> SEQ ID NO 7
<211> LENGTH: 3498
<212> TYPE: DNA
<213> ORGANISM: Artificial Sequence
<220> FEATURE:
<223> OTHER INFORMATION: Nucleotide sequence used for expression in a bacterial cell encoding Cry1Da1_5.

<400> SEQUENCE: 7

```
atggaaataa ataatcaaaa ccaatgtgtg ccttacaatt gtttaagtaa tcctaaggag     60
ataatattag gcgaggaaag gctagaaaca gggaatactg tagcagacat ttcattaggg    120
cttattaatt ttctatattc taattttgta ccaggaggag gatttatagt aggtttacta    180
gaattaatat ggggatttat agggccttcg caatgggata ttttttagc tcaaattgag    240 caattgatta gtcaaagaat agaagaattt gctaggaatc aggcaatttc aagattggag    300
gggctaagca atctttataa ggtctatgtt agagcgttta gcgactggga gaaagatcct    360
actaatcctg ctttaaggga agaaatgcgt atacaattta atgacatgaa tagtgctctc    420
ataacggcta ttccactttt tagagttcaa aattatgaag ttgctctttt atctgtatat    480
gttcaagccg caaacttaca tttatctatt ttaagggatg tttcagtttt cggagaaaga    540
tggggatatg atacagcgac tatcaataat cgctatagtg atctgactag ccttattcat    600
gtttatacta accattgtgt ggatacgtat aatcagggat taaggcgttt ggaaggtcgt    660
tttcttagcg attggattgt atataatcgt ttccggagac aattgacaat ttcagtatta    720
gatattgttg cgttttttcc aaattatgat attagaacat atccaattca aacagctact    780
cagctaacga gggaagtcta tctggattta ccttttatta atgaaaatct ttctcctgca    840
gcaagctatc caacctttc agctgctgaa agtgctataa ttagaagtcc tcatttagta    900
gactttttaa atagctttac catttataca gatagtctgg cacgttctgc atattgggga    960
gggcacttgg taaattcttt ccgcacagga accactacta atttgataag atccccttta   1020
tatggaaggg aaggaaatac agagcgcccc gtaactatta ccgcatcacc tagcgtacca   1080
```

```
atatttagaa cactttcata tagaacaggc cttgacaatt caaatcctgt agctggaatc   1140
gagggagtgg aattccaaaa tactataagt agaagtatct atcgtaaaag cggtccaata   1200
gattctttta gtgaattacc acctcaagat gccagcgtat ctcctgcaat tgggtatagt   1260
caccgtttat gccatgcaac attttttagaa cggattagtg gaccaagaat agcaggcacc   1320
gtattttctt ggacacaccg tagtgccagc cctactaacg aagtaagtcc atctagaatt   1380
acacaaattc catgggtaaa ggcgcatact cttgcatctg gtgcctccgt cattaaaggt   1440
cctggattta caggtggaga tattctgact aggaatagta tgggcgagct ggggacctta   1500
cgagtaacct tcacaggaag attaccacaa agttattata tacgtttccg ttatgcttcg   1560
gtagcaaata ggagtggtac atttagatat tcacagccac cttcgtatgg aatttcattt   1620
ccaaaaacta tggacgcagg tgaaccacta acatctcgtt cgttcgctca tacaacactc   1680
ttcactccaa taaccttttc acgagctcaa gaagaatttg atctatacat ccaatcgggt   1740
gtttatatag atcgaattga atttataccg gttactgcaa catttgaggc agaatatgat   1800
ttagaaagag cgcaaaaggt ggtgaatgcc ctgtttacgt ctacaaacca actagggcta   1860
aaaacagatg tgacggatta tcatattgat caggtatcca atctagttgc gtgtttatcg   1920
gatgaatttt gtctggatga aaagagagaa ttgtccgaga aagttaaaca tgcaaagcga   1980
ctcagtgatg agcggaattt acttcaagat ccaaacttca gagggatcaa taggcaacca   2040
gaccgtggct ggagaggaag tacgatatt actatccaag gaggagatga cgtattcaaa   2100
gagaattacg ttacgctacc gggtaccttt gatgagtgct atccaacgta tttatatcaa   2160
aaaatagatg agtcgaaatt aaaagcctat acccgttatc aattaagagg gtatatcgaa   2220
gatagtcaag acttagaaat ctatttaatt cgttacaatg caaaacacga atagtaaat   2280 gtaccaggta caggaagttt atggcctctt tctgtagaaa atcaaattgg accttgtgga   2340
gaaccgaatc gatgcgcgcc acaccttgaa tggaatcctg atttacactg ttcctgcaga   2400
gacggggaaa aatgtgcaca tcattctcat catttctctt tggacattga tgttggatgt   2460
acagacttaa atgaggactt aggtgtatgg gtgatattca agattaagac gcaagatggc   2520
cacgcacgac tagggaatct agagtttctc gaagagaaac cattattagg agaagcacta   2580
gctcgtgtga aaagagcgga gaaaaaatgg agagacaaac gcgaaacatt acaattggaa   2640
acaactatcg tttataaaga ggcaaaagaa tctgtagatg cttttatttgt aaactctcaa   2700 tatgatagat acaagcgga tacgaacatc gcgatgattc atgcggcaga taaacgcgtt   2760
catagaattc gagaagcgta tctgccggag ctgtctgtga ttccgggtgt caatgcggct   2820
atttttgaag aattagaaga gcgtattttc actgcatttt ccctatatga tgcgagaaat   2880
attattaaaa atgcgatttt caataatggc ttattatgct ggaacgtgaa agggcatgta   2940
gaggtagaag aacaaaacaa tcaccgttca gtcctggtta tcccagaatg ggaggcagaa   3000
gtgtcacaag aggttcgtgt ctgtccaggt cgtggctata tccttcgtgt tacagcgtac   3060
aaagagggat atggagaagg ttgcgtaacg atccatgaga tcgagaacaa tacagacgaa   3120
ctgaaattca caactgtgt agaagaggaa gtatatccaa acaacacggt aacgtgtatt   3180
aattatactg cgactcaaga agaatatgag ggtacgtaca cttctcgtaa tcgaggatat   3240
gacgaagcct atggtaataa cccttccgta ccagctgatt atgcgtcagt ctatgaagaa   3300
aaatcgtata cagatagacg aagagagaat ccttgtgaat ctaacagagg atatggagat   3360
tacacaccac taccagctgg ttatgtaaca aaggaattag agtacttccc agagaccgat   3420
```
aaggtatgga ttgagattgg agaaacagaa ggaacattca tcgtggacag cgtggaatta    3480
ctccttatgg aggaatag                                                  3498

<210> SEQ ID NO 8
<211> LENGTH: 1165
<212> TYPE: PRT
<213> ORGANISM: Artificial Sequence
<220> FEATURE:
<223> OTHER INFORMATION: Amino acid sequence of the engineered
      insecticidal protein Cry1Da1_5.

<400> SEQUENCE: 8

```
Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Lys Val Tyr Val Arg Ala
            100                 105                 110

Phe Ser Asp Trp Glu Lys Asp Pro Thr Asn Pro Ala Leu Arg Glu Glu
        115                 120                 125

Met Arg Ile Gln Phe Asn Asp Met Asn Ser Ala Leu Ile Thr Ala Ile
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
        195                 200                 205

Thr Tyr Asn Gln Gly Leu Arg Arg Leu Glu Gly Arg Phe Leu Ser Asp
    210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
            260                 265                 270

Ile Asn Glu Asn Leu Ser Pro Ala Ala Ser Tyr Pro Thr Phe Ser Ala
        275                 280                 285

Ala Glu Ser Ala Ile Ile Arg Ser Pro His Leu Val Asp Phe Leu Asn
    290                 295                 300

Ser Phe Thr Ile Tyr Thr Asp Ser Leu Ala Arg Ser Ala Tyr Trp Gly
305                 310                 315                 320

Gly His Leu Val Asn Ser Phe Arg Thr Gly Thr Thr Thr Asn Leu Ile
                325                 330                 335

Arg Ser Pro Leu Tyr Gly Arg Glu Gly Asn Thr Glu Arg Pro Val Thr
```

-continued

```
                340                 345                 350
Ile Thr Ala Ser Pro Ser Val Pro Ile Phe Arg Thr Leu Ser Tyr Arg
            355                 360                 365

Thr Gly Leu Asp Asn Ser Asn Pro Val Ala Gly Ile Glu Gly Val Glu
370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
            405                 410                 415

Ile Gly Tyr Ser His Arg Leu Cys His Ala Thr Phe Leu Glu Arg Ile
            420                 425                 430

Ser Gly Pro Arg Ile Ala Gly Thr Val Phe Ser Trp Thr His Arg Ser
            435                 440                 445

Ala Ser Pro Thr Asn Glu Val Ser Pro Ser Arg Ile Thr Gln Ile Pro
        450                 455                 460

Trp Val Lys Ala His Thr Leu Ala Ser Gly Ala Ser Val Ile Lys Gly
465                 470                 475                 480

Pro Gly Phe Thr Gly Gly Asp Ile Leu Thr Arg Asn Ser Met Gly Glu
            485                 490                 495

Leu Gly Thr Leu Arg Val Thr Phe Thr Gly Arg Leu Pro Gln Ser Tyr
            500                 505                 510

Tyr Ile Arg Phe Arg Tyr Ala Ser Val Ala Asn Arg Ser Gly Thr Phe
            515                 520                 525

Arg Tyr Ser Gln Pro Pro Ser Tyr Gly Ile Ser Phe Pro Lys Thr Met
        530                 535                 540

Asp Ala Gly Glu Pro Leu Thr Ser Arg Ser Phe Ala His Thr Thr Leu
545                 550                 555                 560

Phe Thr Pro Ile Thr Phe Ser Arg Ala Gln Glu Glu Phe Asp Leu Tyr
            565                 570                 575

Ile Gln Ser Gly Val Tyr Ile Asp Arg Ile Glu Phe Ile Pro Val Thr
            580                 585                 590

Ala Thr Phe Glu Ala Glu Tyr Asp Leu Glu Arg Ala Gln Lys Val Val
            595                 600                 605

Asn Ala Leu Phe Thr Ser Thr Asn Gln Leu Gly Leu Lys Thr Asp Val
        610                 615                 620

Thr Asp Tyr His Ile Asp Gln Val Ser Asn Leu Val Ala Cys Leu Ser
625                 630                 635                 640

Asp Glu Phe Cys Leu Asp Glu Lys Arg Glu Leu Ser Glu Lys Val Lys
            645                 650                 655

His Ala Lys Arg Leu Ser Asp Glu Arg Asn Leu Leu Gln Asp Pro Asn
            660                 665                 670

Phe Arg Gly Ile Asn Arg Gln Pro Asp Arg Gly Trp Arg Gly Ser Thr
            675                 680                 685

Asp Ile Thr Ile Gln Gly Gly Asp Asp Val Phe Lys Glu Asn Tyr Val
        690                 695                 700

Thr Leu Pro Gly Thr Phe Asp Glu Cys Tyr Pro Thr Tyr Leu Tyr Gln
705                 710                 715                 720

Lys Ile Asp Glu Ser Lys Leu Lys Ala Tyr Thr Arg Tyr Gln Leu Arg
            725                 730                 735

Gly Tyr Ile Glu Asp Ser Gln Asp Leu Glu Ile Tyr Leu Ile Arg Tyr
            740                 745                 750

Asn Ala Lys His Glu Ile Val Asn Val Pro Gly Thr Gly Ser Leu Trp
            755                 760                 765
```

```
Pro Leu Ser Val Glu Asn Gln Ile Gly Pro Cys Gly Glu Pro Asn Arg
    770                 775                 780
Cys Ala Pro His Leu Glu Trp Asn Pro Asp Leu His Cys Ser Cys Arg
785                 790                 795                 800
Asp Gly Glu Lys Cys Ala His His Ser His His Phe Ser Leu Asp Ile
                805                 810                 815
Asp Val Gly Cys Thr Asp Leu Asn Glu Asp Leu Gly Val Trp Val Ile
                820                 825                 830
Phe Lys Ile Lys Thr Gln Asp Gly His Ala Arg Leu Gly Asn Leu Glu
            835                 840                 845
Phe Leu Glu Glu Lys Pro Leu Leu Gly Glu Ala Leu Ala Arg Val Lys
        850                 855                 860
Arg Ala Glu Lys Lys Trp Arg Asp Lys Arg Glu Thr Leu Gln Leu Glu
865                 870                 875                 880
Thr Thr Ile Val Tyr Lys Glu Ala Lys Glu Ser Val Asp Ala Leu Phe
                885                 890                 895
Val Asn Ser Gln Tyr Asp Arg Leu Gln Ala Asp Thr Asn Ile Ala Met
                900                 905                 910
Ile His Ala Ala Asp Lys Arg Val His Arg Ile Arg Glu Ala Tyr Leu
            915                 920                 925
Pro Glu Leu Ser Val Ile Pro Gly Val Asn Ala Ala Ile Phe Glu Glu
        930                 935                 940
Leu Glu Glu Arg Ile Phe Thr Ala Phe Ser Leu Tyr Asp Ala Arg Asn
945                 950                 955                 960
Ile Ile Lys Asn Gly Asp Phe Asn Asn Gly Leu Leu Cys Trp Asn Val
                965                 970                 975
Lys Gly His Val Glu Val Glu Glu Gln Asn Asn His Arg Ser Val Leu
            980                 985                 990
Val Ile Pro Glu Trp Glu Ala Glu Val Ser Gln Glu Val Arg Val Cys
        995                 1000                1005
Pro Gly Arg Gly Tyr Ile Leu Arg Val Thr Ala Tyr Lys Glu Gly
    1010                1015                1020
Tyr Gly Glu Gly Cys Val Thr Ile His Glu Ile Glu Asn Asn Thr
    1025                1030                1035
Asp Glu Leu Lys Phe Asn Asn Cys Val Glu Glu Glu Val Tyr Pro
    1040                1045                1050
Asn Asn Thr Val Thr Cys Ile Asn Tyr Thr Ala Thr Gln Glu Glu
    1055                1060                1065
Tyr Glu Gly Thr Tyr Thr Ser Arg Asn Arg Gly Tyr Asp Glu Ala
    1070                1075                1080
Tyr Gly Asn Asn Pro Ser Val Pro Ala Asp Tyr Ala Ser Val Tyr
    1085                1090                1095
Glu Glu Lys Ser Tyr Thr Asp Arg Arg Arg Glu Asn Pro Cys Glu
    1100                1105                1110
Ser Asn Arg Gly Tyr Gly Asp Tyr Thr Pro Leu Pro Ala Gly Tyr
    1115                1120                1125
Val Thr Lys Glu Leu Glu Tyr Phe Pro Glu Thr Asp Lys Val Trp
    1130                1135                1140
Ile Glu Ile Gly Glu Thr Glu Gly Thr Phe Ile Val Asp Ser Val
    1145                1150                1155
Glu Leu Leu Leu Met Glu Glu
    1160                1165
```

<210> SEQ ID NO 9
<211> LENGTH: 3498
<212> TYPE: DNA
<213> ORGANISM: Artificial Sequence
<220> FEATURE:
<223> OTHER INFORMATION: Nucleotide sequence used for expression in a
      bacterial cell encoding Cry1Da1_6.

<400> SEQUENCE: 9

| | | | | | |
|---|---|---|---|---|---|
| atggaaataa | ataatcaaaa | ccaatgtgtg | ccttacaatt | gtttaagtaa | tcctaaggag | 60 |
| ataatattag | gcgaggaaag | gctagaaaca | gggaatactg | tagcagacat | ttcattaggg | 120 |
| cttattaatt | ttctatattc | taattttgta | ccaggaggag | gatttatagt | aggtttacta | 180 |
| gaattaatat | ggggatttat | agggccttcg | caatgggata | ttttttttagc | tcaaattgag | 240 |
| caattgatta | gtcaaagaat | agaagaattt | gctaggaatc | aggcaatttc | aagattggag | 300 |
| gggctaagca | atctttataa | ggtctatgtt | agagcgttta | gcgactggga | gaaagatcct | 360 |
| actaatcctg | ctttaaggga | agaaatgcgt | atacaattta | atgacatgaa | tagtgctctc | 420 |
| ataacggcta | ttccactttt | tagagttcaa | aattatgaag | ttgctctttt | atctgtatat | 480 |
| gttcaagccg | caaacttaca | tttatctatt | ttaaggggat | tttcagtttt | cggagaaaga | 540 |
| tggggatatg | atacagcgac | tatcaataat | cgctatagtg | atctgactag | ccttattcat | 600 |
| gtttatacta | accattgtgt | ggatacgtat | aatcagggat | taaggcgttt | ggaaggtcgt | 660 |
| tttcttagcg | attggattgt | atataatcgt | ttccggagac | aattgacaat | ttcagtatta | 720 |
| gatattgttg | cgttttttcc | aaattatgat | attagaacat | atccaattca | aacagctact | 780 |
| cagctaacga | gggaagtcta | tctggattta | cctttttatta | atgaaaatct | ttctcctgca | 840 |
| gcaaaatatc | caacctttttc | agctgctgaa | agtgctataa | ttagaagtcc | tcatttagta | 900 |
| gactttttaa | atagctttac | catttataca | gatagtctgg | cacgttctgc | atattgggga | 960 |
| gggcacttgg | taaattcttt | ccgcacagga | accactacta | atttgataag | atcccctta | 1020 |
| tatgaaggg | aaggaaatac | agagcgcccc | gtaactatta | ccgcatcacc | tagcgtacca | 1080 |
| atatttagaa | cactttcata | tccaacaggc | cttgacaatt | caaatcctgt | agctggaatc | 1140 |
| gagggagtgg | aattccaaaa | tactataagt | agaagtatct | atcgtaaaag | cggtccaata | 1200 |
| gattctttta | gtgaattacc | acctcaagat | gccagcgtat | ctcctgcaat | tgggtatagt | 1260 |
| caccgtttat | gccatgcaac | attttttagaa | cggattagtg | gaccaagaat | agcaggcacc | 1320 |
| gtattttctt | ggacacaccg | tagtgccagc | cctactaacg | aagtaagtcc | atctagaatt | 1380 |
| acacaaattc | catgggtaaa | ggcgcatact | cttgcatctg | gtgcctccgt | cattaaaggt | 1440 |
| cctggatta | caggtggaga | tattctgact | aggaatagta | tgggcgagct | ggggaccta | 1500 |
| cgagtaacct | tcacaggaag | attaccacaa | agttattata | tacgttttcg | ttatgcttcg | 1560 |
| gtagcaaata | ggagtggtac | atttagatat | tcacagccac | cttcgtatgg | aatttcattt | 1620 |
| ccaaaaacta | tggacgcagg | tgaaccacta | acatctcgtt | cgttcgctca | tacaacactc | 1680 |
| ttcactccaa | taacctttttc | acgagctcaa | gaagaatttg | atctatacat | ccaatcgggt | 1740 |
| gtttatatag | atcgaattga | atttataccg | gttactgcaa | catttgaggc | agaatatgat | 1800 |
| ttagaaagag | cgcaaaaggt | ggtgaatgcc | ctgtttacgt | ctacaaacca | actagggcta | 1860 |
| aaaacagatg | tgacggatta | tcatattgat | caggtatcca | atctagttgc | gtgtttatcg | 1920 |
| gatgaatttt | gtctggatga | aaagagagaa | ttgtccgaga | agttaaaaca | tgcaaagcga | 1980 |
| ctcagtgatg | agcggaattt | acttcaagat | ccaaacttca | gagggatcaa | taggcaacca | 2040 |

```
gaccgtggct ggagaggaag tacggatatt actatccaag gaggagatga cgtattcaaa    2100
gagaattacg ttacgctacc gggtaccttt gatgagtgct atccaacgta tttatatcaa    2160
aaaatagatg agtcgaaatt aaaagcctat acccgttatc aattaagagg gtatatcgaa    2220
gatagtcaag acttagaaat ctatttaatt cgttacaatg caaaacacga aatagtaaat    2280
gtaccaggta caggaagttt atggcctctt tctgtagaaa atcaaattgg accttgtgga    2340
gaaccgaatc gatgcgcgcc acaccttgaa tggaatcctg atttacactg ttcctgcaga    2400
gacggggaaa atgtgcaca tcattctcat catttctctt tggacattga tgttggatgt    2460
acagacttaa atgaggactt aggtgtatgg gtgatattca agattaagac gcaagatggc    2520
cacgcacgac tagggaatct agagtttctc gaagagaaac cattattagg agaagcacta    2580
gctcgtgtga aaagagcgga gaaaaatgg agagacaaac gcgaaacatt acaattggaa    2640
acaactatcg tttataaaga ggcaaaagaa tctgtagatg ctttatttgt aaactctcaa    2700
tatgatagat acaagcggat acgaacatc gcgatgattc atgcggcaga taaacgcgtt    2760
catagaattc gagaagcgta tctgccggag ctgtctgtga ttccgggtgt caatgcggct    2820 attttgaag aattagaaga gcgtattttc actgcatttt ccctatatga tgcgagaaat    2880
attattaaaa atggcgattt caataatggc ttattatgct ggaacgtgaa agggcatgta    2940
gaggtagaag aacaaaacaa tcaccgttca gtcctggtta tcccagaatg ggaggcagaa    3000
gtgtcacaag aggttcgtgt ctgtccaggt cgtggctata tccttcgtgt tacagcgtac    3060
aaagagggat atggagaagg ttgcgtaacg atccatgaga tcgagaacaa tacagacgaa    3120
ctgaaattca caactgtgt agaagaggaa gtatatccaa acaacacggt aacgtgtatt    3180
aattatactg cgactcaaga agaatatgag ggtacgtaca cttctcgtaa tcgaggatat    3240
gacgaagcct atggtaataa cccttccgta ccagctgatt atgcgtcagt ctatgaagaa    3300
aaatcgtata cagatagacg aagagagaat ccttgtgaat ctaacagagg atatggagat    3360
tacacaccac taccagctgg ttatgtaaca aaggaattag agtacttccc agagaccgat    3420
aaggtatgga ttgagattgg agaaacagaa ggaacattca tcgtggacag cgtggaatta    3480
ctccttatgg aggaatag                                                  3498
```

<210> SEQ ID NO 10
<211> LENGTH: 1165
<212> TYPE: PRT
<213> ORGANISM: Artificial Sequence
<220> FEATURE:
<223> OTHER INFORMATION: Amino acid sequence of the engineered
      insecticidal protein Cry1Da1_6.

<400> SEQUENCE: 10

```
Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95
```

```
Ser Arg Leu Glu Gly Leu Ser Asn Leu Tyr Lys Val Tyr Val Arg Ala
            100                 105                 110

Phe Ser Asp Trp Glu Lys Asp Pro Thr Asn Pro Ala Leu Arg Glu Glu
        115                 120                 125

Met Arg Ile Gln Phe Asn Asp Met Asn Ser Ala Leu Ile Thr Ala Ile
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
        195                 200                 205

Thr Tyr Asn Gln Gly Leu Arg Arg Leu Glu Gly Arg Phe Leu Ser Asp
    210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
            260                 265                 270

Ile Asn Glu Asn Leu Ser Pro Ala Ala Lys Tyr Pro Thr Phe Ser Ala
        275                 280                 285

Ala Glu Ser Ala Ile Ile Arg Ser Pro His Leu Val Asp Phe Leu Asn
    290                 295                 300

Ser Phe Thr Ile Tyr Thr Asp Ser Leu Ala Arg Ser Ala Tyr Trp Gly
305                 310                 315                 320

Gly His Leu Val Asn Ser Phe Arg Thr Gly Thr Thr Asn Leu Ile
                325                 330                 335

Arg Ser Pro Leu Tyr Gly Arg Glu Gly Asn Thr Glu Arg Pro Val Thr
            340                 345                 350

Ile Thr Ala Ser Pro Ser Val Pro Ile Phe Arg Thr Leu Ser Tyr Pro
        355                 360                 365

Thr Gly Leu Asp Asn Ser Asn Pro Val Ala Gly Ile Glu Gly Val Glu
    370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
                405                 410                 415

Ile Gly Tyr Ser His Arg Leu Cys His Ala Thr Phe Leu Glu Arg Ile
            420                 425                 430

Ser Gly Pro Arg Ile Ala Gly Thr Val Phe Ser Trp Thr His Arg Ser
        435                 440                 445

Ala Ser Pro Thr Asn Glu Val Ser Pro Ser Arg Ile Thr Gln Ile Pro
    450                 455                 460

Trp Val Lys Ala His Thr Leu Ala Ser Ala Ser Val Ile Lys Gly
465                 470                 475                 480

Pro Gly Phe Thr Gly Gly Asp Ile Leu Thr Arg Asn Ser Met Gly Glu
                485                 490                 495

Leu Gly Thr Leu Arg Val Thr Phe Thr Gly Arg Leu Pro Gln Ser Tyr
            500                 505                 510

Tyr Ile Arg Phe Arg Tyr Ala Ser Val Ala Asn Arg Ser Gly Thr Phe
```

```
                515                 520                 525
Arg Tyr Ser Gln Pro Ser Tyr Gly Ile Ser Phe Pro Lys Thr Met
530                 535                 540
Asp Ala Gly Glu Pro Leu Thr Ser Arg Ser Phe Ala His Thr Thr Leu
545                 550                 555                 560
Phe Thr Pro Ile Thr Phe Ser Arg Ala Gln Glu Glu Phe Asp Leu Tyr
                565                 570                 575
Ile Gln Ser Gly Val Tyr Ile Asp Arg Ile Glu Phe Ile Pro Val Thr
                580                 585                 590
Ala Thr Phe Glu Ala Glu Tyr Asp Leu Glu Arg Ala Gln Lys Val Val
                595                 600                 605
Asn Ala Leu Phe Thr Ser Thr Asn Gln Leu Gly Leu Lys Thr Asp Val
610                 615                 620
Thr Asp Tyr His Ile Asp Gln Val Ser Asn Leu Val Ala Cys Leu Ser
625                 630                 635                 640
Asp Glu Phe Cys Leu Asp Glu Lys Arg Glu Leu Ser Glu Lys Val Lys
                645                 650                 655
His Ala Lys Arg Leu Ser Asp Glu Arg Asn Leu Leu Gln Asp Pro Asn
                660                 665                 670
Phe Arg Gly Ile Asn Arg Gln Pro Asp Arg Gly Trp Arg Gly Ser Thr
                675                 680                 685
Asp Ile Thr Ile Gln Gly Gly Asp Asp Val Phe Lys Glu Asn Tyr Val
690                 695                 700
Thr Leu Pro Gly Thr Phe Asp Glu Cys Tyr Pro Thr Tyr Leu Tyr Gln
705                 710                 715                 720
Lys Ile Asp Glu Ser Lys Leu Lys Ala Tyr Thr Arg Tyr Gln Leu Arg
                725                 730                 735
Gly Tyr Ile Glu Asp Ser Gln Asp Leu Glu Ile Tyr Leu Ile Arg Tyr
                740                 745                 750
Asn Ala Lys His Glu Ile Val Asn Val Pro Gly Thr Gly Ser Leu Trp
                755                 760                 765
Pro Leu Ser Val Glu Asn Gln Ile Gly Pro Cys Gly Glu Pro Asn Arg
770                 775                 780
Cys Ala Pro His Leu Glu Trp Asn Pro Asp Leu His Cys Ser Cys Arg
785                 790                 795                 800
Asp Gly Glu Lys Cys Ala His His Ser His His Phe Ser Leu Asp Ile
                805                 810                 815
Asp Val Gly Cys Thr Asp Leu Asn Glu Asp Leu Gly Val Trp Val Ile
                820                 825                 830
Phe Lys Ile Lys Thr Gln Asp Gly His Ala Arg Leu Gly Asn Leu Glu
                835                 840                 845
Phe Leu Glu Glu Lys Pro Leu Leu Gly Glu Ala Leu Ala Arg Val Lys
                850                 855                 860
Arg Ala Glu Lys Lys Trp Arg Asp Lys Arg Glu Thr Leu Gln Leu Glu
865                 870                 875                 880
Thr Thr Ile Val Tyr Lys Glu Ala Lys Glu Ser Val Asp Ala Leu Phe
                885                 890                 895
Val Asn Ser Gln Tyr Asp Arg Leu Gln Ala Asp Thr Asn Ile Ala Met
                900                 905                 910
Ile His Ala Ala Asp Lys Arg Val His Arg Ile Arg Glu Ala Tyr Leu
                915                 920                 925
Pro Glu Leu Ser Val Ile Pro Gly Val Asn Ala Ala Ile Phe Glu Glu
                930                 935                 940
```

Leu Glu Glu Arg Ile Phe Thr Ala Phe Ser Leu Tyr Asp Ala Arg Asn
945                 950                 955                 960

Ile Ile Lys Asn Gly Asp Phe Asn Asn Gly Leu Leu Cys Trp Asn Val
            965                 970                 975

Lys Gly His Val Glu Val Glu Glu Gln Asn Asn His Arg Ser Val Leu
        980                 985                 990

Val Ile Pro Glu Trp Glu Ala Glu Val Ser Gln Glu Val Arg Val Cys
            995                1000                1005

Pro Gly Arg Gly Tyr Ile Leu Arg Val Thr Ala Tyr Lys Glu Gly
       1010                1015                1020

Tyr Gly Glu Gly Cys Val Thr Ile His Glu Ile Glu Asn Asn Thr
       1025                1030                1035

Asp Glu Leu Lys Phe Asn Asn Cys Val Glu Glu Glu Val Tyr Pro
       1040                1045                1050

Asn Asn Thr Val Thr Cys Ile Asn Tyr Thr Ala Thr Gln Glu Glu
       1055                1060                1065

Tyr Glu Gly Thr Tyr Thr Ser Arg Asn Arg Gly Tyr Asp Glu Ala
       1070                1075                1080

Tyr Gly Asn Asn Pro Ser Val Pro Ala Asp Tyr Ala Ser Val Tyr
       1085                1090                1095

Glu Glu Lys Ser Tyr Thr Asp Arg Arg Arg Glu Asn Pro Cys Glu
       1100                1105                1110

Ser Asn Arg Gly Tyr Gly Asp Tyr Thr Pro Leu Pro Ala Gly Tyr
       1115                1120                1125

Val Thr Lys Glu Leu Glu Tyr Phe Pro Glu Thr Asp Lys Val Trp
       1130                1135                1140

Ile Glu Ile Gly Glu Thr Glu Gly Thr Phe Ile Val Asp Ser Val
       1145                1150                1155

Glu Leu Leu Leu Met Glu Glu
       1160                1165

<210> SEQ ID NO 11
<211> LENGTH: 3498
<212> TYPE: DNA
<213> ORGANISM: Artificial Sequence
<220> FEATURE:
<223> OTHER INFORMATION: Nucleotide sequence used for expression in a
      bacterial cell encoding Cry1Da1_7.

<400> SEQUENCE: 11
atggaaataa ataatcaaaa ccaatgtgtg ccttacaatt gtttaagtaa tcctaaggag    60
ataatattag gcgaggaaag gctagaaaca gggaatactg tagcagacat ttcattaggg   120
cttattaatt ttctatattc taattttgta ccaggaggag gatttatagt aggtttacta   180
gaattaatat ggggatttat agggccttcg caatgggata tttttttagc tcaaattgag   240
caattgatta gtcaaagaat agaagaattt gctaggaatc aggcaatttc aagattggag   300
gggctaagca atctttataa ggtctatgtt agagcgttta gcgactggga aaagatcct    360 actaatcctg ctttaaggga agaaatgcgt atacaattta tgacatgaa tagtgctctc   420 ataacggcta ttccactttt tagagttcaa aattatgaag ttgctctttt atctgtatat   480
gttcaagccg caaacttaca tttatctatt ttaagggatg tttcagtttt cggagaaaga   540
tggggatatg atacagcgac tatcaataat cgctatagtg atctgactag ccttattcat   600
gtttatacta accattgtgt ggatacgtat aatcaggat taaggcgttt ggaaggtcgt   660

```
tttcttagcg attggattgt atataatcgt ttccggagac aattgacaat ttcagtatta      720
gatattgttg cgtttttttcc aaattatgat attagaacat atccaattca aacagctact     780
cagctaacga gggaagtcta tctggattta cctttatta atgaaaatct ttctcctgca       840
gcagtatatc caaccttttc agctgctgaa agtgctataa ttagaagtcc tcatttagta     900 gacttttta atagctttac catttataca gatagtctgg cacgttctgc atattgggga       960
gggcacttgg taaattcttt ccgcacagga accactacta atttgataag atcccctta      1020 tatggaaggg aaggaaatac agagcgcccc gtaactatta ccgcatcacc tagcgtacca     1080
atatttagaa cactttcata tccaacaggc cttgacaatt caaatcctgt agctggaatc     1140
gagggagtgg aattccaaaa tactataagt agaagtatct atcgtaaaag cggtccaata    1200 gattcttta gtgaattacc acctcaagat gccagcgtat ctcctgcaat tgggtatagt    1260
caccgtttat gccatgcaac atttttagaa cggattagtg gaccaagaat agcaggcacc    1320
gtattttctt ggacacaccg tagtgccagc cctactaacg aagtaagtcc atctagaatt    1380
acacaaattc catgggtaaa ggcgcatact cttgcatctg gtgcctccgt cattaaaggt    1440
cctggattta caggtggaga tattctgact aggaatagta tgggcgagct ggggacctta    1500
cgagtaacct tcacaggaag attaccacaa agttattata tacgtttccg ttatgcttcg    1560
gtagcaaata ggagtggtac atttagatat tcacagccac cttcgtatgg aatttcattt    1620
ccaaaaacta tggacgcagg tgaaccacta acatctcgtt cgttcgctca tacaacactc    1680
ttcactccaa taacctttc acgagctcaa gaagaatttg atctatacat ccaatcgggt    1740
gtttatatag atcgaattga atttataccg gttactgcaa catttgaggc agaatatgat    1800
ttagaaagag cgcaaaaggt ggtgaatgcc ctgtttacgt ctacaaacca actagggcta    1860
aaaacagatg tgacggatta tcatattgat caggtatcca atctagttgc gtgtttatcg    1920
gatgaatttt gtctggatga aaagagagaa ttgtccgaga agttaaaaca tgcaaagcga    1980
ctcagtgatg agcggaattt acttcaagat ccaaacttca gagggatcaa taggcaacca    2040
gaccgtggct ggagaggaag tacggatatt actatccaag gaggagatga cgtattcaaa    2100
gagaattacg ttacgctacc gggtaccttt gatgagtgct atccaacgta tttatatcaa    2160
aaaatagatg agtcgaaatt aaaagcctat acccgttatc aattaagagg gtatatcgaa    2220
gatagtcaag acttagaaat ctatttaatt cgttacaatg caaaacacga atagtaaat    2280 gtaccaggta caggaagttt atggcctctt tctgtagaaa atcaaattgg accttgtgga    2340
gaaccgaatc gatgcgcgcc acaccttgaa tggaatcctg atttacactg ttcctgcaga    2400
gacggggaaa atgtgcaca tcattctcat catttctctt tggacattga tgttggatgt    2460
acagacttaa atgaggactt aggtgtatgg gtgatattca agattaagac gcaagatggc    2520
cacgcacgac tagggaatct agagtttctc gaagagaaac cattattagg agaagcacta    2580
gctcgtgtga aaagagcgga gaaaaaatgg agagacaaac gcgaaacatt acaattggaa    2640
acaactatcg tttataaaga ggcaaaagaa tctgtagatg ctttatttgt aaactctcaa    2700
tatgatagat acaagcgga tacgaacatc gcgatgattc atgcggcaga taaacgcgtt    2760
catagaattc gagaagcgta tctgccggag ctgtctgtga ttccgggtgt caatgcggct    2820 attttgaag aattagaaga gcgtatttc actgcatttt ccctatatga tgcgagaaat    2880
attattaaaa atggcgattt caataatggc ttattatgct ggaacgtgaa agggcatgta    2940
gaggtagaag aacaaaacaa tcaccgttca gtcctggtta tcccagaatg ggaggcagaa    3000
gtgtcacaag aggttcgtgt ctgtccaggt cgtggctata tccttcgtgt tacagcgtac    3060
```

```
aaagagggat atggagaagg ttgcgtaacg atccatgaga tcgagaacaa tacagacgaa   3120
ctgaaattca acaactgtgt agaagaggaa gtatatccaa acaacacggt aacgtgtatt   3180
aattatactg cgactcaaga agaatatgag ggtacgtaca cttctcgtaa tcgaggatat   3240
gacgaagcct atggtaataa cccttccgta ccagctgatt atgcgtcagt ctatgaagaa   3300
aaatcgtata cagatagacg aagagagaat ccttgtgaat ctaacagagg atatggagat   3360
tacacaccac taccagctgg ttatgtaaca aaggaattag agtacttccc agagaccgat   3420
aaggtatgga ttgagattgg agaaacagaa ggaacattca tcgtggacag cgtggaatta   3480
ctccttatgg aggaatag                                                 3498
```

<210> SEQ ID NO 12
<211> LENGTH: 1165
<212> TYPE: PRT
<213> ORGANISM: Artificial sequence
<220> FEATURE:
<223> OTHER INFORMATION: Amino acid sequence of the engineered
      insecticidal protein Cry1Da1_7.

<400> SEQUENCE: 12

```
Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Lys Val Tyr Val Arg Ala
            100                 105                 110

Phe Ser Asp Trp Glu Lys Asp Pro Thr Asn Pro Ala Leu Arg Glu Glu
        115                 120                 125

Met Arg Ile Gln Phe Asn Asp Met Asn Ser Ala Leu Ile Thr Ala Ile
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
        195                 200                 205

Thr Tyr Asn Gln Gly Leu Arg Arg Leu Glu Gly Arg Phe Leu Ser Asp
    210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
            260                 265                 270
```

-continued

```
Ile Asn Glu Asn Leu Ser Pro Ala Val Tyr Pro Thr Phe Ser Ala
            275                 280                 285

Ala Glu Ser Ala Ile Ile Arg Ser Pro His Leu Val Asp Phe Leu Asn
    290                 295                 300

Ser Phe Thr Ile Tyr Thr Asp Ser Leu Ala Arg Ser Ala Tyr Trp Gly
305                 310                 315                 320

Gly His Leu Val Asn Ser Phe Arg Thr Gly Thr Thr Asn Leu Ile
                325                 330                 335

Arg Ser Pro Leu Tyr Gly Arg Glu Gly Asn Thr Glu Arg Pro Val Thr
                340                 345                 350

Ile Thr Ala Ser Pro Ser Val Pro Ile Phe Arg Thr Leu Ser Tyr Pro
            355                 360                 365

Thr Gly Leu Asp Asn Ser Asn Pro Val Ala Gly Ile Glu Gly Val Glu
            370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
                405                 410                 415

Ile Gly Tyr Ser His Arg Leu Cys His Ala Thr Phe Leu Glu Arg Ile
            420                 425                 430

Ser Gly Pro Arg Ile Ala Gly Thr Val Phe Ser Trp Thr His Arg Ser
        435                 440                 445

Ala Ser Pro Thr Asn Glu Val Ser Pro Ser Arg Ile Thr Gln Ile Pro
    450                 455                 460

Trp Val Lys Ala His Thr Leu Ala Ser Gly Ala Ser Val Ile Lys Gly
465                 470                 475                 480

Pro Gly Phe Thr Gly Gly Asp Ile Leu Thr Arg Asn Ser Met Gly Glu
                485                 490                 495

Leu Gly Thr Leu Arg Val Thr Phe Thr Gly Arg Leu Pro Gln Ser Tyr
                500                 505                 510

Tyr Ile Arg Phe Arg Tyr Ala Ser Val Ala Asn Arg Ser Gly Thr Phe
            515                 520                 525

Arg Tyr Ser Gln Pro Pro Ser Tyr Gly Ile Ser Phe Pro Lys Thr Met
    530                 535                 540

Asp Ala Gly Glu Pro Leu Thr Ser Arg Ser Phe Ala His Thr Thr Leu
545                 550                 555                 560

Phe Thr Pro Ile Thr Phe Ser Arg Ala Gln Glu Glu Phe Asp Leu Tyr
                565                 570                 575

Ile Gln Ser Gly Val Tyr Ile Asp Arg Ile Glu Phe Ile Pro Val Thr
                580                 585                 590

Ala Thr Phe Glu Ala Glu Tyr Asp Leu Glu Arg Ala Gln Lys Val Val
            595                 600                 605

Asn Ala Leu Phe Thr Ser Thr Asn Gln Leu Gly Leu Lys Thr Asp Val
    610                 615                 620

Thr Asp Tyr His Ile Asp Gln Val Ser Asn Leu Val Ala Cys Leu Ser
625                 630                 635                 640

Asp Glu Phe Cys Leu Asp Glu Lys Arg Glu Leu Ser Glu Lys Val Lys
                645                 650                 655

His Ala Lys Arg Leu Ser Asp Glu Arg Asn Leu Leu Gln Asp Pro Asn
            660                 665                 670

Phe Arg Gly Ile Asn Arg Gln Pro Asp Arg Gly Trp Arg Gly Ser Thr
            675                 680                 685

Asp Ile Thr Ile Gln Gly Gly Asp Asp Val Phe Lys Glu Asn Tyr Val
```

-continued

```
              690                 695                 700
Thr Leu Pro Gly Thr Phe Asp Glu Cys Tyr Pro Thr Tyr Leu Tyr Gln
705                 710                 715                 720

Lys Ile Asp Glu Ser Lys Leu Lys Ala Tyr Thr Arg Tyr Gln Leu Arg
                725                 730                 735

Gly Tyr Ile Glu Asp Ser Gln Asp Leu Glu Ile Tyr Leu Ile Arg Tyr
                740                 745                 750

Asn Ala Lys His Glu Ile Val Asn Val Pro Gly Thr Gly Ser Leu Trp
                755                 760                 765

Pro Leu Ser Val Glu Asn Gln Ile Gly Pro Cys Gly Glu Pro Asn Arg
770                 775                 780

Cys Ala Pro His Leu Glu Trp Asn Pro Asp Leu His Cys Ser Cys Arg
785                 790                 795                 800

Asp Gly Glu Lys Cys Ala His His Ser His Phe Ser Leu Asp Ile
                805                 810                 815

Asp Val Gly Cys Thr Asp Leu Asn Glu Asp Leu Gly Val Trp Val Ile
                820                 825                 830

Phe Lys Ile Lys Thr Gln Asp Gly His Ala Arg Leu Gly Asn Leu Glu
                835                 840                 845

Phe Leu Glu Glu Lys Pro Leu Leu Gly Glu Ala Leu Ala Arg Val Lys
850                 855                 860

Arg Ala Glu Lys Lys Trp Arg Asp Lys Arg Glu Thr Leu Gln Leu Glu
865                 870                 875                 880

Thr Thr Ile Val Tyr Lys Glu Ala Lys Glu Ser Val Asp Ala Leu Phe
                885                 890                 895

Val Asn Ser Gln Tyr Asp Arg Leu Gln Ala Asp Thr Asn Ile Ala Met
                900                 905                 910

Ile His Ala Ala Asp Lys Arg Val His Arg Ile Arg Glu Ala Tyr Leu
                915                 920                 925

Pro Glu Leu Ser Val Ile Pro Gly Val Asn Ala Ala Ile Phe Glu Glu
                930                 935                 940

Leu Glu Glu Arg Ile Phe Thr Ala Phe Ser Leu Tyr Asp Ala Arg Asn
945                 950                 955                 960

Ile Ile Lys Asn Gly Asp Phe Asn Asn Gly Leu Leu Cys Trp Asn Val
                965                 970                 975

Lys Gly His Val Glu Val Glu Glu Gln Asn Asn His Arg Ser Val Leu
                980                 985                 990

Val Ile Pro Glu Trp Glu Ala Glu  Val Ser Gln Glu Val  Arg Val Cys
                995                1000                 1005

Pro Gly Arg Gly Tyr Ile Leu  Arg Val Thr Ala Tyr  Lys Glu Gly
        1010                 1015                 1020

Tyr Gly Glu Gly Cys Val Thr  Ile His Glu Ile Glu  Asn Asn Thr
        1025                 1030                 1035

Asp Glu  Leu Lys Phe Asn Asn  Cys Val Glu Glu Glu  Val Tyr Pro
        1040                1045                 1050

Asn Asn  Thr Val Thr Cys Ile  Asn Tyr Thr Ala Thr  Gln Glu Glu
        1055                 1060                 1065

Tyr Glu  Gly Thr Tyr Thr Ser  Arg Asn Arg Gly Tyr  Asp Glu Ala
        1070                 1075                 1080

Tyr Gly  Asn Asn Pro Ser Val  Pro Ala Asp Tyr Ala  Ser Val Tyr
        1085                 1090                 1095

Glu Glu  Lys Ser Tyr Thr Asp  Arg Arg Arg Glu Asn  Pro Cys Glu
        1100                 1105                 1110
```

```
Ser Asn Arg Gly Tyr Gly Asp Tyr Thr Pro Leu Pro Ala Gly Tyr
    1115            1120                1125

Val Thr Lys Glu Leu Glu Tyr Phe Pro Glu Thr Asp Lys Val Trp
    1130            1135                1140

Ile Glu Ile Gly Glu Thr Glu Gly Thr Phe Ile Val Asp Ser Val
    1145            1150                1155

Glu Leu Leu Leu Met Glu Glu
    1160            1165

<210> SEQ ID NO 13
<211> LENGTH: 3420
<212> TYPE: DNA
<213> ORGANISM: Artificial sequence
<220> FEATURE:
<223> OTHER INFORMATION: Nucleotide sequence used for expression in a
      bacterial cell encoding TIC844.

<400> SEQUENCE: 13
atggagatca acaaccagaa ccagtgcgtc ccgtacaact gcctgagcaa ccctaaggag      60
atcatcctgg gtgaggaacg cctggagacc ggcaacaccg tagccgacat tagcctgggc     120
ctcatcaact tcctctacag caacttcgtg cccggcggtg gcttcatcgt gggcctcctg     180
gagcttatct ggggcttcat cggcccgtcc cagtgggaca tcttcctcgc ccagatcgag     240
caactgatca gccagcggat cgaggagttc gctaggaacc aggccatctc ccgcctggag     300
ggactctcca acctctacaa ggtgtacgtg cgcgcgttca gcgactggga aaggacccg      360 accaacccgg ccctccgcga ggaaatgcgt atccagttca acgatatgaa ctcggccctc     420
atcaccgcca tcccgctctt ccgcgtgcag aactacgagg tggccctcct gtccgtgtac     480
gttcaagccg ccaacctcca cctctccatc ctccgcgacg tgagcgtgtt cggcgagcgc     540
tggggctacg acaccgccac catcaacaac cgctactccg acctcacctc cctcatccac     600
gtttacacca accactgcgt ggacacgtac aaccagggcc tccgccgcct ggagggccgc     660
ttcctctccg actggatcgt gtacaaccgc ttccgccgcc agctcaccat ctccgtcctg     720
gacatcgtcg ccttcttcc caactacgac atccgcacct accctatcca gaccgccacc     780
cagctcaccc gcgaggtcta cctcgacctc ccgttcatca cgagaaacct cagcccggcc     840
gccagctacc gaccttctc cgccgctgag tccgccatca ttcgcagccc gcacctcgtg     900
gacttcctca actccttcac catctacacc gactccctcg cccgctacgc ctactgggc      960 ggtcacctcg tgaactcctt ccgcaccggc accactacca acctcatccg cagcccgctc    1020
tacggccgcg agggcaacac cgagcgcccg gtgaccatca ccgccagccc gagcgtgccc    1080
atcttccgca ccctcagcta catcaccggc ctggacaaca gcaaccctgt ggcgggcatc    1140
gagggcgtgg agttccagaa caccatctcc aggagcatct accgcaagag cggccctatc    1200
gacagcttca gcgagctgcc tcctcaggac gccagcgtga ccctgccat cggctacagc     1260 cacaggctgt gccacgccac cttcctggag cgcatcagcg ccctcgcat cgcgggcacc    1320 gtgttctcgt ggacccaccg cagcgcctct cctacgaacg aggtgtctcc tagtcgcatc    1380
acccagatcc cttgggtcaa ggcccacacc tggctagtg cgctagtgt catcaagggc      1440 cctggcttca ccgtggtga catcctgacc aggaactcta tgggcgagct gggcactctg    1500
agggtcactt tcactggccg cctgcctcag tcttactaca tccgcttccg ctacgctagt    1560
gtcgctaacc gtctggtac tttccgctac tctcagcctc cgtcttacgg tatctctttc     1620
cctaagacta tggacgctgg tgagcctctg accagtagga gcttcgctca cactactctg    1680
```

-continued

```
ttcactccta tcactttctc tagggctcag gaggagttcg acctgtacat ccagtctggt    1740
gtgtacatcg acaggatcga gttcatcccc gtgaccgcca cgttcgaggc cgagtacgac    1800
cttgagcgcg cccagaaggc tgtcaatgag ctcttcacgt ccagcaatca gatcggcctg    1860
aagaccgacg tcactgacta ccacatcgac caagtctcca acctcgtgga gtgcctctcc    1920
gatgagttct gcctcgacga gaagaaggag ctgtccgaga aggtgaagca tgccaagcgt    1980
ctcagcgacg agaggaatct cctccaggac cccaatttcc gcggcatcaa caggcagctc    2040
gaccgcggct ggcgcggcag caccgacatc acgatccagg cggcgacga tgtgttcaag    2100 gagaactacg tgactctcct gggcactttc gacgagtgct accctaccta cttgtaccag    2160
aagatcgatg agtccaagct caaggcttac actcgctacc agctccgcgg ctacatcgaa    2220
gacagccaag acctcgagat ttacctgatc cgctacaacg ccaagcacga gaccgtcaac    2280
gtgcccggta ctggttccct ctggccgctg agcgccccca gcccgatcgg caagtgtgcc    2340
caccacagcc accacttctc cttggacatc gatgtgggct gcaccgacct gaacgaggac    2400
ctcggagtct gggtcatctt caagatcaag acccaggacg ccacgcgcg cctgggcaac    2460 ctggagttcc tcgaggagaa gcccctggtc ggtgaggctc tggccagggt caagagggct    2520
gagaagaagt ggagggacaa gcgcgagaag ctcgagtggg agaccaacat cgtttacaag    2580
gaggccaagg agagcgtcga cgccctgttc gtgaactccc agtacgaccg cctgcaggcc    2640
gacaccaaca tcgccatgat ccacgctgcc gacaagaggg tgcacagcat cgcgaggcc    2700 tacctgcctg agctgtccgt gatccctggt gtgaacgctg ccatctttga ggagctggag    2760
ggccgcatct ttaccgcatt ctccctgtac gacgcccgca acgtgatcaa gaacggtgac    2820
ttcaacaatg cctcagctg ctggaacgtc aagggccacg tggacgtcga ggaacagaac    2880
aaccaccgct ccgtcctggt cgtcccagag tgggaggctg aggtctccca agaggtccgc    2940
gtctgcccag gccgcggcta cattctcagg gtcaccgctt acaaggaggg ctacggtgag    3000
ggctgtgtga ccatccacga gatcgagaac aacaccgacg agcttaagtt ctccaactgc    3060
gtggaggagg aggtgtaccc aaacaacacc gttacttgca acgactacac cgccacccag    3120
gaggagtacg agggcaccta cacttccagg aacaggggct acgatggtgc ctacgagagc    3180
aacagcagcg ttcctgctga ctacgcttcc gcctacgagg agaaggccta cacggatggc    3240
cgcagggaca acccttgcga gagcaaccgc ggctacggcg actacactcc cctgcccgcc    3300
ggctacgtta ccaaggagct ggagtacttc ccggagactg acaaggtgtg gatcgagatc    3360
ggcgagaccg agggcacctt catcgtggac agcgtggagc tgctcctgat ggaggagtag    3420
```

<210> SEQ ID NO 14
<211> LENGTH: 1139
<212> TYPE: PRT
<213> ORGANISM: Artificial sequence
<220> FEATURE:
<223> OTHER INFORMATION: Amino acid sequence of the chimeric protein TIC844.

<400> SEQUENCE: 14

```
Met Glu Ile Asn Asn Gln Asn Gln Cys Val Pro Tyr Asn Cys Leu Ser
 1               5                  10                  15

Asn Pro Lys Glu Ile Ile Leu Gly Glu Glu Arg Leu Glu Thr Gly Asn
                20                  25                  30

Thr Val Ala Asp Ile Ser Leu Gly Leu Ile Asn Phe Leu Tyr Ser Asn
            35                  40                  45
```

```
Phe Val Pro Gly Gly Phe Ile Val Gly Leu Leu Glu Leu Ile Trp
    50              55                  60
Gly Phe Ile Gly Pro Ser Gln Trp Asp Ile Phe Leu Ala Gln Ile Glu
65              70                  75                  80
Gln Leu Ile Ser Gln Arg Ile Glu Glu Phe Ala Arg Asn Gln Ala Ile
                85                  90                  95
Ser Arg Leu Glu Gly Leu Ser Asn Leu Tyr Lys Val Tyr Val Arg Ala
                100                 105                 110
Phe Ser Asp Trp Glu Lys Asp Pro Thr Asn Pro Ala Leu Arg Glu Glu
        115                 120                 125
Met Arg Ile Gln Phe Asn Asp Met Asn Ser Ala Leu Ile Thr Ala Ile
130                 135                 140
Pro Leu Phe Arg Val Gln Asn Tyr Glu Val Ala Leu Leu Ser Val Tyr
145                 150                 155                 160
Val Gln Ala Ala Asn Leu His Leu Ser Ile Leu Arg Asp Val Ser Val
                165                 170                 175
Phe Gly Glu Arg Trp Gly Tyr Asp Thr Ala Thr Ile Asn Asn Arg Tyr
                180                 185                 190
Ser Asp Leu Thr Ser Leu Ile His Val Tyr Thr Asn His Cys Val Asp
        195                 200                 205
Thr Tyr Asn Gln Gly Leu Arg Arg Leu Glu Gly Arg Phe Leu Ser Asp
210                 215                 220
Trp Ile Val Tyr Asn Arg Phe Arg Arg Gln Leu Thr Ile Ser Val Leu
225                 230                 235                 240
Asp Ile Val Ala Phe Phe Pro Asn Tyr Asp Ile Arg Thr Tyr Pro Ile
                245                 250                 255
Gln Thr Ala Thr Gln Leu Thr Arg Glu Val Tyr Leu Asp Leu Pro Phe
                260                 265                 270
Ile Asn Glu Asn Leu Ser Pro Ala Ala Ser Tyr Pro Thr Phe Ser Ala
        275                 280                 285
Ala Glu Ser Ala Ile Ile Arg Ser Pro His Leu Val Asp Phe Leu Asn
290                 295                 300
Ser Phe Thr Ile Tyr Thr Asp Ser Leu Ala Arg Tyr Ala Tyr Trp Gly
305                 310                 315                 320
Gly His Leu Val Asn Ser Phe Arg Thr Gly Thr Thr Asn Leu Ile
                325                 330                 335
Arg Ser Pro Leu Tyr Gly Arg Glu Gly Asn Thr Glu Arg Pro Val Thr
                340                 345                 350
Ile Thr Ala Ser Pro Ser Val Pro Ile Phe Arg Thr Leu Ser Tyr Ile
        355                 360                 365
Thr Gly Leu Asp Asn Ser Asn Pro Val Ala Gly Ile Glu Gly Val Glu
370                 375                 380
Phe Gln Asn Thr Ile Ser Arg Ser Ile Tyr Arg Lys Ser Gly Pro Ile
385                 390                 395                 400
Asp Ser Phe Ser Glu Leu Pro Pro Gln Asp Ala Ser Val Ser Pro Ala
                405                 410                 415
Ile Gly Tyr Ser His Arg Leu Cys His Ala Thr Phe Leu Glu Arg Ile
                420                 425                 430
Ser Gly Pro Arg Ile Ala Gly Thr Val Phe Ser Trp Thr His Arg Ser
        435                 440                 445
Ala Ser Pro Thr Asn Glu Val Ser Pro Ser Arg Ile Thr Gln Ile Pro
450                 455                 460
Trp Val Lys Ala His Thr Leu Ala Ser Gly Ala Ser Val Ile Lys Gly
```

```
            465                 470                 475                 480
        Pro Gly Phe Thr Gly Gly Asp Ile Leu Thr Arg Asn Ser Met Gly Glu
                        485                 490                 495

Leu Gly Thr Leu Arg Val Thr Phe Thr Gly Arg Leu Pro Gln Ser Tyr
                        500                 505                 510

Tyr Ile Arg Phe Arg Tyr Ala Ser Val Ala Asn Arg Ser Gly Thr Phe
                        515                 520                 525

Arg Tyr Ser Gln Pro Pro Ser Tyr Gly Ile Ser Phe Pro Lys Thr Met
                        530                 535                 540

Asp Ala Gly Glu Pro Leu Thr Ser Arg Ser Phe Ala His Thr Thr Leu
        545                 550                 555                 560

Phe Thr Pro Ile Thr Phe Ser Arg Ala Gln Glu Glu Phe Asp Leu Tyr
                            565                 570                 575

Ile Gln Ser Gly Val Tyr Ile Asp Arg Ile Glu Phe Ile Pro Val Thr
                        580                 585                 590

Ala Thr Phe Glu Ala Glu Tyr Asp Leu Glu Arg Ala Gln Lys Ala Val
                        595                 600                 605

Asn Glu Leu Phe Thr Ser Ser Asn Gln Ile Gly Leu Lys Thr Asp Val
                    610                 615                 620

Thr Asp Tyr His Ile Asp Gln Val Ser Asn Leu Val Glu Cys Leu Ser
        625                 630                 635                 640

Asp Glu Phe Cys Leu Asp Glu Lys Lys Glu Leu Ser Glu Lys Val Lys
                        645                 650                 655

His Ala Lys Arg Leu Ser Asp Glu Arg Asn Leu Leu Gln Asp Pro Asn
                        660                 665                 670

Phe Arg Gly Ile Asn Arg Gln Leu Asp Arg Gly Trp Arg Gly Ser Thr
                        675                 680                 685

Asp Ile Thr Ile Gln Gly Gly Asp Asp Val Phe Lys Glu Asn Tyr Val
                        690                 695                 700

Thr Leu Leu Gly Thr Phe Asp Glu Cys Tyr Pro Thr Tyr Leu Tyr Gln
        705                 710                 715                 720

Lys Ile Asp Glu Ser Lys Leu Lys Ala Tyr Thr Arg Tyr Gln Leu Arg
                        725                 730                 735

Gly Tyr Ile Glu Asp Ser Gln Asp Leu Glu Ile Tyr Leu Ile Arg Tyr
                        740                 745                 750

Asn Ala Lys His Glu Thr Val Asn Val Pro Gly Thr Gly Ser Leu Trp
                    755                 760                 765

Pro Leu Ser Ala Pro Ser Pro Ile Gly Lys Cys Ala His His Ser His
                770                 775                 780

His Phe Ser Leu Asp Ile Asp Val Gly Cys Thr Asp Leu Asn Glu Asp
        785                 790                 795                 800

Leu Gly Val Trp Val Ile Phe Lys Ile Lys Thr Gln Asp Gly His Ala
                        805                 810                 815

Arg Leu Gly Asn Leu Glu Phe Leu Glu Glu Lys Pro Leu Val Gly Glu
                        820                 825                 830

Ala Leu Ala Arg Val Lys Arg Ala Glu Lys Lys Trp Arg Asp Lys Arg
                        835                 840                 845

Glu Lys Leu Glu Trp Glu Thr Asn Ile Val Tyr Lys Glu Ala Lys Glu
                    850                 855                 860

Ser Val Asp Ala Leu Phe Val Asn Ser Gln Tyr Asp Arg Leu Gln Ala
        865                 870                 875                 880

Asp Thr Asn Ile Ala Met Ile His Ala Ala Asp Lys Arg Val His Ser
                        885                 890                 895
```

-continued

Ile Arg Glu Ala Tyr Leu Pro Glu Leu Ser Val Ile Pro Gly Val Asn
            900                 905                 910

Ala Ala Ile Phe Glu Glu Leu Glu Gly Arg Ile Phe Thr Ala Phe Ser
        915                 920                 925

Leu Tyr Asp Ala Arg Asn Val Ile Lys Asn Gly Asp Phe Asn Asn Gly
    930                 935                 940

Leu Ser Cys Trp Asn Val Lys Gly His Val Asp Val Glu Glu Gln Asn
945                 950                 955                 960

Asn His Arg Ser Val Leu Val Val Pro Glu Trp Glu Ala Glu Val Ser
                965                 970                 975

Gln Glu Val Arg Val Cys Pro Gly Arg Gly Tyr Ile Leu Arg Val Thr
            980                 985                 990

Ala Tyr Lys Glu Gly Tyr Gly Glu Gly Cys Val Thr Ile His Glu Ile
        995                 1000                1005

Glu Asn Asn Thr Asp Glu Leu Lys Phe Ser Asn Cys Val Glu Glu
    1010                1015                1020

Glu Val Tyr Pro Asn Asn Thr Val Thr Cys Asn Asp Tyr Thr Ala
    1025                1030                1035

Thr Gln Glu Glu Tyr Glu Gly Thr Tyr Thr Ser Arg Asn Arg Gly
    1040                1045                1050

Tyr Asp Gly Ala Tyr Glu Ser Asn Ser Ser Val Pro Ala Asp Tyr
    1055                1060                1065

Ala Ser Ala Tyr Glu Glu Lys Ala Tyr Thr Asp Gly Arg Arg Asp
    1070                1075                1080

Asn Pro Cys Glu Ser Asn Arg Gly Tyr Gly Asp Tyr Thr Pro Leu
    1085                1090                1095

Pro Ala Gly Tyr Val Thr Lys Glu Leu Glu Tyr Phe Pro Glu Thr
    1100                1105                1110

Asp Lys Val Trp Ile Glu Ile Gly Glu Thr Glu Gly Thr Phe Ile
    1115                1120                1125

Val Asp Ser Val Glu Leu Leu Leu Met Glu Glu
    1130                1135

<210> SEQ ID NO 15
<211> LENGTH: 3420
<212> TYPE: DNA
<213> ORGANISM: Artificial sequence
<220> FEATURE:
<223> OTHER INFORMATION: Nucleotide sequence used for expression in a
      bacterial cell encoding TIC844_2.

<400> SEQUENCE: 15
atggaaataa ataatcaaaa ccaatgtgtg ccttacaatt gtttaagtaa tcctaaggag     60
ataatattag gcgaggaaag gctagaaaca gggaatactg tagcagacat ttcattaggg    120
cttattaatt ttctatattc taattttgta ccaggaggag gatttatagt aggtttacta    180
gaattaatat ggggatttat agggccttcg caatgggata ttttttttagc tcaaattgag   240 caattgatta gtcaaagaat agaagaattt gctaggaatc aggcaatttc aagattggag   300
gggctaagca atctttataa ggtctatgtt agagcgttta gcgactggga gaaagatcct    360
actaatcctg ctttaaggga gaaatgcgt atacaattta tgacatgaa agtgctctc      420 ataacggcta ttccactttt tagagttcaa aattatgaag ttgctctttt atctgtatat    480
gttcaagccg caaacttaca tttatctatt ttaagggtat tttcagtttt cggagaaaga   540
tggggatatg atacagcgac tatcaataat cgctatagtg atctgactag ccttattcat    600

```
gtttatacta accattgtgt ggatacgtat aatcagggat taaggcgttt ggaaggtcgt      660
tttcttagcg attggattgt atataatcgt ttccggagac aattgacaat ttcagtatta      720
gatattgttg cgttttttcc aaattatgat attagaacat atccaattca aacagctact      780
cagctaacga gggaagtcta tctggattta cctttattta tgaaaatct ttctcctgca       840 gcaagctatc caacctttc agctgctgaa agtgctataa ttagaagtcc tcatttagta       900
gactttttaa atagctttac catttataca gatagtctgg cacgttctgc atattgggga     960
gggcacttgg taaattcttt ccgcacagga accactacta atttgataag atcccctta     1020 tatggaaggg aaggaaatac agagcgcccc gtaactatta ccgcatcacc tagcgtacca    1080
atatttagaa cactttcata tattacaggc cttgacaatt cacatcctgt agctggaatc    1140
gagggagtgg aattccaaaa tactataagt agaagtatct atcgtaaaag cggtccaata    1200
gattctttta gtgaattacc acctcaagat gccagcgtat ctcctgcaat tgggtatagt    1260
caccgtttat gccatgcaac attttagaa cggttaagtg gaccaagaat agcaggcacc     1320
gtatttcctt ggacacaccg tagtgccagc cctactaacg aagtaagtcc atctagaatt    1380
acacaaattc catgggtaaa ggcgcatact cttgcatctg gtgcctccgt cattaaaggt    1440
cctggattta caggtggaga tattctgact aggaatagta tgggcgagct ggggacctta    1500
cgagtaacct tcacaggaag attaccacaa agttattata tacgtttccg ttatgcttcg    1560
gtagcaaata ggagtggtac atttagatat tcacagccac cttcgtatgg aatttcattt    1620
ccaaaaacta tggacgcagg tgaaccacta acatctcgtt cgttcgctca tacaacactc    1680
ttcactccaa taccttttc acgagctcaa gaagaatttg atctatacat ccaatcgggt     1740
gtttatatag atcgaattga atttataccg gttactgcaa catttgaggc agaatatgat    1800
ttagaaagag cacaaaaggc ggtgaatgag ctgtttactt cttccaatca aatcgggtta    1860
aaaacagatg tgacggatta tcatattgat caagtatcca atttagttga gtgtttatct    1920
gatgaatttt gtctggatga aaaaaagaa ttgtccgaga agtcaaaca tgcgaagcga      1980 cttagtgatg agcggaattt acttcaagat ccaaacttta gagggatcaa tagacaacta    2040
gaccgtggct ggagaggaag tacgatatt accatccaag gaggcgatga cgtattcaaa     2100
gagaattacg ttacgctatt gggtacctt gatgagtgct atccaacgta tttatatcaa     2160
aaaatagatg agtcgaaatt aaaagccat acccgttacc aattaagagg gtatatcgaa     2220
gatagtcaag acttagaaat ctatttaatt cgctacaatg ccaaacacga aacagtaaat    2280
gtgccaggta cgggttcctt atggccgctt tcagccccaa gtccaatcgg aaaatgtgcc    2340
catcattccc atcatttctc cttggacatt gatgttggat gtacagactt aaatgaggac    2400
ttaggtgtat gggtgatatt caagattaag acgcaagatg gccatgcaag actaggaaat    2460
ctagaatttc tcgaagagaa accattagta ggagaagcac tagctcgtgt gaaaagagcg    2520
gagaaaaaat ggagagacaa acgtgaaaaa ttggaatggg aaacaaatat tgttataaaa    2580
gaggcaaaag aatctgtaga tgctttattt gtaaactctc aatatgatag attacaagcg    2640
gataccaaca tcgcgatgat tcatgcggca gataaacgcg ttcatagcat tcgagaagct    2700
tatctgcctg agctgtctgt gattccgggt gtcaatgcgg ctatttttga agaattagaa    2760
gggcgtattt tcactgcatt ctccctatat gatgcgagaa atgtcattaa aaatggtgat    2820
tttaataatg gcttatcctg ctggaacgtg aaagggcatg tagatgtaga agaacaaaac    2880
aaccaccgtt cggtccttgt tgttccggaa tgggaagcag aagtgtcaca agaagttcgt    2940
```

-continued

```
gtctgtccgg gtcgtggcta tatccttcgt gtcacagcgt acaaggaggg atatggagaa   3000
ggttgcgtaa ccattcatga gatcgagaac aatacagacg aactgaagtt tagcaactgt   3060
gtagaagagg aagtatatcc aaacaacacg gtaacgtgta atgattatac tgcgactcaa   3120
gaagaatatg agggtacgta cacttctcgt aatcgaggat atgacggagc ctatgaaagc   3180
aattcttctg taccagctga ttatgcatca gcctatgaag aaaaagcata tacagatgga   3240
cgaagagaca atccttgtga atctaacaga ggatatgggg attacacacc actaccagct   3300
ggctatgtga caaaagaatt agagtacttc ccagaaaccg ataaggtatg gattgagatc   3360
ggagaaacgg aaggaacatt catcgtggac agcgtggaat tacttcttat ggaggaatag   3420
```

<210> SEQ ID NO 16
<211> LENGTH: 1139
<212> TYPE: PRT
<213> ORGANISM: Artificial sequence
<220> FEATURE:
<223> OTHER INFORMATION: Amino acid sequence of the engineered insecticidal chimeric protein TIC844_2.

<400> SEQUENCE: 16

```
Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Lys Val Tyr Val Arg Ala
            100                 105                 110

Phe Ser Asp Trp Glu Lys Asp Pro Thr Asn Pro Ala Leu Arg Glu Glu
        115                 120                 125

Met Arg Ile Gln Phe Asn Asp Met Asn Ser Ala Leu Ile Thr Ala Ile
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
        195                 200                 205

Thr Tyr Asn Gln Gly Leu Arg Arg Leu Glu Gly Arg Phe Leu Ser Asp
    210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
            260                 265                 270

Ile Asn Glu Asn Leu Ser Pro Ala Ala Ser Tyr Pro Thr Phe Ser Ala
```

```
                    275                 280                 285
Ala Glu Ser Ala Ile Ile Arg Ser Pro His Leu Val Asp Phe Leu Asn
290                 295                 300

Ser Phe Thr Ile Tyr Thr Asp Ser Leu Ala Arg Ser Ala Tyr Trp Gly
305                 310                 315                 320

Gly His Leu Val Asn Ser Phe Arg Thr Gly Thr Thr Asn Leu Ile
                325                 330                 335

Arg Ser Pro Leu Tyr Gly Arg Glu Gly Asn Thr Glu Arg Pro Val Thr
                340                 345                 350

Ile Thr Ala Ser Pro Ser Val Pro Ile Phe Arg Thr Leu Ser Tyr Ile
                355                 360                 365

Thr Gly Leu Asp Asn Ser His Pro Val Ala Gly Ile Glu Gly Val Glu
                370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
                405                 410                 415

Ile Gly Tyr Ser His Arg Leu Cys His Ala Thr Phe Leu Glu Arg Leu
                420                 425                 430

Ser Gly Pro Arg Ile Ala Gly Thr Val Phe Ser Trp Thr His Arg Ser
                435                 440                 445

Ala Ser Pro Thr Asn Glu Val Ser Pro Ser Arg Ile Thr Gln Ile Pro
450                 455                 460

Trp Val Lys Ala His Thr Leu Ala Ser Gly Ala Ser Val Ile Lys Gly
465                 470                 475                 480

Pro Gly Phe Thr Gly Gly Asp Ile Leu Thr Arg Asn Ser Met Gly Glu
                485                 490                 495

Leu Gly Thr Leu Arg Val Thr Phe Thr Gly Arg Leu Pro Gln Ser Tyr
                500                 505                 510

Tyr Ile Arg Phe Arg Tyr Ala Ser Val Ala Asn Arg Ser Gly Thr Phe
                515                 520                 525

Arg Tyr Ser Gln Pro Pro Ser Tyr Gly Ile Ser Phe Pro Lys Thr Met
530                 535                 540

Asp Ala Gly Glu Pro Leu Thr Ser Arg Ser Phe Ala His Thr Thr Leu
545                 550                 555                 560

Phe Thr Pro Ile Thr Phe Ser Arg Ala Gln Glu Glu Phe Asp Leu Tyr
                565                 570                 575

Ile Gln Ser Gly Val Tyr Ile Asp Arg Ile Glu Phe Ile Pro Val Thr
                580                 585                 590

Ala Thr Phe Glu Ala Glu Tyr Asp Leu Glu Arg Ala Gln Lys Ala Val
                595                 600                 605

Asn Glu Leu Phe Thr Ser Ser Asn Gln Ile Gly Leu Lys Thr Asp Val
                610                 615                 620

Thr Asp Tyr His Ile Asp Gln Val Ser Asn Leu Val Glu Cys Leu Ser
625                 630                 635                 640

Asp Glu Phe Cys Leu Asp Glu Lys Lys Glu Leu Ser Glu Lys Val Lys
                645                 650                 655

His Ala Lys Arg Leu Ser Asp Glu Arg Asn Leu Leu Gln Asp Pro Asn
                660                 665                 670

Phe Arg Gly Ile Asn Arg Gln Leu Asp Arg Gly Trp Arg Gly Ser Thr
                675                 680                 685

Asp Ile Thr Ile Gln Gly Gly Asp Asp Val Phe Lys Glu Asn Tyr Val
                690                 695                 700
```

-continued

Thr Leu Leu Gly Thr Phe Asp Glu Cys Tyr Pro Thr Tyr Leu Tyr Gln
705                 710                 715                 720

Lys Ile Asp Glu Ser Lys Leu Lys Ala Tyr Thr Arg Tyr Gln Leu Arg
                725                 730                 735

Gly Tyr Ile Glu Asp Ser Gln Asp Leu Glu Ile Tyr Leu Ile Arg Tyr
            740                 745                 750

Asn Ala Lys His Glu Thr Val Asn Val Pro Gly Thr Gly Ser Leu Trp
        755                 760                 765

Pro Leu Ser Ala Pro Ser Pro Ile Gly Lys Cys Ala His His Ser His
770                 775                 780

His Phe Ser Leu Asp Ile Asp Val Gly Cys Thr Asp Leu Asn Glu Asp
785                 790                 795                 800

Leu Gly Val Trp Val Ile Phe Lys Ile Lys Thr Gln Asp Gly His Ala
                805                 810                 815

Arg Leu Gly Asn Leu Glu Phe Leu Glu Glu Lys Pro Leu Val Gly Glu
            820                 825                 830

Ala Leu Ala Arg Val Lys Arg Ala Glu Lys Lys Trp Arg Asp Lys Arg
        835                 840                 845

Glu Lys Leu Glu Trp Glu Thr Asn Ile Val Tyr Lys Glu Ala Lys Glu
    850                 855                 860

Ser Val Asp Ala Leu Phe Val Asn Ser Gln Tyr Asp Arg Leu Gln Ala
865                 870                 875                 880

Asp Thr Asn Ile Ala Met Ile His Ala Ala Asp Lys Arg Val His Ser
                885                 890                 895

Ile Arg Glu Ala Tyr Leu Pro Glu Leu Ser Val Ile Pro Gly Val Asn
            900                 905                 910

Ala Ala Ile Phe Glu Glu Leu Glu Gly Arg Ile Phe Thr Ala Phe Ser
        915                 920                 925

Leu Tyr Asp Ala Arg Asn Val Ile Lys Asn Gly Asp Phe Asn Asn Gly
    930                 935                 940

Leu Ser Cys Trp Asn Val Lys Gly His Val Asp Val Glu Glu Gln Asn
945                 950                 955                 960

Asn His Arg Ser Val Leu Val Val Pro Glu Trp Glu Ala Glu Val Ser
                965                 970                 975

Gln Glu Val Arg Val Cys Pro Gly Arg Gly Tyr Ile Leu Arg Val Thr
            980                 985                 990

Ala Tyr Lys Glu Gly Tyr Gly Glu Gly Cys Val Thr Ile His Glu Ile
        995                 1000                1005

Glu Asn Asn Thr Asp Glu Leu Lys Phe Ser Asn Cys Val Glu Glu
    1010                1015                1020

Glu Val Tyr Pro Asn Asn Thr Val Thr Cys Asn Asp Tyr Thr Ala
    1025                1030                1035

Thr Gln Glu Glu Tyr Glu Gly Thr Tyr Thr Ser Arg Asn Arg Gly
    1040                1045                1050

Tyr Asp Gly Ala Tyr Glu Ser Asn Ser Ser Val Pro Ala Asp Tyr
    1055                1060                1065

Ala Ser Ala Tyr Glu Glu Lys Ala Tyr Thr Asp Gly Arg Arg Asp
    1070                1075                1080

Asn Pro Cys Glu Ser Asn Arg Gly Tyr Gly Asp Tyr Thr Pro Leu
    1085                1090                1095

Pro Ala Gly Tyr Val Thr Lys Glu Leu Glu Tyr Phe Pro Glu Thr
    1100                1105                1110

Asp Lys Val Trp Ile Glu Ile Gly Glu Thr Glu Gly Thr Phe Ile
    1115                1120                1125

Val Asp Ser Val Glu Leu Leu Leu Met Glu Glu
    1130                1135

<210> SEQ ID NO 17
<211> LENGTH: 3420
<212> TYPE: DNA
<213> ORGANISM: Artificial sequence
<220> FEATURE:
<223> OTHER INFORMATION: Nucleotide sequence used for expression in a
      bacterial cell encoding TIC844_4.

<400> SEQUENCE: 17

| | | |
|---|---|---|
| atggaaataa ataatcaaaa ccaatgtgtg ccttacaatt gtttaagtaa tcctaaggag | 60 |
| ataatattag gcgaggaaag gctagaaaca gggaatactg tagcagacat ttcattaggg | 120 |
| cttattaatt ttctatattc taattttgta ccaggaggag gatttatagt aggtttacta | 180 |
| gaattaatat ggggatttat agggccttcg caatgggata ttttttttagc tcaaattgag | 240 |
| caattgatta gtcaaagaat agaagaattt gctaggaatc aggcaatttc aagattggag | 300 |
| gggctaagca atctttataa ggtctatgtt agagcgttta gcgactggga gaaagatcct | 360 |
| actaatcctg ctttaaggga gaaaatgcgt atacaattta tgacatgaa tagtgctctc | 420 |
| ataacggcta ttccactttt tagagttcaa aattatgaag ttgctctttt atctgtatat | 480 |
| gttcaagccg caaacttaca tttatctatt ttaagggatg tttcagtttt cggagaaaga | 540 |
| tggggatatg atacagcgac tatcaataat cgctatagtg atctgactag ccttattcat | 600 |
| gtttatacta accattgtgt ggatacgtat aatcagggat taaggcgttt ggaaggtcgt | 660 |
| tttcttagcg attggattgt atataatcgt ttccggagac aattgacaat tcagtatta | 720 |
| gatattgttg cgttttttcc aaattatgat attagaacat atccaattca aacagctact | 780 |
| cagctaacga gggaagtcta tctggattta ccttttatta tgaaaatct ttctcctgca | 840 |
| gcaagctatc aaccttttc agctgctgaa agtgctataa ttagaagtcc tcatttagta | 900 |
| gactttttaa atagctttac catttataca gatagtctgg cacgtagtgc atattgggga | 960 |
| gggcacttgg taaattcttt ccgcacagga accactacta atttgataag atccccttta | 1020 |
| tatggaaggg aaggaaatac agagcgcccc gtaactatta ccgcatcacc tagcgtacca | 1080 |
| atatttagaa cactttcata tattacaggc cttgacaatt caaatcctgt agctggaatc | 1140 |
| gagggagtgg aattccaaaa tactataagt agaagtatct atcgtaaaag cggtccaata | 1200 |
| gattctttta gtgaattacc acctcaagat gccagcgtat ctcctgcaat tgggtatagt | 1260 |
| caccgtttat gccatgcaac attttttagaa cggattagtg gaccaagaat agcaggcacc | 1320 |
| gtattttctt ggacacaccg tagtgccagc cctactaacg aagtaagtcc atctagaatt | 1380 |
| acacaaattc catgggtaaa ggcgcatact cttgcatctg gtgcctccgt cattaaaggt | 1440 |
| cctggattta caggtggaga tattctgact aggaatagta tgggcgagct ggggacctta | 1500 |
| cgagtaaacct tcacaggaag attaccacaa agttattata tacgtttccg ttatgcttcg | 1560 |
| gtagcaaata ggagtggtac atttagatat tcacagccac cttcgtatgg aatttcattt | 1620 |
| ccaaaaacta tggacgcagg tgaaccacta acatctcgtt cgttcgctca tacaacactc | 1680 |
| ttcactccaa taacctttc acgagctcaa gaagaatttg atctatacat ccaatcgggt | 1740 |
| gtttatatag atcgaattga atttataccg gttactgcaa catttgaggc agaatatgat | 1800 |
| ttagaaagag cacaaaaggc ggtgaatgag ctgtttactt cttccaatca aatcgggtta | 1860 |

-continued

```
aaaacagatg tgacggatta tcatattgat caagtatcca atttagttga gtgtttatct   1920
gatgaatttt gtctggatga aaaaaaagaa ttgtccgaga aagtcaaaca tgcgaagcga   1980
cttagtgatg agcggaattt acttcaagat ccaaacttta gagggatcaa tagacaacta   2040
gaccgtggct ggagaggaag tacggatatt accatccaag gaggcgatga cgtattcaaa   2100
gagaattacg ttacgctatt gggtaccttt gatgagtgct atccaacgta tttatatcaa   2160
aaaatagatg agtcgaaatt aaaagcctat acccgttacc aattaagagg gtatatcgaa   2220
gatagtcaag acttagaaat ctatttaatt cgctacaatg ccaaacacga aacagtaaat   2280
gtgccaggta cgggttcctt atggccgctt tcagccccaa gtccaatcgg aaaatgtgcc   2340
catcattccc atcatttctc cttggacatt gatgttggat gtacagactt aaatgaggac   2400
ttaggtgtat gggtgatatt caagattaag acgcaagatg gccatgcaag actaggaaat   2460
ctagaatttc tcgaagagaa accattagta ggagaagcac tagctcgtgt gaaaagagcg   2520
gagaaaaaat ggagagacaa acgtgaaaaa ttggaatggg aaacaaatat tgtttataaa   2580
gaggcaaaag aatctgtaga tgctttattt gtaaactctc aatatgatag attacaagcg   2640
gataccaaca tcgcgatgat tcatgcggca gataaacgcg ttcatagcat tcgagaagct   2700
tatctgcctg agctgtctgt gattccgggt gtcaatgcgg ctatttttga agaattagaa   2760
gggcgtattt tcactgcatt ctccctatat gatgcgagaa atgtcattaa aaatggtgat   2820
tttaataatg gcttatcctg ctggaacgtg aaagggcatg tagatgtaga agaacaaaac   2880
aaccaccgtt cggtccttgt tgttccggaa tgggaagcag aagtgtcaca agaagttcgt   2940
gtctgtccgg gtcgtggcta tatccttcgt gtcacagcgt acaaggaggg atatggagaa   3000
ggttgcgtaa ccattcatga gatcgagaac aatacagacg aactgaagtt tagcaactgt   3060
gtagaagagg aagtatatcc aaacaacacg gtaacgtgta atgattatac tgcgactcaa   3120
gaagaatatg agggtacgta cacttctcgt aatcgaggat atgacggagc ctatgaaagc   3180
aattcttctg taccagctga ttatgcatca gcctatgaag aaaaagcata tacagatgga   3240
cgaagagaca atccttgtga atctaacaga ggatatgggg attacacacc actaccagct   3300
ggctatgtga caaaagaatt agagtacttc ccagaaaccg ataaggtatg gattgagatc   3360
ggagaaacgg aaggaacatt catcgtggac agcgtggaat tacttcttat ggaggaatag   3420
```

<210> SEQ ID NO 18
<211> LENGTH: 1139
<212> TYPE: PRT
<213> ORGANISM: Artificial sequence
<220> FEATURE:
<223> OTHER INFORMATION: Amino acid sequence of the engineered
      insecticidal chimeric protein TIC844_4.

<400> SEQUENCE: 18

```
Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
```

```
                        85                  90                  95
Ser Arg Leu Glu Gly Leu Ser Asn Leu Tyr Lys Val Tyr Val Arg Ala
                100                 105                 110

Phe Ser Asp Trp Glu Lys Asp Pro Thr Asn Pro Ala Leu Arg Glu Glu
                115                 120                 125

Met Arg Ile Gln Phe Asn Asp Met Asn Ser Ala Leu Ile Thr Ala Ile
            130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
                180                 185                 190

Ser Asp Leu Thr Ser Leu Ile His Val Tyr Thr Asn His Cys Val Asp
            195                 200                 205

Thr Tyr Asn Gln Gly Leu Arg Arg Leu Glu Gly Arg Phe Leu Ser Asp
        210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
            260                 265                 270

Ile Asn Glu Asn Leu Ser Pro Ala Ala Ser Tyr Pro Thr Phe Ser Ala
        275                 280                 285

Ala Glu Ser Ala Ile Ile Arg Ser Pro His Leu Val Asp Phe Leu Asn
290                 295                 300

Ser Phe Thr Ile Tyr Thr Asp Ser Leu Ala Arg Ser Ala Tyr Trp Gly
305                 310                 315                 320

Gly His Leu Val Asn Ser Phe Arg Thr Gly Thr Thr Thr Asn Leu Ile
                325                 330                 335

Arg Ser Pro Leu Tyr Gly Arg Glu Gly Asn Thr Glu Arg Pro Val Thr
            340                 345                 350

Ile Thr Ala Ser Pro Ser Val Pro Ile Phe Arg Thr Leu Ser Tyr Ile
        355                 360                 365

Thr Gly Leu Asp Asn Ser Asn Pro Val Ala Gly Ile Glu Gly Val Glu
    370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
                405                 410                 415

Ile Gly Tyr Ser His Arg Leu Cys His Ala Thr Phe Leu Glu Arg Ile
            420                 425                 430

Ser Gly Pro Arg Ile Ala Gly Thr Val Phe Ser Trp Thr His Arg Ser
        435                 440                 445

Ala Ser Pro Thr Asn Glu Val Ser Pro Ser Arg Ile Thr Gln Ile Pro
    450                 455                 460

Trp Val Lys Ala His Thr Leu Ala Ser Gly Ala Ser Val Ile Lys Gly
465                 470                 475                 480

Pro Gly Phe Thr Gly Gly Asp Ile Leu Thr Arg Asn Ser Met Gly Glu
                485                 490                 495

Leu Gly Thr Leu Arg Val Thr Phe Thr Gly Arg Leu Pro Gln Ser Tyr
            500                 505                 510
```

```
Tyr Ile Arg Phe Arg Tyr Ala Ser Val Ala Asn Arg Ser Gly Thr Phe
        515                 520                 525
Arg Tyr Ser Gln Pro Pro Ser Tyr Gly Ile Ser Phe Pro Lys Thr Met
        530                 535                 540
Asp Ala Gly Glu Pro Leu Thr Ser Arg Ser Phe Ala His Thr Thr Leu
545                 550                 555                 560
Phe Thr Pro Ile Thr Phe Ser Arg Ala Gln Glu Glu Phe Asp Leu Tyr
                565                 570                 575
Ile Gln Ser Gly Val Tyr Ile Asp Arg Ile Glu Phe Ile Pro Val Thr
                580                 585                 590
Ala Thr Phe Glu Ala Glu Tyr Asp Leu Glu Arg Ala Gln Lys Ala Val
        595                 600                 605
Asn Glu Leu Phe Thr Ser Ser Asn Gln Ile Gly Leu Lys Thr Asp Val
        610                 615                 620
Thr Asp Tyr His Ile Asp Gln Val Ser Asn Leu Val Glu Cys Leu Ser
625                 630                 635                 640
Asp Glu Phe Cys Leu Asp Glu Lys Lys Glu Leu Ser Glu Lys Val Lys
                645                 650                 655
His Ala Lys Arg Leu Ser Asp Glu Arg Asn Leu Leu Gln Asp Pro Asn
        660                 665                 670
Phe Arg Gly Ile Asn Arg Gln Leu Asp Arg Gly Trp Arg Gly Ser Thr
        675                 680                 685
Asp Ile Thr Ile Gln Gly Gly Asp Asp Val Phe Lys Glu Asn Tyr Val
        690                 695                 700
Thr Leu Leu Gly Thr Phe Asp Glu Cys Tyr Pro Thr Tyr Leu Tyr Gln
705                 710                 715                 720
Lys Ile Asp Glu Ser Lys Leu Lys Ala Tyr Thr Arg Tyr Gln Leu Arg
                725                 730                 735
Gly Tyr Ile Glu Asp Ser Gln Asp Leu Glu Ile Tyr Leu Ile Arg Tyr
        740                 745                 750
Asn Ala Lys His Glu Thr Val Asn Val Pro Gly Thr Gly Ser Leu Trp
        755                 760                 765
Pro Leu Ser Ala Pro Ser Pro Ile Gly Lys Cys Ala His His Ser His
        770                 775                 780
His Phe Ser Leu Asp Ile Asp Val Gly Cys Thr Asp Leu Asn Glu Asp
785                 790                 795                 800
Leu Gly Val Trp Val Ile Phe Lys Ile Lys Thr Gln Asp Gly His Ala
                805                 810                 815
Arg Leu Gly Asn Leu Glu Phe Leu Glu Glu Lys Pro Leu Val Gly Glu
        820                 825                 830
Ala Leu Ala Arg Val Lys Arg Ala Glu Lys Lys Trp Arg Asp Lys Arg
        835                 840                 845
Glu Lys Leu Glu Trp Glu Thr Asn Ile Val Tyr Lys Glu Ala Lys Glu
850                 855                 860
Ser Val Asp Ala Leu Phe Val Asn Ser Gln Tyr Asp Arg Leu Gln Ala
865                 870                 875                 880
Asp Thr Asn Ile Ala Met Ile His Ala Ala Asp Lys Arg Val His Ser
                885                 890                 895
Ile Arg Glu Ala Tyr Leu Pro Glu Leu Ser Val Ile Pro Gly Val Asn
        900                 905                 910
Ala Ala Ile Phe Glu Glu Leu Glu Gly Arg Ile Phe Thr Ala Phe Ser
        915                 920                 925
```

| | | | | | | | | | | | | |
|---|---|---|---|---|---|---|---|---|---|---|---|---|
| Leu | Tyr | Asp | Ala | Arg | Asn | Val | Ile | Lys | Asn | Gly | Asp | Phe | Asn | Asn | Gly |
| | 930 | | | | 935 | | | | 940 | | | | | | |

| Leu | Ser | Cys | Trp | Asn | Val | Lys | Gly | His | Val | Asp | Val | Glu | Glu | Gln | Asn |
|---|---|---|---|---|---|---|---|---|---|---|---|---|---|---|---|
| 945 | | | | | 950 | | | | | 955 | | | | | 960 |

| Asn | His | Arg | Ser | Val | Leu | Val | Val | Pro | Glu | Trp | Glu | Ala | Glu | Val | Ser |
|---|---|---|---|---|---|---|---|---|---|---|---|---|---|---|---|
| | | | 965 | | | | | 970 | | | | | 975 | | |

| Gln | Glu | Val | Arg | Val | Cys | Pro | Gly | Arg | Gly | Tyr | Ile | Leu | Arg | Val | Thr |
|---|---|---|---|---|---|---|---|---|---|---|---|---|---|---|---|
| | | 980 | | | | | 985 | | | | | 990 | | | |

| Ala | Tyr | Lys | Glu | Gly | Tyr | Gly | Glu | Gly | Cys | Val | Thr | Ile | His | Glu | Ile |
|---|---|---|---|---|---|---|---|---|---|---|---|---|---|---|---|
| | 995 | | | | | 1000 | | | | | | 1005 | | | |

| Glu | Asn | Asn | Thr | Asp | Glu | Leu | Lys | Phe | Ser | Asn | Cys | Val | Glu | Glu |
|---|---|---|---|---|---|---|---|---|---|---|---|---|---|---|
| 1010 | | | | | 1015 | | | | | 1020 | | | | |

| Glu | Val | Tyr | Pro | Asn | Asn | Thr | Val | Thr | Cys | Asn | Asp | Tyr | Thr | Ala |
|---|---|---|---|---|---|---|---|---|---|---|---|---|---|---|
| 1025 | | | | | 1030 | | | | | 1035 | | | | |

| Thr | Gln | Glu | Glu | Tyr | Glu | Gly | Thr | Tyr | Thr | Ser | Arg | Asn | Arg | Gly |
|---|---|---|---|---|---|---|---|---|---|---|---|---|---|---|
| 1040 | | | | | 1045 | | | | | 1050 | | | | |

| Tyr | Asp | Gly | Ala | Tyr | Glu | Ser | Asn | Ser | Ser | Val | Pro | Ala | Asp | Tyr |
|---|---|---|---|---|---|---|---|---|---|---|---|---|---|---|
| 1055 | | | | | 1060 | | | | | 1065 | | | | |

| Ala | Ser | Ala | Tyr | Glu | Glu | Lys | Ala | Tyr | Thr | Asp | Gly | Arg | Arg | Asp |
|---|---|---|---|---|---|---|---|---|---|---|---|---|---|---|
| 1070 | | | | | 1075 | | | | | 1080 | | | | |

| Asn | Pro | Cys | Glu | Ser | Asn | Arg | Gly | Tyr | Gly | Asp | Tyr | Thr | Pro | Leu |
|---|---|---|---|---|---|---|---|---|---|---|---|---|---|---|
| 1085 | | | | | 1090 | | | | | 1095 | | | | |

| Pro | Ala | Gly | Tyr | Val | Thr | Lys | Glu | Leu | Glu | Tyr | Phe | Pro | Glu | Thr |
|---|---|---|---|---|---|---|---|---|---|---|---|---|---|---|
| 1100 | | | | | 1105 | | | | | 1110 | | | | |

| Asp | Lys | Val | Trp | Ile | Glu | Ile | Gly | Glu | Thr | Glu | Gly | Thr | Phe | Ile |
|---|---|---|---|---|---|---|---|---|---|---|---|---|---|---|
| 1115 | | | | | 1120 | | | | | 1125 | | | | |

| Val | Asp | Ser | Val | Glu | Leu | Leu | Leu | Met | Glu | Glu |
|---|---|---|---|---|---|---|---|---|---|---|
| 1130 | | | | | 1135 | | | | | |

<210> SEQ ID NO 19
<211> LENGTH: 3420
<212> TYPE: DNA
<213> ORGANISM: Artificial sequence
<220> FEATURE:
<223> OTHER INFORMATION: Nucleotide sequence used for expression in a
      bacterial cell encoding TIC844_5.

<400> SEQUENCE: 19

| | | |
|---|---|---|
| atggaaataa ataatcaaaa ccaatgtgtg ccttacaatt gtttaagtaa tcctaaggag | 60 |
| ataatattag gcgaggaaag gctagaaaca gggaatactg tagcagacat tcattaggg | 120 |
| cttattaatt ttctatattc taattttgta ccaggaggag gatttatagt aggtttacta | 180 |
| gaattaatat ggggatttat agggccttcg caatgggata ttttttttagc tcaaattgag | 240 |
| caattgatta gtcaaagaat agaagaattt gctaggaatc aggcaatttc aagattggag | 300 |
| gggctaagca atctttataa ggtctatgtt agagcgttta gcgactggga gaaagatcct | 360 |
| actaatcctg cttaaggga agaaatgcgt atacaattta tgacatgaa tagtgctctc | 420 |
| ataacggcta ttccactttt tagagttcaa aattatgaag ttgctctttt atctgtatat | 480 |
| gttcaagccg caaacttaca tttatctatt ttaagggatg tttcagtttt cggagaaaga | 540 |
| tggggatatg atacagcgac tatcaataat cgctatagtg atctgactag ccttattcat | 600 |
| gtttatacta accattgtgt ggatacgtat aatcagggat taaggcgttt ggaaggtcgt | 660 |
| tttcttagcg attggattgt atataatcgt ttccggagac aattgacaat ttcagtatta | 720 |
| gatattgttg cgttttttcc aaattatgat attagaacat atccaattca aacagctact | 780 |

```
cagctaacga gggaagtcta tctggattta cctttatta atgaaaatct ttctcctgca    840
gcaaaatatc caacctttc agctgctgaa agtgctataa ttagaagtcc tcatttagta    900
gactttttaa atagctttac catttataca gatagtctgg cacgttctgc atattgggga    960
gggcacttgg taaattcttt ccgcacagga accactacta atttgataag atcccctta   1020 tatgaaggg aaggaaatac agagcgcccc gtaactatta ccgcatcacc tagcgtacca   1080
atatttagaa cactttcata tccaacaggc cttgacaatt caaatcctgt agctggaatc   1140
gagggagtgg aattccaaaa tactataagt agaagtatct atcgtaaaag cggtccaata   1200 gattcttta gtgaattacc acctcaagat gccagcgtat ctcctgcaat tgggtatagt   1260
caccgtttat gccatgcaac attttagaa cggattagtg gaccaagaat agcaggcacc   1320 gtatttctt ggacacaccg tagtgccagc cctactaacg aagtaagtcc atctagaatt   1380
acacaaattc catgggtaaa ggcgcatact cttgcatctg gtgcctccgt cattaaaggt   1440
cctggattta caggtggaga tattctgact aggaatagta tgggcgagct ggggaccta   1500 cgagtaacct tcacaggaag attaccacaa agttattata tacgtttccg ttatgcttcg   1560
gtagcaaata ggagtggtac atttagatat tcacagccac cttcgtatgg aatttcattt   1620
ccaaaaacta tggacgcagg tgaaccacta acatctcgtt cgttcgctca tacaacactc   1680
ttcactccaa taacctttc acgagctcaa gaagaatttg atctatacat ccaatcgggt   1740
gtttatatag atcgaattga atttataccg gttactgcaa catttgaggc agaatatgat   1800
ttagaaagag cacaaaaggc ggtgaatgag ctgtttactt cttccaatca aatcgggtta   1860
aaaacagatg tgacggatta tcatattgat caagtatcca atttagttga gtgtttatct   1920
gatgaatttt gtctggatga aaaaaagaa ttgtccgaga agtcaaaca tgcgaagcga   1980 cttagtgatg agcggaattt acttcaagat ccaaacttta gagggatcaa tagacaacta   2040
gaccgtggct ggagaggaag tacggatatt accatccaag gaggcgatga cgtattcaaa   2100
gagaattacg ttacgctatt gggtaccttt gatgagtgct atccaacgta tttatatcaa   2160
aaaatagatg agtcgaaatt aaaagcctat acccgttacc aattaagagg gtatatcgaa   2220
gatagtcaag acttagaaat ctatttaatt cgctacaatg ccaaacacga aacagtaaat   2280
gtgccaggta cgggttcctt atggccgctt tcagccccaa gtccaatcgg aaaatgtgcc   2340
catcattccc atcatttctc cttggacatt gatgttggat gtacagactt aaatgaggac   2400
ttaggtgtat gggtgatatt caagattaag acgcaagatg gccatgcaag actaggaaat   2460 ctagaattc tcgaagagaa accattagta ggagaagcac tagctcgtgt gaaaagagcg   2520 gagaaaaat ggagagacaa acgtgaaaaa ttggaatggg aaacaaatat tgtttataaa   2580
gaggcaaaag aatctgtaga tgctttattt gtaaactctc aatatgatag attacaagcg   2640
gataccaaca tcgcgatgat tcatgcggca gataaacgcg ttcatagcat tcgagaagct   2700
tatctgcctg agctgtctgt gattccgggt gtcaatgcgg ctattttga agaattagaa   2760 gggcgtattt tcactgcatt ctccctatat gatgcgagaa atgtcattaa aaatggtgat   2820
tttaataatg gcttatcctg ctggaacgtg aaagggcatg tagatgtaga agaacaaaac   2880
aaccaccgtt cggtccttgt tgttccgaaa tgggaagcag aagtgtcaca agaagttcgt   2940
gtctgtccgg tcgtggcta tatccttcgt gtcacagcgt acaaggaggg atatggagaa   3000
ggttgcgtaa ccattcatga gatcgagaac aatacagacg aactgaagtt tagcaactgt   3060
gtagaagagg aagtatatcc aaacaacacg gtaacgtgta atgattatac tgcgactcaa   3120
gaagaatatg agggtacgta cacttctcgt aatcgaggat atgacggagc ctatgaaagc   3180
```

```
aattcttctg taccagctga ttatgcatca gcctatgaag aaaaagcata tacagatgga    3240
cgaagagaca atccttgtga atctaacaga ggatatgggg attacacacc actaccagct    3300
ggctatgtga caaaagaatt agagtacttc ccagaaaccg ataaggtatg gattgagatc    3360
ggagaaacgg aaggaacatt catcgtggac agcgtggaat tacttcttat ggaggaatag    3420
```

<210> SEQ ID NO 20
<211> LENGTH: 1139
<212> TYPE: PRT
<213> ORGANISM: Artificial sequence
<220> FEATURE:
<223> OTHER INFORMATION: Amino acid sequence of the engineered
      insecticidal chimeric protein TIC844_5.

<400> SEQUENCE: 20

```
Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Lys Val Tyr Val Arg Ala
            100                 105                 110

Phe Ser Asp Trp Glu Lys Asp Pro Thr Asn Pro Ala Leu Arg Glu Glu
        115                 120                 125

Met Arg Ile Gln Phe Asn Asp Met Asn Ser Ala Leu Ile Thr Ala Ile
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
        195                 200                 205

Thr Tyr Asn Gln Gly Leu Arg Arg Leu Glu Gly Arg Phe Leu Ser Asp
    210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
            260                 265                 270

Ile Asn Glu Asn Leu Ser Pro Ala Ala Lys Tyr Pro Thr Phe Ser Ala
        275                 280                 285

Ala Glu Ser Ala Ile Ile Arg Ser Pro His Leu Val Asp Phe Leu Asn
    290                 295                 300

Ser Phe Thr Ile Tyr Thr Asp Ser Leu Ala Arg Ser Ala Tyr Trp Gly
305                 310                 315                 320
```

-continued

```
Gly His Leu Val Asn Ser Phe Arg Thr Gly Thr Thr Asn Leu Ile
            325                 330                 335

Arg Ser Pro Leu Tyr Gly Arg Glu Gly Asn Thr Glu Arg Pro Val Thr
            340                 345                 350

Ile Thr Ala Ser Pro Ser Val Pro Ile Phe Arg Thr Leu Ser Tyr Pro
            355                 360                 365

Thr Gly Leu Asp Asn Ser Asn Pro Val Ala Gly Ile Glu Gly Val Glu
        370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
            405                 410                 415

Ile Gly Tyr Ser His Arg Leu Cys His Ala Thr Phe Leu Glu Arg Ile
            420                 425                 430

Ser Gly Pro Arg Ile Ala Gly Thr Val Phe Ser Trp Thr His Arg Ser
            435                 440                 445

Ala Ser Pro Thr Asn Glu Val Ser Pro Ser Arg Ile Thr Gln Ile Pro
            450                 455                 460

Trp Val Lys Ala His Thr Leu Ala Ser Gly Ala Ser Val Ile Lys Gly
465                 470                 475                 480

Pro Gly Phe Thr Gly Gly Asp Ile Leu Thr Arg Asn Ser Met Gly Glu
            485                 490                 495

Leu Gly Thr Leu Arg Val Thr Phe Thr Gly Arg Leu Pro Gln Ser Tyr
            500                 505                 510

Tyr Ile Arg Phe Arg Tyr Ala Ser Val Ala Asn Arg Ser Gly Thr Phe
            515                 520                 525

Arg Tyr Ser Gln Pro Pro Ser Tyr Gly Ile Ser Phe Pro Lys Thr Met
            530                 535                 540

Asp Ala Gly Glu Pro Leu Thr Ser Arg Ser Phe Ala His Thr Thr Leu
545                 550                 555                 560

Phe Thr Pro Ile Thr Phe Ser Arg Ala Gln Glu Glu Phe Asp Leu Tyr
            565                 570                 575

Ile Gln Ser Gly Val Tyr Ile Asp Arg Ile Glu Phe Ile Pro Val Thr
            580                 585                 590

Ala Thr Phe Glu Ala Glu Tyr Asp Leu Glu Arg Ala Gln Lys Ala Val
            595                 600                 605

Asn Glu Leu Phe Thr Ser Ser Asn Gln Ile Gly Leu Lys Thr Asp Val
            610                 615                 620

Thr Asp Tyr His Ile Asp Gln Val Ser Asn Leu Val Glu Cys Leu Ser
625                 630                 635                 640

Asp Glu Phe Cys Leu Asp Glu Lys Lys Glu Leu Ser Glu Lys Val Lys
            645                 650                 655

His Ala Lys Arg Leu Ser Asp Glu Arg Asn Leu Leu Gln Asp Pro Asn
            660                 665                 670

Phe Arg Gly Ile Asn Arg Gln Leu Asp Arg Gly Trp Arg Gly Ser Thr
            675                 680                 685

Asp Ile Thr Ile Gln Gly Gly Asp Asp Val Phe Lys Glu Asn Tyr Val
        690                 695                 700

Thr Leu Leu Gly Thr Phe Asp Glu Cys Tyr Pro Thr Tyr Leu Tyr Gln
705                 710                 715                 720

Lys Ile Asp Glu Ser Lys Leu Lys Ala Tyr Thr Arg Tyr Gln Leu Arg
            725                 730                 735
```

```
Gly Tyr Ile Glu Asp Ser Gln Asp Leu Glu Ile Tyr Leu Ile Arg Tyr
                740                 745                 750

Asn Ala Lys His Glu Thr Val Asn Val Pro Gly Thr Gly Ser Leu Trp
                755                 760                 765

Pro Leu Ser Ala Pro Ser Pro Ile Gly Lys Cys Ala His His Ser His
770                 775                 780

His Phe Ser Leu Asp Ile Asp Val Gly Cys Thr Asp Leu Asn Glu Asp
785                 790                 795                 800

Leu Gly Val Trp Val Ile Phe Lys Ile Lys Thr Gln Asp Gly His Ala
                805                 810                 815

Arg Leu Gly Asn Leu Glu Phe Leu Glu Glu Lys Pro Leu Val Gly Glu
                820                 825                 830

Ala Leu Ala Arg Val Lys Arg Ala Glu Lys Lys Trp Arg Asp Lys Arg
                835                 840                 845

Glu Lys Leu Glu Trp Glu Thr Asn Ile Val Tyr Lys Glu Ala Lys Glu
                850                 855                 860

Ser Val Asp Ala Leu Phe Val Asn Ser Gln Tyr Asp Arg Leu Gln Ala
865                 870                 875                 880

Asp Thr Asn Ile Ala Met Ile His Ala Ala Asp Lys Arg Val His Ser
                885                 890                 895

Ile Arg Glu Ala Tyr Leu Pro Glu Leu Ser Val Ile Pro Gly Val Asn
                900                 905                 910

Ala Ala Ile Phe Glu Glu Leu Glu Gly Arg Ile Phe Thr Ala Phe Ser
                915                 920                 925

Leu Tyr Asp Ala Arg Asn Val Ile Lys Asn Gly Asp Phe Asn Asn Gly
                930                 935                 940

Leu Ser Cys Trp Asn Val Lys Gly His Val Asp Val Glu Glu Gln Asn
945                 950                 955                 960

Asn His Arg Ser Val Leu Val Val Pro Glu Trp Glu Ala Glu Val Ser
                965                 970                 975

Gln Glu Val Arg Val Cys Pro Gly Arg Gly Tyr Ile Leu Arg Val Thr
                980                 985                 990

Ala Tyr Lys Glu Gly Tyr Gly Glu Gly Cys Val Thr Ile His Glu Ile
                995                 1000                1005

Glu Asn Asn Thr Asp Glu Leu Lys Phe Ser Asn Cys Val Glu Glu
    1010                1015                1020

Glu Val Tyr Pro Asn Asn Thr Val Thr Cys Asn Asp Tyr Thr Ala
    1025                1030                1035

Thr Gln Glu Glu Tyr Glu Gly Thr Tyr Thr Ser Arg Asn Arg Gly
    1040                1045                1050

Tyr Asp Gly Ala Tyr Glu Ser Asn Ser Ser Val Pro Ala Asp Tyr
    1055                1060                1065

Ala Ser Ala Tyr Glu Glu Lys Ala Tyr Thr Asp Gly Arg Arg Asp
    1070                1075                1080

Asn Pro Cys Glu Ser Asn Arg Gly Tyr Gly Asp Tyr Thr Pro Leu
    1085                1090                1095

Pro Ala Gly Tyr Val Thr Lys Glu Leu Glu Tyr Phe Pro Glu Thr
    1100                1105                1110

Asp Lys Val Trp Ile Glu Ile Gly Glu Thr Glu Gly Thr Phe Ile
    1115                1120                1125

Val Asp Ser Val Glu Leu Leu Leu Met Glu Glu
    1130                1135
```

-continued

```
<210> SEQ ID NO 21
<211> LENGTH: 3420
<212> TYPE: DNA
<213> ORGANISM: Artificial sequence
<220> FEATURE:
<223> OTHER INFORMATION: Nucleotide sequence used for expression in a
      bacterial cell encoding TIC844_6.

<400> SEQUENCE: 21
atggaaataa ataatcaaaa ccaatgtgtg ccttacaatt gtttaagtaa tcctaaggag     60
ataatattag gcgaggaaag gctagaaaca gggaatactg tagcagacat tcattaggg    120 cttattaatt ttctatattc taattttgta ccaggaggag gatttatagt aggtttacta   180
gaattaatat ggggatttat agggccttcg caatgggata tttttttagc tcaaattgag   240
caattgatta gtcaaagaat agaagaattt gctaggaatc aggcaatttc aagattggag   300
gggctaagca atctttataa ggtctatgtt agagcgttta gcgactggga gaaagatcct   360
actaatcctg ctttaaggga gaaatgcgt ataccaattta atgacatgaa tagtgctctc   420
ataacggcta ttccactttt tagagttcaa aattatgaag ttgctctttt atctgtatat   480
gttcaagccg caaacttaca tttatctatt ttaagggatg tttcagtttt cggagaaaga   540
tggggatatg atacagcgac tatcaataat cgctatagtg atctgactag ccttattcat   600
gtttatacta accattgtgt ggatacgtat aatcagggat taaggcgttt ggaaggtcgt   660
tttcttagcg attggattgt atataatcgt ttccggagac aattgacaat tcagtatta   720 gatattgttg cgttttttcc aaattatgat attagaacat atccaattca aacagctact   780
cagctaacga gggaagtcta tctggattta ccttttatta tgaaaatct ttctcctgca   840 gcaagctatc caacctttc agctgctgaa agtgctataa ttagaagtcc tcatttagta   900 gacttttaa atagctttac catttataca gatagtctgg cacgttatgc atattgggga   960
gggcacttgg taaattcttt ccgcacagga accactacta atttgataag atccccttta   1020
tatggaaggg aaggaaatac agagcgcccc gtaactatta ccgcatcacc tagcgtacca   1080
atatttagaa cactttcata tattacaggc cttgacaatc gtaatcctgt agctggaatc   1140
gagggagtgg aattccaaaa tactataagt agaagtatct atcgtaaaag cggtccaata   1200
gattctttta gtgaattacc acctcaagat gccagcgtat ctcctgcaat tgggtatagt   1260
caccgtttat gccatgcaac atttttagaa cggattagtg gaccaagaat agcaggcacc   1320
gtattttctt ggacacaccg tagtgccagc cctactaacg aagtaagtcc atctagaatt   1380
acacaaattc catgggtaaa ggcgcatact cttgcatctg gtgcctccgt cattaaaggt   1440
cctggattta caggtggaga tattctgact aggaatagta tgggcgagct ggggaccttta  1500 cgagtaacct tcacaggaag attaccacaa agttattata tacgtttccg ttatgcttcg   1560
gtagcaaata ggagtggtac atttagatat tcacagccac cttcgtatgg aatttcattt   1620
ccaaaaacta tggacgcagg tgaaccacta acatctcgtt cgttcgctca tacaacactc   1680
ttcactccaa taacctttc acgagctcaa gaagaatttg atctatacat ccaatcgggt   1740
gtttatatag atcgaattga atttataccg gttactgcaa catttgaggc agaatatgat   1800
ttagaaagag cacaaaaggc ggtgaatgag ctgtttactt cttccaatca atcgggtta    1860 aaaacagatg tgacggatta tcatattgat caagtatcca atttagttga gtgtttatct   1920 gatgaattt gtctggatga aaaaaaagaa ttgtccgaga agtcaaaca tgcgaagcga    1980 cttagtgatg agcggaattt acttcaagat ccaaacttta gagggatcaa tagacaacta   2040
gaccgtggct ggagaggaag tacggatatt accatccaag gaggcgatga cgtattcaaa   2100
```

-continued

```
gagaattacg ttacgctatt gggtacctttt gatgagtgct atccaacgta tttatatcaa    2160
aaaatagatg agtcgaaatt aaaagcctat acccgttacc aattaagagg gtatatcgaa    2220
gatagtcaag acttagaaat ctatttaatt cgctacaatg ccaaacacga aacagtaaat    2280
gtgccaggta cgggttcctt atggccgctt tcagccccaa gtccaatcgg aaaatgtgcc    2340
catcattccc atcatttctc cttggacatt gatgttggat gtacagactt aaatgaggac    2400
ttaggtgtat gggtgatatt caagattaag acgcaagatg ccatgcaag actaggaaat    2460 ctagaatttc tcgaagagaa accattagta ggagaagcac tagctcgtgt gaaaagagcg    2520
gagaaaaaat ggagagacaa acgtgaaaaa ttggaatggg aaacaaatat tgtttataaa    2580
gaggcaaaag aatctgtaga tgctttatttt gtaaactctc aatatgatag attacaagcg    2640
gataccaaca tcgcgatgat tcatgcggca gataaacgcg ttcatagcat tcgagaagct    2700
tatctgcctg agctgtctgt gattccgggt gtcaatgcgg ctattttttga agaattagaa    2760 gggcgtatt tcactgcatt ctccctatat gatgcgagaa atgtcattaa aaatggtgat    2820
tttaataatg gcttatcctg ctggaacgtg aaagggcatg tagatgtaga agaacaaaac    2880
aaccaccgtt cggtccttgt tgttccggaa tgggaagcag aagtgtcaca agaagttcgt    2940
gtctgtccgg gtcgtggcta tatccttcgt gtcacagcgt acaaggaggg atatggagaa    3000
ggttgcgtaa ccattcatga gatcgagaac aatacgacg aactgaagtt tagcaactgt    3060
gtagaagagg aagtatatcc aaacaacacg gtaacgtgta atgattatac tgcgactcaa    3120
gaagaatatg agggtacgta cacttctcgt aatcgaggat atgacggagc ctatgaaagc    3180
aattcttctg taccagctga ttatgcatca gcctatgaag aaaaagcata tacagatgga    3240
cgaagagaca atccttgtga atctaacaga ggatatgggg attacacacc actaccagct    3300
ggctatgtga caaaagaatt agagtacttc ccagaaaccg ataaggtatg gattgagatc    3360
ggagaaacgg aaggaacatt catcgtggac agcgtggaat tacttcttat ggaggaatag    3420
```

<210> SEQ ID NO 22
<211> LENGTH: 1139
<212> TYPE: PRT
<213> ORGANISM: Artificial sequence
<220> FEATURE:
<223> OTHER INFORMATION: Amino acid sequence of the engineered
      insecticidal chimeric protein TIC844_6.

<400> SEQUENCE: 22

```
Met Glu Ile Asn Asn Gln Asn Gln Cys Val Pro Tyr Asn Cys Leu Ser
1               5                  10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Lys Val Tyr Val Arg Ala
            100                 105                 110

Phe Ser Asp Trp Glu Lys Asp Pro Thr Asn Pro Ala Leu Arg Glu Glu
        115                 120                 125
```

```
Met Arg Ile Gln Phe Asn Asp Met Asn Ser Ala Leu Ile Thr Ala Ile
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
        195                 200                 205

Thr Tyr Asn Gln Gly Leu Arg Arg Leu Glu Gly Arg Phe Leu Ser Asp
    210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
            260                 265                 270

Ile Asn Glu Asn Leu Ser Pro Ala Ala Ser Tyr Pro Thr Phe Ser Ala
        275                 280                 285

Ala Glu Ser Ala Ile Ile Arg Ser Pro His Leu Val Asp Phe Leu Asn
    290                 295                 300

Ser Phe Thr Ile Tyr Thr Asp Ser Leu Ala Arg Tyr Ala Tyr Trp Gly
305                 310                 315                 320

Gly His Leu Val Asn Ser Phe Arg Thr Gly Thr Thr Thr Asn Leu Ile
                325                 330                 335

Arg Ser Pro Leu Tyr Gly Arg Glu Gly Asn Thr Glu Arg Pro Val Thr
            340                 345                 350

Ile Thr Ala Ser Pro Ser Val Pro Ile Phe Arg Thr Leu Ser Tyr Ile
        355                 360                 365

Thr Gly Leu Asp Asn Arg Asn Pro Val Ala Gly Ile Glu Gly Val Glu
    370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
                405                 410                 415

Ile Gly Tyr Ser His Arg Leu Cys His Ala Thr Phe Leu Glu Arg Ile
            420                 425                 430

Ser Gly Pro Arg Ile Ala Gly Thr Val Phe Ser Trp Thr His Arg Ser
        435                 440                 445

Ala Ser Pro Thr Asn Glu Val Ser Pro Ser Arg Ile Thr Gln Ile Pro
    450                 455                 460

Trp Val Lys Ala His Thr Leu Ala Ser Gly Ala Ser Val Ile Lys Gly
465                 470                 475                 480

Pro Gly Phe Thr Gly Gly Asp Ile Leu Thr Arg Asn Ser Met Gly Glu
                485                 490                 495

Leu Gly Thr Leu Arg Val Thr Phe Thr Gly Arg Leu Pro Gln Ser Tyr
            500                 505                 510

Tyr Ile Arg Phe Arg Tyr Ala Ser Val Ala Asn Arg Ser Gly Thr Phe
        515                 520                 525

Arg Tyr Ser Gln Pro Pro Ser Tyr Gly Ile Ser Phe Pro Lys Thr Met
    530                 535                 540
```

```
Asp Ala Gly Glu Pro Leu Thr Ser Arg Ser Phe Ala His Thr Thr Leu
545                 550                 555                 560

Phe Thr Pro Ile Thr Phe Ser Arg Ala Gln Glu Glu Phe Asp Leu Tyr
            565                 570                 575

Ile Gln Ser Gly Val Tyr Ile Asp Arg Ile Glu Phe Ile Pro Val Thr
                580                 585                 590

Ala Thr Phe Glu Ala Glu Tyr Asp Leu Glu Arg Ala Gln Lys Ala Val
            595                 600                 605

Asn Glu Leu Phe Thr Ser Ser Asn Gln Ile Gly Leu Lys Thr Asp Val
            610                 615                 620

Thr Asp Tyr His Ile Asp Gln Val Ser Asn Leu Val Glu Cys Leu Ser
625                 630                 635                 640

Asp Glu Phe Cys Leu Asp Glu Lys Lys Glu Leu Ser Glu Lys Val Lys
            645                 650                 655

His Ala Lys Arg Leu Ser Asp Glu Arg Asn Leu Leu Gln Asp Pro Asn
            660                 665                 670

Phe Arg Gly Ile Asn Arg Gln Leu Asp Arg Gly Trp Arg Gly Ser Thr
            675                 680                 685

Asp Ile Thr Ile Gln Gly Gly Asp Asp Val Phe Lys Glu Asn Tyr Val
            690                 695                 700

Thr Leu Leu Gly Thr Phe Asp Glu Cys Tyr Pro Thr Tyr Leu Tyr Gln
705                 710                 715                 720

Lys Ile Asp Glu Ser Lys Leu Lys Ala Tyr Thr Arg Tyr Gln Leu Arg
                725                 730                 735

Gly Tyr Ile Glu Asp Ser Gln Asp Leu Glu Ile Tyr Leu Ile Arg Tyr
            740                 745                 750

Asn Ala Lys His Glu Thr Val Asn Val Pro Gly Thr Gly Ser Leu Trp
            755                 760                 765

Pro Leu Ser Ala Pro Ser Pro Ile Gly Lys Cys Ala His His Ser His
770                 775                 780

His Phe Ser Leu Asp Ile Asp Val Gly Cys Thr Asp Leu Asn Glu Asp
785                 790                 795                 800

Leu Gly Val Trp Val Ile Phe Lys Ile Lys Thr Gln Asp Gly His Ala
            805                 810                 815

Arg Leu Gly Asn Leu Glu Phe Leu Glu Glu Lys Pro Leu Val Gly Glu
            820                 825                 830

Ala Leu Ala Arg Val Lys Arg Ala Glu Lys Lys Trp Arg Asp Lys Arg
            835                 840                 845

Glu Lys Leu Glu Trp Glu Thr Asn Ile Val Tyr Lys Glu Ala Lys Glu
850                 855                 860

Ser Val Asp Ala Leu Phe Val Asn Ser Gln Tyr Asp Arg Leu Gln Ala
865                 870                 875                 880

Asp Thr Asn Ile Ala Met Ile His Ala Ala Asp Lys Arg Val His Ser
            885                 890                 895

Ile Arg Glu Ala Tyr Leu Pro Glu Leu Ser Val Ile Pro Gly Val Asn
            900                 905                 910

Ala Ala Ile Phe Glu Glu Leu Glu Gly Arg Ile Phe Thr Ala Phe Ser
            915                 920                 925

Leu Tyr Asp Ala Arg Asn Val Ile Lys Asn Gly Asp Phe Asn Asn Gly
            930                 935                 940

Leu Ser Cys Trp Asn Val Lys Gly His Val Asp Val Glu Glu Gln Asn
945                 950                 955                 960

Asn His Arg Ser Val Leu Val Val Pro Glu Trp Glu Ala Glu Val Ser
```

```
                965                 970                 975
Gln Glu Val Arg Val Cys Pro Gly Arg Gly Tyr Ile Leu Arg Val Thr
                    980                 985                 990
Ala Tyr Lys Glu Gly Tyr Gly Glu Gly Cys Val Thr Ile His Glu Ile
            995                1000                1005
Glu Asn Asn Thr Asp Glu Leu Lys Phe Ser Asn Cys Val Glu Glu
        1010                1015                1020
Glu Val Tyr Pro Asn Asn Thr Val Thr Cys Asn Asp Tyr Thr Ala
    1025                1030                1035
Thr Gln Glu Glu Tyr Glu Gly Thr Tyr Thr Ser Arg Asn Arg Gly
    1040                1045                1050
Tyr Asp Gly Ala Tyr Glu Ser Asn Ser Ser Val Pro Ala Asp Tyr
    1055                1060                1065
Ala Ser Ala Tyr Glu Glu Lys Ala Tyr Thr Asp Gly Arg Arg Asp
    1070                1075                1080
Asn Pro Cys Glu Ser Asn Arg Gly Tyr Gly Asp Tyr Thr Pro Leu
    1085                1090                1095
Pro Ala Gly Tyr Val Thr Lys Glu Leu Glu Tyr Phe Pro Glu Thr
    1100                1105                1110
Asp Lys Val Trp Ile Glu Ile Gly Glu Thr Glu Gly Thr Phe Ile
    1115                1120                1125
Val Asp Ser Val Glu Leu Leu Leu Met Glu Glu
    1130                1135
```

<210> SEQ ID NO 23
<211> LENGTH: 3420
<212> TYPE: DNA
<213> ORGANISM: Artificial sequence
<220> FEATURE:
<223> OTHER INFORMATION: Nucleotide sequence used for expression in a
      bacterial cell encoding TIC844_7.

<400> SEQUENCE: 23

```
atggaaataa ataatcaaaa ccaatgtgtg ccttacaatt gtttaagtaa tcctaaggag      60
ataatattag gcgaggaaag gctagaaaca gggaatactg tagcagacat tccattaggg     120
cttattaatt ttctatattc taattttgta ccaggaggag gatttatagt aggtttacta     180
gaattaatat ggggatttat agggccttcg caatgggata tttttttagc tcaaattgag     240
caattgatta gtcaaagaat agaagaattt gctaggaatc aggcaatttc aagattggag     300
gggctaagca atctttataa ggtctatgtt agagcgttta gcgactggga gaaagatcct     360
actaatcctg ctttaaggga gaaatgcgt atacaattta atgacatgaa tagtgctctc     420
ataacggcta ttccactttt tagagttcaa aattatgaag ttgctctttt atctgtatat     480
gttcaagccg caaacttaca tttatctatt ttaagggatg tttcagtttt cggagaaaga     540
tggggatatg atacagcgac tatcaataat cgctatagtg atctgactag ccttattcat     600
gtttatacta accattgtgt ggatacgtat aatcagggat taaggcgttt ggaaggtcgt     660
tttcttagcg attggattgt atataatcgt ttccggagac aattgacaat tcagtatta     720
gatattgttg cgtttttttcc aaattatgat attagaacat atccaattca acagcactact    780
cagctaacga gggaagtcta tctggattta cctttattaa tgaaaatct ttctcctgca     840
gcaagctatc caacctttc agctgctgaa agtgctataa ttagaagtcc tcatttagta     900
gactttttaa atagctttac catttataca gatagtctgg cacgttctgc atattgggga     960
gggcacttgg taaattcttt ccgcacagga accactacta atttgataag atccccttta    1020
```

```
tatggaaggg aaggaaatac agagcgcccc gtaactatta ccgcatcacc tagcgtacca   1080
atatttagaa cactttcata tagaacaggc cttgacaatt caaatcctgt agctggaatc   1140
gagggagtgg aattccaaaa tactataagt agaagtatct atcgtaaaag cggtccaata   1200
gattctttta gtgaattacc acctcaagat gccagcgtat ctcctgcaat tgggtatagt   1260
caccgtttat gccatgcaac attttagaa cggattagtg gaccaagaat agcaggcacc   1320
gtattttctt ggacacaccg tagtgccagc cctactaacg aagtaagtcc atctagaatt   1380
acacaaattc catgggtaaa ggcgcatact cttgcatctg gtgcctccgt cattaaaggt   1440
cctggattta caggtggaga tattctgact aggaatagta tgggcgagct ggggacctta   1500
cgagtaacct tcacaggaag attaccacaa agttattata tacgtttccg ttatgcttcg   1560
gtagcaaata ggagtggtac atttagatat tcacagccac cttcgtatgg aatttcatt   1620 ccaaaaacta tggacgcagg tgaaccacta acatctcgtt cgttcgctca tacaacactc   1680
ttcactccaa taccttttc acgagctcaa gaagaatttg atctatacat ccaatcgggt   1740
gtttatatag atcgaattga atttataccg gttactgcaa catttgaggc agaatatgat   1800
ttagaaagag cacaaaaggc ggtgaatgag ctgtttactt cttccaatca atcgggtta   1860 aaaacagatg tgacggatta tcatattgat caagtatcca atttagttga gtgtttatct   1920
gatgaatttt gtctggatga aaaaaaagaa ttgtccgaga agtcaaaaca tgcgaagcga   1980
cttagtgatg agcggaattt acttcaagat ccaaacttta gagggatcaa tagacaacta   2040
gaccgtggct ggagaggaag tacggatatt accatccaag gaggcgatga cgtattcaaa   2100
gagaattacg ttacgctatt gggtaccttt gatgagtgct atccaacgta tttatatcaa   2160
aaaatagatg agtcgaaatt aaaagcctat acccgttacc aattaagagg gtatatcgaa   2220
gatagtcaag acttagaaat ctatttaatt cgctacaatg ccaaacacga aacagtaaat   2280
gtgccaggta cgggttcctt atggccgctt tcagccccaa gtccaatcgg aaaatgtgcc   2340
catcattccc atcatttctc cttggacatt gatgttggat gtacagactt aaatgaggac   2400
ttaggtgtat gggtgatatt caagattaag acgcaagatg ccatgcaag actaggaaat   2460 ctagaatttc tcgaagagaa accattagta ggagaagcac tagctcgtgt gaaaagagcg   2520
gagaaaaaat ggagagacaa acgtgaaaaa ttggaatggg aaacaaatat tgtttataaa   2580
gaggcaaaag aatctgtaga tgctttattt gtaaactctc aatatgatag attacaagcg   2640
gataccaaca tcgcgatgat tcatgcggca gataaacgcg ttcatagcat tcgagaagct   2700
tatctgcctg agctgtctgt gattccgggt gtcaatgcgg ctattttga agaattagaa   2760 gggcgtattt tcactgcatt ctccctatat gatgcgagaa atgtcattaa aaatggtgat   2820
tttaataatg gcttatcctg ctggaacgtg aaagggcatg tagatgtaga agaacaaaac   2880
aaccaccgtt cggtccttgt tgttccggaa tgggaagcag aagtgtcaca agaagttcgt   2940
gtctgtccgg gtcgtggcta tatccttcgt gtcacagcgt acaaggaggg atatggagaa   3000
ggttgcgtaa ccattcatga gatcgagaac aatacagacg aactgaagtt tagcaactgt   3060
gtagaagagg aagtatatcc aaacaacacg gtaacgtgta atgattatac tgcgactcaa   3120
gaagaatatg agggtacgta cacttctcgt aatcgaggat atgacggagc ctatgaaagc   3180
aattcttctg taccagctga ttatgcatca gcctatgaag aaaaagcata tacagatgga   3240
cgaagagaca atccttgtga atctaacaga ggatatgggg attacacacc actaccagct   3300
ggctatgtga caaaagaatt agagtacttc ccagaaaccg ataaggtatg gattgagatc   3360
```

```
ggagaaacgg aaggaacatt catcgtggac agcgtggaat tacttcttat ggaggaatag    3420
```

<210> SEQ ID NO 24
<211> LENGTH: 1139
<212> TYPE: PRT
<213> ORGANISM: Artificial sequence
<220> FEATURE:
<223> OTHER INFORMATION: Amino acid sequence of the engineered
      insecticidal chimeric protein TIC844_7.

<400> SEQUENCE: 24

```
Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Lys Val Tyr Val Arg Ala
            100                 105                 110

Phe Ser Asp Trp Glu Lys Asp Pro Thr Asn Pro Ala Leu Arg Glu Glu
        115                 120                 125

Met Arg Ile Gln Phe Asn Asp Met Asn Ser Ala Leu Ile Thr Ala Ile
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
        195                 200                 205

Thr Tyr Asn Gln Gly Leu Arg Arg Leu Glu Gly Arg Phe Leu Ser Asp
    210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
            260                 265                 270

Ile Asn Glu Asn Leu Ser Pro Ala Ala Ser Tyr Pro Thr Phe Ser Ala
        275                 280                 285

Ala Glu Ser Ala Ile Ile Arg Ser Pro His Leu Val Asp Phe Leu Asn
    290                 295                 300

Ser Phe Thr Ile Tyr Thr Asp Ser Leu Ala Arg Ser Ala Tyr Trp Gly
305                 310                 315                 320

Gly His Leu Val Asn Ser Phe Arg Thr Gly Thr Thr Asn Leu Ile
                325                 330                 335

Arg Ser Pro Leu Tyr Gly Arg Glu Gly Asn Thr Glu Arg Pro Val Thr
            340                 345                 350
```

```
Ile Thr Ala Ser Pro Ser Val Pro Ile Phe Arg Thr Leu Ser Tyr Arg
            355                 360                 365

Thr Gly Leu Asp Asn Ser Asn Pro Val Ala Gly Ile Glu Gly Val Glu
370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
                405                 410                 415

Ile Gly Tyr Ser His Arg Leu Cys His Ala Thr Phe Leu Glu Arg Ile
            420                 425                 430

Ser Gly Pro Arg Ile Ala Gly Thr Val Phe Ser Trp Thr His Arg Ser
        435                 440                 445

Ala Ser Pro Thr Asn Glu Val Ser Pro Ser Arg Ile Thr Gln Ile Pro
    450                 455                 460

Trp Val Lys Ala His Thr Leu Ala Ser Gly Ala Ser Val Ile Lys Gly
465                 470                 475                 480

Pro Gly Phe Thr Gly Gly Asp Ile Leu Thr Arg Asn Ser Met Gly Glu
                485                 490                 495

Leu Gly Thr Leu Arg Val Thr Phe Thr Gly Arg Leu Pro Gln Ser Tyr
            500                 505                 510

Tyr Ile Arg Phe Arg Tyr Ala Ser Val Ala Asn Arg Ser Gly Thr Phe
        515                 520                 525

Arg Tyr Ser Gln Pro Pro Ser Tyr Gly Ile Ser Phe Pro Lys Thr Met
    530                 535                 540

Asp Ala Gly Glu Pro Leu Thr Ser Arg Ser Phe Ala His Thr Thr Leu
545                 550                 555                 560

Phe Thr Pro Ile Thr Phe Ser Arg Ala Gln Glu Glu Phe Asp Leu Tyr
                565                 570                 575

Ile Gln Ser Gly Val Tyr Ile Asp Arg Ile Glu Phe Ile Pro Val Thr
            580                 585                 590

Ala Thr Phe Glu Ala Glu Tyr Asp Leu Glu Arg Ala Gln Lys Ala Val
        595                 600                 605

Asn Glu Leu Phe Thr Ser Ser Asn Gln Ile Gly Leu Lys Thr Asp Val
    610                 615                 620

Thr Asp Tyr His Ile Asp Gln Val Ser Asn Leu Val Glu Cys Leu Ser
625                 630                 635                 640

Asp Glu Phe Cys Leu Asp Glu Lys Lys Glu Leu Ser Glu Lys Val Lys
                645                 650                 655

His Ala Lys Arg Leu Ser Asp Glu Arg Asn Leu Leu Gln Asp Pro Asn
            660                 665                 670

Phe Arg Gly Ile Asn Arg Gln Leu Asp Arg Gly Trp Arg Gly Ser Thr
        675                 680                 685

Asp Ile Thr Ile Gln Gly Gly Asp Asp Val Phe Lys Glu Asn Tyr Val
    690                 695                 700

Thr Leu Leu Gly Thr Phe Asp Glu Cys Tyr Pro Thr Tyr Leu Tyr Gln
705                 710                 715                 720

Lys Ile Asp Glu Ser Lys Leu Lys Ala Tyr Thr Arg Tyr Gln Leu Arg
                725                 730                 735

Gly Tyr Ile Glu Asp Ser Gln Asp Leu Glu Ile Tyr Leu Ile Arg Tyr
            740                 745                 750

Asn Ala Lys His Glu Thr Val Asn Val Pro Gly Thr Gly Ser Leu Trp
        755                 760                 765

Pro Leu Ser Ala Pro Ser Pro Ile Gly Lys Cys Ala His His Ser His
```

His Phe Ser Leu Asp Ile Asp Val Gly Cys Thr Asp Leu Asn Glu Asp
785                 790                 795                 800

Leu Gly Val Trp Val Ile Phe Lys Ile Lys Thr Gln Asp Gly His Ala
            805                 810                 815

Arg Leu Gly Asn Leu Glu Phe Leu Glu Lys Pro Leu Val Gly Glu
        820                 825                 830

Ala Leu Ala Arg Val Lys Arg Ala Glu Lys Lys Trp Arg Asp Lys Arg
        835                 840                 845

Glu Lys Leu Glu Trp Glu Thr Asn Ile Val Tyr Lys Glu Ala Lys Glu
    850                 855                 860

Ser Val Asp Ala Leu Phe Val Asn Ser Gln Tyr Asp Arg Leu Gln Ala
865                 870                 875                 880

Asp Thr Asn Ile Ala Met Ile His Ala Ala Asp Lys Arg Val His Ser
            885                 890                 895

Ile Arg Glu Ala Tyr Leu Pro Glu Leu Ser Val Ile Pro Gly Val Asn
        900                 905                 910

Ala Ala Ile Phe Glu Glu Leu Glu Gly Arg Ile Phe Thr Ala Phe Ser
        915                 920                 925

Leu Tyr Asp Ala Arg Asn Val Ile Lys Asn Gly Asp Phe Asn Asn Gly
    930                 935                 940

Leu Ser Cys Trp Asn Val Lys Gly His Val Asp Val Glu Glu Gln Asn
945                 950                 955                 960

Asn His Arg Ser Val Leu Val Val Pro Glu Trp Glu Ala Glu Val Ser
            965                 970                 975

Gln Glu Val Arg Val Cys Pro Gly Arg Gly Tyr Ile Leu Arg Val Thr
        980                 985                 990

Ala Tyr Lys Glu Gly Tyr Gly Glu  Gly Cys Val Thr Ile  His Glu Ile
        995                 1000                1005

Glu Asn  Asn Thr Asp Glu Leu  Lys Phe Ser Asn Cys  Val Glu Glu
    1010                1015                1020

Glu Val  Tyr Pro Asn Asn Thr  Val Thr Cys Asn Asp  Tyr Thr Ala
    1025                1030                1035

Thr Gln  Glu Glu Tyr Glu Gly  Thr Tyr Thr Ser Arg  Asn Arg Gly
    1040                1045                1050

Tyr Asp  Gly Ala Tyr Glu Ser  Asn Ser Ser Val Pro  Ala Asp Tyr
    1055                1060                1065

Ala Ser  Ala Tyr Glu Glu Lys  Ala Tyr Thr Asp Gly  Arg Arg Asp
    1070                1075                1080

Asn Pro  Cys Glu Ser Asn Arg  Gly Tyr Gly Asp Tyr  Thr Pro Leu
    1085                1090                1095

Pro Ala  Gly Tyr Val Thr Lys  Glu Leu Glu Tyr Phe  Pro Glu Thr
    1100                1105                1110

Asp Lys  Val Trp Ile Glu Ile  Gly Glu Thr Glu Gly  Thr Phe Ile
    1115                1120                1125

Val Asp  Ser Val Glu Leu Leu  Leu Met Glu Glu
    1130                1135

<210> SEQ ID NO 25
<211> LENGTH: 3420
<212> TYPE: DNA
<213> ORGANISM: Artificial sequence
<220> FEATURE:
<223> OTHER INFORMATION: Nucleotide sequence used for expression in a
      bacterial cell encoding TIC844_8.

<400> SEQUENCE: 25

```
atggaaataa ataatcaaaa ccaatgtgtg ccttacaatt gtttaagtaa tcctaaggag    60
ataatattag gcgaggaaag gctagaaaca gggaatactg tagcagacat ttcattaggg   120
cttattaatt ttctatattc taattttgta ccaggaggag gatttatagt aggtttacta   180
gaattaatat ggggatttat agggccttcg caatgggata ttttttttagc tcaaattgag   240
caattgatta gtcaaagaat agaagaattt gctaggaatc aggcaatttc aagattggag   300
gggctaagca atctttataa ggtctatgtt agagcgttta gcgactggga gaaagatcct   360
actaatcctg ctttaaggga gaaaatgcgt atacaattta tgacatgaa tagtgctctc    420
ataacggcta ttccactttt tagagttcaa aattatgaag ttgctctttt atctgtatat   480
gttcaagccg caaacttaca tttatctatt ttaagggatg tttcagtttt cggagaaaga   540
tggggatatg atacagcgac tatcaataat cgctatagtg atctgactag ccttattcat   600
gtttatacta accattgtgt ggatacgtat aatcagggat taaggcgttt ggaaggtcgt   660
tttcttagcg attggattgt atataatcgt ttccggagac aattgacaat ttcagtatta   720
gatattgttg cgttttttcc aaattatgat attagaacat atccaattca aacagctact   780
cagctaacga gggaagtcta tctggattta ccttttatta tgaaaatct ttctcctgca    840
gcagtatatc caccttttc agctgctgaa agtgctataa ttagaagtcc tcatttagta   900
gactttttaa atagctttac catttataca gatagtctgg cacgttctgc atattgggga   960
gggcacttgg taaattcttt ccgcacagga accactacta atttgataag atcccctta  1020
tatggaaggg aaggaaatac agagcgcccc gtaactatta ccgcatcacc tagcgtacca  1080
atatttagaa cactttcata tccaacaggc cttgacaatt caaatcctgt agctggaatc  1140
gagggagtgg aattccaaaa tactataagt agaagtatct atcgtaaaag cggtccaata  1200
gattctttta gtgaattacc acctcaagat gccagcgtat ctcctgcaat tgggtatagt  1260
caccgtttat gccatgcaac atttttagaa cggattagtg gaccaagaat agcaggcacc  1320
gtattttctt ggacacaccg tagtgccagc cctactaacg aagtaagtcc atctagaatt  1380
acacaaattc catgggtaaa ggcgcatact cttgcatctg gtgcctccgt cattaaaggt  1440
cctggattta caggtggaga tattctgact aggaatagta tgggcgagct ggggaccta  1500
cgagtaacct tcacaggaag attaccacaa agttattata tacgtttccg ttatgcttcg  1560
gtagcaaata ggagtggtac atttagatat tcacagccac cttcgtatgg aatttcatt  1620
ccaaaaacta tggacgcagg tgaaccacta acatctcgtt cgttcgctca tacaacactc  1680
ttcactccaa taacctttc acgagctcaa gaagaatttg atctatacat ccaatcgggt  1740
gtttatatag atcgaattga atttataccg gttactgcaa catttgaggc agaatatgat  1800
ttagaaagag cacaaaaggc ggtgaatgag ctgtttactt cttccaatca aatcgggtta  1860
aaaacagatg tgacggatta tcatattgat caagtatcca atttagttga gtgtttatct  1920
gatgaatttt gtctggatga aaaaaaagaa ttgtccgaga agtcaaaca tgcgaagcga  1980
cttagtgatg agcggaattt acttcaagat ccaaacttta gagggatcaa tagacaacta  2040
gaccgtggct ggagaggaag tacgatatt accatccaag gaggcgatga cgtattcaaa  2100
gagaattacg ttacgctatt gggtaccttt gatgagtgct atccaacgta tttatatcaa  2160
aaaatagatg agtcgaaatt aaaagcctat acccgttacc aattaagagg gtatatcgaa  2220
gatagtcaag acttagaaat ctatttaatt cgctacaatg ccaaacacga aacagtaaat  2280
```

```
gtgccaggta cgggttcctt atggccgctt tcagccccaa gtccaatcgg aaaatgtgcc    2340
catcattccc atcatttctc cttggacatt gatgttggat gtacagactt aaatgaggac    2400
ttaggtgtat gggtgatatt caagattaag acgcaagatg gccatgcaag actaggaaat    2460
ctagaatttc tcgaagagaa accattagta ggagaagcac tagctcgtgt gaaaagagcg    2520
gagaaaaaat ggagagacaa acgtgaaaaa ttggaatggg aaacaaatat tgtttataaa    2580
gaggcaaaag aatctgtaga tgctttattt gtaaactctc aatatgatag attacaagcg    2640
gataccaaca tcgcgatgat tcatgcggca gataaacgcg ttcatagcat tcgagaagct    2700
tatctgcctg agctgtctgt gattccgggt gtcaatgcgg ctattttga agaattagaa    2760 gggcgtattt tcactgcatt ctccctatat gatgcgagaa atgtcattaa aaatggtgat    2820
tttaataatg gcttatcctg ctggaacgtg aaagggcatg tagatgtaga agaacaaaac    2880
aaccaccgtt cggtccttgt tgttccggaa tgggaagcag aagtgtcaca agaagttcgt    2940
gtctgtccgg tcgtggcta tatccttcgt gtcacagcgt acaaggaggg atatggagaa    3000
ggttgcgtaa ccattcatga gatcgagaac aatacagacg aactgaagtt tagcaactgt    3060
gtagaagagg aagtatatcc aaacaacacg gtaacgtgta atgattatac tgcgactcaa    3120
gaagaatatg agggtacgta cacttctcgt aatcgaggat atgacggagc ctatgaaagc    3180
aattcttctg taccagctga ttatgcatca gcctatgaag aaaaagcata tacagatgga    3240
cgaagagaca tccttgtga atctaacaga ggatatgggg attacacacc actaccagct    3300
ggctatgtga caaaagaatt agagtacttc ccagaaaccg ataaggtatg gattgagatc    3360
ggagaaacgg aaggaacatt catcgtggac agcgtggaat tacttcttat ggaggaatag    3420

<210> SEQ ID NO 26
<211> LENGTH: 1139
<212> TYPE: PRT
<213> ORGANISM: Artificial sequence
<220> FEATURE:
<223> OTHER INFORMATION: Amino acid sequence of the engineered
      insecticidal chimeric protein TIC844_8.

<400> SEQUENCE: 26

Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Lys Val Tyr Val Arg Ala
            100                 105                 110

Phe Ser Asp Trp Glu Lys Asp Pro Thr Asn Pro Ala Leu Arg Glu Glu
        115                 120                 125

Met Arg Ile Gln Phe Asn Asp Met Asn Ser Ala Leu Ile Thr Ala Ile
    130                 135                 140

Pro Leu Phe Arg Val Gln Asn Tyr Glu Val Ala Leu Leu Ser Val Tyr
145                 150                 155                 160
```

```
Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
        195                 200                 205

Thr Tyr Asn Gln Gly Leu Arg Arg Leu Glu Gly Arg Phe Leu Ser Asp
    210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
            260                 265                 270

Ile Asn Glu Asn Leu Ser Pro Ala Ala Val Tyr Pro Thr Phe Ser Ala
        275                 280                 285

Ala Glu Ser Ala Ile Ile Arg Ser Pro His Leu Val Asp Phe Leu Asn
    290                 295                 300

Ser Phe Thr Ile Tyr Thr Asp Ser Leu Ala Arg Ser Ala Tyr Trp Gly
305                 310                 315                 320

Gly His Leu Val Asn Ser Phe Arg Thr Gly Thr Thr Asn Leu Ile
                325                 330                 335

Arg Ser Pro Leu Tyr Gly Arg Glu Gly Asn Thr Glu Arg Pro Val Thr
            340                 345                 350

Ile Thr Ala Ser Pro Ser Val Pro Ile Phe Arg Thr Leu Ser Tyr Pro
        355                 360                 365

Thr Gly Leu Asp Asn Ser Asn Pro Val Ala Gly Ile Glu Gly Val Glu
    370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
                405                 410                 415

Ile Gly Tyr Ser His Arg Leu Cys His Ala Thr Phe Leu Glu Arg Ile
            420                 425                 430

Ser Gly Pro Arg Ile Ala Gly Thr Val Phe Ser Trp Thr His Arg Ser
        435                 440                 445

Ala Ser Pro Thr Asn Glu Val Ser Pro Ser Arg Ile Thr Gln Ile Pro
    450                 455                 460

Trp Val Lys Ala His Thr Leu Ala Ser Gly Ala Ser Val Ile Lys Gly
465                 470                 475                 480

Pro Gly Phe Thr Gly Gly Asp Ile Leu Thr Arg Asn Ser Met Gly Glu
                485                 490                 495

Leu Gly Thr Leu Arg Val Thr Phe Thr Gly Arg Leu Pro Gln Ser Tyr
            500                 505                 510

Tyr Ile Arg Phe Arg Tyr Ala Ser Val Ala Asn Arg Ser Gly Thr Phe
        515                 520                 525

Arg Tyr Ser Gln Pro Pro Ser Tyr Gly Ile Ser Phe Pro Lys Thr Met
    530                 535                 540

Asp Ala Gly Glu Pro Leu Thr Ser Arg Ser Phe Ala His Thr Thr Leu
545                 550                 555                 560

Phe Thr Pro Ile Thr Phe Ser Arg Ala Gln Glu Glu Phe Asp Leu Tyr
                565                 570                 575

Ile Gln Ser Gly Val Tyr Ile Asp Arg Ile Glu Phe Ile Pro Val Thr
```

```
                580             585             590
Ala Thr Phe Glu Ala Glu Tyr Asp Leu Glu Arg Ala Gln Lys Ala Val
            595                 600             605
Asn Glu Leu Phe Thr Ser Ser Asn Gln Ile Gly Leu Lys Thr Asp Val
    610                 615                 620
Thr Asp Tyr His Ile Asp Gln Val Ser Asn Leu Val Glu Cys Leu Ser
625                 630                 635                 640
Asp Glu Phe Cys Leu Asp Glu Lys Lys Glu Leu Ser Glu Lys Val Lys
                645                 650                 655
His Ala Lys Arg Leu Ser Asp Glu Arg Asn Leu Leu Gln Asp Pro Asn
            660                 665                 670
Phe Arg Gly Ile Asn Arg Gln Leu Asp Arg Gly Trp Arg Gly Ser Thr
        675                 680                 685
Asp Ile Thr Ile Gln Gly Gly Asp Asp Val Phe Lys Glu Asn Tyr Val
    690                 695                 700
Thr Leu Leu Gly Thr Phe Asp Glu Cys Tyr Pro Thr Tyr Leu Tyr Gln
705                 710                 715                 720
Lys Ile Asp Glu Ser Lys Leu Lys Ala Tyr Thr Arg Tyr Gln Leu Arg
                725                 730                 735
Gly Tyr Ile Glu Asp Ser Gln Asp Leu Glu Ile Tyr Leu Ile Arg Tyr
            740                 745                 750
Asn Ala Lys His Glu Thr Val Asn Val Pro Gly Thr Gly Ser Leu Trp
        755                 760                 765
Pro Leu Ser Ala Pro Ser Pro Ile Gly Lys Cys Ala His His Ser His
    770                 775                 780
His Phe Ser Leu Asp Ile Asp Val Gly Cys Thr Asp Leu Asn Glu Asp
785                 790                 795                 800
Leu Gly Val Trp Val Ile Phe Lys Ile Lys Thr Gln Asp Gly His Ala
                805                 810                 815
Arg Leu Gly Asn Leu Glu Phe Leu Glu Glu Lys Pro Leu Val Gly Glu
            820                 825                 830
Ala Leu Ala Arg Val Lys Arg Ala Glu Lys Lys Trp Arg Asp Lys Arg
        835                 840                 845
Glu Lys Leu Glu Trp Glu Thr Asn Ile Val Tyr Lys Glu Ala Lys Glu
    850                 855                 860
Ser Val Asp Ala Leu Phe Val Asn Ser Gln Tyr Asp Arg Leu Gln Ala
865                 870                 875                 880
Asp Thr Asn Ile Ala Met Ile His Ala Ala Asp Lys Arg Val His Ser
                885                 890                 895
Ile Arg Glu Ala Tyr Leu Pro Glu Leu Ser Val Ile Pro Gly Val Asn
            900                 905                 910
Ala Ala Ile Phe Glu Glu Leu Glu Gly Arg Ile Phe Thr Ala Phe Ser
        915                 920                 925
Leu Tyr Asp Ala Arg Asn Val Ile Lys Asn Gly Asp Phe Asn Asn Gly
    930                 935                 940
Leu Ser Cys Trp Asn Val Lys Gly His Val Asp Val Glu Glu Gln Asn
945                 950                 955                 960
Asn His Arg Ser Val Leu Val Val Pro Glu Trp Glu Ala Glu Val Ser
                965                 970                 975
Gln Glu Val Arg Val Cys Pro Gly Arg Gly Tyr Ile Leu Arg Val Thr
            980                 985                 990
Ala Tyr Lys Glu Gly Tyr Gly Glu Gly Cys Val Thr Ile His Glu Ile
        995                 1000                1005
```

```
Glu Asn  Asn Thr Asp Glu Leu  Lys Phe Ser Asn Cys  Val Glu Glu
    1010                 1015                 1020

Glu Val  Tyr Pro Asn Asn Thr  Val Thr Cys Asn Asp  Tyr Thr Ala
    1025                 1030                 1035

Thr Gln  Glu Glu Tyr Glu Gly  Thr Tyr Thr Ser Arg  Asn Arg Gly
    1040                 1045                 1050

Tyr Asp  Gly Ala Tyr Glu Ser  Asn Ser Ser Val Pro  Ala Asp Tyr
    1055                 1060                 1065

Ala Ser  Ala Tyr Glu Glu Lys  Ala Tyr Thr Asp Gly  Arg Arg Asp
    1070                 1075                 1080

Asn Pro  Cys Glu Ser Asn Arg  Gly Tyr Gly Asp Tyr  Thr Pro Leu
    1085                 1090                 1095

Pro Ala  Gly Tyr Val Thr Lys  Glu Leu Glu Tyr Phe  Pro Glu Thr
    1100                 1105                 1110

Asp Lys  Val Trp Ile Glu Ile  Gly Glu Thr Glu Gly  Thr Phe Ile
    1115                 1120                 1125

Val Asp  Ser Val Glu Leu Leu  Leu Met Glu Glu
    1130                 1135
```

<210> SEQ ID NO 27
<211> LENGTH: 3498
<212> TYPE: DNA
<213> ORGANISM: Artificial sequence
<220> FEATURE:
<223> OTHER INFORMATION: Synthetic DNA sequence designed for plant expression encoding Cry1Da1.

<400> SEQUENCE: 27

```
atggagatca acaaccagaa ccagtgcgtc ccgtacaact gcctgagcaa ccctaaggag     60
atcatcctgg gtgaggaacg cctggagacc ggcaacaccg tagccgacat tagcctgggc    120
ctcatcaact tcctctacag caacttcgtg cccggcggtg gcttcatcgt gggcctcctg    180
gagcttatct ggggcttcat cggcccgtcc cagtgggaca tcttcctcgc ccagatcgag    240
caactgatca gccagcggat cgaggagttc gctaggaacc aggccatctc ccgcctggag    300
ggactctcca acctctacaa ggtgtacgtg cgcgcgttca gcgactggga gaaggacccg    360
accaacccgg ccctccgcga ggaaatgcgt atccagttca acgatatgaa ctcggccctc    420
atcaccgcca tcccgctctt ccgcgtgcag aactacgagg tggccctcct gtccgtgtac    480
gttcaagccg ccaacctcca cctctccatc ctccgcgacg tgagcgtgtt cggcgagcgc    540
tggggctacg acaccgccac catcaacaac cgctactccg acctcacctc cctcatccac    600
gtttacacca accactgcgt ggacacgtac aaccagggcc tccgccgcct ggagggccgc    660
ttcctctccg actggatcgt gtacaaccgc ttccgccgcc agctcaccat ctccgtcctg    720
gacatcgtcg ccttctttcc caactacgac atccgcacct accctatcca gaccgccacc    780
cagctcaccc gcgaggtcta cctcgacctc ccgttcatca acgagaacct cagcccggcc    840
gccagctacc cgaccttctc cgccgctgag tccgccatca ttcgcagccc gcacctcgtg    900
gacttcctca actccttcac catctacacc gactccctcg cccgctacgc ctactggggc    960
ggtcacctcg tgaactcctt ccgcaccggc accactacca acctcatccg cagcccgctc   1020
tacggccgcg agggcaacac cgagcgcccg gtgaccatca ccgccagccc gagcgtgccc   1080
atcttccgca ccctcagcta catcaccggc ctggacaaca gcaaccctgt ggcgggcatc   1140
gagggcgtgg agttccagaa caccatctcc aggagcatct accgcaagag cggccctatc   1200
```

```
gacagcttca gcgagctgcc tcctcaggac gccagcgtga gccctgccat cggctacagc   1260
cacaggctgt gccacgccac cttcctggag cgcatcagcg ccctcgcat cgcgggcacc   1320
gtgttctcgt ggacccaccg cagcgcctct cctacgaacg aggtgtctcc tagtcgcatc   1380
acccagatcc cttgggtcaa ggcccacacc ctggctagtg cgctagtgt catcaagggc   1440
cctggcttca ccggtggtga catcctgacc aggaactcta tgggcgagct gggcactctg   1500
agggtcactt tcactggccg cctgcctcag tcttactaca tccgcttccg ctacgctagt   1560
gtcgctaacc gctctggtac tttccgctac tctcagcctc cgtcttacgg tatctctttc   1620
cctaagacta tggacgctgg tgagcctctg accagtagga gcttcgctca cactactctg   1680
ttcactccta tcactttctc tagggctcag gaggagttcg acctgtacat ccagtctggt   1740
gtgtacatcg acaggatcga gttcatcccc gtgaccgcca cgttcgaggc cgagtacgac   1800
cttgagcgcg cccagaaggt ggtgaacgcc ctcttcacta gcactaacca gctaggcctg   1860
aagactgacg tgaccgacta ccacatcgac caagtgagca acctagtggc ctgcctctcc   1920
gacgagttct gcctcgacga aagcgcgag ctgtccgaga aggtgaagca cgccaagcgc   1980
ctctccgacg agcgcaacct gctccaggac cccaacttca ggggcatcaa caggcagccc   2040
gaccgcggct ggcgcggctc caccgacatc accatccagg gcggtgacga cgtattcaag   2100
gagaactacg ttaccctccc cggcaccttc gacgagtgtt accccaccta cctctaccag   2160
aagatcgacg agtccaagct gaaggcctac acccgctacc agctccgcgg ctacatcgag   2220
gactcccagg acctggaaat ctacctcatc cgctacaacg ccaagcacga gatcgtgaac   2280
gtgcctggca ccggcagcct ctggcctctc agcgtggaga accagatcgg cccttgcggc   2340
gagcctaacc gctgcgcccc tcacctcgag tggaaccctg acctccactg ctcgtgcagg   2400
gacggcgaga agtgcgccca ccatagccac cacttctctc tggacatcga cgtgggctgc   2460
accgacctga cgaggacct gggcgtgtgg gttatcttca agatcaagac caggacggt   2520
cacgccaggc tgggtaacct ggagttcctt gaggaaaagc ctctgctggg tgaggccctg   2580
gccagggtca agagggctga agaaaatgg agggataaga gggagaccct gcagctggag   2640
accactatcg tctacaagga ggctaaggag tctgtcgatg ctctgttcgt caactctcag   2700
tacgatagac tgcaagctga taccaacatc gctatgatcc acgctgcgga taagcgggtc   2760
caccggatcc gggaggctta ccttccggag cttttctgtca tcccgggtgt caacgctgcg   2820
atcttcgagg aacttgagga acggatcttc actgcgttta gtctttacga tgcgcggaac   2880
atcatcaaga acggggactt caacaatggt ctgctgtgct ggaacgtcaa gggtcatgtc   2940
gaggtcgagg aacaaaacaa tcatcgtagt gtccttgtca ttcctgagtg ggaggcggag   3000
gtctctcaag aggtccgtgt ttgcccgggg cgtgggtaca ttcttcgtgt tactgcgtac   3060
aaggagggt acggggaggg gtgcgttact attcatgaga ttgagaacaa tactgatgag   3120
cttaagttca caattgtgt tgaggaggag gtttacccga acaatactgt tacgtgcatc   3180
aactacacgg caacgcaaga ggaatacgag gggacgtaca cctcgcgtaa tagagggtat   3240
gatgaggcgt acggaaacaa cccgtcggtt ccagcagatt atgcctcggt ttatgaggag   3300
aagtcgtaca cggatagacg acgcgagaat ccatgtgagt caaatcgagg atacggagat   3360
tacacaccat taccagcagg atacgttaca aaggagttgg aatacttccc ggaaacagat   3420
aaagtttgga ttgaaatcgg agaaacagaa ggaacattca tcgtcgactc agtagaattg   3480
ttgttgatgg aagaatga                                                3498
```

<210> SEQ ID NO 28
<211> LENGTH: 1165
<212> TYPE: PRT
<213> ORGANISM: Artificial sequence
<220> FEATURE:
<223> OTHER INFORMATION: Amino acid sequence of Cry1Da1 encoded by a
      synthetic DNA sequence.

<400> SEQUENCE: 28

```
Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

Thr Val Ala Asp Ile Ser Leu Gly Leu Ile Asn Phe Leu Tyr Ser Asn
        35                  40                  45

Phe Val Pro Gly Gly Gly Phe Ile Val Gly Leu Leu Glu Leu Ile Trp
    50                  55                  60

Gly Phe Ile Gly Pro Ser Gln Trp Asp Ile Phe Leu Ala Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Lys Val Tyr Val Arg Ala
            100                 105                 110

Phe Ser Asp Trp Glu Lys Asp Pro Thr Asn Pro Ala Leu Arg Glu Glu
        115                 120                 125

Met Arg Ile Gln Phe Asn Asp Met Asn Ser Ala Leu Ile Thr Ala Ile
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
        195                 200                 205

Thr Tyr Asn Gln Gly Leu Arg Arg Leu Glu Gly Arg Phe Leu Ser Asp
    210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
            260                 265                 270

Ile Asn Glu Asn Leu Ser Pro Ala Ala Ser Tyr Pro Thr Phe Ser Ala
        275                 280                 285

Ala Glu Ser Ala Ile Ile Arg Ser Pro His Leu Val Asp Phe Leu Asn
    290                 295                 300

Ser Phe Thr Ile Tyr Thr Asp Ser Leu Ala Arg Tyr Ala Tyr Trp Gly
305                 310                 315                 320

Gly His Leu Val Asn Ser Phe Arg Thr Gly Thr Thr Thr Asn Leu Ile
                325                 330                 335

Arg Ser Pro Leu Tyr Gly Arg Glu Gly Asn Thr Glu Arg Pro Val Thr
            340                 345                 350

Ile Thr Ala Ser Pro Ser Val Pro Ile Phe Arg Thr Leu Ser Tyr Ile
        355                 360                 365
```

```
Thr Gly Leu Asp Asn Ser Asn Pro Val Ala Gly Ile Glu Gly Val Glu
    370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
                405                 410                 415

Ile Gly Tyr Ser His Arg Leu Cys His Ala Thr Phe Leu Glu Arg Ile
                420                 425                 430

Ser Gly Pro Arg Ile Ala Gly Thr Val Phe Ser Trp Thr His Arg Ser
            435                 440                 445

Ala Ser Pro Thr Asn Glu Val Ser Pro Ser Arg Ile Thr Gln Ile Pro
450                 455                 460

Trp Val Lys Ala His Thr Leu Ala Ser Gly Ala Ser Val Ile Lys Gly
465                 470                 475                 480

Pro Gly Phe Thr Gly Gly Asp Ile Leu Thr Arg Asn Ser Met Gly Glu
                485                 490                 495

Leu Gly Thr Leu Arg Val Thr Phe Thr Gly Arg Leu Pro Gln Ser Tyr
            500                 505                 510

Tyr Ile Arg Phe Arg Tyr Ala Ser Val Ala Asn Arg Ser Gly Thr Phe
        515                 520                 525

Arg Tyr Ser Gln Pro Pro Ser Tyr Gly Ile Ser Phe Pro Lys Thr Met
    530                 535                 540

Asp Ala Gly Glu Pro Leu Thr Ser Arg Ser Phe Ala His Thr Thr Leu
545                 550                 555                 560

Phe Thr Pro Ile Thr Phe Ser Arg Ala Gln Glu Glu Phe Asp Leu Tyr
                565                 570                 575

Ile Gln Ser Gly Val Tyr Ile Asp Arg Ile Glu Phe Ile Pro Val Thr
            580                 585                 590

Ala Thr Phe Glu Ala Glu Tyr Asp Leu Glu Arg Ala Gln Lys Val Val
        595                 600                 605

Asn Ala Leu Phe Thr Ser Thr Asn Gln Leu Gly Leu Lys Thr Asp Val
    610                 615                 620

Thr Asp Tyr His Ile Asp Gln Val Ser Asn Leu Val Ala Cys Leu Ser
625                 630                 635                 640

Asp Glu Phe Cys Leu Asp Glu Lys Arg Glu Leu Ser Glu Lys Val Lys
                645                 650                 655

His Ala Lys Arg Leu Ser Asp Glu Arg Asn Leu Leu Gln Asp Pro Asn
            660                 665                 670

Phe Arg Gly Ile Asn Arg Gln Pro Asp Arg Gly Trp Arg Gly Ser Thr
        675                 680                 685

Asp Ile Thr Ile Gln Gly Gly Asp Asp Val Phe Lys Glu Asn Tyr Val
    690                 695                 700

Thr Leu Pro Gly Thr Phe Asp Glu Cys Tyr Pro Thr Tyr Leu Tyr Gln
705                 710                 715                 720

Lys Ile Asp Glu Ser Lys Leu Lys Ala Tyr Thr Arg Tyr Gln Leu Arg
                725                 730                 735

Gly Tyr Ile Glu Asp Ser Gln Asp Leu Glu Ile Tyr Leu Ile Arg Tyr
            740                 745                 750

Asn Ala Lys His Glu Ile Val Asn Val Pro Gly Thr Gly Ser Leu Trp
        755                 760                 765

Pro Leu Ser Val Glu Asn Gln Ile Gly Pro Cys Gly Glu Pro Asn Arg
    770                 775                 780

Cys Ala Pro His Leu Glu Trp Asn Pro Asp Leu His Cys Ser Cys Arg
```

-continued

```
            785                 790                 795                 800
Asp Gly Glu Lys Cys Ala His His Ser His His Phe Ser Leu Asp Ile
                805                 810                 815

Asp Val Gly Cys Thr Asp Leu Asn Glu Asp Leu Gly Val Trp Val Ile
                820                 825                 830

Phe Lys Ile Lys Thr Gln Asp Gly His Ala Arg Leu Gly Asn Leu Glu
                835                 840                 845

Phe Leu Glu Glu Lys Pro Leu Leu Gly Glu Ala Leu Ala Arg Val Lys
850                 855                 860

Arg Ala Glu Lys Lys Trp Arg Asp Lys Arg Glu Thr Leu Gln Leu Glu
865                 870                 875                 880

Thr Thr Ile Val Tyr Lys Glu Ala Lys Glu Ser Val Asp Ala Leu Phe
                885                 890                 895

Val Asn Ser Gln Tyr Asp Arg Leu Gln Ala Asp Thr Asn Ile Ala Met
                900                 905                 910

Ile His Ala Ala Asp Lys Arg Val His Arg Ile Arg Glu Ala Tyr Leu
                915                 920                 925

Pro Glu Leu Ser Val Ile Pro Gly Val Asn Ala Ala Ile Phe Glu Glu
                930                 935                 940

Leu Glu Glu Arg Ile Phe Thr Ala Phe Ser Leu Tyr Asp Ala Arg Asn
945                 950                 955                 960

Ile Ile Lys Asn Gly Asp Phe Asn Asn Gly Leu Leu Cys Trp Asn Val
                965                 970                 975

Lys Gly His Val Glu Val Glu Glu Gln Asn Asn His Arg Ser Val Leu
                980                 985                 990

Val Ile Pro Glu Trp Glu Ala Glu  Val Ser Gln Glu Val  Arg Val Cys
                995                 1000                1005

Pro Gly Arg Gly Tyr Ile Leu  Arg Val Thr Ala Tyr  Lys Glu Gly
        1010                1015                1020

Tyr Gly Glu Gly Cys Val Thr  Ile His Glu Ile Glu  Asn Asn Thr
        1025                1030                1035

Asp Glu Leu Lys Phe Asn Asn  Cys Val Glu Glu Glu  Val Tyr Pro
        1040                1045                1050

Asn Asn Thr Val Thr Cys Ile  Asn Tyr Thr Ala Thr  Gln Glu Glu
        1055                1060                1065

Tyr Glu Gly Thr Tyr Thr Ser  Arg Asn Arg Gly Tyr  Asp Glu Ala
        1070                1075                1080

Tyr Gly Asn Asn Pro Ser Val  Pro Ala Asp Tyr Ala  Ser Val Tyr
        1085                1090                1095

Glu Glu Lys Ser Tyr Thr Asp  Arg Arg Arg Glu Asn  Pro Cys Glu
        1100                1105                1110

Ser Asn Arg Gly Tyr Gly Asp  Tyr Thr Pro Leu Pro  Ala Gly Tyr
        1115                1120                1125

Val Thr Lys Glu Leu Glu Tyr  Phe Pro Glu Thr Asp  Lys Val Trp
        1130                1135                1140

Ile Glu Ile Gly Glu Thr Glu  Gly Thr Phe Ile Val  Asp Ser Val
        1145                1150                1155

Glu Leu Leu Leu Met Glu Glu
        1160                1165

<210> SEQ ID NO 29
<211> LENGTH: 3501
<212> TYPE: DNA
<213> ORGANISM: Artificial sequence
```

<220> FEATURE:
<223> OTHER INFORMATION: Synthetic DNA sequence designed for plant
expression encoding Cry1Da1 with an additional Alanine residue
      inserted at position 2.

<400> SEQUENCE: 29

```
atggctgaga tcaacaacca gaaccagtgc gtcccgtaca actgcctgag caaccctaag      60
gagatcatcc tgggtgagga acgcctggag accggcaaca ccgtagccga cattagcctg     120
ggcctcatca acttcctcta cagcaacttc gtgcccggcg gtggcttcat cgtgggcctc     180
ctggagctta tctggggctt catcggcccg tcccagtggg acatcttcct cgcccagatc     240
gagcaactga tcagccagcg gatcgaggag ttcgctagga accaggccat ctcccgcctg     300
gagggactct ccaacctcta caaggtgtac gtgcgcgcgt tcagcgactg ggagaaggac     360
ccgaccaacc cggccctccg cgaggaaatg cgtatccagt tcaacgatat gaactcggcc     420
ctcatcaccg ccatcccgct cttccgcgtg cagaactacg aggtggccct cctgtccgtg     480
tacgttcaag ccgccaacct ccacctctcc atcctccgcg acgtgagcgt gttcggcgag     540
cgctggggct acgacaccgc caccatcaac aaccgctact ccgacctcac ctccctcatc     600
cacgtttaca ccaaccactg cgtggacacg tacaaccagg gcctccgccg cctggagggc     660
cgcttcctct ccgactggat cgtgtacaac cgcttccgcc gccagctcac catctccgtc     720
ctggacatcg tcgccttctt tcccaactac gacatccgca cctaccctat ccagaccgcc     780
acccagctca cccgcgaggt ctacctcgac ctcccgttca tcaacgagaa cctcagcccg     840
gccgccagct acccgacctt ctccgccgct gagtccgcca tcattcgcag cccgcacctc     900
gtggacttcc tcaactcctt caccatctac accgactccc tcgcccgcta cgcctactgg     960
ggcggtcacc tcgtgaactc cttccgcacc ggcaccacta ccaacctcat ccgcagcccg    1020
ctctacggcc gcgagggcaa caccgagcgc ccggtgacca tcaccgccag cccgagcgtg    1080
cccatcttcc gcaccctcag ctacatcacc ggcctggaca acagcaaccc tgtggcgggc    1140
atcgagggcg tggagttcca gaacaccatc tccaggagca tctaccgcaa gagcggccct    1200
atcgacagct tcagcgagct gcctcctcag gacgccagcg tgagccctgc catcggctac    1260
agccacaggc tgtgccacgc caccttcctg gagcgcatca gcggccctcg catcgcgggc    1320
accgtgttct cgtggaccca ccgcagcgcc tctcctacga acgaggtgtc tcctagtcgc    1380
atcacccaga tcccttgggt caaggcccac accctggcta gtggcgctag tgtcatcaag    1440
ggccctggct tcaccggtgg tgacatcctg accaggaact ctatgggcga gctgggcact    1500
ctgagggtca ctttcactgg ccgcctgcct cagtcttact acatccgctt ccgctacgct    1560
agtgtcgcta accgctctgg tactttccgc tactctcagc ctccgtctta cggtatctct    1620
ttccctaaga ctatggacgc tggtgagcct ctgaccagta ggagcttcgc tcacactact    1680
ctgttcactc ctatcacttt ctctagggct caggaggagt tcgacctgta catccagtct    1740
ggtgtgtaca tcgacaggat cgagttcatc cccgtgaccg ccacgttcga ggccgagtac    1800
gaccttgagc gcgcccagaa ggtggtgaac gccctcttca ctagcactaa ccagctaggc    1860
ctgaagactg acgtgaccga ctaccacatc gaccaagtga gcaacctagt ggcctgcctc    1920
tccgacgagt tctgcctcga cgagaagcgc gagctgtccg agaaggtgaa gcacgccaag    1980
cgcctctccg acgagcgcaa cctgctccag gaccccaact tcaggggcat caacaggcag    2040
cccgaccgcg gctggcgcgg ctccaccgac atcaccatcc agggcggtga cgacgtattc    2100
aaggagaact acgttaccct ccccggcacc ttcgacgagt gttaccccac ctacctctac    2160
```

-continued

```
cagaagatcg acgagtccaa gctgaaggcc tacacccgct accagctccg cggctacatc   2220
gaggactccc aggacctgga aatctacctc atccgctaca acgccaagca cgagatcgtg   2280
aacgtgcctg gcaccggcag cctctggcct ctcagcgtgg agaaccagat cggcccttgc   2340
ggcgagccta accgctgcgc ccctcacctc gagtggaacc ctgacctcca ctgctcgtgc   2400
agggacggcg agaagtgcgc ccaccatagc caccacttct ctctggacat cgacgtgggc   2460
tgcaccgacc tgaacgagga cctgggcgtg tgggttatct tcaagatcaa gacccaggac   2520
ggtcacgcca ggctgggtaa cctggagttc cttgaggaaa agcctctgct gggtgaggcc   2580
ctggccaggg tcaagagggc tgagaagaaa tggagggata agagggagac cctgcagctg   2640
gagaccacta tcgtctacaa ggaggctaag gagtctgtcg atgctctgtt cgtcaactct   2700
cagtacgata gactgcaagc tgataccaac atcgctatga tccacgctgc ggataagcgg   2760
gtccaccgga tccgggaggc ttaccttccg gagctttctg tcatcccggg tgtcaacgct   2820
gcgatcttcg aggaacttga ggaacggatc ttcactgcgt ttagtcttta cgatgcgcgg   2880
aacatcatca agaacgggga cttcaacaat ggtctgctgt gctggaacgt caagggtcat   2940
gtcgaggtcg aggaacaaaa caatcatcgt agtgtccttg tcattcctga gtgggaggcg   3000
gaggtctctc aagaggtccg tgtttgcccg gggcgtgggt acattcttcg tgttactgcg   3060
tacaaggagg ggtacgggga ggggtgcgtt actattcatg agattgagaa caatactgat   3120
gagcttaagt tcaacaattg tgttgaggag gaggtttacc cgaacaatac tgttacgtgc   3180
atcaactaca cggcaacgca agaggaatac gaggggacgt acacctcgcg taatagaggg   3240
tatgatgagg cgtacggaaa caacccgtcg gttccagcag attatgcctc ggtttatgag   3300
gagaagtcgt acacggatag acgacgcgag aatccatgtg agtcaaatcg aggatacgga   3360
gattacacac cattaccagc aggatacgtt acaaaggagt tggaatactt cccggaaaca   3420
gataaagttt ggattgaaat cggagaaaca gaaggaacat tcatcgtcga ctcagtagaa   3480
ttgttgttga tggaagaatg a                                             3501
```

```

<210> SEQ ID NO 30
<211> LENGTH: 1166
<212> TYPE: PRT
<213> ORGANISM: Artificial sequence
<220> FEATURE:
<223> OTHER INFORMATION: Amino acid sequence of Cry1Da1 encoded by a
      synthetic DNA sequence wherein an additional Alanine residue has
      been inserted at position 2.

<400> SEQUENCE: 30

Met Ala Glu Ile Asn Asn Gln Asn Gln Cys Val Pro Tyr Asn Cys Leu
1               5                   10                  15

Ser Asn Pro Lys Glu Ile Ile Leu Gly Glu Glu Arg Leu Glu Thr Gly
            20                  25                  30

Asn Thr Val Ala Asp Ile Ser Leu Gly Leu Ile Asn Phe Leu Tyr Ser
        35                  40                  45

Asn Phe Val Pro Gly Gly Gly Phe Ile Val Gly Leu Leu Glu Leu Ile
    50                  55                  60

Trp Gly Phe Ile Gly Pro Ser Gln Trp Asp Ile Phe Leu Ala Gln Ile
65                  70                  75                  80

Glu Gln Leu Ile Ser Gln Arg Ile Glu Glu Phe Ala Arg Asn Gln Ala
                85                  90                  95

Ile Ser Arg Leu Glu Gly Leu Ser Asn Leu Tyr Lys Val Tyr Val Arg
            100                 105                 110
```

```
Ala Phe Ser Asp Trp Glu Lys Asp Pro Thr Asn Pro Ala Leu Arg Glu
        115                 120                 125

Glu Met Arg Ile Gln Phe Asn Asp Met Asn Ser Ala Leu Ile Thr Ala
    130                 135                 140

Ile Pro Leu Phe Arg Val Gln Asn Tyr Glu Val Ala Leu Leu Ser Val
145                 150                 155                 160

Tyr Val Gln Ala Ala Asn Leu His Leu Ser Ile Leu Arg Asp Val Ser
                165                 170                 175

Val Phe Gly Glu Arg Trp Gly Tyr Asp Thr Ala Thr Ile Asn Asn Arg
            180                 185                 190

Tyr Ser Asp Leu Thr Ser Leu Ile His Val Tyr Thr Asn His Cys Val
        195                 200                 205

Asp Thr Tyr Asn Gln Gly Leu Arg Arg Leu Glu Gly Arg Phe Leu Ser
    210                 215                 220

Asp Trp Ile Val Tyr Asn Arg Phe Arg Arg Gln Leu Thr Ile Ser Val
225                 230                 235                 240

Leu Asp Ile Val Ala Phe Phe Pro Asn Tyr Asp Ile Arg Thr Tyr Pro
                245                 250                 255

Ile Gln Thr Ala Thr Gln Leu Thr Arg Glu Val Tyr Leu Asp Leu Pro
            260                 265                 270

Phe Ile Asn Glu Asn Leu Ser Pro Ala Ala Ser Tyr Pro Thr Phe Ser
        275                 280                 285

Ala Ala Glu Ser Ala Ile Ile Arg Ser Pro His Leu Val Asp Phe Leu
    290                 295                 300

Asn Ser Phe Thr Ile Tyr Thr Asp Ser Leu Ala Arg Tyr Ala Tyr Trp
305                 310                 315                 320

Gly Gly His Leu Val Asn Ser Phe Arg Thr Gly Thr Thr Asn Leu
                325                 330                 335

Ile Arg Ser Pro Leu Tyr Gly Arg Glu Gly Asn Thr Glu Arg Pro Val
            340                 345                 350

Thr Ile Thr Ala Ser Pro Ser Val Pro Ile Phe Arg Thr Leu Ser Tyr
        355                 360                 365

Ile Thr Gly Leu Asp Asn Ser Asn Pro Val Ala Gly Ile Glu Gly Val
370                 375                 380

Glu Phe Gln Asn Thr Ile Ser Arg Ser Ile Tyr Arg Lys Ser Gly Pro
385                 390                 395                 400

Ile Asp Ser Phe Ser Glu Leu Pro Pro Gln Asp Ala Ser Val Ser Pro
                405                 410                 415

Ala Ile Gly Tyr Ser His Arg Leu Cys His Ala Thr Phe Leu Glu Arg
            420                 425                 430

Ile Ser Gly Pro Arg Ile Ala Gly Thr Val Phe Ser Trp Thr His Arg
        435                 440                 445

Ser Ala Ser Pro Thr Asn Glu Val Ser Pro Ser Arg Ile Thr Gln Ile
    450                 455                 460

Pro Trp Val Lys Ala His Thr Leu Ala Ser Gly Ala Ser Val Ile Lys
465                 470                 475                 480

Gly Pro Gly Phe Thr Gly Gly Asp Ile Leu Thr Arg Asn Ser Met Gly
                485                 490                 495

Glu Leu Gly Thr Leu Arg Val Thr Phe Thr Gly Arg Leu Pro Gln Ser
            500                 505                 510

Tyr Tyr Ile Arg Phe Arg Tyr Ala Ser Val Ala Asn Arg Ser Gly Thr
        515                 520                 525

Phe Arg Tyr Ser Gln Pro Pro Ser Tyr Gly Ile Ser Phe Pro Lys Thr
```

```
                530             535             540
Met Asp Ala Gly Glu Pro Leu Thr Ser Arg Ser Phe Ala His Thr Thr
545                 550             555             560

Leu Phe Thr Pro Ile Thr Phe Ser Arg Ala Gln Glu Phe Asp Leu
                565             570             575

Tyr Ile Gln Ser Gly Val Tyr Ile Asp Arg Ile Glu Phe Ile Pro Val
                580             585             590

Thr Ala Thr Phe Glu Ala Glu Tyr Asp Leu Glu Arg Ala Gln Lys Val
            595             600             605

Val Asn Ala Leu Phe Thr Ser Thr Asn Gln Leu Gly Leu Lys Thr Asp
610             615             620

Val Thr Asp Tyr His Ile Asp Gln Val Ser Asn Leu Val Ala Cys Leu
625             630             635             640

Ser Asp Glu Phe Cys Leu Asp Glu Lys Arg Glu Leu Ser Glu Lys Val
                645             650             655

Lys His Ala Lys Arg Leu Ser Asp Glu Arg Asn Leu Leu Gln Asp Pro
                660             665             670

Asn Phe Arg Gly Ile Asn Arg Gln Pro Asp Arg Gly Trp Arg Gly Ser
            675             680             685

Thr Asp Ile Thr Ile Gln Gly Gly Asp Asp Val Phe Lys Glu Asn Tyr
690             695             700

Val Thr Leu Pro Gly Thr Phe Asp Glu Cys Tyr Pro Thr Tyr Leu Tyr
705             710             715             720

Gln Lys Ile Asp Glu Ser Lys Leu Lys Ala Tyr Thr Arg Tyr Gln Leu
                725             730             735

Arg Gly Tyr Ile Glu Asp Ser Gln Asp Leu Glu Ile Tyr Leu Ile Arg
            740             745             750

Tyr Asn Ala Lys His Glu Ile Val Asn Val Pro Gly Thr Gly Ser Leu
            755             760             765

Trp Pro Leu Ser Val Glu Asn Gln Ile Gly Pro Cys Gly Glu Pro Asn
770             775             780

Arg Cys Ala Pro His Leu Glu Trp Asn Pro Asp Leu His Cys Ser Cys
785             790             795             800

Arg Asp Gly Glu Lys Cys Ala His His Ser His His Phe Ser Leu Asp
                805             810             815

Ile Asp Val Gly Cys Thr Asp Leu Asn Glu Asp Leu Gly Val Trp Val
            820             825             830

Ile Phe Lys Ile Lys Thr Gln Asp Gly His Ala Arg Leu Gly Asn Leu
            835             840             845

Glu Phe Leu Glu Glu Lys Pro Leu Leu Gly Glu Ala Leu Ala Arg Val
850             855             860

Lys Arg Ala Glu Lys Lys Trp Arg Asp Lys Arg Glu Thr Leu Gln Leu
865             870             875             880

Glu Thr Thr Ile Val Tyr Lys Glu Ala Lys Glu Ser Val Asp Ala Leu
                885             890             895

Phe Val Asn Ser Gln Tyr Asp Arg Leu Gln Ala Asp Thr Asn Ile Ala
                900             905             910

Met Ile His Ala Ala Asp Lys Arg Val His Arg Ile Arg Glu Ala Tyr
            915             920             925

Leu Pro Glu Leu Ser Val Ile Pro Gly Val Asn Ala Ala Ile Phe Glu
            930             935             940

Glu Leu Glu Glu Arg Ile Phe Thr Ala Phe Ser Leu Tyr Asp Ala Arg
945             950             955             960
```

```
Asn Ile Ile Lys Asn Gly Asp Phe Asn Asn Gly Leu Leu Cys Trp Asn
                965                 970                 975

Val Lys Gly His Val Glu Val Glu Glu Gln Asn Asn His Arg Ser Val
            980                 985                 990

Leu Val Ile Pro Glu Trp Glu Ala  Glu Val Ser Gln Glu  Val Arg Val
        995                 1000                 1005

Cys Pro  Gly Arg Gly Tyr Ile  Leu Arg Val Thr Ala  Tyr Lys Glu
    1010                 1015                 1020

Gly Tyr  Gly Glu Gly Cys Val  Thr Ile His Glu Ile  Glu Asn Asn
    1025                 1030                 1035

Thr Asp  Glu Leu Lys Phe Asn  Asn Cys Val Glu Glu  Glu Val Tyr
    1040                 1045                 1050

Pro Asn  Asn Thr Val Thr Cys  Ile Asn Tyr Thr Ala  Thr Gln Glu
    1055                 1060                 1065

Glu Tyr  Glu Gly Thr Tyr Thr  Ser Arg Asn Arg Gly  Tyr Asp Glu
    1070                 1075                 1080

Ala Tyr  Gly Asn Asn Pro Ser  Val Pro Ala Asp Tyr  Ala Ser Val
    1085                 1090                 1095

Tyr Glu  Glu Lys Ser Tyr Thr  Asp Arg Arg Arg Glu  Asn Pro Cys
    1100                 1105                 1110

Glu Ser  Asn Arg Gly Tyr Gly  Asp Tyr Thr Pro Leu  Pro Ala Gly
    1115                 1120                 1125

Tyr Val  Thr Lys Glu Leu Glu  Tyr Phe Pro Glu Thr  Asp Lys Val
    1130                 1135                 1140

Trp Ile  Glu Ile Gly Glu Thr  Glu Gly Thr Phe Ile  Val Asp Ser
    1145                 1150                 1155

Val Glu  Leu Leu Leu Met Glu  Glu
    1160                 1165
```

```
<210> SEQ ID NO 31
<211> LENGTH: 3501
<212> TYPE: DNA
<213> ORGANISM: Artificial sequence
<220> FEATURE:
<223> OTHER INFORMATION: Synthetic DNA sequence designed for plant
      expression encoding Cry1Da1_3 with an additional Alanine residue
      inserted at position 2.

<400> SEQUENCE: 31
atggctgaga tcaacaacca gaaccagtgc gtcccgtaca actgcctgag caaccctaag     60
gagatcatcc tgggtgagga acgcctggag accggcaaca ccgtagccga cattagcctg    120
ggcctcatca acttcctcta cagcaacttc gtgcccggcg gtggcttcat cgtgggcctc    180
ctggagctta tctggggctt catcggcccg tcccagtggg acatcttcct cgcccagatc    240
gagcaactga tcagccagcg gatcgaggag ttcgctagga accaggccat ctcccgcctg    300
gagggactct ccaacctcta caaggtgtac gtgcgcgcgt tcagcgactg ggagaaggac    360
ccgaccaacc cggccctccg cgaggaaatg cgtatccagt tcaacgatat gaactcggcc    420
ctcatcaccg ccatcccgct cttccgcgtg cagaactacg aggtggccct cctgtccgtg    480
tacgttcaag ccgccaacct ccacctctcc atcctccgcg acgtgagcgt gttcggcgag    540
cgctggggct acgacaccgc caccatcaac aaccgctact ccgacctcac ctccctcatc    600
cacgtttaca ccaaccactg cgtggacacg tacaaccagg gcctccgccg cctggagggc    660
cgcttcctct ccgactggat cgtgtacaac cgcttccgcc gccagctcac catctccgtc    720
```

|  |  |  |  |  |
|---|---|---|---|---|
| ctggacatcg | tcgccttctt | tcccaactac | gacatccgca | cctaccctat ccagaccgcc | 780 |
| acccagctca | cccgcgaggt | ctacctcgac | ctcccgttca | tcaacgagaa cctcagcccg | 840 |
| gccgccagct | acccgacctt | ctccgccgct | gagtccgcca | tcattcgcag cccgcacctc | 900 |
| gtggacttcc | tcaactcctt | caccatctac | accgactccc | tcgcccgcag cgcctactgg | 960 |
| ggcggtcacc | tcgtgaactc | cttccgcacc | ggcaccacta | ccaacctcat ccgcagcccg | 1020 |
| ctctacggcc | gcgagggcaa | caccgagcgc | ccggtgacca | tcaccgccag cccgagcgtg | 1080 |
| cccatcttcc | gcaccctcag | ctacatcacc | ggcctggaca | acagcaaccc tgtggcgggc | 1140 |
| atcgagggcg | tggagttcca | gaacaccatc | tccaggagca | tctaccgcaa gagcggccct | 1200 |
| atcgacagct | tcagcgagct | gcctcctcag | gacgccagcg | tgagccctgc catcggctac | 1260 |
| agccacaggc | tgtgccacgc | caccttcctg | gagcgcatca | gcggccctcg catcgcgggc | 1320 |
| accgtgttct | cgtggaccca | ccgcagcgcc | tctcctacga | acgaggtgtc tcctagtcgc | 1380 |
| atcacccaga | tcccttgggt | caaggcccac | accctggcta | gtggcgctag tgtcatcaag | 1440 |
| ggccctggct | tcaccggtgg | tgacatcctg | accaggaact | ctatgggcga gctgggcact | 1500 |
| ctgagggtca | ctttcactgg | ccgcctgcct | cagtcttact | acatccgctt ccgctacgct | 1560 |
| agtgtcgcta | accgctctgg | tactttccgc | tactctcagc | ctccgtctta cggtatctct | 1620 |
| ttccctaaga | ctatgacgc | tggtgagcct | ctgaccagta | ggagcttcgc tcacactact | 1680 |
| ctgttcactc | ctatcacttt | tctagggct | caggaggagt | tcgacctgta catccagtct | 1740 |
| ggtgtgtaca | tcgacaggat | cgagttcatc | cccgtgaccg | ccacgttcga ggccgagtac | 1800 |
| gaccttgagc | gcgcccagaa | ggtggtgaac | gccctcttca | ctagcactaa ccagctaggc | 1860 |
| ctgaagactg | acgtgaccga | ctaccacatc | gaccaagtga | gcaacctagt ggcctgcctc | 1920 |
| tccgacgagt | tctgcctcga | cgagaagcgc | gagctgtccg | agaaggtgaa gcacgccaag | 1980 |
| cgcctctccg | acgagcgcaa | cctgctccag | gaccccaact | tcaggggcat caacaggcag | 2040 |
| cccgaccgcg | gctggcgcgg | ctccaccgac | atcaccatcc | agggcggtga cgacgtattc | 2100 |
| aaggagaact | acgttaccct | ccccggcacc | ttcgacgagt | gttaccccac ctacctctac | 2160 |
| cagaagatcg | acgagtccaa | gctgaaggcc | tacacccgct | accagctccg cggctacatc | 2220 |
| gaggactccc | aggacctgga | aatctacctc | atccgctaca | acgccaagca cgagatcgtg | 2280 |
| aacgtgcctg | gcaccggcag | cctctggcct | ctcagcgtgg | agaaccagat cggcccttgc | 2340 |
| ggcgagccta | accgctgcgc | ccctcacctc | gagtggaacc | ctgacctcca ctgctcgtgc | 2400 |
| agggacggcg | agaagtgcgc | ccaccatagc | caccacttct | ctctggacat cgacgtgggc | 2460 |
| tgcaccgacc | tgaacgagga | cctgggcgtg | tgggttatct | tcaagatcaa gacccaggac | 2520 |
| ggtcacgcca | gctgggtaa | cctggagttc | cttgaggaaa | agcctctgct gggtgaggcc | 2580 |
| ctggccaggg | tcaagagggc | tgagaagaaa | tggagggata | agaggagac cctgcagctg | 2640 |
| gagaccacta | tcgtctacaa | ggaggctaag | gagtctgtcg | atgctctgtt cgtcaactct | 2700 |
| cagtacgata | gactgcaagc | tgataccaac | atcgctatga | tccacgctgc ggataagcgg | 2760 |
| gtccaccgga | tccggaggc | ttaccttccg | gagctttctg | tcatcccggg tgtcaacgct | 2820 |
| gcgatcttcg | aggaacttga | ggaacggatc | ttcactgcgt | ttagtctta cgatgcgcgg | 2880 |
| aacatcatca | gaacgggga | cttcaacaat | ggtctgctgt | gctggaacgt caagggtcat | 2940 |
| gtcgaggtcg | aggaacaaaa | caatcatcgt | agtgtccttg | tcattcctga gtgggaggcg | 3000 |
| gaggtctctc | aagaggtccg | tgtttgcccg | gggcgtgggg | acattcttcg tgttactgcg | 3060 |
| tacaaggagg | ggtacgggga | ggggtgcgtt | actattcatg | agattgagaa caatactgat | 3120 |

```
gagcttaagt tcaacaattg tgttgaggag gaggtttacc cgaacaatac tgttacgtgc    3180
atcaactaca cggcaacgca agaggaatac gaggggacgt acacctcgcg taatagaggg    3240
tatgatgagg cgtacggaaa caacccgtcg gttccagcag attatgcctc ggtttatgag    3300
gagaagtcgt acacggatag acgacgcgag aatccatgtg agtcaaatcg aggatacgga    3360
gattacacac cattaccagc aggatacgtt acaaaggagt tggaatactt cccggaaaca    3420
gataaagttt ggattgaaat cggagaaaca gaaggaacat tcatcgtcga ctcagtagaa    3480
ttgttgttga tggaagaatg a                                              3501
```

<210> SEQ ID NO 32  
<211> LENGTH: 1166  
<212> TYPE: PRT  
<213> ORGANISM: Artificial sequence  
<220> FEATURE:  
<223> OTHER INFORMATION: Amino acid sequence of the engineered insecticidal protein Cry1Da1_3 encoded by a synthetic DNA sequence wherein an additional Alanine residue has been inserted at position 2.

<400> SEQUENCE: 32

```
Met Ala Glu Ile Asn Asn Gln Asn Gln Cys Val Pro Tyr Asn Cys Leu
1               5                   10                  15

Ser Asn Pro Lys Glu Ile Ile Leu Gly Glu Glu Arg Leu Glu Thr Gly
            20                  25                  30

Asn Thr Val Ala Asp Ile Ser Leu Gly Leu Ile Asn Phe Leu Tyr Ser
        35                  40                  45

Asn Phe Val Pro Gly Gly Gly Phe Ile Val Gly Leu Leu Glu Leu Ile
    50                  55                  60

Trp Gly Phe Ile Gly Pro Ser Gln Trp Asp Ile Phe Leu Ala Gln Ile
65                  70                  75                  80

Glu Gln Leu Ile Ser Gln Arg Ile Glu Glu Phe Ala Arg Asn Gln Ala
                85                  90                  95

Ile Ser Arg Leu Glu Gly Leu Ser Asn Leu Tyr Lys Val Tyr Val Arg
            100                 105                 110

Ala Phe Ser Asp Trp Glu Lys Asp Pro Thr Asn Pro Ala Leu Arg Glu
        115                 120                 125

Glu Met Arg Ile Gln Phe Asn Asp Met Asn Ser Ala Leu Ile Thr Ala
    130                 135                 140

Ile Pro Leu Phe Arg Val Gln Asn Tyr Glu Val Ala Leu Leu Ser Val
145                 150                 155                 160

Tyr Val Gln Ala Ala Asn Leu His Leu Ser Ile Leu Arg Asp Val Ser
                165                 170                 175

Val Phe Gly Glu Arg Trp Gly Tyr Asp Thr Ala Thr Ile Asn Asn Arg
            180                 185                 190

Tyr Ser Asp Leu Thr Ser Leu Ile His Val Tyr Thr Asn His Cys Val
        195                 200                 205

Asp Thr Tyr Asn Gln Gly Leu Arg Arg Leu Glu Gly Arg Phe Leu Ser
    210                 215                 220

Asp Trp Ile Val Tyr Asn Arg Phe Arg Arg Gln Leu Thr Ile Ser Val
225                 230                 235                 240

Leu Asp Ile Val Ala Phe Phe Pro Asn Tyr Asp Ile Arg Thr Tyr Pro
                245                 250                 255

Ile Gln Thr Ala Thr Gln Leu Thr Arg Glu Val Tyr Leu Asp Leu Pro
            260                 265                 270
```

```
Phe Ile Asn Glu Asn Leu Ser Pro Ala Ala Ser Tyr Pro Thr Phe Ser
            275                 280                 285

Ala Ala Glu Ser Ala Ile Ile Arg Ser Pro His Leu Val Asp Phe Leu
290                 295                 300

Asn Ser Phe Thr Ile Tyr Thr Asp Ser Leu Ala Arg Ser Ala Tyr Trp
305                 310                 315                 320

Gly Gly His Leu Val Asn Ser Phe Arg Thr Gly Thr Thr Asn Leu
                325                 330                 335

Ile Arg Ser Pro Leu Tyr Gly Arg Gly Asn Thr Glu Arg Pro Val
                340                 345                 350

Thr Ile Thr Ala Ser Pro Ser Val Pro Ile Phe Arg Thr Leu Ser Tyr
            355                 360                 365

Ile Thr Gly Leu Asp Asn Ser Asn Pro Val Ala Gly Ile Glu Gly Val
370                 375                 380

Glu Phe Gln Asn Thr Ile Ser Arg Ser Ile Tyr Arg Lys Ser Gly Pro
385                 390                 395                 400

Ile Asp Ser Phe Ser Glu Leu Pro Pro Gln Asp Ala Ser Val Ser Pro
                405                 410                 415

Ala Ile Gly Tyr Ser His Arg Leu Cys His Ala Thr Phe Leu Glu Arg
                420                 425                 430

Ile Ser Gly Pro Arg Ile Ala Gly Thr Val Phe Ser Trp Thr His Arg
            435                 440                 445

Ser Ala Ser Pro Thr Asn Glu Val Ser Pro Ser Arg Ile Thr Gln Ile
            450                 455                 460

Pro Trp Val Lys Ala His Thr Leu Ala Ser Gly Ala Ser Val Ile Lys
465                 470                 475                 480

Gly Pro Gly Phe Thr Gly Gly Asp Ile Leu Thr Arg Asn Ser Met Gly
                485                 490                 495

Glu Leu Gly Thr Leu Arg Val Thr Phe Thr Gly Arg Leu Pro Gln Ser
                500                 505                 510

Tyr Tyr Ile Arg Phe Arg Tyr Ala Ser Val Ala Asn Arg Ser Gly Thr
            515                 520                 525

Phe Arg Tyr Ser Gln Pro Pro Ser Tyr Gly Ile Ser Phe Pro Lys Thr
530                 535                 540

Met Asp Ala Gly Glu Pro Leu Thr Ser Arg Ser Phe Ala His Thr Thr
545                 550                 555                 560

Leu Phe Thr Pro Ile Thr Phe Ser Arg Ala Gln Glu Glu Phe Asp Leu
                565                 570                 575

Tyr Ile Gln Ser Gly Val Tyr Ile Asp Arg Ile Glu Phe Ile Pro Val
                580                 585                 590

Thr Ala Thr Phe Glu Ala Glu Tyr Asp Leu Glu Arg Ala Gln Lys Val
            595                 600                 605

Val Asn Ala Leu Phe Thr Ser Thr Asn Gln Leu Gly Leu Lys Thr Asp
610                 615                 620

Val Thr Asp Tyr His Ile Asp Gln Val Ser Asn Leu Val Ala Cys Leu
625                 630                 635                 640

Ser Asp Glu Phe Cys Leu Asp Glu Lys Arg Glu Leu Ser Glu Lys Val
                645                 650                 655

Lys His Ala Lys Arg Leu Ser Asp Glu Arg Asn Leu Leu Gln Asp Pro
                660                 665                 670

Asn Phe Arg Gly Ile Asn Arg Gln Pro Asp Arg Gly Trp Arg Gly Ser
            675                 680                 685

Thr Asp Ile Thr Ile Gln Gly Gly Asp Asp Val Phe Lys Glu Asn Tyr
```

```
                690           695           700
Val Thr Leu Pro Gly Thr Phe Asp Glu Cys Tyr Pro Thr Tyr Leu Tyr
705           710           715           720

Gln Lys Ile Asp Glu Ser Lys Leu Lys Ala Tyr Thr Arg Tyr Gln Leu
            725           730           735

Arg Gly Tyr Ile Glu Asp Ser Gln Asp Leu Glu Ile Tyr Leu Ile Arg
            740           745           750

Tyr Asn Ala Lys His Glu Ile Val Asn Val Pro Gly Thr Gly Ser Leu
            755           760           765

Trp Pro Leu Ser Val Glu Asn Gln Ile Gly Pro Cys Gly Glu Pro Asn
770           775           780

Arg Cys Ala Pro His Leu Glu Trp Asn Pro Asp Leu His Cys Ser Cys
785           790           795           800

Arg Asp Gly Glu Lys Cys Ala His His Ser His His Phe Ser Leu Asp
            805           810           815

Ile Asp Val Gly Cys Thr Asp Leu Asn Glu Asp Leu Gly Val Trp Val
            820           825           830

Ile Phe Lys Ile Lys Thr Gln Asp Gly His Ala Arg Leu Gly Asn Leu
            835           840           845

Glu Phe Leu Glu Glu Lys Pro Leu Leu Gly Glu Ala Leu Ala Arg Val
850           855           860

Lys Arg Ala Glu Lys Lys Trp Arg Asp Lys Arg Glu Thr Leu Gln Leu
865           870           875           880

Glu Thr Thr Ile Val Tyr Lys Glu Ala Lys Glu Ser Val Asp Ala Leu
            885           890           895

Phe Val Asn Ser Gln Tyr Asp Arg Leu Gln Ala Asp Thr Asn Ile Ala
            900           905           910

Met Ile His Ala Ala Asp Lys Arg Val His Arg Ile Arg Glu Ala Tyr
            915           920           925

Leu Pro Glu Leu Ser Val Ile Pro Gly Val Asn Ala Ala Ile Phe Glu
            930           935           940

Glu Leu Glu Glu Arg Ile Phe Thr Ala Phe Ser Leu Tyr Asp Ala Arg
945           950           955           960

Asn Ile Ile Lys Asn Gly Asp Phe Asn Asn Gly Leu Leu Cys Trp Asn
            965           970           975

Val Lys Gly His Val Glu Val Glu Glu Gln Asn Asn His Arg Ser Val
            980           985           990

Leu Val Ile Pro Glu Trp Glu Ala  Glu Val Ser Gln Glu  Val Arg Val
            995           1000          1005

Cys Pro  Gly Arg Gly Tyr Ile  Leu Arg Val Thr Ala  Tyr Lys Glu
     1010          1015          1020

Gly Tyr  Gly Glu Gly Cys Val  Thr Ile His Glu Ile  Glu Asn Asn
     1025          1030          1035

Thr Asp  Glu Leu Lys Phe Asn  Asn Cys Val Glu Glu  Glu Val Tyr
     1040          1045          1050

Pro Asn  Asn Thr Val Thr Cys  Ile Asn Tyr Thr Ala  Thr Gln Glu
     1055          1060          1065

Glu Tyr  Glu Gly Thr Tyr Thr  Ser Arg Asn Arg Gly  Tyr Asp Glu
     1070          1075          1080

Ala Tyr  Gly Asn Asn Pro Ser  Val Pro Ala Asp Tyr  Ala Ser Val
     1085          1090          1095

Tyr Glu  Glu Lys Ser Tyr Thr  Asp Arg Arg Arg Glu  Asn Pro Cys
     1100          1105          1110
```

Glu Ser Asn Arg Gly Tyr Gly Asp Tyr Thr Pro Leu Pro Ala Gly
    1115                1120                1125

Tyr Val Thr Lys Glu Leu Glu Tyr Phe Pro Glu Thr Asp Lys Val
    1130                1135                1140

Trp Ile Glu Ile Gly Glu Thr Glu Gly Thr Phe Ile Val Asp Ser
    1145                1150                1155

Val Glu Leu Leu Leu Met Glu Glu
    1160                1165

<210> SEQ ID NO 33
<211> LENGTH: 3501
<212> TYPE: DNA
<213> ORGANISM: Artificial sequence
<220> FEATURE:
<223> OTHER INFORMATION: Synthetic DNA sequence designed for plant
      expression encoding Cry1Da1_4 with an additional Alanine residue
      inserted at position 2.

<400> SEQUENCE: 33

| | |
|---|---|
| atggctgaga tcaacaacca gaaccagtgc gtcccgtaca actgcctgag caaccctaag | 60 |
| gagatcatcc tgggtgagga acgcctggag accggcaaca ccgtagccga cattagcctg | 120 |
| ggcctcatca acttcctcta cagcaacttc gtgcccggcg gtggcttcat cgtgggcctc | 180 |
| ctggagctta tctggggctt catcggcccg tcccagtggg acatcttcct cgcccagatc | 240 |
| gagcaactga tcagccagcg gatcgaggag ttcgctagga accaggccat ctcccgcctg | 300 |
| gagggactct ccaacctcta caaggtgtac gtgcgcgcgt tcagcgactg ggagaaggac | 360 |
| ccgaccaacc cggccctccg cgaggaaatg cgtatccagt tcaacgatat gaactcggcc | 420 |
| ctcatcaccg ccatcccgct cttccgcgtg cagaactacg aggtggccct cctgtccgtg | 480 |
| tacgttcaag ccgccaacct ccacctctcc atcctccgcg acgtgagcgt gttcggcgag | 540 |
| cgctggggct acgacaccgc caccatcaac aaccgctact ccgacctcac ctccctcatc | 600 |
| cacgtttaca ccaaccactg cgtggacacg tacaaccagg gcctccgccg cctggagggc | 660 |
| cgcttcctct ccgactggat cgtgtacaac cgcttccgcc gccagctcac catctccgtc | 720 |
| ctggacatcg tcgccttctt tcccaactac gacatccgca cctaccctat ccagaccgcc | 780 |
| acccagctca cccgcgaggt ctacctcgac ctcccgttca tcaacgagaa cctcagcccg | 840 |
| gccgccagct acccgaccTT ctccgccgct gagtccgcca tcattcgcag cccgcacctc | 900 |
| gtggacttcc tcaactcctt caccatctac accgactccc tcgcccgcta cgcctactgg | 960 |
| ggcggtcacc tcgtgaactc cttccgcacc ggcaccacta ccaacctcat ccgcagcccg | 1020 |
| ctctacggcc gcgagggcaa caccgagcgc ccggtgacca tcaccgccag ccgagcgtg | 1080 |
| cccatcttcc gcaccctcag ctacatcacc ggcctggaca caggaaccc tgtggcgggc | 1140 |
| atcgagggcg tggagttcca gaacaccatc tccaggagca tctaccgcaa gagcggccct | 1200 |
| atcgacagct tcagcgagct gcctcctcag gacgccagcg tgagccctgc catcggctac | 1260 |
| agccacaggc tgtgccacgc caccttcctg gagcgcatca gcggccctcg catcgcgggc | 1320 |
| accgtgttct cgtggaccca ccgcagcgcc tctcctacga acgaggtgtc tcctagtcgc | 1380 |
| atcacccaga tcccttgggt caaggcccac accctggcta gtggcgctag tgtcatcaag | 1440 |
| ggccctggct tcaccggtgg tgacatcctg accaggaact ctatgggcga gctgggcact | 1500 |
| ctgagggtca ctttcactgg ccgcctgcct cagtcttact acatccgctt ccgctacgct | 1560 |
| agtgtcgcta accgctctgg tactttccgc tactctcagc ctccgtctta cggtatctct | 1620 |

```
ttccctaaga ctatggacgc tggtgagcct ctgaccagta ggagcttcgc tcacactact    1680
ctgttcactc ctatcacttt ctctagggct caggaggagt tcgacctgta catccagtct    1740
ggtgtgtaca tcgacaggat cgagttcatc cccgtgaccg ccacgttcga ggccgagtac    1800
gaccttgagc gcgcccagaa ggtggtgaac gccctcttca ctagcactaa ccagctaggc    1860
ctgaagactg acgtgaccga ctaccacatc gaccaagtga gcaacctagt ggcctgcctc    1920
tccgacgagt tctgcctcga cgagaagcgc gagctgtccg agaaggtgaa gcacgccaag    1980
cgcctctccg acgagcgcaa cctgctccag gaccccaact tcagggggcat caacaggcag    2040 cccgaccgcg gctggcgcgg ctccaccgac atcaccatcc agggcggtga cgacgtattc    2100
aaggagaact acgttaccct ccccggcacc ttcgacgagt gttaccccac ctacctctac    2160
cagaagatcg acgagtccaa gctgaaggcc tacacccgct accagctccg cggctacatc    2220
gaggactccc aggacctgga aatctacctc atccgctaca acgccaagca cgagatcgtg    2280
aacgtgcctg gcaccggcag cctctggcct ctcagcgtgg agaaccagat cggcccttgc    2340
ggcgagccta accgctgcgc ccctcacctc gagtggaacc ctgacctcca ctgctcgtgc    2400
agggacggcg agaagtgcgc caccatagc caccacttct ctctggacat cgacgtgggc    2460
tgcaccgacc tgaacgagga cctgggcgtg tgggttatct tcaagatcaa gacccaggac    2520
ggtcacgcca ggctgggtaa cctggagttc cttgaggaaa agcctctgct gggtgaggcc    2580
ctggccaggg tcaagagggc tgagaagaaa tggagggata gagggagac cctgcagctg    2640 gagaccacta tcgtctacaa ggaggctaag gagtctgtcg atgctctgtt cgtcaactct    2700
cagtacgata gactgcaagc tgataccaac atcgctatga tccacgctgc ggataagcgg    2760
gtccaccgga tccgggaggc ttaccttccg gagctttctg tcatcccggg tgtcaacgct    2820
gcgatcttcg aggaacttga ggaacggatc ttcactgcgt ttagtcttta cgatgcgcgg    2880
aacatcatca agaacgggga cttcaacaat ggtctgctgt gctggaacgt caagggtcat    2940
gtcgaggtcg aggaacaaaa caatcatcgt agtgtccttg tcattcctga gtgggaggcg    3000
gaggtctctc aagaggtccg tgtttgcccg gggcgtgggt acattcttcg tgttactgcg    3060
tacaaggagg ggtacgggga ggggtgcgtt actattcatg agattgagaa caatactgat    3120
gagcttaagt tcaacaattg tgttgaggag gaggtttacc cgaacaatac tgttacgtgc    3180
atcaactaca cggcaacgca agaggaatac gaggggacgt acacctcgcg taatagaggg    3240
tatgatgagg cgtacggaaa caacccgtcg gttccagcag attatgcctc ggtttatgag    3300
gagaagtcgt acacggatag acgacgcgag aatccatgtg agtcaaatcg aggatacgga    3360
gattacacac cattaccagc aggatacgtt acaaaggagt tggaatactt cccggaaaca    3420
gataaagttt ggattgaaat cggagaaaca gaaggaacat tcatcgtcga ctcagtagaa    3480
ttgttgttga tggaagaatg a                                             3501
```

<210> SEQ ID NO 34
<211> LENGTH: 1166
<212> TYPE: PRT
<213> ORGANISM: Artificial sequence
<220> FEATURE:
<223> OTHER INFORMATION: Amino acid sequence of the engineered
      insecticidal protein Cry1Da1_4 encoded by a synthetic DNA sequence
      wherein an additional Alanine residue has been inserted at
      position 2.

<400> SEQUENCE: 34

Met Ala Glu Ile Asn Asn Gln Asn Gln Cys Val Pro Tyr Asn Cys Leu
1               5                   10                  15

```
Ser Asn Pro Lys Glu Ile Ile Leu Gly Glu Arg Leu Glu Thr Gly
            20                  25                  30

Asn Thr Val Ala Asp Ile Ser Leu Gly Leu Ile Asn Phe Leu Tyr Ser
            35                  40                  45

Asn Phe Val Pro Gly Gly Phe Ile Val Gly Leu Leu Glu Leu Ile
 50                  55                  60

Trp Gly Phe Ile Gly Pro Ser Gln Trp Asp Ile Phe Leu Ala Gln Ile
 65                  70                  75                  80

Glu Gln Leu Ile Ser Gln Arg Ile Glu Glu Phe Ala Arg Asn Gln Ala
                85                  90                  95

Ile Ser Arg Leu Glu Gly Leu Ser Asn Leu Tyr Lys Val Tyr Val Arg
            100                 105                 110

Ala Phe Ser Asp Trp Glu Lys Asp Pro Thr Asn Pro Ala Leu Arg Glu
            115                 120                 125

Glu Met Arg Ile Gln Phe Asn Asp Met Asn Ser Ala Leu Ile Thr Ala
 130                 135                 140

Ile Pro Leu Phe Arg Val Gln Asn Tyr Glu Val Ala Leu Leu Ser Val
145                 150                 155                 160

Tyr Val Gln Ala Ala Asn Leu His Leu Ser Ile Leu Arg Asp Val Ser
            165                 170                 175

Val Phe Gly Glu Arg Trp Gly Tyr Asp Thr Ala Thr Ile Asn Asn Arg
            180                 185                 190

Tyr Ser Asp Leu Thr Ser Leu Ile His Val Tyr Thr Asn His Cys Val
            195                 200                 205

Asp Thr Tyr Asn Gln Gly Leu Arg Arg Leu Glu Gly Arg Phe Leu Ser
 210                 215                 220

Asp Trp Ile Val Tyr Asn Arg Phe Arg Arg Gln Leu Thr Ile Ser Val
225                 230                 235                 240

Leu Asp Ile Val Ala Phe Phe Pro Asn Tyr Asp Ile Arg Thr Tyr Pro
            245                 250                 255

Ile Gln Thr Ala Thr Gln Leu Thr Arg Glu Val Tyr Leu Asp Leu Pro
            260                 265                 270

Phe Ile Asn Glu Asn Leu Ser Pro Ala Ala Ser Tyr Pro Thr Phe Ser
 275                 280                 285

Ala Ala Glu Ser Ala Ile Ile Arg Ser Pro His Leu Val Asp Phe Leu
 290                 295                 300

Asn Ser Phe Thr Ile Tyr Thr Asp Ser Leu Ala Arg Tyr Ala Tyr Trp
305                 310                 315                 320

Gly Gly His Leu Val Asn Ser Phe Arg Thr Gly Thr Thr Asn Leu
            325                 330                 335

Ile Arg Ser Pro Leu Tyr Gly Arg Glu Gly Asn Thr Glu Arg Pro Val
            340                 345                 350

Thr Ile Thr Ala Ser Pro Ser Val Pro Ile Phe Arg Thr Leu Ser Tyr
            355                 360                 365

Ile Thr Gly Leu Asp Asn Arg Asn Pro Val Ala Gly Ile Glu Gly Val
 370                 375                 380

Glu Phe Gln Asn Thr Ile Ser Arg Ser Ile Tyr Arg Lys Ser Gly Pro
385                 390                 395                 400

Ile Asp Ser Phe Ser Glu Leu Pro Pro Gln Asp Ala Ser Val Ser Pro
            405                 410                 415

Ala Ile Gly Tyr Ser His Arg Leu Cys His Ala Thr Phe Leu Glu Arg
            420                 425                 430
```

-continued

```
Ile Ser Gly Pro Arg Ile Ala Gly Thr Val Phe Ser Trp Thr His Arg
        435                 440                 445

Ser Ala Ser Pro Thr Asn Glu Val Ser Pro Ser Arg Ile Thr Gln Ile
450                 455                 460

Pro Trp Val Lys Ala His Thr Leu Ala Ser Gly Ala Ser Val Ile Lys
465                 470                 475                 480

Gly Pro Gly Phe Thr Gly Gly Asp Ile Leu Thr Arg Asn Ser Met Gly
                485                 490                 495

Glu Leu Gly Thr Leu Arg Val Thr Phe Thr Gly Arg Leu Pro Gln Ser
            500                 505                 510

Tyr Tyr Ile Arg Phe Arg Tyr Ala Ser Val Ala Asn Arg Ser Gly Thr
        515                 520                 525

Phe Arg Tyr Ser Gln Pro Pro Ser Tyr Gly Ile Ser Phe Pro Lys Thr
    530                 535                 540

Met Asp Ala Gly Glu Pro Leu Thr Ser Arg Ser Phe Ala His Thr Thr
545                 550                 555                 560

Leu Phe Thr Pro Ile Thr Phe Ser Arg Ala Gln Glu Glu Phe Asp Leu
                565                 570                 575

Tyr Ile Gln Ser Gly Val Tyr Ile Asp Arg Ile Glu Phe Ile Pro Val
            580                 585                 590

Thr Ala Thr Phe Glu Ala Glu Tyr Asp Leu Glu Arg Ala Gln Lys Val
        595                 600                 605

Val Asn Ala Leu Phe Thr Ser Thr Asn Gln Leu Gly Leu Lys Thr Asp
    610                 615                 620

Val Thr Asp Tyr His Ile Asp Gln Val Ser Asn Leu Val Ala Cys Leu
625                 630                 635                 640

Ser Asp Glu Phe Cys Leu Asp Glu Lys Arg Glu Leu Ser Glu Lys Val
                645                 650                 655

Lys His Ala Lys Arg Leu Ser Asp Glu Arg Asn Leu Leu Gln Asp Pro
            660                 665                 670

Asn Phe Arg Gly Ile Asn Arg Gln Pro Asp Arg Gly Trp Arg Gly Ser
        675                 680                 685

Thr Asp Ile Thr Ile Gln Gly Gly Asp Asp Val Phe Lys Glu Asn Tyr
    690                 695                 700

Val Thr Leu Pro Gly Thr Phe Asp Glu Cys Tyr Pro Thr Tyr Leu Tyr
705                 710                 715                 720

Gln Lys Ile Asp Glu Ser Lys Leu Lys Ala Tyr Thr Arg Tyr Gln Leu
                725                 730                 735

Arg Gly Tyr Ile Glu Asp Ser Gln Asp Leu Glu Ile Tyr Leu Ile Arg
            740                 745                 750

Tyr Asn Ala Lys His Glu Ile Val Asn Val Pro Gly Thr Gly Ser Leu
        755                 760                 765

Trp Pro Leu Ser Val Glu Asn Gln Ile Gly Pro Cys Gly Glu Pro Asn
    770                 775                 780

Arg Cys Ala Pro His Leu Glu Trp Asn Pro Asp Leu His Cys Ser Cys
785                 790                 795                 800

Arg Asp Gly Glu Lys Cys Ala His His Ser His His Phe Ser Leu Asp
                805                 810                 815

Ile Asp Val Gly Cys Thr Asp Leu Asn Glu Asp Leu Gly Val Trp Val
            820                 825                 830

Ile Phe Lys Ile Lys Thr Gln Asp Gly His Ala Arg Leu Gly Asn Leu
        835                 840                 845

Glu Phe Leu Glu Glu Lys Pro Leu Leu Gly Glu Ala Leu Ala Arg Val
```

```
                      850                855               860
Lys Arg Ala Glu Lys Lys Trp Arg Asp Lys Arg Glu Thr Leu Gln Leu
865                 870                875                880

Glu Thr Thr Ile Val Tyr Lys Glu Ala Lys Glu Ser Val Asp Ala Leu
                    885                890                895

Phe Val Asn Ser Gln Tyr Asp Arg Leu Gln Ala Asp Thr Asn Ile Ala
                900                905                910

Met Ile His Ala Ala Asp Lys Arg Val His Arg Ile Arg Glu Ala Tyr
                915                920                925

Leu Pro Glu Leu Ser Val Ile Pro Gly Val Asn Ala Ala Ile Phe Glu
                930                935                940

Glu Leu Glu Glu Arg Ile Phe Thr Ala Phe Ser Leu Tyr Asp Ala Arg
945                 950                955                960

Asn Ile Ile Lys Asn Gly Asp Phe Asn Asn Gly Leu Leu Cys Trp Asn
                    965                970                975

Val Lys Gly His Val Glu Val Glu Glu Gln Asn Asn His Arg Ser Val
                980                985                990

Leu Val Ile Pro Glu Trp Glu Ala  Glu Val Ser Gln Glu  Val Arg Val
            995                1000                1005

Cys Pro  Gly Arg Gly Tyr Ile  Leu Arg Val Thr Ala  Tyr Lys Glu
    1010                1015                1020

Gly Tyr  Gly Glu Gly Cys Val  Thr Ile His Glu Ile  Glu Asn Asn
    1025                1030                1035

Thr Asp  Glu Leu Lys Phe Asn  Asn Cys Val Glu Glu  Glu Val Tyr
    1040                1045                1050

Pro Asn  Asn Thr Val Thr Cys  Ile Asn Tyr Thr Ala  Thr Gln Glu
    1055                1060                1065

Glu Tyr  Glu Gly Thr Tyr Thr  Ser Arg Asn Arg Gly  Tyr Asp Glu
    1070                1075                1080

Ala Tyr  Gly Asn Asn Pro Ser  Val Pro Ala Asp Tyr  Ala Ser Val
    1085                1090                1095

Tyr Glu  Glu Lys Ser Tyr Thr  Asp Arg Arg Arg Glu  Asn Pro Cys
    1100                1105                1110

Glu Ser  Asn Arg Gly Tyr Gly  Asp Tyr Thr Pro Leu  Pro Ala Gly
    1115                1120                1125

Tyr Val  Thr Lys Glu Leu Glu  Tyr Phe Pro Glu Thr  Asp Lys Val
    1130                1135                1140

Trp Ile  Glu Ile Gly Glu Thr  Glu Gly Thr Phe Ile  Val Asp Ser
    1145                1150                1155

Val Glu  Leu Leu Leu Met Glu  Glu
    1160                1165

<210> SEQ ID NO 35
<211> LENGTH: 3501
<212> TYPE: DNA
<213> ORGANISM: Artificial sequence
<220> FEATURE:
<223> OTHER INFORMATION: Synthetic DNA sequence designed for plant
      expression encoding Cry1Da1_5 with an additional Alanine residue
      inserted at position 2.

<400> SEQUENCE: 35
atggctgaga tcaacaacca gaaccagtgc gtcccgtaca actgcctgag caaccctaag      60
gagatcatcc tgggtgagga acgctggag accggcaaca ccgtagccga cattagcctg     120
ggcctcatca acttcctcta cagcaacttc gtgcccggcg gtggcttcat cgtgggcctc     180
```

```
ctggagctta tctggggctt catcggcccg tcccagtggg acatcttcct cgcccagatc      240
gagcaactga tcagccagcg gatcgaggag ttcgctagga accaggccat ctcccgcctg      300
gagggactct ccaacctcta caaggtgtac gtgcgcgcgt tcagcgactg ggagaaggac      360
ccgaccaacc cggccctccg cgaggaaatg cgtatccagt tcaacgatat gaactcggcc      420
ctcatcaccg ccatcccgct cttccgcgtg cagaactacg aggtggccct cctgtccgtg      480
tacgttcaag ccgccaacct ccacctctcc atcctccgcg acgtgagcgt gttcggcgag      540
cgctggggct acgacaccgc caccatcaac aaccgctact ccgacctcac ctccctcatc      600
cacgtttaca ccaaccactg cgtggacacg tacaaccagg cctccgccg cctggagggc       660 cgcttcctct ccgactggat cgtgtacaac cgcttccgcc gccagctcac catctccgtc      720
ctggacatcg tcgccttctt tcccaactac gacatccgca cctaccctat ccagaccgcc      780
acccagctca cccgcgaggt ctacctcgac ctcccgttca tcaacgagaa cctcagcccg      840
gccgccagct acccgacctt ctccgccgct gagtccgcca tcattcgcag cccgcacctc      900
gtggacttcc tcaactcctt caccatctac accgactccc tcgcccgcag cgcctactgg      960
ggcggtcacc tcgtgaactc cttccgcacc ggcaccacta ccaacctcat ccgcagcccg     1020
ctctacggcc gcgagggcaa caccgagcgc ccggtgacca tcaccgccag cccgagcgtg     1080
cccatcttcc gcaccctcag ctaccgcacc ggcctggaca acagcaaccc tgtggcgggc     1140
atcgagggcg tggagttcca gaacaccatc tccaggagca tctaccgcaa gagcggccct     1200
atcgacagct tcagcgagct gcctcctcag gacgccagcg tgagccctgc catcggctac     1260
agccacaggc tgtgccacgc caccttcctg gagcgcatca gcggccctcg catcgcgggc     1320
accgtgttct cgtggaccca ccgcagcgcc tctcctacga acgaggtgtc tcctagtcgc     1380
atcacccaga tcccttgggt caaggcccac accctggcta gtggcgctag tgtcatcaag     1440
ggccctggct tcaccggtgg tgacatcctg accaggaact ctatgggcga gctgggcact     1500
ctgagggtca ctttcactgg ccgcctgcct cagtcttact acatccgctt ccgctacgct     1560
agtgtcgcta accgctctgg tactttccgc tactctcagc ctccgtctta cggtatctct     1620
ttccctaaga ctatggacgc tggtgagcct ctgaccagta ggagcttcgc tcacactact     1680
ctgttcactc ctatcacttt tctctagggct caggaggagt tcgacctgta catccagtct     1740
ggtgtgtaca tcgacaggat cgagttcatc cccgtgaccg ccacgttcga ggccgagtac     1800
gaccttgagc gcgcccagaa ggtggtgaac gccctcttca ctagcactaa ccagctaggc     1860
ctgaagactg acgtgaccga ctaccacatc gaccaagtga gcaacctagt ggcctgcctc     1920
tccgacgagt tctgcctcga cgagaagcgc gagctgtccg agaaggtgaa gcacgccaag     1980
cgcctctccg acgagcgcaa cctgctccag gaccccaact tcaggggcat caacaggcag     2040
cccgaccgcg gctggcgcgg ctccaccgac atcaccatcc agggcggtga cgacgtattc     2100
aaggagaact acgttaccct ccccggcacc ttcgacgagt gttacccccac ctacctctac     2160 cagaagatcg acgagtccaa gctgaaggcc tacacccgct accagctccg cggctacatc     2220
gaggactccc aggacctgga aatctacctc atccgctaca cgccaagca cgagatcgtg     2280 aacgtgcctg gcaccggcag cctctggcct ctcagcgtgg agaaccagat cggcccttgc     2340
ggcgagccta accgctgcgc ccctcacctc gagtggaacc ctgacctcca ctgctcgtgc     2400
agggacggca gaagtgcgc ccaccatagc caccacttct ctctggacat cgacgtgggc      2460
tgcaccgacc tgaacgagga cctgggcgtg tgggttatct tcaagatcaa gacccaggac     2520
```

-continued

```
ggtcacgcca ggctgggtaa cctggagttc cttgaggaaa agcctctgct gggtgaggcc    2580
ctggccaggg tcaagagggc tgagaagaaa tggagggata agagggagac cctgcagctg    2640
gagaccacta tcgtctacaa ggaggctaag gagtctgtcg atgctctgtt cgtcaactct    2700
cagtacgata gactgcaagc tgataccaac atcgctatga tccacgctgc ggataagcgg    2760
gtccaccgga tccgggaggc ttaccttccg gagctttctg tcatcccggg tgtcaacgct    2820
gcgatcttcg aggaacttga ggaacggatc ttcactgcgt ttagtcttta cgatgcgcgg    2880
aacatcatca agaacgggga cttcaacaat ggtctgctgt gctggaacgt caagggtcat    2940
gtcgaggtcg aggaacaaaa caatcatcgt agtgtccttg tcattcctga gtgggaggcg    3000
gaggtctctc aagaggtccg tgtttgcccg gggcgtgggt acattcttcg tgttactgcg    3060
tacaaggagg ggtacgggga ggggtgcgtt actattcatg agattgagaa caatactgat    3120
gagcttaagt tcaacaattg tgttgaggag gaggtttacc cgaacaatac tgttacgtgc    3180
atcaactaca cggcaacgca agaggaatac gaggggacgt acacctcgcg taatagaggg    3240
tatgatgagg cgtacggaaa caacccgtcg gttccagcag attatgcctc ggtttatgag    3300
gagaagtcgt acacggatag acgacgcgag aatccatgtg agtcaaatcg aggatacgga    3360
gattacacac cattaccagc aggatacgtt acaaaggagt tggaatactt cccggaaaca    3420
gataaagttt ggattgaaat cggagaaaca gaaggaacat tcatcgtcga ctcagtagaa    3480
ttgttgttga tggaagaatg a                                              3501
```

<210> SEQ ID NO 36
<211> LENGTH: 1166
<212> TYPE: PRT
<213> ORGANISM: Artificial sequence
<220> FEATURE:
<223> OTHER INFORMATION: Amino acid sequence of the engineered
      insecticidal protein Cry1Da1_5 encoded by a synthetic DNA sequence
      wherein an additional Alanine residue has been inserted at
      position 2.

<400> SEQUENCE: 36

```
Met Ala Glu Ile Asn Asn Gln Asn Gln Cys Val Pro Tyr Asn Cys Leu
1               5                   10                  15

Ser Asn Pro Lys Glu Ile Ile Leu Gly Glu Glu Arg Leu Glu Thr Gly
                20                  25                  30

Asn Thr Val Ala Asp Ile Ser Leu Gly Leu Ile Asn Phe Leu Tyr Ser
            35                  40                  45

Asn Phe Val Pro Gly Gly Gly Phe Ile Val Gly Leu Leu Glu Leu Ile
        50                  55                  60

Trp Gly Phe Ile Gly Pro Ser Gln Trp Asp Ile Phe Leu Ala Gln Ile
65                  70                  75                  80

Glu Gln Leu Ile Ser Gln Arg Ile Glu Glu Phe Ala Arg Asn Gln Ala
                85                  90                  95

Ile Ser Arg Leu Glu Gly Leu Ser Asn Leu Tyr Lys Val Tyr Val Arg
            100                 105                 110

Ala Phe Ser Asp Trp Glu Lys Asp Pro Thr Asn Pro Ala Leu Arg Glu
        115                 120                 125

Glu Met Arg Ile Gln Phe Asn Asp Met Asn Ser Ala Leu Ile Thr Ala
    130                 135                 140

Ile Pro Leu Phe Arg Val Gln Asn Tyr Glu Val Ala Leu Leu Ser Val
145                 150                 155                 160

Tyr Val Gln Ala Ala Asn Leu His Leu Ser Ile Leu Arg Asp Val Ser
                165                 170                 175
```

```
Val Phe Gly Glu Arg Trp Gly Tyr Asp Thr Ala Thr Ile Asn Asn Arg
            180                 185                 190

Tyr Ser Asp Leu Thr Ser Leu Ile His Val Tyr Thr Asn His Cys Val
        195                 200                 205

Asp Thr Tyr Asn Gln Gly Leu Arg Arg Leu Glu Gly Arg Phe Leu Ser
        210                 215                 220

Asp Trp Ile Val Tyr Asn Arg Phe Arg Arg Gln Leu Thr Ile Ser Val
225                 230                 235                 240

Leu Asp Ile Val Ala Phe Phe Pro Asn Tyr Asp Ile Arg Thr Tyr Pro
                245                 250                 255

Ile Gln Thr Ala Thr Gln Leu Thr Arg Glu Val Tyr Leu Asp Leu Pro
                260                 265                 270

Phe Ile Asn Glu Asn Leu Ser Pro Ala Ala Ser Tyr Pro Thr Phe Ser
            275                 280                 285

Ala Ala Glu Ser Ala Ile Ile Arg Ser Pro His Leu Val Asp Phe Leu
        290                 295                 300

Asn Ser Phe Thr Ile Tyr Thr Asp Ser Leu Ala Arg Ser Ala Tyr Trp
305                 310                 315                 320

Gly Gly His Leu Val Asn Ser Phe Arg Thr Gly Thr Thr Thr Asn Leu
                325                 330                 335

Ile Arg Ser Pro Leu Tyr Gly Arg Glu Gly Asn Thr Glu Arg Pro Val
            340                 345                 350

Thr Ile Thr Ala Ser Pro Ser Val Pro Ile Phe Arg Thr Leu Ser Tyr
        355                 360                 365

Arg Thr Gly Leu Asp Asn Ser Asn Pro Val Ala Gly Ile Glu Gly Val
        370                 375                 380

Glu Phe Gln Asn Thr Ile Ser Arg Ser Ile Tyr Arg Lys Ser Gly Pro
385                 390                 395                 400

Ile Asp Ser Phe Ser Glu Leu Pro Pro Gln Asp Ala Ser Val Ser Pro
                405                 410                 415

Ala Ile Gly Tyr Ser His Arg Leu Cys His Ala Thr Phe Leu Glu Arg
                420                 425                 430

Ile Ser Gly Pro Arg Ile Ala Gly Thr Val Phe Ser Trp Thr His Arg
            435                 440                 445

Ser Ala Ser Pro Thr Asn Glu Val Ser Pro Ser Arg Ile Thr Gln Ile
        450                 455                 460

Pro Trp Val Lys Ala His Thr Leu Ala Ser Gly Ala Ser Val Ile Lys
465                 470                 475                 480

Gly Pro Gly Phe Thr Gly Gly Asp Ile Leu Thr Arg Asn Ser Met Gly
                485                 490                 495

Glu Leu Gly Thr Leu Arg Val Thr Phe Thr Gly Arg Leu Pro Gln Ser
            500                 505                 510

Tyr Tyr Ile Arg Phe Arg Tyr Ala Ser Val Ala Asn Arg Ser Gly Thr
        515                 520                 525

Phe Arg Tyr Ser Gln Pro Pro Ser Tyr Gly Ile Ser Phe Pro Lys Thr
        530                 535                 540

Met Asp Ala Gly Glu Pro Leu Thr Ser Arg Ser Phe Ala His Thr Thr
545                 550                 555                 560

Leu Phe Thr Pro Ile Thr Phe Ser Arg Ala Gln Glu Glu Phe Asp Leu
                565                 570                 575

Tyr Ile Gln Ser Gly Val Tyr Ile Asp Arg Ile Glu Phe Ile Pro Val
            580                 585                 590
```

-continued

Thr Ala Thr Phe Glu Ala Glu Tyr Asp Leu Glu Arg Ala Gln Lys Val
            595                 600                 605

Val Asn Ala Leu Phe Thr Ser Thr Asn Gln Leu Gly Leu Lys Thr Asp
610                 615                 620

Val Thr Asp Tyr His Ile Asp Gln Val Ser Asn Leu Val Ala Cys Leu
625                 630                 635                 640

Ser Asp Glu Phe Cys Leu Asp Glu Lys Arg Glu Leu Ser Glu Lys Val
            645                 650                 655

Lys His Ala Lys Arg Leu Ser Asp Glu Arg Asn Leu Leu Gln Asp Pro
                660                 665                 670

Asn Phe Arg Gly Ile Asn Arg Gln Pro Asp Arg Gly Trp Arg Gly Ser
            675                 680                 685

Thr Asp Ile Thr Ile Gln Gly Gly Asp Asp Val Phe Lys Glu Asn Tyr
        690                 695                 700

Val Thr Leu Pro Gly Thr Phe Asp Glu Cys Tyr Pro Thr Tyr Leu Tyr
705                 710                 715                 720

Gln Lys Ile Asp Glu Ser Lys Leu Lys Ala Tyr Thr Arg Tyr Gln Leu
                725                 730                 735

Arg Gly Tyr Ile Glu Asp Ser Gln Asp Leu Glu Ile Tyr Leu Ile Arg
            740                 745                 750

Tyr Asn Ala Lys His Glu Ile Val Asn Val Pro Gly Thr Gly Ser Leu
        755                 760                 765

Trp Pro Leu Ser Val Glu Asn Gln Ile Gly Pro Cys Gly Glu Pro Asn
        770                 775                 780

Arg Cys Ala Pro His Leu Glu Trp Asn Pro Asp Leu His Cys Ser Cys
785                 790                 795                 800

Arg Asp Gly Glu Lys Cys Ala His His Ser His His Phe Ser Leu Asp
                805                 810                 815

Ile Asp Val Gly Cys Thr Asp Leu Asn Glu Asp Leu Gly Val Trp Val
            820                 825                 830

Ile Phe Lys Ile Lys Thr Gln Asp Gly His Ala Arg Leu Gly Asn Leu
        835                 840                 845

Glu Phe Leu Glu Glu Lys Pro Leu Leu Gly Glu Ala Leu Ala Arg Val
850                 855                 860

Lys Arg Ala Glu Lys Lys Trp Arg Asp Lys Arg Glu Thr Leu Gln Leu
865                 870                 875                 880

Glu Thr Thr Ile Val Tyr Lys Glu Ala Lys Glu Ser Val Asp Ala Leu
                885                 890                 895

Phe Val Asn Ser Gln Tyr Asp Arg Leu Gln Ala Asp Thr Asn Ile Ala
            900                 905                 910

Met Ile His Ala Ala Asp Lys Arg Val His Arg Ile Arg Glu Ala Tyr
        915                 920                 925

Leu Pro Glu Leu Ser Val Ile Pro Gly Val Asn Ala Ala Ile Phe Glu
        930                 935                 940

Glu Leu Glu Glu Arg Ile Phe Thr Ala Phe Ser Leu Tyr Asp Ala Arg
945                 950                 955                 960

Asn Ile Ile Lys Asn Gly Asp Phe Asn Asn Gly Leu Leu Cys Trp Asn
                965                 970                 975

Val Lys Gly His Val Glu Val Glu Glu Gln Asn Asn His Arg Ser Val
            980                 985                 990

Leu Val Ile Pro Glu Trp Glu Ala Glu Val Ser Gln Glu Val Arg Val
        995                 1000                1005

Cys Pro Gly Arg Gly Tyr Ile Leu Arg Val Thr Ala Tyr Lys Glu

```
    1010                1015                1020

Gly Tyr  Gly Glu Gly Cys Val  Thr Ile His Glu Ile  Glu Asn Asn
    1025                1030                1035

Thr Asp  Glu Leu Lys Phe Asn  Asn Cys Val Glu Glu  Glu Val Tyr
    1040                1045                1050

Pro Asn  Asn Thr Val Thr Cys  Ile Asn Tyr Thr Ala  Thr Gln Glu
    1055                1060                1065

Glu Tyr  Glu Gly Thr Tyr Thr  Ser Arg Asn Arg Gly  Tyr Asp Glu
    1070                1075                1080

Ala Tyr  Gly Asn Asn Pro Ser  Val Pro Ala Asp Tyr  Ala Ser Val
    1085                1090                1095

Tyr Glu  Glu Lys Ser Tyr Thr  Asp Arg Arg Arg Glu  Asn Pro Cys
    1100                1105                1110

Glu Ser  Asn Arg Gly Tyr Gly  Asp Tyr Thr Pro Leu  Pro Ala Gly
    1115                1120                1125

Tyr Val  Thr Lys Glu Leu Glu  Tyr Phe Pro Glu Thr  Asp Lys Val
    1130                1135                1140

Trp Ile  Glu Ile Gly Glu Thr  Glu Gly Thr Phe Ile  Val Asp Ser
    1145                1150                1155

Val Glu  Leu Leu Leu Met Glu  Glu
    1160                1165
```

<210> SEQ ID NO 37
<211> LENGTH: 3501
<212> TYPE: DNA
<213> ORGANISM: Artificial sequence
<220> FEATURE:
<223> OTHER INFORMATION: Synthetic DNA sequence designed for plant expression encoding Cry1Da1_6 with an additional Alanine residue inserted at position 2.

<400> SEQUENCE: 37

```
atggctgaga tcaacaacca gaaccagtgc gtcccgtaca actgcctgag caaccctaag     60
gagatcatcc tgggtgagga acgcctggag accggcaaca ccgtagccga cattagcctg    120
ggcctcatca acttcctcta cagcaacttc gtgcccggcg gtggcttcat cgtgggcctc    180
ctggagctta tctggggctt catcggcccg tcccagtggg acatcttcct cgcccagatc    240
gagcaactga tcagccagcg gatcgaggag ttcgctagga accaggccat ctcccgcctg    300
gagggactct ccaacctcta caaggtgtac gtgcgcgcgt tcagcgactg ggagaaggac    360
ccgaccaacc cggccctccg cgaggaaatg cgtatccagt tcaacgatat gaactcggcc    420
ctcatcaccg ccatcccgct cttccgcgtg cagaactacg aggtggccct cctgtccgtg    480
tacgttcaag ccgccaacct ccacctctcc atcctccgcg acgtgagcgt gttcggcgag    540
cgctggggct acgacaccgc caccatcaac aaccgctact ccgacctcac ctccctcatc    600
cacgtttaca ccaaccactg cgtggacacg tacaaccagg gcctccgccg cctggagggc    660
cgcttcctct ccgactggat cgtgtacaac cgcttccgcc gccagctcac catctccgtc    720
ctggacatcg tcgccttctt tcccaactac gacatccgca cctaccctat ccagaccgcc    780
acccagctca cccgcgaggt ctacctcgac ctcccgttca tcaacgagaa cctcagcccg    840
gccgccaagt acccgacctt ctccgccgct gagtccgcca tcattcgcag cccgcacctc    900
gtggacttcc tcaactcctt caccatctac accgactccc tcgcccgcag cgcctactgg    960
ggcggtcacc tcgtgaactc cttccgcacc ggcaccacta ccaacctcat ccgcagcccg   1020
ctctacggcc gcgagggcaa caccgagcgc ccggtgacca tcaccgccag cccgagcgtg   1080
```

```
cccatcttcc gcaccctcag ctaccccacc ggcctggaca acagcaaccc tgtggcgggc      1140
atcgagggcg tggagttcca gaacaccatc tccaggagca tctaccgcaa gagcggccct      1200
atcgacagct tcagcgagct gcctcctcag gacgccagcg tgagccctgc catcggctac      1260
agccacaggc tgtgccacgc caccttcctg gagcgcatca gcggccctcg catcgcgggc      1320
accgtgttct cgtggaccca ccgcagcgcc tctcctacga acgaggtgtc tcctagtcgc      1380
atcacccaga tcccttgggt caaggccac  accctggcta gtggcgctag tgtcatcaag      1440
ggccctggct tcaccggtgg tgacatcctg accaggaact ctatgggcga gctgggcact      1500
ctgagggtca ctttcactgg ccgcctgcct cagtcttact acatccgctt ccgctacgct      1560
agtgtcgcta accgctctgg tactttccgc tactctcagc ctccgtctta cggtatctct      1620
ttccctaaga ctatggacgc tggtgagcct ctgaccagta ggagcttcgc tcacactact      1680
ctgttcactc ctatcacttt tctagggct  caggaggagt tcgacctgta catccagtct      1740
ggtgtgtaca tcgacaggat cgagttcatc cccgtgaccg ccacgttcga ggccgagtac      1800
gaccttgagc gcgcccagaa ggtggtgaac gccctcttca ctagcactaa ccagctaggc      1860
ctgaagactg acgtgaccga ctaccacatc gaccaagtga gcaacctagt ggcctgcctc      1920
tccgacgagt tctgcctcga cgagaagcgc gagctgtccg agaaggtgaa gcacgccaag      1980
cgcctctccg acgagcgcaa cctgctccag gaccccaact tcaggggcat caacaggcag      2040
cccgaccgcg gctggcgcgg ctccaccgac atcaccatcc agggcggtga cgacgtattc      2100
aaggagaact acgttaccct ccccggcacc ttcgacgagt gttacccac  ctacctctac      2160 cagaagatcg acgagtccaa gctgaaggcc tacacccgct accagctccg cggctacatc      2220
gaggactccc aggacctgga aatctacctc atccgctaca cgccaagca  cgagatcgtg      2280 aacgtgcctg gcaccggcag cctctggcct ctcagcgtgg agaaccagat cggcccttgc      2340
ggcgagccta accgctgcgc ccctcacctc gagtggaacc ctgacctcca ctgctcgtgc      2400
agggacggcg agaagtgcgc ccaccatagc caccacttct ctctggacat cgacgtgggc      2460
tgcaccgacc tgaacgagga cctgggcgtg tgggttatct tcaagatcaa gacccaggac      2520
ggtcacgcca ggctgggtaa cctggagttc cttgaggaaa agcctctgct gggtgaggcc      2580
ctggccaggg tcaagagggc tgagaagaaa tggagggata agaggagac cctgcagctg       2640 gagaccacta tcgtctacaa ggaggctaag gagtctgtcg atgctctgtt cgtcaactct      2700
cagtacgata gactgcaagc tgataccaac atcgctatga tccacgctgc ggataagcgg      2760
gtccaccgga tccgggaggc ttaccttccg gagctttctg tcatcccggg tgtcaacgct      2820
gcgatcttcg aggaacttga ggaacggatc ttcactgcgt ttagtcttta cgatgcgcgg      2880
aacatcatca gaacgggga  cttcaacaat ggtctgctgt gctggaacgt caagggtcat      2940
gtcgaggtcg aggaacaaaa caatcatcgt agtgtccttg tcattcctga gtgggaggcg      3000
gaggtctctc aagaggtccg tgtttgcccg gggcgtgggt acattcttcg tgttactgcg      3060
tacaaggagg ggtacgggga ggggtgcgtt actattcatg agattgagaa caatactgat      3120
gagcttaagt tcaacaattg tgttgaggag gaggtttacc cgaacaatac tgttacgtgc      3180
atcaactaca cggcaacgca agaggaatac gaggggacgt acacctcgcg taatagaggg      3240
tatgatgagg cgtacggaaa caacccgtcg gttccagcag attatgcctc ggtttatgag      3300
gagaagtcgt acacggatag acgacgcgag aatccatgtg agtcaaatcg aggatacgga      3360
gattacacac cattaccagc aggatacgtt acaaaggagt tggaatactt cccggaaaca      3420
```

```
gataaagttt ggattgaaat cggagaaaca gaaggaacat tcatcgtcga ctcagtagaa      3480
ttgttgttga tggaagaatg a                                                3501
```

<210> SEQ ID NO 38
<211> LENGTH: 1166
<212> TYPE: PRT
<213> ORGANISM: Artificial sequence
<220> FEATURE:
<223> OTHER INFORMATION: Amino acid sequence of the engineered
      insecticidal protein Cry1Da1_6 encoded by a synthetic DNA sequence
      wherein an additional Alanine residue has been inserted at
      position 2.

<400> SEQUENCE: 38

```
Met Ala Glu Ile Asn Asn Gln Asn Gln Cys Val Pro Tyr Asn Cys Leu
1               5                   10                  15

Ser Asn Pro Lys Glu Ile Ile Leu Gly Glu Glu Arg Leu Glu Thr Gly
            20                  25                  30

Asn Thr Val Ala Asp Ile Ser Leu Gly Leu Ile Asn Phe Leu Tyr Ser
        35                  40                  45

Asn Phe Val Pro Gly Gly Gly Phe Ile Val Gly Leu Leu Glu Leu Ile
    50                  55                  60

Trp Gly Phe Ile Gly Pro Ser Gln Trp Asp Ile Phe Leu Ala Gln Ile
65                  70                  75                  80

Glu Gln Leu Ile Ser Gln Arg Ile Glu Glu Phe Ala Arg Asn Gln Ala
                85                  90                  95

Ile Ser Arg Leu Glu Gly Leu Ser Asn Leu Tyr Lys Val Tyr Val Arg
            100                 105                 110

Ala Phe Ser Asp Trp Glu Lys Asp Pro Thr Asn Pro Ala Leu Arg Glu
        115                 120                 125

Glu Met Arg Ile Gln Phe Asn Asp Met Asn Ser Ala Leu Ile Thr Ala
    130                 135                 140

Ile Pro Leu Phe Arg Val Gln Asn Tyr Glu Val Ala Leu Leu Ser Val
145                 150                 155                 160

Tyr Val Gln Ala Ala Asn Leu His Leu Ser Ile Leu Arg Asp Val Ser
                165                 170                 175

Val Phe Gly Glu Arg Trp Gly Tyr Asp Thr Ala Thr Ile Asn Asn Arg
            180                 185                 190

Tyr Ser Asp Leu Thr Ser Leu Ile His Val Tyr Thr Asn His Cys Val
        195                 200                 205

Asp Thr Tyr Asn Gln Gly Leu Arg Arg Leu Glu Gly Arg Phe Leu Ser
    210                 215                 220

Asp Trp Ile Val Tyr Asn Arg Phe Arg Arg Gln Leu Thr Ile Ser Val
225                 230                 235                 240

Leu Asp Ile Val Ala Phe Phe Pro Asn Tyr Asp Ile Arg Thr Tyr Pro
                245                 250                 255

Ile Gln Thr Ala Thr Gln Leu Thr Arg Glu Val Tyr Leu Asp Leu Pro
            260                 265                 270

Phe Ile Asn Glu Asn Leu Ser Pro Ala Ala Lys Tyr Pro Thr Phe Ser
        275                 280                 285

Ala Ala Glu Ser Ala Ile Ile Arg Ser Pro His Leu Val Asp Phe Leu
    290                 295                 300

Asn Ser Phe Thr Ile Tyr Thr Asp Ser Leu Ala Arg Ser Ala Tyr Trp
305                 310                 315                 320

Gly Gly His Leu Val Asn Ser Phe Arg Thr Gly Thr Thr Thr Asn Leu
                325                 330                 335
```

```
Ile Arg Ser Pro Leu Tyr Gly Arg Glu Gly Asn Thr Glu Arg Pro Val
            340                 345                 350

Thr Ile Thr Ala Ser Pro Ser Val Pro Ile Phe Arg Thr Leu Ser Tyr
            355                 360                 365

Pro Thr Gly Leu Asp Asn Ser Asn Pro Val Ala Gly Ile Glu Gly Val
370                 375                 380

Glu Phe Gln Asn Thr Ile Ser Arg Ser Ile Tyr Arg Lys Ser Gly Pro
385                 390                 395                 400

Ile Asp Ser Phe Ser Glu Leu Pro Pro Gln Asp Ala Ser Val Ser Pro
                405                 410                 415

Ala Ile Gly Tyr Ser His Arg Leu Cys His Ala Thr Phe Leu Glu Arg
            420                 425                 430

Ile Ser Gly Pro Arg Ile Ala Gly Thr Val Phe Ser Trp Thr His Arg
            435                 440                 445

Ser Ala Ser Pro Thr Asn Glu Val Ser Pro Ser Arg Ile Thr Gln Ile
    450                 455                 460

Pro Trp Val Lys Ala His Thr Leu Ala Ser Gly Ala Ser Val Ile Lys
465                 470                 475                 480

Gly Pro Gly Phe Thr Gly Gly Asp Ile Leu Thr Arg Asn Ser Met Gly
                485                 490                 495

Glu Leu Gly Thr Leu Arg Val Thr Phe Thr Gly Arg Leu Pro Gln Ser
                500                 505                 510

Tyr Tyr Ile Arg Phe Arg Tyr Ala Ser Val Ala Asn Arg Ser Gly Thr
            515                 520                 525

Phe Arg Tyr Ser Gln Pro Pro Ser Tyr Gly Ile Ser Phe Pro Lys Thr
            530                 535                 540

Met Asp Ala Gly Glu Pro Leu Thr Ser Arg Ser Phe Ala His Thr Thr
545                 550                 555                 560

Leu Phe Thr Pro Ile Thr Phe Ser Arg Ala Gln Glu Glu Phe Asp Leu
                565                 570                 575

Tyr Ile Gln Ser Gly Val Tyr Ile Asp Arg Ile Glu Phe Ile Pro Val
            580                 585                 590

Thr Ala Thr Phe Glu Ala Glu Tyr Asp Leu Glu Arg Ala Gln Lys Val
            595                 600                 605

Val Asn Ala Leu Phe Thr Ser Thr Asn Gln Leu Gly Leu Lys Thr Asp
610                 615                 620

Val Thr Asp Tyr His Ile Asp Gln Val Ser Asn Leu Val Ala Cys Leu
625                 630                 635                 640

Ser Asp Glu Phe Cys Leu Asp Glu Lys Arg Glu Leu Ser Glu Lys Val
                645                 650                 655

Lys His Ala Lys Arg Leu Ser Asp Glu Arg Asn Leu Leu Gln Asp Pro
            660                 665                 670

Asn Phe Arg Gly Ile Asn Arg Gln Pro Asp Arg Gly Trp Arg Gly Ser
            675                 680                 685

Thr Asp Ile Thr Ile Gln Gly Gly Asp Asp Val Phe Lys Glu Asn Tyr
            690                 695                 700

Val Thr Leu Pro Gly Thr Phe Asp Glu Cys Tyr Pro Thr Tyr Leu Tyr
705                 710                 715                 720

Gln Lys Ile Asp Glu Ser Lys Leu Lys Ala Tyr Thr Arg Tyr Gln Leu
                725                 730                 735

Arg Gly Tyr Ile Glu Asp Ser Gln Asp Leu Glu Ile Tyr Leu Ile Arg
            740                 745                 750
```

```
Tyr Asn Ala Lys His Glu Ile Val Asn Val Pro Gly Thr Gly Ser Leu
        755                 760                 765

Trp Pro Leu Ser Val Glu Asn Gln Ile Gly Pro Cys Gly Pro Asn
770                 775                 780

Arg Cys Ala Pro His Leu Glu Trp Asn Pro Asp Leu His Cys Ser Cys
785                 790                 795                 800

Arg Asp Gly Glu Lys Cys Ala His His Ser His His Phe Ser Leu Asp
                805                 810                 815

Ile Asp Val Gly Cys Thr Asp Leu Asn Glu Asp Leu Gly Val Trp Val
        820                 825                 830

Ile Phe Lys Ile Lys Thr Gln Asp Gly His Ala Arg Leu Gly Asn Leu
        835                 840                 845

Glu Phe Leu Glu Glu Lys Pro Leu Leu Gly Glu Ala Leu Ala Arg Val
850                 855                 860

Lys Arg Ala Glu Lys Lys Trp Arg Asp Lys Arg Glu Thr Leu Gln Leu
865                 870                 875                 880

Glu Thr Thr Ile Val Tyr Lys Glu Ala Lys Glu Ser Val Asp Ala Leu
                885                 890                 895

Phe Val Asn Ser Gln Tyr Asp Arg Leu Gln Ala Asp Thr Asn Ile Ala
                900                 905                 910

Met Ile His Ala Ala Asp Lys Arg Val His Arg Ile Arg Glu Ala Tyr
        915                 920                 925

Leu Pro Glu Leu Ser Val Ile Pro Gly Val Asn Ala Ala Ile Phe Glu
        930                 935                 940

Glu Leu Glu Glu Arg Ile Phe Thr Ala Phe Ser Leu Tyr Asp Ala Arg
945                 950                 955                 960

Asn Ile Ile Lys Asn Gly Asp Phe Asn Asn Gly Leu Leu Cys Trp Asn
                965                 970                 975

Val Lys Gly His Val Glu Val Glu Glu Gln Asn Asn His Arg Ser Val
                980                 985                 990

Leu Val Ile Pro Glu Trp Glu Ala Glu Val Ser Gln Glu Val Arg Val
        995                 1000                1005

Cys Pro Gly Arg Gly Tyr Ile Leu Arg Val Thr Ala Tyr Lys Glu
1010                1015                1020

Gly Tyr Gly Glu Gly Cys Val Thr Ile His Glu Ile Glu Asn Asn
1025                1030                1035

Thr Asp Glu Leu Lys Phe Asn Asn Cys Val Glu Glu Glu Val Tyr
1040                1045                1050

Pro Asn Asn Thr Val Thr Cys Ile Asn Tyr Thr Ala Thr Gln Glu
1055                1060                1065

Glu Tyr Glu Gly Thr Tyr Thr Ser Arg Asn Arg Gly Tyr Asp Glu
1070                1075                1080

Ala Tyr Gly Asn Asn Pro Ser Val Pro Ala Asp Tyr Ala Ser Val
1085                1090                1095

Tyr Glu Glu Lys Ser Tyr Thr Asp Arg Arg Arg Glu Asn Pro Cys
1100                1105                1110

Glu Ser Asn Arg Gly Tyr Gly Asp Tyr Thr Pro Leu Pro Ala Gly
1115                1120                1125

Tyr Val Thr Lys Glu Leu Glu Tyr Phe Pro Glu Thr Asp Lys Val
1130                1135                1140

Trp Ile Glu Ile Gly Glu Thr Glu Gly Thr Phe Ile Val Asp Ser
1145                1150                1155

Val Glu Leu Leu Leu Met Glu Glu
```

1160        1165

<210> SEQ ID NO 39
<211> LENGTH: 3501
<212> TYPE: DNA
<213> ORGANISM: Artificial sequence
<220> FEATURE:
<223> OTHER INFORMATION: Synthetic DNA sequence designed for plant
      expression encoding Cry1Da1_7 with an additional Alanine residue inserted at position 2.

<400> SEQUENCE: 39
atggctgaga tcaacaacca gaaccagtgc gtcccgtaca actgcctgag caaccctaag 60
gagatcatcc tgggtgagga acgcctggag accggcaaca ccgtagccga cattagcctg 120
ggcctcatca acttcctcta cagcaacttc gtgcccggcg gtggcttcat cgtgggcctc 180
ctggagctta tctggggctt catcggcccg tcccagtggg acatcttcct cgcccagatc 240
gagcaactga tcagccagcg gatcgaggag ttcgctagga accaggccat ctcccgcctg 300
gagggactct ccaacctcta caaggtgtac gtgcgcgcgt tcagcgactg ggagaaggac 360
ccgaccaacc cggccctccg cgaggaaatg cgtatccagt tcaacgatat gaactcggcc 420
ctcatcaccg ccatcccgct cttccgcgtg cagaactacg aggtggccct cctgtccgtg 480
tacgttcaag ccgccaacct ccacctctcc atcctccgcg acgtgagcgt gttcggcgag 540
cgctggggct acgacaccgc caccatcaac aaccgctact ccgacctcac ctccctcatc 600
cacgtttaca ccaaccactg cgtggacacg tacaaccagg gcctccgccg cctggagggc 660
cgcttcctct ccgactggat cgtgtacaac cgcttccgcc gccagctcac catctccgtc 720
ctggacatcg tcgccttctt tcccaactac gacatccgca cctaccctat ccagaccgcc 780
acccagctca cccgcgaggt ctacctcgac ctcccgttca tcaacgagaa cctcagcccg 840
gccgccgtct acccgacctt ctccgccgct gagtccgcca tcattcgcag cccgcacctc 900
gtggacttcc tcaactcctt caccatctac accgactccc tcgcccgcag cgcctactgg 960
ggcggtcacc tcgtgaactc cttccgcacc ggcaccacta ccaacctcat ccgcagcccg 1020
ctctacggcc gcgagggcaa caccgagcgc ccggtgacca tcaccgccag cccgagcgtg 1080
cccatcttcc gcaccctcag ctaccccacc ggcctggaca acagcaaccc tgtggcgggc 1140
atcgagggcg tggagttcca gaacaccatc tccaggagca tctaccgcaa gagcggccct 1200
atcgacagct tcagcgagct gcctcctcag gacgccagcg tgagccctgc catcggctac 1260
agccacaggc tgtgccacgc caccttcctg gagcgcatca gcggccctcg catcgcgggc 1320
accgtgttct cgtggaccca ccgcagcgcc tctcctacga acgaggtgtc tcctagtcgc 1380
atcacccaga tcccttgggt caaggcccac accctggcta gtggcgctag tgtcatcaag 1440
ggccctggct tcaccggtgg tgacatcctg accaggaact ctatgggcga gctgggcact 1500
ctgagggtca ctttcactgg ccgcctgcct cagtcttact acatccgctt ccgctacgct 1560
agtgtcgcta accgctctgg tactttccgc tactctcagc ctccgtctta cggtatctct 1620
ttccctaaga ctatggacgc tggtgagcct ctgaccagta ggagcttcgc tcacactact 1680
ctgttcactc ctatcacttt ctctagggct caggaggagt tcgacctgta catccagtct 1740
ggtgtgtaca tcgacaggat cgagttcatc cccgtgaccg ccacgttcga ggccgagtac 1800
gaccttgagc gcgcccagaa ggtggtgaac gccctcttca ctagcactaa ccagctaggc 1860
ctgaagactg acgtgaccga ctaccacatc gaccaagtga gcaacctagt ggcctgcctc 1920
tccgacgagt tctgcctcga cgagaagcgc gagctgtccg agaaggtgaa gcacgccaag 1980

```
cgcctctccg acgagcgcaa cctgctccag acccccaact tcaggggcat caacaggcag    2040
cccgaccgcg gctggcgcgg ctccaccgac atcaccatcc agggcggtga cgacgtattc    2100
aaggagaact acgttaccct ccccggcacc ttcgacgagt gttaccccac ctacctctac    2160
cagaagatcg acgagtccaa gctgaaggcc tacacccgct accagctccg cggctacatc    2220
gaggactccc aggacctgga aatctacctc atccgctaca acgccaagca cgagatcgtg    2280
aacgtgcctg gcaccggcag cctctggcct ctcagcgtgg agaaccagat cggcccttgc    2340
ggcgagccta accgctgcgc ccctcacctc gagtggaacc ctgacctcca ctgctcgtgc    2400
agggacggcg agaagtgcgc ccaccatagc caccacttct ctctggacat cgacgtgggc    2460
tgcaccgacc tgaacgagga cctgggcgtg tgggttatct tcaagatcaa gacccaggac    2520
ggtcacgcca gctgggtaa cctggagttc cttgaggaaa agcctctgct gggtgaggcc    2580
ctggccaggg tcaagagggc tgagaagaaa tggagggata gagggagac cctgcagctg    2640 gagaccacta tcgtctacaa ggaggctaag gagtctgtcg atgctctgtt cgtcaactct    2700
cagtacgata gactgcaagc tgataccaac atcgctatga tccacgctgc ggataagcgg    2760
gtccaccgga tccgggaggc ttaccttccg gagctttctg tcatcccggg tgtcaacgct    2820
gcgatcttcg aggaacttga ggaacggatc ttcactgcgt ttagtcttta cgatgcgcgg    2880
aacatcatca gaacgggga cttcaacaat ggtctgctgt gctggaacgt caagggtcat    2940
gtcgaggtcg aggaacaaaa caatcatcgt agtgtccttg tcattcctga gtgggaggcg    3000
gaggtctctc aagaggtccg tgtttgcccg gggcgtgggt acattcttcg tgttactgcg    3060
tacaaggagg ggtacgggga ggggtgcgtt actattcatg agattgagaa caatactgat    3120
gagcttaagt tcaacaattg tgttgaggag gaggttttacc cgaacaatac tgttacgtgc    3180
atcaactaca cggcaacgca agaggaatac gaggggacgt acacctcgcg taatagaggg    3240
tatgatgagg cgtacggaaa caacccgtcg gttccagcag attatgcctc ggtttatgag    3300
gagaagtcgt acacggatag acgacgcgag aatccatgtg agtcaaatcg aggatacgga    3360
gattacacac cattaccagc aggatacgtt acaaaggagt tggaatactt cccggaaaca    3420
gataaagttt ggattgaaat cggagaaaca gaaggaacat tcatcgtcga ctcagtagaa    3480
ttgttgttga tggaagaatg a                                              3501
```

<210> SEQ ID NO 40
<211> LENGTH: 1166
<212> TYPE: PRT
<213> ORGANISM: Artificial sequence
<220> FEATURE:
<223> OTHER INFORMATION: Amino acid sequence of the engineered
      insecticidal protein Cry1Da1_7 encoded by a synthetic DNA sequence
      wherein an additional Alanine residue has been inserted at
      position 2.

<400> SEQUENCE: 40

Met Ala Glu Ile Asn Asn Gln Asn Gln Cys Val Pro Tyr Asn Cys Leu
1               5                   10                  15

Ser Asn Pro Lys Glu Ile Ile Leu Gly Glu Glu Arg Leu Glu Thr Gly
            20                  25                  30

Asn Thr Val Ala Asp Ile Ser Leu Gly Leu Ile Asn Phe Leu Tyr Ser
        35                  40                  45

Asn Phe Val Pro Gly Gly Gly Phe Ile Val Gly Leu Leu Glu Leu Ile
    50                  55                  60

Trp Gly Phe Ile Gly Pro Ser Gln Trp Asp Ile Phe Leu Ala Gln Ile

-continued

```
             65                  70                  75                  80
Glu Gln Leu Ile Ser Gln Arg Ile Glu Glu Phe Ala Arg Asn Gln Ala
                     85                  90                  95
Ile Ser Arg Leu Glu Gly Leu Ser Asn Leu Tyr Lys Val Tyr Val Arg
                100                 105                 110
Ala Phe Ser Asp Trp Glu Lys Asp Pro Thr Asn Pro Ala Leu Arg Glu
                115                 120                 125
Glu Met Arg Ile Gln Phe Asn Asp Met Asn Ser Ala Leu Ile Thr Ala
            130                 135                 140
Ile Pro Leu Phe Arg Val Gln Asn Tyr Glu Val Ala Leu Leu Ser Val
145                 150                 155                 160
Tyr Val Gln Ala Ala Asn Leu His Leu Ser Ile Leu Arg Asp Val Ser
                    165                 170                 175
Val Phe Gly Glu Arg Trp Gly Tyr Asp Thr Ala Thr Ile Asn Asn Arg
                180                 185                 190
Tyr Ser Asp Leu Thr Ser Leu Ile His Val Tyr Thr Asn His Cys Val
                195                 200                 205
Asp Thr Tyr Asn Gln Gly Leu Arg Arg Leu Glu Gly Arg Phe Leu Ser
            210                 215                 220
Asp Trp Ile Val Tyr Asn Arg Phe Arg Arg Gln Leu Thr Ile Ser Val
225                 230                 235                 240
Leu Asp Ile Val Ala Phe Phe Pro Asn Tyr Asp Ile Arg Thr Tyr Pro
                    245                 250                 255
Ile Gln Thr Ala Thr Gln Leu Thr Arg Glu Val Tyr Leu Asp Leu Pro
                260                 265                 270
Phe Ile Asn Glu Asn Leu Ser Pro Ala Ala Val Tyr Pro Thr Phe Ser
            275                 280                 285
Ala Ala Glu Ser Ala Ile Ile Arg Ser Pro His Leu Val Asp Phe Leu
            290                 295                 300
Asn Ser Phe Thr Ile Tyr Thr Asp Ser Leu Ala Arg Ser Ala Tyr Trp
305                 310                 315                 320
Gly Gly His Leu Val Asn Ser Phe Arg Thr Gly Thr Thr Thr Asn Leu
                    325                 330                 335
Ile Arg Ser Pro Leu Tyr Gly Arg Glu Gly Asn Thr Glu Arg Pro Val
                340                 345                 350
Thr Ile Thr Ala Ser Pro Ser Val Pro Ile Phe Arg Thr Leu Ser Tyr
            355                 360                 365
Pro Thr Gly Leu Asp Asn Ser Asn Pro Val Ala Gly Ile Glu Gly Val
370                 375                 380
Glu Phe Gln Asn Thr Ile Ser Arg Ser Ile Tyr Arg Lys Ser Gly Pro
385                 390                 395                 400
Ile Asp Ser Phe Ser Glu Leu Pro Pro Gln Asp Ala Ser Val Ser Pro
                    405                 410                 415
Ala Ile Gly Tyr Ser His Arg Leu Cys His Ala Thr Phe Leu Glu Arg
                420                 425                 430
Ile Ser Gly Pro Arg Ile Ala Gly Thr Val Phe Ser Trp Thr His Arg
            435                 440                 445
Ser Ala Ser Pro Thr Asn Glu Val Ser Pro Ser Arg Ile Thr Gln Ile
            450                 455                 460
Pro Trp Val Lys Ala His Thr Leu Ala Ser Gly Ala Ser Val Ile Lys
465                 470                 475                 480
Gly Pro Gly Phe Thr Gly Gly Asp Ile Leu Thr Arg Asn Ser Met Gly
                    485                 490                 495
```

```
Glu Leu Gly Thr Leu Arg Val Thr Phe Thr Gly Arg Leu Pro Gln Ser
            500                 505                 510

Tyr Tyr Ile Arg Phe Arg Tyr Ala Ser Val Ala Asn Arg Ser Gly Thr
            515                 520                 525

Phe Arg Tyr Ser Gln Pro Pro Ser Tyr Gly Ile Ser Phe Pro Lys Thr
            530                 535                 540

Met Asp Ala Gly Glu Pro Leu Thr Ser Arg Ser Phe Ala His Thr Thr
545                 550                 555                 560

Leu Phe Thr Pro Ile Thr Phe Ser Arg Ala Gln Glu Glu Phe Asp Leu
                565                 570                 575

Tyr Ile Gln Ser Gly Val Tyr Ile Asp Arg Ile Glu Phe Ile Pro Val
            580                 585                 590

Thr Ala Thr Phe Glu Ala Glu Tyr Asp Leu Glu Arg Ala Gln Lys Val
            595                 600                 605

Val Asn Ala Leu Phe Thr Ser Thr Asn Gln Leu Gly Leu Lys Thr Asp
            610                 615                 620

Val Thr Asp Tyr His Ile Asp Gln Val Ser Asn Leu Val Ala Cys Leu
625                 630                 635                 640

Ser Asp Glu Phe Cys Leu Asp Glu Lys Arg Glu Leu Ser Glu Lys Val
                645                 650                 655

Lys His Ala Lys Arg Leu Ser Asp Glu Arg Asn Leu Leu Gln Asp Pro
            660                 665                 670

Asn Phe Arg Gly Ile Asn Arg Gln Pro Asp Arg Gly Trp Arg Gly Ser
            675                 680                 685

Thr Asp Ile Thr Ile Gln Gly Gly Asp Asp Val Phe Lys Glu Asn Tyr
            690                 695                 700

Val Thr Leu Pro Gly Thr Phe Asp Glu Cys Tyr Pro Thr Tyr Leu Tyr
705                 710                 715                 720

Gln Lys Ile Asp Glu Ser Lys Leu Lys Ala Tyr Thr Arg Tyr Gln Leu
                725                 730                 735

Arg Gly Tyr Ile Glu Asp Ser Gln Asp Leu Glu Ile Tyr Leu Ile Arg
            740                 745                 750

Tyr Asn Ala Lys His Glu Ile Val Asn Val Pro Gly Thr Gly Ser Leu
            755                 760                 765

Trp Pro Leu Ser Val Glu Asn Gln Ile Gly Pro Cys Gly Glu Pro Asn
            770                 775                 780

Arg Cys Ala Pro His Leu Glu Trp Asn Pro Asp Leu His Cys Ser Cys
785                 790                 795                 800

Arg Asp Gly Glu Lys Cys Ala His His Ser His His Phe Ser Leu Asp
                805                 810                 815

Ile Asp Val Gly Cys Thr Asp Leu Asn Glu Asp Leu Gly Val Trp Val
            820                 825                 830

Ile Phe Lys Ile Lys Thr Gln Asp Gly His Ala Arg Leu Gly Asn Leu
            835                 840                 845

Glu Phe Leu Glu Glu Lys Pro Leu Leu Gly Glu Ala Leu Ala Arg Val
            850                 855                 860

Lys Arg Ala Glu Lys Lys Trp Arg Asp Lys Arg Glu Thr Leu Gln Leu
865                 870                 875                 880

Glu Thr Thr Ile Val Tyr Lys Glu Ala Lys Glu Ser Val Asp Ala Leu
                885                 890                 895

Phe Val Asn Ser Gln Tyr Asp Arg Leu Gln Ala Asp Thr Asn Ile Ala
            900                 905                 910
```

```
Met Ile His Ala Ala Asp Lys Arg Val His Arg Ile Arg Glu Ala Tyr
        915                 920                 925

Leu Pro Glu Leu Ser Val Ile Pro Gly Val Asn Ala Ala Ile Phe Glu
    930                 935                 940

Glu Leu Glu Glu Arg Ile Phe Thr Ala Phe Ser Leu Tyr Asp Ala Arg
945                 950                 955                 960

Asn Ile Ile Lys Asn Gly Asp Phe Asn Asn Gly Leu Leu Cys Trp Asn
                965                 970                 975

Val Lys Gly His Val Glu Val Glu Glu Gln Asn Asn His Arg Ser Val
            980                 985                 990

Leu Val Ile Pro Glu Trp Glu Ala  Glu Val Ser Gln Glu  Val Arg Val
            995                 1000                 1005

Cys Pro Gly Arg Gly Tyr Ile  Leu Arg Val Thr Ala  Tyr Lys Glu
    1010                1015                1020

Gly Tyr Gly Glu Gly Cys Val  Thr Ile His Glu Ile  Glu Asn Asn
    1025                1030                1035

Thr Asp Glu Leu Lys Phe Asn  Asn Cys Val Glu Glu  Val Tyr
    1040                1045                1050

Pro Asn Asn Thr Val Thr Cys  Ile Asn Tyr Thr Ala  Thr Gln Glu
    1055                1060                1065

Glu Tyr Glu Gly Thr Tyr Thr  Ser Arg Asn Arg Gly  Tyr Asp Glu
    1070                1075                1080

Ala Tyr Gly Asn Asn Pro Ser  Val Pro Ala Asp Tyr  Ala Ser Val
    1085                1090                1095

Tyr Glu Glu Lys Ser Tyr Thr  Asp Arg Arg Arg Glu  Asn Pro Cys
    1100                1105                1110

Glu Ser Asn Arg Gly Tyr Gly  Asp Tyr Thr Pro Leu  Pro Ala Gly
    1115                1120                1125

Tyr Val Thr Lys Glu Leu Glu  Tyr Phe Pro Glu Thr  Asp Lys Val
    1130                1135                1140

Trp Ile Glu Ile Gly Glu Thr  Glu Gly Thr Phe Ile  Val Asp Ser
    1145                1150                1155

Val Glu  Leu Leu Leu Met Glu  Glu
    1160                1165

<210> SEQ ID NO 41
<211> LENGTH: 3423
<212> TYPE: DNA
<213> ORGANISM: Artificial sequence
<220> FEATURE:
<223> OTHER INFORMATION: Synthetic DNA sequence designed for plant
      expression encoding TIC844 with an additional Alanine residue
      inserted at position 2.

<400> SEQUENCE: 41
atggctgaga tcaacaacca gaaccagtgc gtcccgtaca actgcctgag caaccctaag     60
gagatcatcc tgggtgagga acgcctggag accggcaaca ccgtagccga cattagcctg    120
ggcctcatca acttcctcta cagcaacttc gtgcccggcg gtggcttcat cgtgggcctc    180
ctggagctta tctggggctt catcggcccg tcccagtggg acatcttcct cgcccagatc    240
gagcaactga tcagccagcg gatcgaggag ttcgctagga accaggccat ctcccgcctg    300
gagggactct ccaacctcta caaggtgtac gtgcgcgcgt tcagcgactg ggagaaggac    360
ccgaccaacc cggccctccg cgaggaaatg cgtatccagt tcaacgatat gaactcggcc    420
ctcatcaccg ccatcccgct cttccgcgtg cagaactacg aggtggccct cctgtccgtg    480
```

-continued

```
tacgttcaag ccgccaacct ccacctctcc atcctccgcg acgtgagcgt gttcggcgag    540
cgctggggct acgacaccgc caccatcaac aaccgctact ccgacctcac ctccctcatc    600
cacgtttaca ccaaccactg cgtggacacg tacaaccagg gcctccgccg cctggagggc    660
cgcttcctct ccgactggat cgtgtacaac cgcttccgcc gccagctcac catctccgtc    720
ctggacatcg tcgccttctt tcccaactac gacatccgca cctaccctat ccagaccgcc    780
acccagctca cccgcgaggt ctacctcgac ctcccgttca tcaacgagaa cctcagcccg    840
gccgccagct acccgacctt ctccgccgct gagtccgcca tcattcgcag cccgcacctc    900
gtggacttcc tcaactcctt caccatctac accgactccc tcgcccgcta cgcctactgg    960
ggcggtcacc tcgtgaactc cttccgcacc ggcaccacta ccaacctcat ccgcagcccg   1020
ctctacggcc gcgagggcaa caccgagcgc ccggtgacca tcaccgccag cccgagcgtg   1080
cccatcttcc gcaccctcag ctacatcacc ggcctggaca acagcaaccc tgtggcgggc   1140
atcgagggcg tggagttcca gaacaccatc tccaggagca tctaccgcaa gagcggccct   1200
atcgacagct tcagcgagct gcctcctcag gacgccagcg tgagccctgc catcggctac   1260
agccacaggc tgtgccacgc caccttcctg gagcgcatca gcggccctcg catcgcgggc   1320
accgtgttct cgtggaccca ccgcagcgcc tctcctacga acgaggtgtc tcctagtcgc   1380
atcacccaga tcccttgggt caaggcccac accctggcta gtggcgctag tgtcatcaag   1440
ggccctggct tcaccggtgg tgacatcctg accaggaact ctatgggcga gctgggcact   1500
ctgagggtca ctttcactgg ccgcctgcct cagtcttact acatccgctt ccgctacgct   1560
agtgtcgcta accgctctgg tactttccgc tactctcagc ctccgtctta cggtatctct   1620
ttccctaaga ctatggacgc tggtgagcct ctgaccagta ggagcttcgc tcacactact   1680
ctgttcactc ctatcacttt tctctagggct caggaggagt tcgacctgta catccagtct   1740
ggtgtgtaca tcgacaggat cgagttcatc cccgtgaccg ccacgttcga ggccgagtac   1800
gaccttgagc gcgcccagaa ggctgtcaat gagctcttca cgtccagcaa tcagatcggc   1860
ctgaagaccg acgtcactga ctaccacatc gaccaagtct ccaacctcgt ggagtgcctc   1920
tccgatgagt tctgcctcga cgagaagaag gagctgtccg agaaggtgaa gcatgccaag   1980
cgtctcagcg acgagaggaa tctcctccag gaccccaatt ccgcggcat caacaggcag   2040
ctcgaccgcg gctggcgcgg cagcaccgac atcacgatcc agggcggcga cgatgtgttc   2100
aaggagaact acgtgactct cctgggcact ttcgacgagt gctaccctac ctacttgtac   2160
cagaagatcg atgagtccaa gctcaaggct tacactcgct accagctccg cggctacatc   2220
gaagacagcc aagacctcga gatttacctg atccgctaca acgccaagca cgagaccgtc   2280
aacgtgcccg gtactggttc cctctggccg ctgagcgccc ccagcccgat cggcaagtgt   2340
gcccaccaca gccaccactt ctccttggac atcgatgtgg gctgcaccga cctgaacgag   2400
gacctcggag tctgggtcat cttcaagatc aagacccagg acggccacgc gcgcctgggc   2460
aacctggagt cctcgagga gaagcccctg gtcggtgagg ctctggccag ggtcaagagg   2520
gctgagaaga agtggaggga caagcgcgag aagctcgagt gggagaccaa catcgtttac   2580
aaggaggcca aggagagcgt cgacgccctg ttcgtgaact cccagtacga ccgcctgcag   2640
gccgacacca acatcgccat gatccacgct gccgacaaga gggtgcacag cattcgcgag   2700
gcctacctgc ctgagctgtc cgtgatccct ggtgtgaacg ctgccatctt tgaggagctg   2760
gagggccgca tctttacccgc attctccctg tacgacgccc gcaacgtgat caagaacggt   2820
gacttcaaca atggcctcag ctgctggaac gtcaagggcc acgtggacgt cgaggaacag   2880
```

```
aacaaccacc gctccgtcct ggtcgtccca gagtgggagg ctgaggtctc ccaagaggtc    2940
cgcgtctgcc caggccgcgg ctacattctc agggtcaccg cttacaagga gggctacggt    3000
gagggctgtg tgaccatcca cgagatcgag aacaacaccg acgagcttaa gttctccaac    3060
tgcgtggagg aggaggtgta cccaaacaac accgttactt gcaacgacta caccgccacc    3120
caggaggagt acgagggcac ctacacttcc aggaacaggg gctacgatgg tgcctacgag    3180
agcaacagca gcgttcctgc tgactacgct tccgcctacg aggagaaggc ctacacggat    3240
ggccgcaggg acaaccettg cgagagcaac cgcggctacg gcgactacac tccectgccc    3300 gccggctacg ttaccaagga gctggagtac ttcccggaga ctgacaaggt gtggatcgag    3360
atcggcgaga ccgagggcac cttcatcgtg gacagcgtgg agctgctcct gatggaggag    3420
tag                                                                  3423
```

<210> SEQ ID NO 42
<211> LENGTH: 1140
<212> TYPE: PRT
<213> ORGANISM: Artificial sequence
<220> FEATURE:
<223> OTHER INFORMATION: Amino acid sequence of the chimeric protein
      TIC844 encoded by a synthetic DNA sequence wherein an additional
      Alanine residue has been inserted at position 2.

<400> SEQUENCE: 42

```
Met Ala Glu Ile Asn Asn Gln Asn Gln Cys Val Pro Tyr Asn Cys Leu
1               5                   10                  15

Ser Asn Pro Lys Glu Ile Ile Leu Gly Glu Glu Arg Leu Glu Thr Gly
            20                  25                  30

Asn Thr Val Ala Asp Ile Ser Leu Gly Leu Ile Asn Phe Leu Tyr Ser
        35                  40                  45

Asn Phe Val Pro Gly Gly Gly Phe Ile Val Gly Leu Leu Glu Leu Ile
    50                  55                  60

Trp Gly Phe Ile Gly Pro Ser Gln Trp Asp Ile Phe Leu Ala Gln Ile
65                  70                  75                  80

Glu Gln Leu Ile Ser Gln Arg Ile Glu Glu Phe Ala Arg Asn Gln Ala
                85                  90                  95

Ile Ser Arg Leu Glu Gly Leu Ser Asn Leu Tyr Lys Val Tyr Val Arg
            100                 105                 110

Ala Phe Ser Asp Trp Glu Lys Asp Pro Thr Asn Pro Ala Leu Arg Glu
        115                 120                 125

Glu Met Arg Ile Gln Phe Asn Asp Met Asn Ser Ala Leu Ile Thr Ala
    130                 135                 140

Ile Pro Leu Phe Arg Val Gln Asn Tyr Glu Val Ala Leu Leu Ser Val
145                 150                 155                 160

Tyr Val Gln Ala Ala Asn Leu His Leu Ser Ile Leu Arg Asp Val Ser
                165                 170                 175

Val Phe Gly Glu Arg Trp Gly Tyr Asp Thr Ala Thr Ile Asn Asn Arg
            180                 185                 190

Tyr Ser Asp Leu Thr Ser Leu Ile His Val Tyr Thr Asn His Cys Val
        195                 200                 205

Asp Thr Tyr Asn Gln Gly Leu Arg Arg Leu Glu Gly Arg Phe Leu Ser
    210                 215                 220

Asp Trp Ile Val Tyr Asn Arg Phe Arg Arg Gln Leu Thr Ile Ser Val
225                 230                 235                 240

Leu Asp Ile Val Ala Phe Phe Pro Asn Tyr Asp Ile Arg Thr Tyr Pro
```

-continued

```
                245                 250                 255
Ile Gln Thr Ala Thr Gln Leu Thr Arg Glu Val Tyr Leu Asp Leu Pro
            260                 265                 270
Phe Ile Asn Glu Asn Leu Ser Pro Ala Ala Ser Tyr Pro Thr Phe Ser
            275                 280                 285
Ala Ala Glu Ser Ala Ile Ile Arg Ser Pro His Leu Val Asp Phe Leu
            290                 295                 300
Asn Ser Phe Thr Ile Tyr Thr Asp Ser Leu Ala Arg Tyr Ala Tyr Trp
305                 310                 315                 320
Gly Gly His Leu Val Asn Ser Phe Arg Thr Gly Thr Thr Asn Leu
            325                 330                 335
Ile Arg Ser Pro Leu Tyr Gly Arg Glu Gly Asn Thr Glu Arg Pro Val
            340                 345                 350
Thr Ile Thr Ala Ser Pro Ser Val Pro Ile Phe Arg Thr Leu Ser Tyr
            355                 360                 365
Ile Thr Gly Leu Asp Asn Ser Asn Pro Val Ala Gly Ile Glu Gly Val
            370                 375                 380
Glu Phe Gln Asn Thr Ile Ser Arg Ser Ile Tyr Arg Lys Ser Gly Pro
385                 390                 395                 400
Ile Asp Ser Phe Ser Glu Leu Pro Pro Gln Asp Ala Ser Val Ser Pro
                405                 410                 415
Ala Ile Gly Tyr Ser His Arg Leu Cys His Ala Thr Phe Leu Glu Arg
            420                 425                 430
Ile Ser Gly Pro Arg Ile Ala Gly Thr Val Phe Ser Trp Thr His Arg
            435                 440                 445
Ser Ala Ser Pro Thr Asn Glu Val Ser Pro Ser Arg Ile Thr Gln Ile
            450                 455                 460
Pro Trp Val Lys Ala His Thr Leu Ala Ser Gly Ala Ser Val Ile Lys
465                 470                 475                 480
Gly Pro Gly Phe Thr Gly Gly Asp Ile Leu Thr Arg Asn Ser Met Gly
                485                 490                 495
Glu Leu Gly Thr Leu Arg Val Thr Phe Thr Gly Arg Leu Pro Gln Ser
            500                 505                 510
Tyr Tyr Ile Arg Phe Arg Tyr Ala Ser Val Ala Asn Arg Ser Gly Thr
            515                 520                 525
Phe Arg Tyr Ser Gln Pro Pro Ser Tyr Gly Ile Ser Phe Pro Lys Thr
            530                 535                 540
Met Asp Ala Gly Glu Pro Leu Thr Ser Arg Ser Phe Ala His Thr Thr
545                 550                 555                 560
Leu Phe Thr Pro Ile Thr Phe Ser Arg Ala Gln Glu Glu Phe Asp Leu
                565                 570                 575
Tyr Ile Gln Ser Gly Val Tyr Ile Asp Arg Ile Glu Phe Ile Pro Val
            580                 585                 590
Thr Ala Thr Phe Glu Ala Glu Tyr Asp Leu Glu Arg Ala Gln Lys Ala
            595                 600                 605
Val Asn Glu Leu Phe Thr Ser Ser Asn Gln Ile Gly Leu Lys Thr Asp
            610                 615                 620
Val Thr Asp Tyr His Ile Asp Gln Val Ser Asn Leu Val Glu Cys Leu
625                 630                 635                 640
Ser Asp Glu Phe Cys Leu Asp Glu Lys Lys Glu Leu Ser Glu Lys Val
                645                 650                 655
Lys His Ala Lys Arg Leu Ser Asp Glu Arg Asn Leu Leu Gln Asp Pro
            660                 665                 670
```

```
Asn Phe Arg Gly Ile Asn Arg Gln Leu Asp Arg Gly Trp Arg Gly Ser
        675                 680                 685

Thr Asp Ile Thr Ile Gln Gly Gly Asp Asp Val Phe Lys Glu Asn Tyr
690                 695                 700

Val Thr Leu Leu Gly Thr Phe Asp Glu Cys Tyr Pro Thr Tyr Leu Tyr
705                 710                 715                 720

Gln Lys Ile Asp Glu Ser Lys Leu Lys Ala Tyr Thr Arg Tyr Gln Leu
                725                 730                 735

Arg Gly Tyr Ile Glu Asp Ser Gln Asp Leu Glu Ile Tyr Leu Ile Arg
            740                 745                 750

Tyr Asn Ala Lys His Glu Thr Val Asn Val Pro Gly Thr Gly Ser Leu
                755                 760                 765

Trp Pro Leu Ser Ala Pro Ser Pro Ile Gly Lys Cys Ala His His Ser
770                 775                 780

His His Phe Ser Leu Asp Ile Asp Val Gly Cys Thr Asp Leu Asn Glu
785                 790                 795                 800

Asp Leu Gly Val Trp Val Ile Phe Lys Ile Lys Thr Gln Asp Gly His
                805                 810                 815

Ala Arg Leu Gly Asn Leu Glu Phe Leu Glu Lys Pro Leu Val Gly
                820                 825                 830

Glu Ala Leu Ala Arg Val Lys Arg Ala Glu Lys Lys Trp Arg Asp Lys
835                 840                 845

Arg Glu Lys Leu Glu Trp Glu Thr Asn Ile Val Tyr Lys Glu Ala Lys
850                 855                 860

Glu Ser Val Asp Ala Leu Phe Val Asn Ser Gln Tyr Asp Arg Leu Gln
865                 870                 875                 880

Ala Asp Thr Asn Ile Ala Met Ile His Ala Ala Asp Lys Arg Val His
                885                 890                 895

Ser Ile Arg Glu Ala Tyr Leu Pro Glu Leu Ser Val Ile Pro Gly Val
            900                 905                 910

Asn Ala Ala Ile Phe Glu Glu Leu Glu Gly Arg Ile Phe Thr Ala Phe
            915                 920                 925

Ser Leu Tyr Asp Ala Arg Asn Val Ile Lys Asn Gly Asp Phe Asn Asn
930                 935                 940

Gly Leu Ser Cys Trp Asn Val Lys Gly His Val Asp Val Glu Glu Gln
945                 950                 955                 960

Asn Asn His Arg Ser Val Leu Val Pro Glu Trp Glu Ala Glu Val
            965                 970                 975

Ser Gln Glu Val Arg Val Cys Pro Gly Arg Gly Tyr Ile Leu Arg Val
            980                 985                 990

Thr Ala Tyr Lys Glu Gly Tyr Gly Glu Gly Cys Val Thr Ile His Glu
            995                 1000                1005

Ile Glu Asn Asn Thr Asp Glu Leu Lys Phe Ser Asn Cys Val Glu
    1010                1015                1020

Glu Glu Val Tyr Pro Asn Asn Thr Val Thr Cys Asn Asp Tyr Thr
    1025                1030                1035

Ala Thr Gln Glu Glu Tyr Gly Thr Tyr Thr Ser Arg Asn Arg
    1040                1045                1050

Gly Tyr Asp Gly Ala Tyr Glu Ser Asn Ser Ser Val Pro Ala Asp
    1055                1060                1065

Tyr Ala Ser Ala Tyr Glu Glu Lys Ala Tyr Thr Asp Gly Arg Arg
    1070                1075                1080
```

| | | | | | | | | | | |
|---|---|---|---|---|---|---|---|---|---|---|
|Asp|Asn|Pro|Cys|Glu|Ser|Asn|Arg|Gly|Tyr|Gly|Asp|Tyr|Thr|Pro|
| |1085| | | | |1090| | | |1095| | | | |

| | | | | | | | | | |
|---|---|---|---|---|---|---|---|---|---|
|Leu|Pro|Ala|Gly|Tyr|Val|Thr|Lys|Glu|Leu|Glu|Tyr|Phe|Pro|Glu|
| |1100| | | | |1105| | | |1110| | | | |

| | | | | | | | | | |
|---|---|---|---|---|---|---|---|---|---|
|Thr|Asp|Lys|Val|Trp|Ile|Glu|Ile|Gly|Glu|Thr|Glu|Gly|Thr|Phe|
| |1115| | | | |1120| | | |1125| | | | |

| | | | | | | | | | |
|---|---|---|---|---|---|---|---|---|---|
|Ile|Val|Asp|Ser|Val|Glu|Leu|Leu|Leu|Met|Glu|Glu|
| |1130| | | | |1135| | | |1140| |

```
<210> SEQ ID NO 43
<211> LENGTH: 3423
<212> TYPE: DNA
<213> ORGANISM: Artificial
<220> FEATURE:
<223> OTHER INFORMATION: Synthetic DNA sequence designed for plant
      expression encoding TIC844_8 with an additional Alanine residue
      inserted at position 2.

<400> SEQUENCE: 43
```

| | |
|---|---|
|atggctgaga tcaacaacca gaaccagtgc gtcccgtaca actgcctgag caaccctaag|60|
|gagatcatcc tgggtgagga acgcctggag accggcaaca ccgtagccga cattagcctg|120|
|ggcctcatca acttcctcta cagcaacttc gtgcccggcg tggcttcat cgtgggcctc|180|
|ctggagctta tctggggctt catcggcccg tcccagtggg acatcttcct cgcccagatc|240|
|gagcaactga tcagccagcg gatcgaggag ttcgctagga accaggccat ctcccgcctg|300|
|gagggactct ccaacctcta caaggtgtac gtgcgcgcgt tcagcgactg ggagaaggac|360|
|ccgaccaacc cggccctccg cgaggaaatg cgtatccagt tcaacgatat gaactcggcc|420|
|ctcatcaccg ccatcccgct cttccgcgtg cagaactacg aggtggccct cctgtccgtg|480|
|tacgttcaag ccgccaacct ccacctctcc atcctccgcg acgtgagcgt gttcggcgag|540|
|cgctggggct acgacaccgc caccatcaac aaccgctact ccgacctcac ctccctcatc|600|
|cacgtttaca ccaaccactg cgtggacacg tacaaccagg gcctccgccg cctggagggc|660|
|cgcttcctct ccgactggat cgtgtacaac cgcttccgcc gccagctcac catctccgtc|720|
|ctggacatcg tcgccttctt tcccaactac gacatccgca cctacccttat ccagaccgcc|780|
|acccagctca cccgcgaggt ctacctcgac ctcccgttca tcaacgagaa cctcagcccg|840|
|gccgccgtct acccgacctt ctccgccgct gagtccgcca tcattcgcag cccgcacctc|900|
|gtggacttcc tcaactcctt caccatctac accgactccc tcgcccgcag cgcctactgg|960|
|ggcggtcacc tcgtgaactc cttccgcacc ggcaccacta ccaacctcat ccgcagcccg|1020|
|ctctacggcc gcgagggcaa caccgagcgc ccggtgacca tcaccgccag cccgagcgtg|1080|
|cccatcttcc gcaccctcag ctaccccacc ggcctggaca cagcaaccc tgtggcgggc|1140|
|atcgagggcg tggagttcca gaacaccatc tccaggagca tctaccgcaa gagcggccct|1200|
|atcgacagct tcagcgagct gcctcctcag gacgccagcg tgagccctgc catcggctac|1260|
|agccacaggc tgtgccacgc caccttcctg gagcgcatca gcggccctcg catcgcgggc|1320|
|accgtgttct cgtggaccca ccgcagcgcc tctcctacga acgaggtgtc tcctagtcgc|1380|
|atcacccaga tccttgggt caaggccac accctggcta gtggcgctag tgtcatcaag|1440|
|ggccctggct tcaccggtgg tgacatcctg accaggaact ctatgggcga gctgggcact|1500|
|ctgagggtca ctttcactgg ccgcctgcct cagtcttact acatccgctt ccgctacgct|1560|
|agtgtcgcta accgctctgg tactttccgc tactctcagc ctccgtctta cggtatctct|1620|
|ttccctaaga ctatggacgc tggtgagcct ctgaccagta ggagcttcgc tcacactact|1680|

```
ctgttcactc ctatcacttt ctctagggct caggaggagt tcgacctgta catccagtct    1740
ggtgtgtaca tcgacaggat cgagttcatc cccgtgaccg ccacgttcga ggccgagtac    1800
gaccttgagc gcgcccagaa ggctgtcaat gagctcttca cgtccagcaa tcagatcggc    1860
ctgaagaccg acgtcactga ctaccacatc gaccaagtct ccaacctcgt ggagtgcctc    1920
tccgatgagt tctgcctcga cgagaagaag gagctgtccg agaaggtgaa gcatgccaag    1980
cgtctcagcg acgagaggaa tctcctccag gaccccaatt ccgcggcat caacaggcag    2040 ctcgaccgcg gctggcgcgg cagcaccgac atcacgatcc agggcggcga cgatgtgttc    2100
aaggagaact acgtgactct cctgggcact ttcgacgagt gctaccctac ctacttgtac    2160
cagaagatcg atgagtccaa gctcaaggct tacactcgct accagctccg cggctacatc    2220
gaagacagcc aagacctcga gatttacctg atccgctaca acgccaagca cgagaccgtc    2280
aacgtgcccg gtactggttc cctctggccg ctgagcgccc ccagcccgat cggcaagtgt    2340
gcccaccaca gccaccactt ctccttggac atcgatgtgg gctgcaccga cctgaacgag    2400
gacctcggag tctgggtcat cttcaagatc aagacccagg acggccacgc gcgcctgggc    2460
aacctggagt tcctcgagga gaagcccctg gtcggtgagg ctctggccag ggtcaagagg    2520
gctgagaaga agtggaggga caagcgcgag aagctcgagt gggagaccaa catcgtttac    2580
aaggaggcca aggagagcgt cgacgccctg ttcgtgaact cccagtacga ccgcctgcag    2640
gccgacacca acatcgccat gatccacgct gccgacaaga gggtgcacag cattcgcgag    2700
gcctacctgc ctgagctgtc cgtgatccct ggtgtgaacg ctgccatctt tgaggagctg    2760
gagggccgca tctttaccgc attctccctg tacgacgccc gcaacgtgat caagaacggt    2820
gacttcaaca atggcctcag ctgctggaac gtcaagggcc acgtggacgt cgaggaacag    2880
aacaaccacc gctccgtcct ggtcgtccca gagtgggagg ctgaggtctc ccaagaggtc    2940
cgcgtctgcc caggccgcgg ctacattctc agggtcaccg cttacaagga gggctacggt    3000
gagggctgtg tgaccatcca cgagatcgag aacaacaccg acgagcttaa gttctccaac    3060
tgcgtggagg aggaggtgta cccaaacaac accgttactt gcaacgacta caccgccacc    3120
caggaggagt acgagggcac ctacacttcc aggaacaggg gctacgatgg tgcctacgag    3180
agcaacagca gcgttcctgc tgactacgct tccgcctacg aggagaaggc ctacacggat    3240
ggccgcaggg acaaccctg cgagagcaac cgcggctacg cgactacac tcccctgccc    3300 gccggctacg ttaccaagga gctggagtac ttcccggaga ctgacaaggt gtggatcgag    3360
atcggcgaga ccgagggcac cttcatcgtg gacagcgtgg agctgctcct gatggaggag    3420
tag                                                                  3423
```

<210> SEQ ID NO 44
<211> LENGTH: 1140
<212> TYPE: PRT
<213> ORGANISM: Artificial
<220> FEATURE:
<223> OTHER INFORMATION: Amino acid sequence of the engineered
      insecticidal chimeric protein TIC844_8 encoded by a synthetic DNA
      sequence wherein an additional Alanine residue has been inserted
      at position 2.

<400> SEQUENCE: 44

Met Ala Glu Ile Asn Asn Gln Asn Gln Cys Val Pro Tyr Asn Cys Leu
1               5                   10                  15

Ser Asn Pro Lys Glu Ile Ile Leu Gly Glu Glu Arg Leu Glu Thr Gly
            20                  25                  30

```
Asn Thr Val Ala Asp Ile Ser Leu Gly Leu Ile Asn Phe Leu Tyr Ser
         35                  40                  45

Asn Phe Val Pro Gly Gly Phe Ile Val Gly Leu Leu Glu Leu Ile
 50                  55                  60

Trp Gly Phe Ile Gly Pro Ser Gln Trp Asp Ile Phe Leu Ala Gln Ile
 65                  70                  75                  80

Glu Gln Leu Ile Ser Gln Arg Ile Glu Phe Ala Arg Asn Gln Ala
                 85                  90                  95

Ile Ser Arg Leu Glu Gly Leu Ser Asn Leu Tyr Lys Val Tyr Val Arg
                100                 105                 110

Ala Phe Ser Asp Trp Glu Lys Asp Pro Thr Asn Pro Ala Leu Arg Glu
                115                 120                 125

Glu Met Arg Ile Gln Phe Asn Asp Met Asn Ser Ala Leu Ile Thr Ala
        130                 135                 140

Ile Pro Leu Phe Arg Val Gln Asn Tyr Glu Val Ala Leu Leu Ser Val
145                 150                 155                 160

Tyr Val Gln Ala Ala Asn Leu His Leu Ser Ile Leu Arg Asp Val Ser
                165                 170                 175

Val Phe Gly Glu Arg Trp Gly Tyr Asp Thr Ala Thr Ile Asn Asn Arg
        180                 185                 190

Tyr Ser Asp Leu Thr Ser Leu Ile His Val Tyr Thr Asn His Cys Val
        195                 200                 205

Asp Thr Tyr Asn Gln Gly Leu Arg Arg Leu Glu Gly Arg Phe Leu Ser
        210                 215                 220

Asp Trp Ile Val Tyr Asn Arg Phe Arg Arg Gln Leu Thr Ile Ser Val
225                 230                 235                 240

Leu Asp Ile Val Ala Phe Phe Pro Asn Tyr Asp Ile Arg Thr Tyr Pro
                245                 250                 255

Ile Gln Thr Ala Thr Gln Leu Thr Arg Glu Val Tyr Leu Asp Leu Pro
                260                 265                 270

Phe Ile Asn Glu Asn Leu Ser Pro Ala Ala Val Tyr Pro Thr Phe Ser
        275                 280                 285

Ala Ala Glu Ser Ala Ile Ile Arg Ser Pro His Leu Val Asp Phe Leu
        290                 295                 300

Asn Ser Phe Thr Ile Tyr Thr Asp Ser Leu Ala Arg Ser Ala Tyr Trp
305                 310                 315                 320

Gly Gly His Leu Val Asn Ser Phe Arg Thr Gly Thr Thr Asn Leu
                325                 330                 335

Ile Arg Ser Pro Leu Tyr Gly Arg Glu Gly Asn Thr Glu Arg Pro Val
                340                 345                 350

Thr Ile Thr Ala Ser Pro Ser Val Pro Ile Phe Arg Thr Leu Ser Tyr
        355                 360                 365

Pro Thr Gly Leu Asp Asn Ser Asn Pro Val Ala Gly Ile Glu Gly Val
        370                 375                 380

Glu Phe Gln Asn Thr Ile Ser Arg Ser Ile Tyr Arg Lys Ser Gly Pro
385                 390                 395                 400

Ile Asp Ser Phe Ser Glu Leu Pro Pro Gln Asp Ala Ser Val Ser Pro
                405                 410                 415

Ala Ile Gly Tyr Ser His Arg Leu Cys His Ala Thr Phe Leu Glu Arg
                420                 425                 430

Ile Ser Gly Pro Arg Ile Ala Gly Thr Val Phe Ser Trp Thr His Arg
        435                 440                 445
```

-continued

```
Ser Ala Ser Pro Thr Asn Glu Val Ser Pro Ser Arg Ile Thr Gln Ile
450                 455                 460
Pro Trp Val Lys Ala His Thr Leu Ala Ser Gly Ala Ser Val Ile Lys
465                 470                 475                 480
Gly Pro Gly Phe Thr Gly Gly Asp Ile Leu Thr Arg Asn Ser Met Gly
                    485                 490                 495
Glu Leu Gly Thr Leu Arg Val Thr Phe Thr Gly Arg Leu Pro Gln Ser
                500                 505                 510
Tyr Tyr Ile Arg Phe Arg Tyr Ala Ser Val Ala Asn Arg Ser Gly Thr
                515                 520                 525
Phe Arg Tyr Ser Gln Pro Pro Ser Tyr Gly Ile Ser Phe Pro Lys Thr
530                 535                 540
Met Asp Ala Gly Glu Pro Leu Thr Ser Arg Ser Phe Ala His Thr Thr
545                 550                 555                 560
Leu Phe Thr Pro Ile Thr Phe Ser Arg Ala Gln Glu Glu Phe Asp Leu
                565                 570                 575
Tyr Ile Gln Ser Gly Val Tyr Ile Asp Arg Ile Glu Phe Ile Pro Val
                580                 585                 590
Thr Ala Thr Phe Glu Ala Glu Tyr Asp Leu Glu Arg Ala Gln Lys Ala
                595                 600                 605
Val Asn Glu Leu Phe Thr Ser Ser Asn Gln Ile Gly Leu Lys Thr Asp
610                 615                 620
Val Thr Asp Tyr His Ile Asp Gln Val Ser Asn Leu Val Glu Cys Leu
625                 630                 635                 640
Ser Asp Glu Phe Cys Leu Asp Glu Lys Lys Glu Leu Ser Glu Lys Val
                645                 650                 655
Lys His Ala Lys Arg Leu Ser Asp Glu Arg Asn Leu Leu Gln Asp Pro
                660                 665                 670
Asn Phe Arg Gly Ile Asn Arg Gln Leu Asp Arg Gly Trp Arg Gly Ser
                675                 680                 685
Thr Asp Ile Thr Ile Gln Gly Gly Asp Asp Val Phe Lys Glu Asn Tyr
690                 695                 700
Val Thr Leu Leu Gly Thr Phe Asp Glu Cys Tyr Pro Thr Tyr Leu Tyr
705                 710                 715                 720
Gln Lys Ile Asp Glu Ser Lys Leu Lys Ala Tyr Thr Arg Tyr Gln Leu
                725                 730                 735
Arg Gly Tyr Ile Glu Asp Ser Gln Asp Leu Glu Ile Tyr Leu Ile Arg
                740                 745                 750
Tyr Asn Ala Lys His Glu Thr Val Asn Val Pro Gly Thr Gly Ser Leu
                755                 760                 765
Trp Pro Leu Ser Ala Pro Ser Pro Ile Gly Lys Cys Ala His His Ser
770                 775                 780
His His Phe Ser Leu Asp Ile Asp Val Gly Cys Thr Asp Leu Asn Glu
785                 790                 795                 800
Asp Leu Gly Val Trp Val Ile Phe Lys Ile Lys Thr Gln Asp Gly His
                805                 810                 815
Ala Arg Leu Gly Asn Leu Glu Phe Leu Glu Glu Lys Pro Leu Val Gly
                820                 825                 830
Glu Ala Leu Ala Arg Val Lys Arg Ala Glu Lys Lys Trp Arg Asp Lys
                835                 840                 845
Arg Glu Lys Leu Glu Trp Glu Thr Asn Ile Val Tyr Lys Glu Ala Lys
850                 855                 860
Glu Ser Val Asp Ala Leu Phe Val Asn Ser Gln Tyr Asp Arg Leu Gln
```

```
865                870                875                880
Ala Asp Thr Asn Ile Ala Met Ile His Ala Ala Asp Lys Arg Val His
                885                890                895
Ser Ile Arg Glu Ala Tyr Leu Pro Glu Leu Ser Val Ile Pro Gly Val
                900                905                910
Asn Ala Ala Ile Phe Glu Glu Leu Glu Gly Arg Ile Phe Thr Ala Phe
                915                920                925
Ser Leu Tyr Asp Ala Arg Asn Val Ile Lys Asn Gly Asp Phe Asn Asn
        930                935                940
Gly Leu Ser Cys Trp Asn Val Lys Gly His Val Asp Val Glu Glu Gln
945                950                955                960
Asn Asn His Arg Ser Val Leu Val Val Pro Glu Trp Glu Ala Glu Val
                965                970                975
Ser Gln Glu Val Arg Val Cys Pro Gly Arg Gly Tyr Ile Leu Arg Val
                980                985                990
Thr Ala Tyr Lys Glu Gly Tyr Gly Glu Gly Cys Val Thr Ile His Glu
                995                1000               1005
Ile Glu Asn Asn Thr Asp Glu Leu Lys Phe Ser Asn Cys Val Glu
        1010               1015               1020
Glu Glu Val Tyr Pro Asn Asn Thr Val Thr Cys Asn Asp Tyr Thr
        1025               1030               1035
Ala Thr Gln Glu Glu Tyr Glu Gly Thr Tyr Thr Ser Arg Asn Arg
        1040               1045               1050
Gly Tyr Asp Gly Ala Tyr Glu Ser Asn Ser Ser Val Pro Ala Asp
        1055               1060               1065
Tyr Ala Ser Ala Tyr Glu Glu Lys Ala Tyr Thr Asp Gly Arg Arg
        1070               1075               1080
Asp Asn Pro Cys Glu Ser Asn Arg Gly Tyr Gly Asp Tyr Thr Pro
        1085               1090               1095
Leu Pro Ala Gly Tyr Val Thr Lys Glu Leu Glu Tyr Phe Pro Glu
        1100               1105               1110
Thr Asp Lys Val Trp Ile Glu Ile Gly Glu Thr Glu Gly Thr Phe
        1115               1120               1125
Ile Val Asp Ser Val Glu Leu Leu Leu Met Glu Glu
        1130               1135               1140
```

LEPIDOPTERAN-ACTIVE CRY1DA1 AMINO ACID SEQUENCE VARIANT PROTEINS

REFERENCE TO RELATED APPLICATIONS

This application claims the benefit of U.S. Provisional Applications 62/064,994, filed Oct. 16, 2014, and 62/065,017, filed Oct. 17, 2014, which are each incorporated herein by reference in their entirety.

INCORPORATION OF SEQUENCE LISTING

A computer readable form of the Sequence Listing is filed herewith by electronic submission. The Sequence Listing is incorporated by reference in its entirety, is contained in the file created on Oct. 14, 2015, having the file name P34223US02_SEQ.txt, and which is 327,225 bytes in size (as measured in the MS-Windows® operating system).

FIELD OF THE INVENTION

The invention generally relates to the field of insect inhibitory proteins. A novel class of engineered proteins exhibiting insect inhibitory activity against agriculturally-relevant pests of crop plants and seeds is disclosed. In particular, the disclosed class of engineered inhibitory proteins has insecticidal activity against the Lepidopteran order of insect pests. Plants, plant parts, and seeds containing a polynucleotide construct encoding one or more of the disclosed engineered inhibitory proteins are provided.

BACKGROUND OF THE INVENTION

*Helicoverpa zea* is a significant Lepidopteran pest of major agricultural crops, including corn, cotton, and soy. Known as the corn earworm (CEW), cotton bollworm (CBW), and soy podworm (SPW), this polyphagous insect species is particularly difficult to control with insecticidal proteins from *Bacillus thuringiensis* (Bt) or other bacterial species. *H. zea* is considered at risk for resistance development to current insect control traits, given its ability to feed on many different crops and the current absence of a high-dose control strategy. Accordingly, new modes of action (MoA) are required to ensure the durability of transgenic plants protected from *H. zea* feeding damage.

The Cry1Da1 protein is a Lepidopteran-active protein that was first described by Hofte, et al. "Nucleotide sequence and deduced amino acid sequence of a new Lepidoptera-specific crystal protein gene from *Bacillus thuringiensis.*" *Nucleic Acids Res.* 18(18) (1990): 5545. This protein exhibits excellent insecticidal activity towards *Spodoptera* species including *Spodoptera frugiperda* (fall armyworm, FAW), a pest of several row crops, including corn, cotton and soybean. However, Cry1Da1 exhibits low-to-moderate activity towards a variety of other major Lepidopteran pests, including bollworms (e.g., *Helicoverpa armigera* and *H. zea*), borers (e.g., *Ostrinia nubilalis* and *Diatraea grandiosella*) and soybean looper (*Pseudoplusia includens*). Because of its narrow insecticidal spectrum and its inability to provide commercial-level protection against a range of important Lepidopteran agricultural pests such as CEW, the Cry1Da1 insecticidal protein has limited value as a transgenic plant insect control trait. As a result, no current commercial varieties of insect-protected crops utilize Cry1Da1 as a plant-incorporated protectant.

Despite its narrow insecticidal spectrum, Cry1Da1 is an interesting insecticidal protein because it appears that the Cry1Da1 protein uses an alternative MoA for controlling certain Lepidopteran pests. Evidence for this comes from studies with multiple resistant insect colonies. For example, field-derived colonies of *Plutella xylostella* (diamondback moth) and *Pectinophora gossypiella* (pink bollworm) that are resistant to Cry1Ac intoxication retain full sensitivity to the Cry1Da1 protein (Tabashnik, et al. "Cross-Resistance of Pink Bollworm (*Pectinophora gossypiella*) to *Bacillus thuringiensis* toxins." *Appl. Environ. Microbiol.* 66 (2000): 4582-4584; Tabashnik, et al. "Cross-Resistance to *Bacillus thuringiensis* Toxin Cry1Ja in a Strain of Diamondback Moth Adapted to Artificial Diet." *J. Invert. Pathol.* 76: (2000): 81-83.). These lines of evidence indicate that Cry1Da1 recognizes Lepidopteran midgut receptors distinct from those recognized by Lepidopteran-active proteins currently deployed in transgenic crops, including Cry1Ac, Cry1Ab, Cry1A.105, Cry1Fa, Cry2Ae, and Cry2Ab2. In view of this apparent novel MoA, optimization of Cry1Da1-like proteins for improved activity against a broader spectrum of *Helicoverpa* species while maintaining or increasing their insecticidal activity towards *Spodoptera* would create a high-value plant-incorporated protectant for insect resistance management.

SUMMARY OF THE INVENTION

In the present invention, several amino acid sequence variants of the TIC844 and Cry1Da scaffold proteins have been identified that exhibit markedly improved activity (compared to the Cry1Da1 native toxin) towards *H. zea* while retaining excellent activity towards *S. frugiperda*. The improved variants of TIC844 and Cry1Da have been engineered to be expressed in crop plants (e.g., corn, soybean, cotton, sugarcane), and provide novel options for in-planta resistance management and Lepidopteran insect pest control in view of the apparent unique mode-of-action of Cry1Da coupled with the engineered improvement in activity against *H. zea*.

The engineered Lepidopteran toxic proteins described herein (referred to as "engineered toxin proteins", "engineered toxic proteins", or "engineered insecticidal proteins") are derivatives of the naturally occurring *Bacillus thuringiensis* insecticidal toxin Cry1Da1 (SEQ ID NO:2) or the chimeric homolog of Cry1Da1, TIC844 (SEQ ID NO:14), which comprises the Cry1Da1 core toxin but substitutes the Cry1Ab3 protoxin for the native Cry1Da1 protoxin domain. The engineered insecticidal proteins of the present invention each contain at least one amino acid substitution, one amino acid addition, or one amino acid deletion compared to the scaffold proteins set forth in any of SEQ ID NO:2 or SEQ ID NO:14. The engineered insecticidal proteins of the present invention are particularly toxic to insects of the *Helicoverpa zea* (corn earworm, soy podworm, cotton bollworm) and *Spodoptera frugiperda* (fall armyworm) species. While the scaffold proteins TIC844 (SEQ ID NO:14) and Cry1Da1 (SEQ ID NO:2) display low toxicity to *H. zea*, the engineered insecticidal proteins of the present invention exhibit surprising and unexpectedly improved insecticidal activity and an enhanced insecticidal spectrum against Lepidopteran insect pests including *H. zea*.

In certain embodiments, an engineered insecticidal protein comprising an amino acid sequence as set forth in any of SEQ ID NO:44, SEQ ID NO: 40, SEQ ID NO: 12, SEQ ID NO:26, SEQ ID NO:4, SEQ ID NO:6, SEQ ID NO:8, SEQ ID NO:10, SEQ ID NO:16, SEQ ID NO:18, SEQ ID NO:20, SEQ ID NO:22, SEQ ID NO:24, SEQ ID NO:32, SEQ ID NO:34, SEQ ID NO:36, SEQ ID NO:38 or SEQ ID NO:42, or an insect inhibitory fragment thereof is disclosed. In certain embodiments, the engineered insecticidal protein exhibits inhibitory activity against an insect species of the order Lepidoptera. The target Lepidopteran pest species inhibited by the Lepidopteran toxic proteins of the present invention include at least fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Chrysodeixis includens*), velvetbean caterpillar (*Anticarsia gemmatalis*), green cloverworm (*Hypena scabs*), tobacco budworm (*Heliothis virescens*), granulate cutworm (*Agrotis subterranea*), armyworm (*Pseudaletia unipuncta*), western cutworm (*Agrotis orthogonia*), European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*), codling moth (*Cydia pomonella*), grape berry moth (*Endopiza viteana*), oriental fruit moth (*Grapholita molesta*), sunflower bud moth (*Suleima helianthana*), diamondback moth (*Plutella xylostella*), pink bollworm (*Pectinophora gossypiella*), pink stem borer (*Sesamia inferens*), gypsy moth (*Lymantria dispar*), cotton leaf worm (*Alabama argillacea*), fruit tree leaf roller (*Archips argyrospila*), European leafroller (*Archips rosana*), Asiatic rice borer, or rice stem borer (*Chilo suppressalis*), rice leaf roller (*Cnaphalocrocis medinalis*), corn root webworm (*Crambus caliginosellus*), bluegrass webworm (*Crambus teterrellus*), southwestern corn borer (*Diatraea grandiosella*)), sugarcane borer (*Diatraea saccharalis*), spiny bollworm (*Earias insulana*), spotted bollworm (*Earias vittella*), Old World cotton bollworm (*Helicoverpa armigera*), corn earworm, soy podworm or cotton bollworm (*Helicoverpa zea*), sod webworm (*Herpetogramma licarsisalis*), European grape vine moth (*Lobesia botrana*), citrus leafminer (*Phyllocnistis citrella*), large white butterfly (*Pieris brassicae*), imported cabbageworm, or small white butterfly (*Pieris rapae*), tobacco cutworm, or cluster caterpillar (*Spodoptera litura*), and tomato leafminer (*Tuta absoluta*).

Also disclosed herein is a polynucleotide encoding an engineered insecticidal protein or pesticidal fragment thereof, wherein the polynucleotide is operably linked to a heterologous promoter and the engineered insecticidal protein comprises the amino acid sequence as set forth in any of SEQ ID NO:44, SEQ ID NO: 40, SEQ ID NO: 12, SEQ ID NO:26, SEQ ID NO:4, SEQ ID NO:6, SEQ ID NO:8, SEQ ID NO:10, SEQ ID NO:16, SEQ ID NO:18, SEQ ID NO:20, SEQ ID NO:22, SEQ ID NO:24, SEQ ID NO:32, SEQ ID NO:34, SEQ ID NO:36, SEQ ID NO:38 or SEQ ID NO:42.

In another embodiment, disclosed herein is a polynucleotide encoding an engineered insecticidal protein, wherein the polynucleotide comprises a nucleotide sequence that optionally hybridizes under stringent conditions to the reverse complement of the polynucleotide sequence as set forth in any of SEQ ID NO: 43, SEQ ID NO: 39, SEQ ID NO: 11, SEQ ID NO: 11, SEQ ID NO: 25, SEQ ID NO: 3, SEQ ID NO: 5, SEQ ID NO: 7, SEQ ID NO: 9, SEQ ID NO: 15, SEQ ID NO: 17, SEQ ID NO: 19, SEQ ID NO: 21, SEQ ID NO: 23, SEQ ID NO:31, SEQ ID NO: 33, SEQ ID NO: 35, SEQ ID NO: 37 or SEQ ID NO: 41; or encodes the engineered insecticidal protein comprising an amino acid sequence as set forth in any of SEQ ID NO:44, SEQ ID NO: 40, SEQ ID NO: 12, SEQ ID NO:26, SEQ ID NO:4, SEQ ID NO:6, SEQ ID NO:8, SEQ ID NO:10, SEQ ID NO:16, SEQ ID NO:18, SEQ ID NO:20, SEQ ID NO:22, SEQ ID NO:24, SEQ ID NO:32, SEQ ID NO:34, SEQ ID NO:36, SEQ ID NO:38 or SEQ ID NO:42.

Also provided herein is a host cell comprising the polynucleotide set forth in any of SEQ ID NO: 43, SEQ ID NO: 39, SEQ ID NO: 11, SEQ ID NO: 11, SEQ ID NO: 25, SEQ ID NO: 3, SEQ ID NO: 5, SEQ ID NO: 7, SEQ ID NO: 9, SEQ ID NO: 15, SEQ ID NO: 17, SEQ ID NO: 19, SEQ ID NO: 21, SEQ ID NO: 23, SEQ ID NO:31, SEQ ID NO: 33, SEQ ID NO: 35, SEQ ID NO: 37 or SEQ ID NO: 41, wherein the host cell is selected from the group consisting of a bacterial host cell or a plant host cell. Contemplated bacterial host cells include bacterial host cells selected from the group consisting of *Agrobacterium*, *Rhizobium*, *Bacillus*, *Brevibacillus*, *Escherichia*, *Pseudomonas*, *Klebsiella*, and *Erwinia*, wherein the *Bacillus* species is a *Bacillus cereus* or a *Bacillus thuringiensis*, said *Brevibacillus* is a *Brevibacillus laterosperous*, and said *Escherichia* is an *Escherichia coli*. Further, contemplated plant host cells include monocots or dicots.

In yet another embodiment, provided herein is an insect inhibitory composition comprising an engineered insecticidal protein comprising an amino acid sequence as set forth in any of SEQ ID NO:44, SEQ ID NO: 40, SEQ ID NO: 12, SEQ ID NO:26, SEQ ID NO:4, SEQ ID NO:6, SEQ ID NO:8, SEQ ID NO:10, SEQ ID NO:16, SEQ ID NO:18, SEQ ID NO:20, SEQ ID NO:22, SEQ ID NO:24, SEQ ID NO:32, SEQ ID NO:34, SEQ ID NO:36, SEQ ID NO:38 or SEQ ID NO:42 or an insect inhibitory fragment thereof. It is contemplated that this insect inhibitory composition can further comprise at least one insect inhibitory agent different from the engineered insecticidal protein. Contemplated insect inhibitory agents include an insect inhibitory protein, an insect inhibitory dsRNA molecule, and an insect inhibitory chemistry. It is contemplated that the at least one other pesticidal agent can exhibit activity against one or more pest species of the orders Lepidoptera, Coleoptera, Hemiptera, Homoptera, or Thysanoptera.

Also disclosed herein are is a seed comprising an insect inhibitory effective amount of an engineered insecticidal protein comprising the amino acid sequence as set forth in any of SEQ ID NO:44, SEQ ID NO: 40, SEQ ID NO: 12, SEQ ID NO:26, SEQ ID NO:4, SEQ ID NO:6, SEQ ID NO:8, SEQ ID NO:10, SEQ ID NO:16, SEQ ID NO:18, SEQ ID NO:20, SEQ ID NO:22, SEQ ID NO:24, SEQ ID NO:32, SEQ ID NO:34, SEQ ID NO:36, SEQ ID NO:38 or SEQ ID NO:42; or a polynucleotide set forth in any of SEQ ID NO: 43, SEQ ID NO: 39, SEQ ID NO: 11, SEQ ID NO: 11, SEQ ID NO: 25, SEQ ID NO: 3, SEQ ID NO: 5, SEQ ID NO: 7, SEQ ID NO: 9, SEQ ID NO: 15, SEQ ID NO: 17, SEQ ID NO: 19, SEQ ID NO: 21, SEQ ID NO: 23, SEQ ID NO:31, SEQ ID NO: 33, SEQ ID NO: 35, SEQ ID NO: 37 or SEQ ID NO: 41.

A method for controlling a Lepidopteran pest, the method comprising contacting the Lepidopteran pest with an inhibitory amount of an engineered insecticidal protein is also disclosed herein in another embodiment.

In yet another embodiment, disclosed herein is a transgenic plant cell, plant or plant part comprising an engineered insecticidal protein Methods are provided for controlling a Lepidopteran pest, comprising exposing the pest to the transgenic plant cell, plant or plant part comprising an engineered insecticidal protein. Commodity products derived from the plant cell, plant or plant part comprising an engineered insecticidal protein wherein the product comprises a detectable amount of the engineered insecticidal protein are also contemplated. Contemplated commodity products include plant biomass, oil, meal, animal feed, flour, flakes, bran, lint, hulls, and processed seed Another method disclosed herein is a method of producing a seed comprising the engineered insecticidal protein, the method comprising: planting at least one seed comprising the engineered insecticidal protein; growing plants from said seed; and harvesting seed from the plants, wherein said harvested seed comprises the engineered insecticidal protein.

Yet another method disclosed in this application is a method of inhibiting Lepidopteran pests from feeding on a crop plant comprising modifying one or more amino acid residue(s) of SEQ ID NO: 2 or SEQ ID NO:14 through substitution of the one or more amino acid residue(s) to produce a modified SEQ ID NO:2 or SEQ ID NO:14; and making available a Lepidopteran-inhibiting amount of the modified SEQ ID NO: 2 or SEQ ID NO:14 within, on the surface, or in the vicinity of tissues of said crop plant; wherein the SEQ ID NO:2 or SEQ ID NO:14 modified amino acid residue is selected from the group consisting of serine at position 282 replaced by lysine or valine, tyrosine at position 316 replaced by serine, isoleucine at position 368 replaced by proline or arginine, serine at 374 replaced by arginine, asparagine at position 375 replaced by histidine, and isoleucine at position 432 replaced by leucine.

Recombinant polynucleotide molecules that encode the engineered insecticidal proteins of the present invention are also provided. Contemplated recombinant polynucleotide molecules comprise a polynucleotide sequence selected from the group consisting of SEQ ID NO: 43, SEQ ID NO: 39, SEQ ID NO: 11, SEQ ID NO: 11, SEQ ID NO: 25, SEQ ID NO: 3, SEQ ID NO: 5, SEQ ID NO: 7, SEQ ID NO: 9, SEQ ID NO: 15, SEQ ID NO: 17, SEQ ID NO: 19, SEQ ID NO: 21, SEQ ID NO: 23, SEQ ID NO:31, SEQ ID NO: 33, SEQ ID NO: 35, SEQ ID NO: 37 or SEQ ID NO: 41; and optionally a polynucleotide sequence encoding an insect inhibitory agent different from the engineered insecticidal protein.

Another method disclosed in this application is method for increasing the Lepidopteran activity and enhancing the Lepidopteran inhibitory spectrum of a scaffold protein, the method comprising modifying one or more amino acid residue(s) of SEQ ID NO: 2 or SEQ ID NO: 14 through substitution of the amino acid residue(s) to produce an engineered insecticidal protein, wherein the SEQ ID NO:2 or SEQ ID NO:14 modified amino acid residue is selected from the group consisting of serine at position 282 replaced by lysine or valine, tyrosine at position 316 replaced by serine, isoleucine at position 368 replaced by proline or arginine, serine at 374 replaced by arginine, asparagine at position 375 replaced by histidine, and isoleucine at position 432 replaced by leucine. In certain embodiments of this method, the engineered insecticidal protein has at least an eight-fold increase in *Helicoverpa zea* lethality relative to the scaffold protein Other embodiments, features, and advantages of the invention will be apparent from the following detailed description, the examples, and the claims.

BRIEF DESCRIPTION OF THE DRAWINGS

FIG. 1 illustrates the $MIC_{50}$ values of the scaffold protein TIC844 (SEQ ID NO: 14) compared to the engineered insecticidal protein TIC844_8 (SEQ ID NO: 26) for two different *Helicoverpa zea* (CEW) colonies, Union City and Benzon.

BRIEF DESCRIPTION OF THE SEQUENCES

SEQ ID NO:1 is a nucleotide sequence encoding a Cry1Da1 protein.
SEQ ID NO:2 is an amino acid sequence of a Cry1Da1 protein toxin.
SEQ ID NO:3 is a nucleotide sequence encoding a Cry1Da1_3 protein.
SEQ ID NO:4 is an amino acid sequence of a Cry1Da1_3 protein toxin.
SEQ ID NO:5 is a nucleotide sequence encoding a Cry1Da1_4 protein.
SEQ ID NO:6 is an amino acid sequence of a Cry1Da1_4 protein toxin.
SEQ ID NO:7 is a nucleotide sequence encoding a Cry1Da1_5 protein.
SEQ ID NO:8 is an amino acid sequence of a Cry1Da1_5 protein toxin.
SEQ ID NO:9 is a nucleotide sequence encoding a Cry1Da1_6 protein.
SEQ ID NO:10 is an amino acid sequence of a Cry1Da1_6 protein toxin.
SEQ ID NO:11 is a nucleotide sequence encoding a Cry1Da1_7 protein.
SEQ ID NO:12 is an amino acid sequence of a Cry1Da1_7 protein toxin.
SEQ ID NO:13 is a nucleotide sequence encoding a TIC844 protein.
SEQ ID NO:14 is an amino acid sequence of a TIC844 protein toxin.
SEQ ID NO:15 is a nucleotide sequence encoding a TIC844_2 protein.
SEQ ID NO:16 is an amino acid sequence of a TIC844_2 protein toxin.
SEQ ID NO:17 is a nucleotide sequence encoding a TIC844_4 protein.
SEQ ID NO:18 is an amino acid sequence of a TIC844_4 protein toxin.
SEQ ID NO:19 is a nucleotide sequence encoding a TIC844_5 protein.
SEQ ID NO:20 is an amino acid sequence of a TIC844_5 protein toxin.
SEQ ID NO:21 is a nucleotide sequence encoding a TIC844_6 protein.
SEQ ID NO:22 is an amino acid sequence of a TIC844_6 protein toxin.
SEQ ID NO:23 is a nucleotide sequence encoding a TIC844_7 protein.
SEQ ID NO:24 is an amino acid sequence of a TIC844_7 protein toxin.
SEQ ID NO:25 is a nucleotide sequence encoding a TIC844_8 protein.
SEQ ID NO:26 is an amino acid sequence of a TIC844_8 protein toxin.
SEQ ID NO:27 is a polynucleotide sequence designed for use in expressing a Cry1Da1 protein in plants.
SEQ ID NO:28 is an amino acid sequence of a Cry1Da1 protein toxin.
SEQ ID NO:29 is a polynucleotide sequence designed for use in expressing a Cry1Da1_2.nno protein in plants.
SEQ ID NO:30 is an amino acid sequence of a Cry1Da1_2.nno protein toxin.
SEQ ID NO:31 is a polynucleotide sequence designed for use in expressing a Cry1Da1_3.nno protein in plants.
SEQ ID NO:32 is an amino acid sequence of a Cry1Da1_3.nno protein toxin.

SEQ ID NO:33 is a polynucleotide sequence designed for use in expressing a Cry1Da1_4.nno protein in plants.

SEQ ID NO:34 is an amino acid sequence of a Cry1Da1_4.nno protein toxin.

SEQ ID NO:35 is a polynucleotide sequence designed for use in expressing a Cry1Da1_5.nno protein in plants.

SEQ ID NO:36 is an amino acid sequence of a Cry1Da1_5.nno protein toxin.

SEQ ID NO:37 is a polynucleotide sequence designed for use in expressing a Cry1Da1_6.nno protein in plants.

SEQ ID NO:38 is an amino acid sequence of a Cry1Da1_6.nno protein toxin.

SEQ ID NO:39 is a polynucleotide sequence designed for use in expressing a Cry1Da1_7.nno protein in plants.

SEQ ID NO:40 is an amino acid sequence of a Cry1Da1_7.nno protein toxin.

SEQ ID NO:41 is a polynucleotide sequence designed for use in expressing a TIC844_9.nno protein in plants.

SEQ ID NO:42 is an amino acid sequence of a TIC844_9.nno protein toxin.

SEQ ID NO:43 is a polynucleotide sequence designed for use in expressing a TIC844_11.nno protein in plants.

SEQ ID NO:44 is an amino acid sequence of a TIC844_11.nno protein toxin.

DETAILED DESCRIPTION OF THE INVENTION

Engineered insecticidal proteins that exhibit surprisingly higher levels of toxic activity against Lepidopteran species and a broader insecticidal spectrum compared to other previously known Lepidopteran insecticidal proteins are provided herein. These engineered insecticidal proteins are derived from insecticidal scaffold proteins, which serve as templates for various amino acid modifications. Examples of such insecticidal scaffold proteins include but are not limited to Cry1Da1 and TIC844 (a homolog of Cry1Da1). TIC844 comprises the Cry1Da1 core toxin (i.e., domains I, II and III) but utilizes the Cry1Ab3 protoxin domain to ensure good expression in *Bacillus thuringiensis* (Bt). Expression of Cry1Da1 in Bt is poor when using the native Cry1Da1 protoxin domain. However, as demonstrated in this application, the expression of Cry1Da1 core toxin is remarkably improved in acrystalliferous strains of Bt when the native protoxin domain is removed and the Cry1Da1 core toxin coding segment is fused in frame with a segment encoding the Cry1Ab3 protoxin domain. Notably, the scaffold proteins TIC844 (SEQ ID NO:14) and Cry1Da1 (SEQ ID NO:2) do not exhibit the commercially useful Lepidopteran inhibitory spectrum and improved Lepidopteran inhibitory activity observed in the engineered insecticidal proteins.

The engineered insecticidal proteins disclosed herein are related by amino acid modifications such that the modified proteins exhibit enhanced Lepidopteran inhibitory spectrum and/or improved Lepidopteran inhibitory activity compared to the parent scaffold protein, TIC844 or Cry1Da1. The phrases "more active", "improved activity", "enhanced specificity", "increased toxic potency", "increased toxicity", "improved Lepidopteran inhibitory activity", "greater Lepidopteran inhibitory activity", and "enhanced Lepidopteran inhibitory spectrum" refer to a comparison of the activity of an engineered insecticidal protein to the activity of a scaffold protein (TIC844 or Cry1Da1) against a Lepidopteran insect, wherein the activity attributed to the engineered insecticidal protein is greater than the activity attributed to the scaffold protein. In certain embodiments, the engineered insecticidal proteins provided herein exhibit an enhanced Lepidopteran inhibitory spectrum and/or improved or greater Lepidopteran inhibitory activity when compared to the activities of the scaffold TIC844 or Cry1Da1 protein where the Lepidopteran pest species include, but are not limited to, *Helicoverpa zea* and *Spodoptera frugiperda*.

As used herein, the terms and phrases "active" or "activity"; "pesticidal activity" or "pesticidal"; or "insecticidal activity", "insect inhibitory", "insecticidal", or "an insect inhibitory amount", refer to efficacy of a toxic agent, such as an insecticidal protein, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of a disclosed engineered insecticidal protein) or killing (causing the morbidity, mortality, or reduced fecundity of) a pest. Similarly, a "Lepidopteran inhibitory amount" refers to an amount of a toxic agent, such as an insecticidal protein, that results in any measurable inhibition of Lepidopteran viability, Lepidopteran growth, Lepidopteran development, Lepidopteran reproduction, Lepidopteran feeding behavior, Lepidopteran mating behavior and/or any measurable decrease in the adverse effects caused to a plant by Lepidopteran feeding. These terms are intended to include the result of providing a pesticidally effective amount of a toxic agent to a pest where the exposure of the pest to the toxic agent results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic agent in or on the plant. In general, pesticidal activity refers to the ability of a toxic agent to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera. The toxic agent can be produced by the plant or can be applied to the plant or to the environment within the location where the plant is located.

A pesticidally effective amount of a toxic agent, when provided in the diet of a target pest, exhibits pesticidal activity when the toxic is ingested by the pest. A toxic agent can be a pesticidal protein or one or more chemical agents known in the art. Pesticidal or insecticidal chemical agents and pesticidal or insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Pesticidal or insecticidal protein agents include the engineered insecticidal proteins set forth in this application, as well as other proteinaceous toxic agents including those that target Lepidopteran pest species, as well as protein toxins that are used to control other plant pests such as Cry proteins available in the art for use in controlling Coleopteran, Hemipteran and Homopteran species.

The term "segment" or "fragment" is used herein to describe consecutive amino acid or nucleic acid sequences that are shorter than the complete amino acid or nucleic acid sequence describing the engineered insecticidal proteins.

It is intended that reference to a pest, particularly a pest of a crop plant, means insect pests of crop plants, particularly those Lepidopteran insect pests that are controlled by the disclosed engineered insecticidal proteins. However, reference to a pest can also include Coleopteran, Hemipteran and Homopteran insect pests of plants, as well as nematodes and fungi, when toxic agents targeting these pests are co-localized or present together with the disclosed engineered insecticidal proteins.

The disclosed engineered insecticidal proteins exhibit insecticidal activity towards insect pest from the Lepidopteran insect species, including adults, pupae, larvae, and neonates, The armyworm (*Spodoptera exigua*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabs*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*) and gypsy moth (*Lymantria dispar*). Other insect pests of order Lepidoptera include, e.g., *Alabama argillacea* (cotton leaf worm), *Archips argyrospila* (fruit tree leaf roller), *Archips rosana* (European leafroller) and other *Archips* species, *Chilo suppressalis* (Asiatic rice borer, or rice stem borer), *Cnaphalocrocis medinalis* (rice leaf roller), *Crambus caliginosellus* (corn root webworm), *Crambus teterrellus* (bluegrass webworm), *Diatraea grandiosella* (southwestern corn borer), *Diatraea saccharalis* (surgarcane borer), *Earias insulana* (spiny bollworm), *Earias vittella* (spotted bollworm), *Helicoverpa armigera* (American bollworm), *Helicoverpa zea* (corn earworm or cotton bollworm), *Heliothis virescens* (tobacco budworm), *Herpetogramma licarsisalis* (sod webworm), *Lobesia botrana* (European grape vine moth), *Phyllocnistis citrella* (citrus leafminer), *Pieris brassicae* (large white butterfly), *Pieris rapae* (imported cabbageworm, or small white butterfly), *Plutella xylostella* (diamondback moth), *Spodoptera exigua* (beet armyworm), *Spodoptera litura* (tobacco cutworm, cluster caterpillar), and *Tuta absoluta* (tomato leafminer).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of a naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further in the Examples, repetitive rounds of engineering, testing and selecting of over two thousand (2000) amino acid sequence variants of TIC844 and Cry1Da1 resulted in the identification of certain amino acid residues that may be substituted, inserted or deleted from the given scaffold protein to produce engineered insecticidal proteins that exhibit an expanded Lepidopteran inhibitory spectrum and/or improved Lepidopteran inhibitory activity (i.e., more toxic; less insecticidal protein required to obtain same level of mortality) when compared to the spectrum and activity of the baseline scaffold proteins, TIC844 or Cry1Da1. These repetitive rounds of engineering, testing and selecting also resulted in the identification of neutral amino acid residue substitutions, insertions or deletions in the TIC844 and Cry1Da1 scaffold proteins that do not change the proteins' insect inhibitory spectrum or activity. The specific amino acid residues in the TIC844 and Cry1Da1 scaffold that can be modified to yield an enhanced Lepidopteran inhibitory spectrum and/or improved Lepidopteran inhibitory activity relative to TIC844 or Cry1Da1 are identified herein. In certain embodiments, the engineered insecticidal protein provided herein can exhibit about an eight fold or greater Lepidopteran inhibitory activity against a Lepidopteran pest species than a scaffold protein of SEQ ID NO:14 (TIC844) or SEQ ID NO:2 (Cry1Da1).

The "engineering" in these repetitive rounds included identifying relevant residues in the scaffold protein to modify to create a modified test protein, and cloning and expressing the resultant modified test proteins. The atomic structure of the scaffold proteins was used to guide and complement semi-random approaches of selecting amino acid residues to modify for engineering. The "testing" in these repetitive rounds included comparing the Lepidopteran species activities of a modified test protein to its parent scaffold protein. The "selecting" in these repetitive rounds included identifying modified test proteins with improved activity (improved variants) and the relevant residues which were engineered to create these improved variants (these improved variants are referred to herein as "engineered insecticidal proteins").

Examples of methods for testing and selecting engineered insecticidal proteins include administering identical amounts of a modified test protein and of a scaffold protein (TIC844 or Cry1Da1) to an insect pest under controlled assay conditions and measuring and comparing the potency of the modified test and scaffold proteins. Another method for testing and selecting engineered insecticidal proteins includes determining the protein doses (e.g., protein concentration in diet) of a modified test protein and of a scaffold protein (TIC844 or Cry1Da1) which elicit equivalent insect population responses under controlled assay conditions (i.e., obtaining a dose response curve). A statistically robust dose response value used for comparison would be the median lethal concentration ($LC_{50}$) required to kill 50% of a test population or the molting inhibition concentration ("$MIC_{50}$"), the median concentration required to inhibit molting by 50%).

In certain embodiments, the engineered insecticidal proteins described herein include at least one amino acid modification of the following relative positions of TIC844 (SEQ ID NO:14) or Cry1Da1 (SEQ ID NO:2): serine at position 282 replaced by lysine or valine, tyrosine at position 316 replaced by serine, isoleucine at position 368 replaced by proline or arginine, serine at 374 replaced by arginine, asparagine at position 375 replaced by histidine, and isoleucine at position 432 replaced by leucine. The engineered insecticidal proteins can also include at least two, three, four, or more of these amino acid substitutions or deletions within the same engineered insecticidal protein sequence.

The engineered insecticidal proteins that include these amino acid modifications include the proteins set forth as SEQ ID NO:4, SEQ ID NO:6, SEQ ID NO:8, SEQ ID NO:10, SEQ ID NO:12, SEQ ID NO:16, SEQ ID NO:18, SEQ ID NO:20, SEQ ID NO:22, SEQ ID NO:24, SEQ ID NO:26, SEQ ID NO:32, SEQ ID NO:34, SEQ ID NO:36, SEQ ID NO:38, SEQ ID NO:40, and SEQ ID NO:44, and insect inhibitory fragments thereof. Each of these engineered insecticidal proteins has a measured mass of about 132 k-Daltons. Individual characteristics of the insecticidal scaffold proteins TIC844 and Cry1Da1 and the engineered insecticidal proteins derived therefrom are reported in Table 1.

TABLE 1

Characteristics of TIC844, Cry1Da1 and the Engineered Insecticidal Proteins.

| Protein (Name/SEQ ID NO.) | Molecular Weight (in Daltons) | Amino Acid Length | Isoelectric Point | Charge at PH 7.0 | No. of Strongly Basic (−) Amino Acids | No. of Strongly Acidic Amino Acids | No. of Hydrophobic Amino Acids | No. of Polar Amino Acids |
|---|---|---|---|---|---|---|---|---|
| Cry1Da1/NO:2 | 132481.87 | 1165 | 5.087 | −39.319 | 113 | 156 | 388 | 347 |
| Cry1Da1_3/NO:4 | 132405.77 | 1165 | 5.087 | −39.318 | 113 | 156 | 388 | 347 |
| Cry1Da1_4/NO:6 | 132550.98 | 1165 | 5.112 | −38.319 | 114 | 156 | 388 | 346 |
| Cry1Da1_5/NO:8 | 132448.80 | 1165 | 5.112 | −38.318 | 114 | 156 | 387 | 347 |
| Cry1Da1_6/NO:10 | 132430.82 | 1165 | 5.112 | −38.319 | 114 | 156 | 387 | 346 |
| Cry1Da1_7/NO:12 | 132401.78 | 1165 | 5.087 | −39.318 | 113 | 156 | 388 | 346 |
| TIC844/NO:14 | 129182.91 | 1139 | 5.026 | −39.540 | 110 | 153 | 382 | 340 |
| TIC844_2/NO:16 | 129129.85 | 1139 | 5.048 | −39.373 | 110 | 153 | 382 | 339 |
| TIC844_4/NO:18 | 129106.81 | 1139 | 5.026 | −39.539 | 110 | 153 | 382 | 340 |
| TIC844_5/NO:20 | 1291118.08 | 1069 | 5.325 | −27.535 | 105 | 136 | 363 | 321 |
| TIC844_6/NO:22 | 129252.02 | 1139 | 5.050 | −38.540 | 111 | 153 | 382 | 339 |
| TIC844_7/NO:24 | 129149.84 | 1139 | 5.050 | −38.539 | 111 | 153 | 381 | 340 |
| TIC844_8/NO:26 | 129102.82 | 1139 | 5.026 | −39.539 | 110 | 153 | 382 | 339 |
| Cry1Da1/NO:28 | 132481.87 | 1165 | 5.087 | −39.319 | 113 | 156 | 388 | 347 |
| Cry1Da1_2.nno/NO:30 | 132552.95 | 1166 | 5.087 | −39.319 | 113 | 156 | 389 | 347 |
| Cry1Da1_3.nno/NO:32 | 132476.85 | 1166 | 5.087 | −39.318 | 113 | 156 | 389 | 347 |
| Cry1Da1_4.nno/NO:34 | 132622.06 | 1166 | 5.112 | −38.319 | 114 | 156 | 389 | 346 |
| Cry1Da1_5.nno/NO:36 | 132519.88 | 1166 | 5.112 | −38.318 | 114 | 156 | 388 | 347 |
| Cry1Da1_6.nno/NO:38 | 132501.90 | 1166 | 5.112 | −39.319 | 114 | 156 | 388 | 346 |
| Cry1Da1_7.nno/NO:40 | 132472.86 | 1166 | 5.087 | −39.318 | 113 | 156 | 389 | 346 |
| TIC8449.nno/NO:42 | 129253.99 | 1140 | 5.026 | −39.540 | 110 | 153 | 383 | 340 |
| TIC84411.nno/NO:44 | 129173.90 | 1140 | 5.026 | −39.539 | 110 | 153 | 383 | 339 |

Fragments of the engineered insecticidal proteins described herein can be truncated forms wherein one or more amino acids are deleted from the N-terminal end, C-terminal end, the middle of the protein, or combinations thereof without a loss of insect inhibitory activity. These fragments should retain the insect inhibitory activity of the parent engineered insecticidal protein.

Proteins that resemble the engineered insecticidal proteins can be identified by comparison to each other using various computer based algorithms known in the art. For example, amino acid sequence identities of proteins related to the engineered insecticidal proteins can be analyzed using a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et at (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment.

As described further in the Examples of this application, synthetic or artificial sequences encoding the scaffold proteins and the engineered insecticidal proteins were designed for use in plants. Exemplary synthetic nucleotide sequences that were designed for use in plants are set forth in SEQ ID NO:27 (Cry1Da1.nno), SEQ ID NO:29 (Cry1Da1_2.nno), SEQ ID NO:31 (Cry1Da1_3.nno), SEQ ID NO:33 (Cry1Da1_4.nno), SEQ ID NO:35 (Cry1Da1_5.nno), SEQ ID NO:37 (Cry1Da1_6.nno), SEQ ID NO:39 (Cry1Da1_7.nno), SEQ ID NO:41 (TIC844_9.nno) and SEQ ID NO:43 (TIC844_11.nno).

Expression cassettes and vectors containing these synthetic or artificial nucleotide sequences were constructed and introduced into corn, cotton and soybean plant cells in accordance with transformation methods and techniques known in the art. Transformed cells were regenerated into transformed plants that were observed to be expressing the engineered insecticidal protein or the scaffold protein. To test pesticidal activity, bioassays were performed in the presence of Lepidopteran pest larvae using plant leaf disks obtained from the transformed plants.

Recombinant nucleic acid molecule compositions that encode the engineered insecticidal proteins are contemplated. For example, an engineered insecticidal protein can be expressed with recombinant DNA constructs in which a polynucleotide molecule with an ORF encoding the engineered insecticidal protein is operably linked to genetic expression elements such as a promoter and any other regulatory element necessary for expression in the system for which the construct is intended. Non-limiting examples include a plant-functional promoter operably linked to the synthetic engineered insecticidal protein encoding sequences for expression of the engineered insecticidal protein in plants or a Bt-functional promoter operably linked to an engineered insecticidal protein encoding sequence for expression of the protein in a Bt bacterium or other *Bacillus* species. Other elements can be operably linked to the engineered insecticidal protein encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herein include, but are not limited to, a heterologous promoter operably linked to a polynucleotide such as SEQ ID NO:3, SEQ ID NO:5, SEQ ID NO:7, SEQ ID NO:9, SEQ ID NO:11, SEQ ID NO:15, SEQ ID NO:17, SEQ ID NO:19, SEQ ID NO:21, SEQ ID NO:23, SEQ ID NO:25, SEQ ID NO:31, SEQ ID NO:33, SEQ ID NO:35, SEQ ID NO:37, SEQ ID NO:39 and SEQ ID NO:43, that encodes the polypeptide or protein having the amino acid sequence as set forth in SEQ ID NO:4 (Cry1Da1_3), SEQ ID NO:6 (Cry1Da1_4), SEQ ID NO:8 (Cry1Da1_5), SEQ ID NO:10 (Cry1Da1_6), SEQ ID NO:12 (Cry1Da1_7), SEQ ID NO:16 (TIC844_2), SEQ ID NO:18 (TIC844_4), SEQ ID NO:20 (TIC844_5), SEQ ID NO:22 (TIC844_6), SEQ ID NO:24 (TIC844_7), SEQ ID NO:26 (TIC844_8), SEQ ID NO:32 (Cry1Da1_3.nno), SEQ ID NO:34 (Cry1Da1_4.nno), SEQ ID NO:36 (Cry1Da1_5.nno), SEQ ID NO:38 (Cry1Da1_6.nno), SEQ ID NO:40 (Cry1Da1_7.nno) and SEQ ID NO:44 (TIC844_11.nno). A heterologous promoter can also be operably linked to synthetic DNA coding sequences encoding a plastid targeted engineered insecticidal protein and untargeted engineered insecticidal protein. It is contemplated that the codons of a recombinant nucleic acid molecule encoding for an engineered insecticidal protein disclosed herein can be substituted by synonymous codons (known in the art as a silent substitution).

A recombinant DNA molecule or construct comprising an engineered insecticidal protein encoding sequence can further comprise a region of DNA that encodes for one or more toxic agents which can be configured to concomitantly express or co-express with a DNA sequence encoding an engineered insecticidal protein, a protein different from an engineered insecticidal protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA molecule or construct can be assembled so that all proteins or dsRNA molecules are expressed from one promoter or each protein or dsRNA molecule is under separate promoter control or some combination thereof. The proteins of this invention can be expressed from a multi-gene expression system in which an engineered insecticidal protein is expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked expression cassettes, each expressing a different protein or other toxic agent such as one or more dsRNA molecules.

Recombinant nucleic acid molecules or recombinant DNA constructs comprising an engineered insecticidal protein encoding sequence can be delivered to host cells by vectors, e.g., a plasmid, baculovirus, synthetic chromosome, virion, cosmid, phagemid, phage, or viral vector. Such vectors can be used to achieve stable or transient expression of an engineered insecticidal protein encoding sequence in a host cell, or subsequent expression of the encoded polypeptide. An exogenous recombinant polynucleotide or recombinant DNA construct that comprises an engineered insecticidal protein sequence encoding sequence and that is introduced into a host cell is referred herein as a “transgene”.

Transgenic bacteria, transgenic plant cells, transgenic plants, and transgenic plant parts that contain a polynucleotide that encodes any one or more of the engineered insecticidal proteins are provided herein. The term “bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a dicotyledonous cell or a monocotyledonous cell. Contemplated plants and plant cells include, but are not limited to, alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise Lepidoptera-inhibitory amounts of an engineered insecticidal proteins are provided. Such plants can be made by introducing a polynucleotide that encodes the engineered insecticidal proteins provided in this application into a plant cell, and selecting a plant derived from said plant cell that expresses an insect or Lepidoptera-inhibitory amount of the engineered insecticidal protein. Plants can be derived from the plant cells by regeneration, seed, pollen, or meristem transformation techniques. Methods for transforming plants are known in the art.

Plants expressing the engineered insecticidal proteins can be crossed by breeding with transgenic events expressing other insecticidal proteins and/or expressing other transgenic traits such as other insect control traits, herbicide tolerance genes, genes conferring yield or stress tolerance traits, and the like, or such traits can be combined in a single vector so that the traits are all linked.

Processed plant products, wherein the processed product comprises a detectable amount of an engineered insecticidal protein, an insect inhibitory segment or fragment thereof, or any distinguishing portion thereof, are also disclosed in this application. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of an engineered insecticidal protein.

Methods of controlling insects, in particular Lepidoptera infestations of crop plants, with the engineered insecticidal proteins are also disclosed in this application. Such methods can comprise growing a plant comprising an insect- or Lepidoptera-inhibitory amount of the engineered insecticidal protein. In certain embodiments, such methods can further comprise any one or more of: (i) applying any composition comprising or encoding an engineered insecticidal protein to a plant or a seed that gives rise to a plant; and (ii) transforming a plant or a plant cell that gives rise to a plant with a polynucleotide encoding an engineered insecticidal protein. In general, it is contemplated that engineered insecticidal protein can be provided in a composition, provided in a microorganism, or provided in a transgenic plant to confer insect inhibitory activity against Lepidopteran insects.

In certain embodiments, the engineered insecticidal protein is the insecticidally active ingredient of an insect inhibitory composition prepared by culturing recombinant *Bacillus* or any other recombinant bacterial cell transformed to express an engineered insecticidal protein under conditions suitable for expression. Such a composition can be prepared by desiccation, lyophilization, homogenization, extraction, filtration, centrifugation, sedimentation, or concentration of a culture of such recombinant cells expressing/producing the engineered insecticidal protein. Such a process can result in a *Bacillus* or other entomopathogenic bacterial cell extract, cell suspension, cell homogenate, cell lysate, cell supernatant, cell filtrate, or cell pellet. By obtaining the engineered insecticidal protein so produced, a composition that includes the engineered insecticidal protein can include bacterial cells, bacterial spores, and parasporal inclusion bodies and can be formulated for various uses, including as agricultural insect inhibitory spray products or as insect inhibitory formulations in diet bioassays.

In an embodiment, in order to reduce the likelihood of resistance development, an insect inhibitory composition or transgenic plant comprising an engineered insecticidal protein can further comprise at least one additional toxic agent that exhibits insect inhibitory activity against the same Lepidopteran insect species, but which is different from the engineered insecticidal protein. Possible additional toxic agents for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide(s) for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. patent Publication Ser. No. 10/525,318), Cry1C (U.S. Pat. No. 6,033,874), Cry1D, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), DIG-3 (U.S. Patent Publication 2013-0219570 A1), DIG-5 (U.S. Patent Publication 2010-0317569 A1), DIG-11 (U.S. Patent Publication 2010-0319093 A1), AflP-1A and derivatives thereof (U.S. Patent Publication 2014-0033361 A1), AflP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput 1063 (U.S. Patent Publication 2014-0007292 A1), Pput 1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1); and the like.

In other embodiments, an insect inhibitory composition or transgenic plant can further comprise at least one additional toxic agent that exhibits insect inhibitory activity to an insect pest that is not inhibited by the engineered insecticidal proteins of the present invention (such as Coleopteran, Hemipteran and Homopteran pests), in order to expand the spectrum of insect inhibition obtained.

Such additional toxic agent for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), axmi207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-0210462 A1), and $\overline{\omega}$-Hexatoxin-Hv1a (U.S. Patent Application Publication US2014-0366227 A1).

Such additional toxic agent for the control of Hemipteran pests may be selected from the group consisting of Hemipteran-active proteins such as, but not limited to, TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Additional polypeptides for the control of Coleopteran, Lepidopteran, and Hemipteran insect pests can be found on the *Bacillus thuringiensis* toxin nomenclature website maintained by Neil Crickmore (on the world wide web at btnomenclature.info).

Engineered insecticidal protein-encoding sequences and sequences having a substantial percentage identity to the engineered insecticidal proteins can be identified using methods known to those of ordinary skill in the art such as polymerase chain reaction (PCR), thermal amplification and hybridization. For example, the engineered insecticidal proteins can be used to produce antibodies that bind specifically to related proteins, and can be used to screen for and to find other proteins that are closely related.

Furthermore, nucleotide sequences encoding the engineered insecticidal proteins can be used as probes and primers for screening to identify other members of the class using thermal-cycle or isothermal amplification and hybridization methods. For example, oligonucleotides derived from sequences as set forth in SEQ ID NO: 3 can be used to determine the presence or absence of an engineered insecticidal transgene in a deoxyribonucleic acid sample derived from a commodity product. Given the sensitivity of certain nucleic acid detection methods that employ oligonucleotides, it is anticipated that oligonucleotides derived from sequences as set forth in any of SEQ ID NO: 3 can be used to detect the respective engineered insecticidal protein in commodity products derived from pooled sources where only a fraction of the commodity product is derived from a transgenic plant containing any of SEQ ID NO: 3.

Other features and advantages of the invention will be apparent from the following Examples and claims.

EXAMPLES

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

Example 1

Design of Modified Test Proteins and Sample Preparation for Insect Bioassay Testing This Example illustrates the methods undertaken to identify relevant amino acid residues in the scaffold proteins to modify to create modified test proteins, and the cloning and expressing of the resultant modified test proteins.

Several molecular engineering techniques were employed in a tiered approach to construct improved variants of Cry1Da1 having an enhanced Lepidopteran inhibitory spectrum and/or improved Lepidopteran inhibitory activity compared to the scaffold proteins of Cry1Da1 and TIC844, a homolog of Cry1Da1. The first tier, or initial round of design, was primarily hypothesis driven. The second and third tiers were statistically-driven rounds of design. For example, in the second tier of design, statistically non-deleterious mutations were combined with putative beneficial mutations to produce double mutations which satisfied defined statistical criteria. In the third tier of design, all the data from the previous tests was analyzed using multiple statistical methods. Only mutations showing statistically significant improvement in more than one statistical method were selected to the final pool of mutations. The variants designed in this tier contained one or two more positive mutations from variants previously confirmed positive. Thus, the third tier design significantly enriched the active variants compared to the first and second tier. As demonstrated in the subsequent Examples, the use of the three-tiered design strategy identified both single and synergistic mutations that provided significant improvement in activity against CEW for certain improved variants relative to the TIC844 and Cry1Da1 scaffolds.

The methods which were utilized to create the modified test proteins included, but were not limited to, semi-random modifications, directed modifications of variances in alignment of TIC844/Cry1Da1 with other native *Bacillus thuringensis* (Bt) proteins, and structure/function assisted design. Examples of utilized molecular engineering techniques include the following.

Receptor binding. Susceptibility of Lepidopteran pests, specifically Corn Earworm (CEW, *Helicoverpa zea*) to Cry1Da1/TIC844 improved variants may be attributable to different targeted gut receptors. Designs which were utilized to improve binding to receptors in the gut, thus increasing toxicity, included: (1) mutating every position in the apical loops of domain II to all amino-acid types; and (2) swapping all possible combinations of the apical loops of domain II with those from other Cry1Da1 homologs (e.g., Cry1Db1, Cry1Dc1) and CEW-active three-domain toxins (e.g., Cry1Bb1, Cry1Ja1 and Cry2Ab2).

Alignment based approaches. Alignment of Cry1Da1 with other homologs (e.g., Cry1Db1 and Cry1Dc1) was used to identify regions of variability. As a result of the alignment, one hundred fifty (150) positions and two hundred ninety five (295) unique single mutations were identified. These positions were located throughout the three domains. Positions within four (4) amino acids from one another were grouped together. Only mutations from the same parental sequences were nominated for every group of positions, rendering one hundred thirty two (132) unique variants.

Surface mutagenesis approaches. The polynucleotides encoding the surface positions in domains II and III of the scaffold proteins were mutagenized by a scan. Amino acid residues were modified to alanine where an alanine was not already present in the scaffold protein. At surface positions where the native residues were lysine, arginine mutations were introduced in addition to the alanine mutations. The rational for the lysine to arginine mutations was based on the observation that Lepidopteran-active toxins tend to have very few lysine and many arginine and, therefore, it was hypothesized that changing the surface lysine positions in domains II and III to arginine would increase the Lepidopteran activity of the modified test protein.

Alteration of proteolytic events. The proteolytic process was hypothesized to be an important aspect of the activity of three-domain toxins in the Lepidopteran insect guts. In order to test this, several sets of mutations were made to potentially alter any proteolytic cleavage. Potential cleavage sites are located at the N-terminus and between domain III and the protoxin. The mutational positions included predicted loop regions from the N-terminus to the beginning of helix 4 and from the C-terminus of domain III to ~40 amino acids into the protoxin. Generally, glycine residues were hypothesized to promote proteolysis either through proteolytic site recognition or by increasing the protein flexibility, thereby rendering it more susceptible to proteolytic cleavage. Further, trypsin and chymotripsin are two proteases that are widely accepted as viable proteases in Lepidopteran midguts. Lysine residues provide recognition sites for trypsin and tyrosine residues provide recognition sites for chymotripsin. Thus, selected mutational positions in the potential cleavage sites were mutated to either glycine, lysine or tyrosine.

Potential hot-spot mutations from other CEW-active toxins. Activity and absence of activity data against CEW for a large set of proteins (including chimeras, fragments and native sequences) was analyzed. Information gained from a statistical analysis of this data was utilized to identify potential specific mutations or positions for mutation that would be likely to increase CEW activity in the resultant modified test proteins.

The modified test proteins which resulted from the molecular engineering methodologies described above were cloned using methods known in the art into a recombinant Bt plasmid expression vector downstream of a sporulation specific expression promoter and transformed into an acrystalliferous Bt host cell.

Example 2

Testing of Modified Test Proteins in Diet Bioassays Against Lepidopteran Pests

This Example illustrates the testing of the modified test proteins created from the engineering efforts described in Example 1.

From the engineering efforts described in Example 1, about two thousand five hundred (2,500) recombinant Bt strains were produced which expressed more than two thousand three hundred (2,300) different modified test proteins. These modified test proteins were expressed in Bt and assayed for toxicity to various species of Lepidoptera. Feeding assays were conducted with neonate larvae (<24 hour post hatch) of various Lepidopteran species, including corn earworm (CEW, *Helicoverpa zea*) and fall armyworm (FAW, *Spodoptera frugiperda*). Insect eggs for the CEW testing were obtained from two different laboratory colonies: Benson Research, Carlisle, PA and Monsanto Company, Union City, Tenn. All of the expressed modified test proteins were tested on CEW and some of those modified test proteins demonstrating improved activity against CEW compared to their parent scaffold proteins were tested on FAW, in addition to performing additional bioassays to confirm CEW activity.

Various protocols for bioassays and scoring insects for mortality and stunting are known in the art. Variations of methods, such as those described in PCT Patent Application Publication No. WO 2012/139004 and in U.S. Pat. No. 7,927,598, were used.

Example 3

Modified Test Proteins Exhibiting Improved CEW Activity

This Example illustrates the discovery of an enhanced Lepidopteran inhibitory spectrum and/or improved or greater Lepidopteran inhibitory activity for some of the modified test proteins when compared to the activities of the scaffold TIC844 or Cry1Da1 proteins in multiple testing rounds.

The modified tests proteins created from the engineering efforts described in Example 1 and tested in insect bioassay as described in Example 2 were tested in repetitive rounds in which the Lepidopteran species activities of the modified test proteins were compared to their respective parent scaffold proteins (i.e., TIC844 or Cry1Da1). In a first round, three hundred and seventy (370) different modified test proteins demonstrated increased toxicity against CEW relative to TIC844 or Cry1Da1 in diet bioassays. In each of these diet bioassays, identical amounts of the protein (either modified test protein or scaffold protein) was provided to CEW under controlled single-dose assay conditions. The potency of the modified test proteins and scaffold proteins was determined by measuring and comparing the observed mortality and stunting of each of the modified test protein bioassays to the observed mortality and stunting of the parent scaffold protein bioassays.

Of the three hundred and seventy (370) modified test proteins which demonstrated increased toxicity against CEW when compared to the scaffold proteins in single-dose assay screens, about one hundred eighty (180) of them were further tested in FAW bioassays to determine whether these modified test proteins maintained or exhibited increased FAW activity compared to their scaffold protein parents. About forty (40) to fifty (50) of these modified test proteins exhibited similar or better FAW activity than their parent scaffold proteins. These further-screened modified test proteins were also tested in additional CEW bioassays to confirm CEW activity. These rounds of selecting and testing modified test proteins which demonstrated improved CEW activity while maintaining or improving FAW activity resulted in a final list of improved variants (referred to herein as the "engineered insecticidal proteins"). Table 2 identifies these engineered insecticidal proteins and the amino acid mutations in each engineered insecticidal protein. Table 2 also demonstrates the activity of the scaffold and the engineered insecticidal proteins against CEW and FAW (insecticidal activity is demonstrated in $LC_{50}$ value (the toxin concentration required to kill 50% of an insect population during a fixed exposure duration. The lower the $LC_{50}$ value, the greater the toxicity) and the $MIC_{50}$ value (the concentration required to inhibit molting to a specific instar of 50% of the larvae during a fixed exposure duration). This Table demonstrates that the engineered insecticidal proteins have improved CEW-activity, while maintaining or improving FAW activity.

TABLE 2

Amino Acid Mutations and Activity Data for Scaffold Proteins and Engineered Insecticidal Proteins.

| Protein (Name/SEQ ID NO.) | Amino Acid Mutations* | $LC_{50}$ ($\mu g/cm^2$) against CEW Benzon colony with spore-crystal bioassay prep | $MIC_{50}$ ($\mu g/cm^2$) against CEW Benzon colony with spore-crystal bioassay prep |
|---|---|---|---|
| Cry1Da1/ NO:2, 28 | None (scaffold protein) | NA** | ~3.0 |
| Cry1Da1_3/ NO:4 | Cry1Da1 + Y316S | NA** | NA** |
| Cry1Da1_4/ NO:6 | Cry1Da1 + S374R | NA** | NA** |
| Cry1Da1_5/ NO:8 | Cry1Da1 + Y316S_I368R | NA** | NA** |
| Cry1Da1_6/ NO:10 | Cry1Da1 + S282K_Y316S_I368P | NA** | NA** |
| Cry1Da1_7/ NO:12 | Cry1Da1 + S282V_Y316S_I368P | NA** | NA** |
| TIC844/ NO:14 | None (scaffold protein) | 41.90 | 3.73 |
| TIC844_2/ NO:16 | TIC844 + Y316S_N375H_I432L | 0.81 | 0.65 |
| TIC844_4/ NO:18 | TIC844 + Y316S | 0.98 | 0.57 |
| TIC844_5/ NO:20 | TIC844 + S282K_Y316S_I368P | 0.32 | 0.33 |
| TIC844_6/ NO:22 | TIC844 + S374R | 4.09 | 1.39 |
| TIC844_7/ NO:24 | TIC844 + Y316S_I368R | 0.93 | 0.61 |
| TIC844_8/ NO:26 | TIC844 + S282V_Y316S_I368P | 0.221 | .064 |

*The amino acid mutations are identified using the standard IUPAC amino acid code. See IUPAC-IUB Joint Commission on Biochemical Nomenclature. Nomenclature and Symbolism for Amino Acids and Peptides. Eur. J. Biochem. 138:9-37(1984). The first amino acid sequence abbreviation indicates the original amino acid in the given scaffold protein, the number represents the position of the amino acid, and the second amino acid sequence abbreviation indicates the amino acid placed in that position in the improved variant protein.
**The core toxin of Cry1Da1 is identical to the core toxin of TIC844.

Further demonstrating the enhanced Lepidopteran inhibitory spectrum and improved Lepidopteran inhibitory activity of the engineered insecticidal proteins, the lethality of engineered insecticidal protein TIC844_8 relative to its parent scaffold protein is demonstrated in FIG. 1. The bar chart of FIG. 1 demonstrates the $MIC_{50}$ values of TIC844_8 compared to the scaffold protein TIC844 for two different CEW colonies, Union City and Benzon. The bioassay results depicted in FIG. 1 were calculated from sucrose gradient-purified bioassay preparations. The reason these secondary bioassays were run with sucrose gradient-purified preparation of the proteins opposed to spore-crystal preparations of the proteins was to ensure that the improved activity of TIC844_8 persisted with more extensive purification. Further, the Union City colony was tested to confirm the improved activity observed on the Benzon colony. As demonstrated in FIG. 1, the mutations in three residues for TIC844_8 (S282V_Y316S_I368P), imparted an 8-fold improvement in CEW lethality, relative to TIC844, for the Union City colony and a 50-fold improvement in CEW lethality, relative to TIC844, for the Benzon colony.

Even further demonstrating enhanced Lepidopteran inhibitory spectrum and improved Lepidopteran inhibitory activity of the engineered insecticidal proteins, the insect activity profiles for TIC844 and TIC844_8 from diet bioassay studies, conducted against a broad spectrum of Lepidopteran insect species, are shown in Table 3. The insects tested against in the bioassay studies in Table 3 include black cutworm (BCW, *Agrotis ipsilon*), corn earworm (CEW, *Helicoverpa zea*), fall armyworm (FAW, *Spodoptera frugiperda*), southern armyworm (SAW, *Spodoptera eridiania*), cabbage looper (CLW, *Trichoplusia ni*), European corn borer (ECB, *Ostrinia nubilalis*), southwestern corn borer (SWC, *Diatraea grandiosella*), tobacco budworm (TBW, *Heliothis virescens*), velvetbean caterpillars (VBC, *Anticarsia gemmatalis*), soybean looper (SBL, *Chrysodeixis includes*), and sugarcane borer (SCB, *Diatraea saccharalis*). This Table 3 demonstrates the enhanced Lepidopteran inhibitory spectrum of TIC844_8 compared to the parent scaffold protein TIC844, specifically with improved activity against CEW and VBC.

TABLE 3

Insect activity spectrum for TIC844 and TIC844_8.

| SEQ ID NO. | Protein | BCW | CEW | FAW | SAW | CLW | ECB | SWC | TBW | VBC | SBL | SCB |
|---|---|---|---|---|---|---|---|---|---|---|---|---|
| 26 | TIC844_8 |  | * | * | * | * |  |  |  | * | * | * |
| 14 | TIC844 |  |  | * | * | * |  |  |  |  | * | * |

* Active against the indicated insect species.

The enhanced Lepidopteran inhibitory spectrum of the engineered insecticidal proteins is further demonstrated in Table 4 which depicts the insect activity profile for certain engineered insecticidal proteins from diet bioassay studies. The insects tested against in the bioassay studies in Table 4 include Old World cotton bollworm (CBW, *Helicoverpa armigera*), tobacco cutworm (TCW, *Spodoptera litura*), beet armyworm (BAW, *Spodoptera exigua*), pink bollworm (PBW, *Pectinophora gossypiella*), pink stem borer (PSB, *Sesamia inferens*) and spotted bollworm (SBW, *Earias vitella*). The results depicted in Table 4 demonstrates the enhanced Lepidopteran inhibitory spectrum of the listed engineered insecticidal proteins compared to the scaffold protein Cry1Da1, specifically with improved activity against CBW, PBW (Cry1Ac resistant), PBW (field collected) and SBW.

TABLE 4

Insect Activity Profile Comparison for Cry1Da1 and Engineered Insecticidal Proteins.

| SEQ ID NO. | Protein | CBW | TCW | BAW | PBW (Lab raised) | PBW (Cry1Ac resistant) | PBW (Field collected) | PSB | SBW |
|---|---|---|---|---|---|---|---|---|---|
| 2 | Cry1Da1 |  | + | + | + | + | + | + |  |
| 12 | Cry1Da1_7 | + | + | + | + | + | + |  | + |
| 18 | TIC844_4 | + | + | + | + | + |  |  | + |
| 20 | TIC844_5 | + | + | + | + | + |  |  | + |
| 24 | TIC844_7 | + | + | + | + | + |  |  |  |

+ Active against the indicated insect species.

Example 4

Synthesis of Genes Encoding Engineered Insecticidal Proteins and Scaffold Proteins for Expression in Plants This Example illustrates the synthesis of polynucleotides encoding engineered insecticidal proteins and scaffold proteins for expression in plants.

Nucleotide sequences encoding scaffold proteins and engineered insecticidal proteins for expression in plants were designed and synthesized according to methods generally described in U.S. Pat. No. 5,500,365, avoiding certain inimical problem sequences such as ATTTA and A/T rich plant polyadenylation sequences while preserving the amino acid sequence of the original scaffold or engineered insecticidal protein. The nucleotide sequences for these genes encoding engineered insecticidal proteins and scaffold proteins for expression in plants are listed below in Table 5.

TABLE 5

Polynucleotide Sequences Designed for Use in Plants Encoding Scaffold and Engineered Insecticidal Proteins.

| NUCLE-OTIDE SEQ ID NO. | PROTEIN | VARIANT |
|---|---|---|
| 27 | Cry1Da1.nno | None (scaffold protein) |
| 29 | Cry1Da1_2.nno | Cry1Da1 + A2** |
| 31 | Cry1Da1_3.nno | Cry1Da1 + Y316S + A2 |
| 33 | Cry1Da1_4.nno | Cry1Da1 + S374R + A2 |
| 35 | Cry1Da1_5.nno | Cry1Da1 + S374R + A2 |
| 37 | Cry1Da1_6.nno | Cry1Da1 + S282K_Y316S_I368P + A2 |
| 39 | Cry1Da1_7.nno | Cry1Da1 + S282V_Y316S_I368P + A2 |
| 41 | TIC844_9.nno | TIC844 + A2 |
| 43 | TIC844_11.nno | TIC844 + S282V_Y316S_I368P + A2 |

**Variant designation "A2" indicates insertion of an alanine residue at amino acid position 2 compared to the native sequence for cloning purposes into plant expression vectors.

Example 5

Expression Cassettes for Expression of Engineered Insecticidal Proteins in Plants This Example illustrates the construction of expression cassettes comprising polynucleotide sequences designed for use in plants which encode scaffold and engineered insecticidal proteins.

A variety of plant expression cassettes were constructed with the polynucleotide sequences encoding scaffold and engineered insecticidal proteins designed for plant expression provided in Table 5. Such expression cassettes are useful for transient expression in plant protoplasts or transformation of plant cells. Typical expression cassettes were designed with respect to the eventual placement of the protein within the cell. One set of expression cassettes was designed in a manner to allow the protein to be translated and remain in the cytosol. Another set of expression cassettes was designed to have a transit peptide contiguous with the toxin protein to allow targeting to an organelle of the cell such as the chloroplast or plastid. All expression cassettes were designed to begin at the 5' end with a promoter, which can be comprised of multiple promoter elements, enhancer elements, or other expression elements known to those of ordinary skill in the art operably linked to boost the expression of the transgene. The promoter sequence was usually followed contiguously with one or more leader sequences 3' to the promoter. An intron sequence was usually provided 3' to the leader sequence to improve expression of the transgene. A coding sequence for the toxin or transit peptide and coding sequence for the toxin was usually located 3' to the operably linked promoter, leader and intron configuration. A 3 'UTR sequence was usually provided 3' of the coding sequence to facilitate termination of transcription and to provide sequences important for the polyadenylation of the resulting transcript. All of the elements described above were operably linked and arranged sequentially, often with additional sequences provided for the construction of the expression cassette.

Example 6

Transformation Vectors Containing a Scaffold or Engineered Insecticidal Protein Expression Cassette This Example illustrates the incorporation of scaffold or engineered insecticidal proteins into plant tissues.

Methods for producing a transgenic plant which expresses a nucleic acid segment encoding a scaffold protein or an engineered insecticidal protein can be done utilizing variations of methods well known in the art. In general, the method comprises transforming a suitable host cell with a DNA segment which contains a promoter operatively linked to a coding region that encodes one or more of the engineered insecticidal proteins or scaffold proteins. Such a coding region is generally operatively linked to a transcription-terminating region, whereby the promoter is capable of driving the transcription of the coding region in the cell, and hence providing the cell the ability to produce the polypeptide in vivo. Vectors, plasmids, cosmids, and DNA segments for use in transforming such cells will generally comprise operons, genes, or gene-derived sequences, either native or synthetically-derived, and particularly those encoding the disclosed engineered insecticidal proteins. These DNA constructs can further include structures such as promoters, enhancers, polylinkers, or other gene sequences which can have regulating activity upon the particular genes of interest. The resultant transgenic plant, plant parts and plant cells are tested for the expression and bioactivity of the encoded protein.

Examples of methods which can be modified for obtaining transgenic plants that express Lepidopteran-active proteins include those describing, for example, Cry1A proteins (U.S. Pat. No. 5,880,275), Cry1B (U.S. patent application Ser. No. 10/525,318), Cry1C (U.S. Pat. No. 6,033,874), Cry1A/F chimeras (U.S. Pat. Nos. 7,070,982; 6,962,705, and 6,713,063), and a Cry2Ab protein (U.S. Pat. No. 7,064,249).

Example 7

Lepidopteran Activity of Engineered Insecticidal Proteins in Stably Transformed Corn This Example illustrates the inhibitory activity exhibited by the engineered insecticidal proteins against Lepidopteran pests when expressed in corn plants and provided as a diet to the respective insect pest.

R0 transgenic corn plants expressing Cry1Da1 and Cry1Da1_7.nno proteins were produced using vectors containing the expression cassettes described in Example 6. F1 transgenic corn plants were grown from seed produced by pollinating ears of non-transformed wild-type commercial germplasm plants with pollen from R0 transformants.

The transformed cells were induced to form plants by methods known in the art. Bioassays using plant leaf disks were performed analogous to those described in U.S. Pat. No. 8,344,207. A non-transformed plant was used to obtain tissue for a negative control. Multiple transformation events from each binary vector were assessed, and the results were tabulated.

The insecticidal activity of transgenic corn plants expressing Cry1Da1 and Cry1Da1_7.nno proteins at F1 and R0 is provided in Table 6, in addition to activity against transgenic corn plants expressing Cry1Da1 and Cry1Da1_7.nno proteins at F1 in the field. Specifically, Table 6 demonstrates the Lepidopteran activity profile for Cry1Da1_7.nno compared to the parent scaffold protein Cry1Da1 when tested against CEW, FAW, and SWC. As can be seen in Table 6, unlike Cry1Da1, Cry1Da1_7.nno demonstrates activity against both CEW and FAW in R0 and F1 bioassay and F1 field tests.

TABLE 6

Insect activity profile for Cry1Da1 and Cry1Da1_7.nno expressed in corn plants.

| Protein | CEW | | | FAW | | | SWC | | |
|---|---|---|---|---|---|---|---|---|---|
| (SEQ ID NO.) | R0 | F1 | Field | R0 | F1 | Field | R0 | F1 | Field |
| Cry1Da1 (28) | − | NT | NT | + | NT | NT | − | NT | NT |
| Cry1Da1_7.nno (40) | + | + | + | + | + | + | − | − | − |

+ Active against insect species; − Inactive against insect species; NT Not Tested

Example 8

Lepidopteran Activity of Engineered Insecticidal Proteins in Stably Transformed Cotton This Example illustrates the inhibitory activity exhibited by the engineered insecticidal proteins against Lepidopteran pests when expressed in cotton plants and provided as a diet to the respective insect pest.

Cotton plants expressing Cry1Da1_7.nno and TIC844_11.nno proteins were produced using vectors containing the expression cassettes described in Example 6. The transformed cells were induced to form plants by methods known in the art. Cotton leaf tissue was used in bioassay as described in Example 7 and tested against CBW, FAW, Tobacco budworm (TBW, *Heliothis virescens*), and SBL. Table 7 shows the activity observed against these Lepidopteran species in stably transformed $R_0$ generation cotton. As can be seen in Table 7, Cry1Da1_7.nno and TIC844_11.nno demonstrated activity against two or more Lepidopteran pest species in stably transformed $R_0$ generation cotton.

TABLE 7

Bioassay activity profile of Cry1Da1_7.nno, and TIC844_11.nno expressed in $R_0$ generation cotton.

| Toxin | CBW | FAW | TBW | SBL |
|---|---|---|---|---|
| Cry1Da1_7.nno (SEQ ID NO: 40) | + | + | + | + |
| TIC844_11.nno (SEQ ID NO: 44) | + | + | − | + |

+ Active against insect species; − Inactive against insect species.

Selected transformed events were used to produce $R_1$ plants. $R_1$ plants expressing Cry1Da1_7.nno were assayed for resistance to CBW, FAW and SBL. Leaf, square and boll tissues were used in bioassay, in addition to field tests conducted in screenhouses. Table 8 shows the activity observed in these tests. As demonstrated in Table 8, Cry1Da1_7.nno demonstrated activity against CBW, FAW and SBL in bioassay and field tests.

TABLE 8

Insect activity profile of Cry1Da1_7.nno expressed in $R_1$ generation cotton.

| | CBW | | | FAW | | | SBL | Screenhouse | |
|---|---|---|---|---|---|---|---|---|---|
| Toxin | Leaf | Square | Boll | Leaf | Square | Boll | Leaf | CBW | FAW |
| Cry1Da1_7.nno (SEQ ID NO:40) | + | + | + | + | + | + | + | + | + |

+ Active against insect species; − Inactive against insect species.

Example 9

Lepidopteran Activity of Engineered Insecticidal Proteins in Stably Transformed Soybean This Example illustrates the inhibitory activity exhibited by the engineered insecticidal proteins against Lepidopteran pests when expressed in soybean plants and provided as a diet to the respective insect pest.

Soybean plants expressing Cry1Da1_7.nno, TIC844_9.nno and TIC844_11.nno proteins were produced using vectors containing the expression cassettes described in Example 6. Leaf tissue was harvested and used in bioassay as described in Example 7 or, alternatively, lyophilized tissue was used in the insect diet for bioassay. Bioassay was performed against various Lepidopteran species, including SAW, SBL and Soybean Pod Worm (SPW, *Helicoverpa zea*). Table 9 shows the activity observed against these Lepidopteran pests in stably transformed R0 generation soybeans. As can be seen in Table 9, Cry1Da1_7.nno and TIC844_11.nno demonstrated activity against SPW, SAW and SBL. TIC844_9.nno (TIC844 plus a bonus alanine for cloning) did not demonstrate activity against SPW.

TABLE 9

Bioassay activity profile of Cry1Da1_7.nno, TIC844_9.nno and TIC844_11.nno expressed in $R_0$ generation soybean.

| Toxin | SPW | SAW | SBL |
|---|---|---|---|
| Cry1Da1_7.nno (SEQ ID NO: 40) | + | + | + |
| TIC844_11.nno (SEQ ID NO: 44) | + | + | + |
| TIC844_9.nno (SEQ ID NO: 42) | − | + | + |

+ Active against insect species; − Inactive against insect species.

Selected transformed events were used to produce $R_1$ plants. $R_1$ plants expressing Cry1Da1_7.nno were assayed for resistance to SAW, SBL, SPW and Velvetbean caterpillar (VBC, *Anticarsia gemmatalis*). Leaf tissue was harvested from the $R_1$ generation plants and used in a feeding bioassay. Table 10 shows the activity observed in these tests. As demonstrated in Table 10, Cry1Da1_7.nno demonstrated activity against SPW, SAW and SBL.

TABLE 10

Bioassay activity profile of Cry1Da1_7.nno expressed in $R_1$ generation soybean.

| Toxin | SPW | SAW | SBL | VBC |
|---|---|---|---|---|
| Cry1Da1_7.nno (SEQ ID NO: 40) | + | + | + | − |

+ Active against insect species; − Inactive against insect species.

Table 11 shows the results of field tests conducted in screenhouses with stably transformed $R_1$ generation soybean plants expressing Cry1Da1_7.nno. Species used to infest plants in the screenhouses include Black armyworm (BLAW, *Spodoptera cosmioides*), Bean shoot moth (BSM, *Crocidosema aporema*), South American podworm (SAPW, *Helicoverpa gelotopoeon*), Sunflower looper (SFL, *Rachiplusia nu*) and VBC. Table 11 shows the activity observed in these tests. As demonstrated in Table 11, Cry1Da1_7.nno demonstrated activity against BLAW, SAPW and SFL.

TABLE 11

Activity profile of Cry1Da1_7.nno expressed in $R_1$ generation soybean tested in screenhouse field tests.

| Toxin | BLAW | BSM | SAPW | SFL | VBC |
|---|---|---|---|---|---|
| Cry1Da1_7.nno (SEQ ID NO: 40) | + | − | + | + | − |

+ Active against insect species; − Inactive against insect species.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

What is claimed is:

1. An engineered insecticidal protein comprising the amino acid sequence as set forth in SEQ ID NO:40.

2. The engineered insecticidal protein of claim 1, wherein the engineered insecticidal protein exhibits inhibitory activity against an insect species of the order Lepidoptera.

3. The engineered insecticidal protein of claim 2, wherein the Lepidoptera is selected from the group consisting of a *Spodoptera* and a *Helicoverpa*.

4. The engineered insecticidal protein of claim 2, wherein the Lepidoptera is selected from the group consisting of *Helicoverpa zea* and *Spodoptera frugiperda*.

5. The engineered insecticidal protein of claim 1, encoded by a polynucleotide operably linked to a heterologous promoter.

6. The engineered insecticidal protein of claim 5, wherein said engineered insecticidal protein is encoded by a polynucleotide comprising a nucleotide sequence that hybridizes to the reverse complement of the polynucleotide sequence as set forth in SEQ ID NO: 39.

7. A host cell comprising the polynucleotide of SEQ ID NO: 39, wherein said polynucleotide is present within a host cell selected from the group consisting of a bacterial host cell and a plant host cell.

8. The host cell of claim 7, wherein said bacterial host cell is selected from the group consisting of *Agrobacterium*, *Rhizobium*, *Bacillus*, *Brevibacillus*, *Escherichia*, *Pseudomonas*, *Klebsiella*, and *Erwinia*.

9. The host cell of claim 7, wherein said plant host cell is selected from the group of plants consisting of a monocot plant cell and a dicot plant cell.

10. An insect inhibitory composition comprising the engineered insecticidal protein of claim 1, wherein said protein is present in an insect inhibitory amount.

11. The insect inhibitory composition of claim 10, wherein said composition further comprises a second insect inhibitory agent different from said engineered insecticidal protein.

12. The insect inhibitory composition of claim 11, wherein said second insect inhibitory agent is selected from the group consisting of an insect inhibitory protein and an insect inhibitory dsRNA molecule.

13. The insect inhibitory composition of claim 12, wherein said second pesticidal agent exhibits activity against one or more pest species selected from the group of orders consisting of Lepidoptera, Coleoptera, Hemiptera, Homoptera, and Thysanoptera.

14. A seed comprising the full length polynucleotide set forth in SEQ ID NO: 39, wherein said polynucleotide is operably linked to a heterologous promoter.

15. A method of controlling a Lepidopteran pest comprising contacting said Lepidopteran pest with an insect inhibitory amount of the engineered insecticidal protein of claim 1.

16. A transgenic plant or plant part comprising the engineered insecticidal protein of claim 1 and a polynucleotide having the nucleotide sequence as set forth in SEQ ID NO:39, wherein said engineered insecticidal protein is present in an insect inhibitory amount.

17. A method of controlling a Lepidopteran pest, said method comprising exposing said pest to the transgenic plant or plant part of claim 16.

18. A commodity product comprising a detectable amount of the engineered insecticidal protein of claim 1 or a detectable amount of a polynucleotide having the sequence as set forth in SEQ ID NO:39.

19. The commodity product of claim 18, wherein said commodity product is selected from the group consisting of plant biomass, oil, meal, animal feed, flour, flakes, bran, lint, hulls, and processed seed.

20. A method of producing a seed comprising the engineered insecticidal protein of claim 1, the method comprising:
   a. planting at least one seed comprising a polynucleotide having the sequence as set forth in SEQ ID NO:39;
   b. growing a plant from said seed; and
   c. harvesting progeny seed from said plant,
   wherein said harvested seed comprises said polynucleotide.

* * * * *